(12) United States Patent
Fischer et al.

(10) Patent No.: US 11,697,829 B2
(45) Date of Patent: *Jul. 11, 2023

(54) CHEMOAUTOTROPHIC CELLS COMPRISING AN ENGINEERED CARBON FIXATION PATHWAY

(71) Applicant: Ginkgo Bioworks, Inc., Boston, MA (US)

(72) Inventors: Curt R. Fischer, Boston, MA (US); Austin J. Che, Boston, MA (US); Reshma P. Shetty, Boston, MA (US); Jason R. Kelly, Boston, MA (US)

(73) Assignee: Ginkgo Bioworks, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/943,819

(22) Filed: Jul. 30, 2020

(65) Prior Publication Data

US 2021/0010037 A1    Jan. 14, 2021

Related U.S. Application Data

(63) Continuation of application No. 15/867,209, filed on Jan. 10, 2018, now Pat. No. 10,801,045, which is a continuation of application No. 14/354,354, filed as application No. PCT/US2012/062540 on Oct. 30, 2012, now Pat. No. 9,902,980, which is a continuation-in-part of application No. 13/285,919, filed on Oct. 31, 2011, now Pat. No. 8,349,587.

(51) Int. Cl.
| | |
|---|---|
| *C12P 7/40* | (2006.01) |
| *C12P 5/00* | (2006.01) |
| *C12P 7/00* | (2006.01) |
| *C12P 7/16* | (2006.01) |
| *C12N 9/04* | (2006.01) |
| *C12N 9/02* | (2006.01) |
| *C12N 15/52* | (2006.01) |
| *C12N 15/70* | (2006.01) |

(52) U.S. Cl.
CPC ............. *C12P 7/40* (2013.01); *C12N 9/0006* (2013.01); *C12N 9/0051* (2013.01); *C12N 15/52* (2013.01); *C12N 15/70* (2013.01); *C12P 5/00* (2013.01); *C12P 7/00* (2013.01); *C12P 7/16* (2013.01); *C12Y 101/05006* (2013.01); *C12Y 108/05004* (2013.01); *Y02E 50/10* (2013.01)

(58) Field of Classification Search
None
See application file for complete search history.

(56) References Cited

U.S. PATENT DOCUMENTS

| | | | |
|---|---|---|---|
| 1,746,464 A | 2/1930 | Fischer | |
| 5,302,525 A | 4/1994 | Groleau et al. | |
| 7,118,896 B2 | 10/2006 | Kalscheuer et al. | |
| 7,256,016 B2 | 8/2007 | San et al. | |
| 7,803,589 B2 | 9/2010 | Burk et al. | |
| 7,923,227 B2 | 4/2011 | Hickey et al. | |
| 7,981,647 B2 | 7/2011 | Berry et al. | |
| 8,349,587 B2 * | 1/2013 | Fischer | C12P 5/00 |
| | | | 435/41 |
| 9,322,000 B2 | 4/2016 | Brautaset et al. | |
| 9,902,980 B2 * | 2/2018 | Fischer | C12Y 108/05004 |
| 10,006,033 B2 | 6/2018 | Liao et al. | |
| 10,563,180 B2 | 2/2020 | Andrae et al. | |
| 10,801,045 B2 * | 10/2020 | Fischer | C12N 15/70 |
| 2003/0157636 A1 | 8/2003 | Figueira et al. | |
| 2004/0142435 A1 | 7/2004 | Gunji et al. | |
| 2007/0264688 A1 | 11/2007 | Venter et al. | |
| 2007/0269862 A1 | 11/2007 | Glass et al. | |
| 2010/0086958 A1 | 4/2010 | Davis et al. | |
| 2010/0228067 A1 | 9/2010 | Peterson et al. | |
| 2012/0064622 A1 | 3/2012 | Fischer et al. | |
| 2015/0037853 A1 | 2/2015 | Fischer et al. | |
| 2015/0267177 A1 | 9/2015 | Brautaset et al. | |
| 2015/0315599 A1 | 11/2015 | Shetty et al. | |
| 2016/0017339 A1 | 1/2016 | Liao et al. | |
| 2016/0060635 A1 | 3/2016 | Liao et al. | |
| 2016/0237410 A1 | 8/2016 | Andrae et al. | |

(Continued)

FOREIGN PATENT DOCUMENTS

| | | |
|---|---|---|
| CN | 107267472 A | 10/2017 |
| WO | WO 2007/041872 A1 | 4/2007 |
| WO | WO 2007/139925 A2 | 12/2007 |

(Continued)

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Abelson et al., Carbon Isotope Fractionation in Formation of Amino Acids by Photosynthetic Organisms. Proc Natl Acad Sci USA. 47(5): 623-632 (1961).
Accession No. AXX60695, 3 pages (Jun. 10, 2010).
Agrawal, P. et al., An algorithm for operating a fed-batch fermentor at optimum specific growth rate. Biotechnology and Bioengineering. 33: 115-125 (1989).

(Continued)

*Primary Examiner* — Christian L Fronda
(74) *Attorney, Agent, or Firm* — Wolf, Greenfield & Sacks, P.C.

(57) ABSTRACT

The present disclosure identifies pathways, mechanisms, systems and methods to confer chemoautotrophic production of carbon-based products of interest, such as sugars, alcohols, chemicals, amino acids, polymers, fatty acids and their derivatives, hydrocarbons, isoprenoids, and intermediates thereof, in organisms such that these organisms efficiently convert inorganic carbon to organic carbon-based products of interest using inorganic energy, such as formate, and in particular the use of organisms for the commercial production of various carbon-based products of interest.

18 Claims, 29 Drawing Sheets

Specification includes a Sequence Listing.

(56) References Cited

U.S. PATENT DOCUMENTS

| | | |
|---|---|---|
| 2018/0223317 A1 | 8/2018 | Fischer et al. |
| 2019/0048310 A1 | 2/2019 | Papoutsakis et al. |

FOREIGN PATENT DOCUMENTS

| | | |
|---|---|---|
| WO | WO 2007/140339 A2 | 12/2007 |
| WO | WO 2009/022754 A1 | 2/2009 |
| WO | WO 2009/154753 A2 | 12/2009 |
| WO | WO 2010/028262 A1 | 3/2010 |
| WO | WO 2011/028264 A1 | 3/2010 |
| WO | WO 2010/042197 A1 | 4/2010 |
| WO | WO 2010/070295 A1 | 6/2010 |
| WO | WO 2011/088425 A2 | 7/2011 |
| WO | WO 2013/066848 A1 | 5/2013 |
| WO | WO 2014/089436 A1 | 6/2014 |
| WO | WO 2017/123775 A1 | 7/2017 |
| WO | WO 2020/214940 A1 | 10/2020 |

OTHER PUBLICATIONS

Aharoni et al., Identification of the SAAT Gene Involved in Strawberry Flavor Biogenesis by Use of DNA Microarrays. The Plant Cell. 12: 647-661 (2000).

Alber et al., Malonyl-Coenzyme A Reductase in the Modified 3-Hydroxypropionate Cycle for Autotrophic Carbon Fixation in Archaeal *Metallosphaera* and *Sulfolobus* spp. Journal of Bacteriology. 188(24): 8551-8559 (2006).

Alber et al., Propionyl-Coenzyme a Synthase from Chloroflexus aurantiacus, as Key Ensyme of the 3-Hydroxypropionate Cycle for Autotrophic $CO_2$ Fixation. The Journal of Biological Chemistry. 277(14): 12137-12143 (2002).

Andersen et al., New Unstable Variants of Green Fluorescent Protein for Studies of Transient Gene Expression in Bacteria. Applied and Environmental Microbiology. 64(6): 2240-2246 (1998).

Anderson et al., Environmental Signal Integration by a Modular AND Gate. Molecular Systems Biology. 3:133 (2007).

Aoshima et al., A Novel Biotin Protein Required for Reductive Carboxylation of 2-Oxoglutarate by Isocitrate Dehydrogenase in Hydrogenobacter thermophilus TK-6. Molecular Microbiology. 51(3): 791-798 (2004).

Aoshima et al., A Novel Enzyme, Citryl-CoA Lyase, Catalysing the Second Step of the Citrate Cleavage Reaction in Hydrogenobacter thermophilus TK-6. Molecular Microbiology. 52(3): 763-770 (2004).

Aoshima et al., A Novel Enzyme, Citryl-CoA Synthetase, Catalysing the First Step of the Citrate Cleavage Reaction in Hydrogenobacter thermophilus TK-6. Molecular Microbiology. 52(3): 751-761 (2004).

Aoshima et al., A Novel Oxalosuccinate-Forming Enzyme Involved in the Reductive Carboxylation of 2-Oxoglutarate in Hydrogenobacter thermophilus TK-6. Molecular Microbiology. 62(3): 748-759 (2006).

Baba et al., Construction of *Escherichia coli* K-12 In-Frame, Single-Gene Knockout Mutants: The Keio Collection. Molecular Systems Biology. 2006.2008 (2006).

Bai et al., Ethanol Fermentation Technologies from Sugar and Starch Feedstocks. Biotechnology Advances. 26(1): 89-105 (2008).

Bailer et al., Determination of Saponifiable Glycerol in 'Bio-Diesel'. Fresenius' Journal of Analytical Chemistry. 340(3): 186 (1991).

Bar-Even et al., Design and Analysis of Synthetic Carbon Fixation Pathways. Proc Natl Acad Sci USA. 107(19): 8889-8894 (2010).

Bassham et al., The Path of Carbon in Photosynthesis. XXI. The Cyclic Regeneration of Carbon Dioxide Acceptor. Radiation Laboratory and Department of Chemistry, University of California, Berkeley. 76:1760-1770(1954).

Bayer et al., "Synthesis of Methyl Halides from Biomass Using Engineered Microbes," JACS. 131(18): 6508-6515 (2009).

Berrios-Rivera et al., "The Effect of the NAPRTase Overexpression on the Total Levels of NAD, The $NADH/NAD^+$ Ratio, and the Distribution of Metabolites in *Escherichia coli*," 4(3): 238-247 (2002).

Bourque, D. et al., High cell density production of poly-beta-hydroxybutyrate (PHB) from methanol by Methylobacterium extorquens: production of high-molecular-mass PHB, Appl. Microbiol. Biotechnol., 44: 367-376 (1995).

Brugna-Guiral et al., "[NiFe] Hydrogenases from the Hyperthermophilic Bacterium *Aquifex aeolicus*: Properties, Function, and Phylogenetics," Extremophiles. 7(2):145-157 (2003).

Buchanan et al., "A Reverse KREBS Cycle in Photosynthesis: Consensus at Last," Photosynthesis Research. 24: 47-53 (1990).

Burgdorf et al., "The Soluble $NAD^+$-Reducing [NiFe]-Hydrogenase from Ralstonia eutropha H16 Consists of Six Subunits and can be Specifically Activated by NADPH," Journal of Bacteriology. 187(9): 3122-3132 (2005).

Camilli et al., "Bacterial Small-Molecule Signaling Pathways," Science. 311(5794): 1113-1116 (2006).

Campbell et al., "Adaptations to Submarine Hydrothermal Environments Exemplified by the Genome of Nautilia profundicola," PLoS Genetics. 5(2): e1000362 (2009).

Campbell et al., "Growth and Phylogenetic Properties of Novel Bacteria Belonging to the Epsilon Subdivision of the Preteobacteria Enriched from Alvinella pompejana and Deep-Sea Hydrothermal Vents," Applied and Environmental Microbiology. 67(10):4566-4572 (2001).

Canton et al., "Refinement and Standardization of Synthetic Biological Parts and Devices," Nature Biotechnology. 26(7): 787-793 (2008).

Cheesbrough et al., "Alkane Biosynthesis by Decarbonylation of Aldehydes Catalyzed by a Particulate Preparation from Pisum sativum," Proc. Natl. Acad. Sci. USA. 81(21): 6613-6617 (1984).

Chen et al., "Biosynthesis of Ansatrienin (Mycotrienin) and Naphthomycin Identification and Analysis of Two Separate Biosynthetic Gene Clusters in Streptomyces collinus Tu 1892," European Journal of Biochemistry. 261(1): 98-107 (1999).

Chica, R.A. et al., Semi-rational approaches to engineering enzyme activity: combining the benefits of directed evolution and rational design, Current Opinion in Biotechnology, 16: 378-384 (2005).

Chin et al., "Improved NADPH Supply for Xylitol Production by Engineered *Escherichia coli* with Glycolytic Mutations," Biotechnol. Prog. 27(2): 333-341 (2011).

Cline, Joel. "Spectrophotometric Determination of Hydrogen Sulfide in Natural Waters," Limnology and Oceanography. 14(3): 454-458 (1969).

Contador, C.A. et al., Ensemble modeling for strain development of L-lysine-producing *Escherichia coli*, Metabolic Engineering, 11: 221-233 (2009).

Cropp et al., "Identification of a Cyclohexylcarbonyl CoA Biosynthetic Gene Cluster and Application in the Production of Doramectin," Nature Biotechnology. 18(9): 980-983 (2000).

Crowther, Gregory J. et al., Formate as the main branch point for methylotrophic metabolism in Methylobacterium extorquens AM1, Journal of Bacteriology, 190(14): 5057-5062 (2008).

Davis et al., "Design, Construction and Characterization of a Set of Insulated Bacterial Promoters," Nucleic Acids Research, doi:10.1093 (2010).

Dellomonaco et al., "Engineered Reversal of the β-oxidation Cycle for the Synthesis of Fuels and Chemicals," Nature. 476(7360): 355-361 (2011).

Dennis et al., "Alkane Biosynthesis by Decarbonylation of Aldehyde Catalyzed by a Microsomal Preparation from Botryococcus brraunii," Archives of Biochemistry and Biophysics. 287(2): 268-275 (1991).

Denoya et al., "A Second Branched-Chain α-Keto Acid Dehydrogenase Gene Cluster (bkdFGH) from Streptomyces avermitilis: Its Relationship to Avermectin Biosynthesis and the Construction of a bkdF Mutant Suitable for the Production of Novel Antiparasitic Avermectins," Journal of Bacteriology. 177(12): 3504-3511 (1995).

Deshpande, Mukund, "Ethanol Production from Cellulose by Coupled Saccharification/Fermentation Using *Saccharomyces cerevisiae* and Cellulase Complex from Sclerotium rolfsii UV-8 Mutant," Applied Biochemistry and Biotechnology. 36(3): 227-234 (1992).

(56) References Cited

OTHER PUBLICATIONS

Dettman et al., "Controls on the Stable Isotope Composition of Seasonal Growth Bands in Aragonitic Fresh-Water Bivalves (*Unionidae*)," Geochimica et Cosmochimica Acta. 63(7/8): 1049-1057 (1999).
Dunham, M.J., Experimental Evolution in Yeast: A practical guide, Methods in Enzymology, 470: 487-507 (2010).
Edgar, Roger C., "MUSCLE: A Multiple Sequence Alignment Method with Reduced Time and Space Complexity," BMC Bioinformatics. 5: 113 (2004).
Edgar, Roger C., "MUSCLE: Multiple Sequence Alignment with High Accuracy and High Throughput," Nucleic Acids Research. 32(5): 1792-1797 (2004).
Edwards et al., "Characterizing the Metabolic Phenotype: A Phenotype Phase Plane Analysis," Biotechnology and Bioengineering. 77(1): 27-36 (2002).
Eisenreich et al., "Retrobiosynthetic Analysis of Carbon Fixation in the Phototrophic Eubacterium *Chloroflexus aurantiacus*," Eur. J. Biochem. 215(3): 619-632 (1993).
Evans et al., "[$^{13}$C]Propionate Oxidation in Wild-Type and Citrate Synthase Mutant *Escherichia coli*: Evidence for Multiple Pathways of Propionate Utilization," Biochem. J. 291:927-932 (1993).
Evans et al., "A New Ferredoxin-Dependent Carbon Reduction Cycle in a Photosynthetic Bacterium," Biochemistry. 55(4): 928-934 (1966).
Evdokimov, E.V. et al., Mikrobiologiya, 61(4): 652-659 (1992).
Farquhar et al., "Carbon Isotope Discrimination and Photosynthesis," Annu. Rev. Plant Physiol. Plant Mol. Biol. 40: 503-537 (1989).
Ferenci et al., "Purification and Properties of 3-Hexulose Phosphate Synthase and Phospho-3-Hexuloisomerase from Methylococcus capsulatus," Biochem. J. 144(3): 477-486 (1974).
Fischer et al., Assessment of heterologous butyrate and butanol pathway activity by measurement of intracellular pathway intermediates in recombinant *Escherichia coli*, Applied Microbial Biotechnology 88: 265-275 (2010).
Fogel et al., "Prokaryotic Genome Size and SSU rDNA Copy Number: Estimation of Microbial Relative Abundance from a Mixed Population," Microbial Ecology. 38(2): 93-113 (1999).
Fong et al., "Metabolic Gene-Deletion Strains of *Escherichia coli* Evolve to Computationally Predicted Growth Phenotypes," Nature Genetics. 36(10): 1056-1058 (2004).
Fong et al., "Predicting Specificity in bZIP Coiled-Coil Protein Interactions," Genome Biology. 5(2): R11.1-R11.10 (2004).
Friedmann et al., "Properties of R-Citramalyl-Coenzyme A Lyase and Its Role in the Autotrophic 3-Hydroxypropionate Cycle of Chloroflexus aurantiacus," Journal of Bacteriology. 189(7): 2906-2914 (2007).
Friedmann et al., "Properties of Succinyl-Coenzyme A: L-Malate Coenzyme A Transferase and Its Role in the Autotrophic 3-Hydroxypropionate Cycle of Chloroflexus aurantiacus," Journal of Bacteriology. 188(7): 2646-2655 (2006).
Gehring and Arnon. "Purification and Properties of α-Ketoglutarate Synthase from a Photosynthetic Bacterium," The Journal of Biological Chemistry. 247(21): 6963-6969 (1972).
Gerhold et al., "DNA Chips: Promising Toys Have Become Powerful Tools," Trends in Biochemical Science. 24(5):168-173 (1999).
Grantham et al., "Codon Catalog Usage and the Genome Hypothesis," Nucleic Acids Research. 8(1): r49-r62 (1980).
Greene et al., "Artificially Evolved Synechococcus PCC6301 Rubisco Variants Exhibit Improvements in Folding and Catalytic Efficiency," Biochem. J. 404(3):571-524 (2007).
Griesbeck et al., "Biological Sulfide Oxidation: Sulfide-Quinone Reductase (SQR), the Primary Reaction," Recent Research Developments in Microbiology. 4:129-203 (2000).
Gul-Karaguler et al., "A Single Mutation in the NAD-specific Formate Dehydrogenase from Candida methylica Allows the Enzyme to Use NADP," Biotechnology Letters. 23(4):283-287 (2001).
Gutteridge et al., "Expression of Bacterial Rubisco Genes in *Escherichia coli*," Phil. Trans. R. Soc. Lond. B. 313:433-445 (1986).

Han and Reynolds. "A Novel Alternative Anaplerotic Pathway to the Glyoxylate Cycle in Streptomycetes," Journal of Bacteriology. 179(16): 5157-5164 (1997).
Harms, N. and Van Spanning, R.J.M., C1 Metabolism in Paracoccus denitrificans: Genetics of Paracoccus denitrificans, Journal of Bioenergetics and Biomembranes, 23(2): 187-209 (1991).
Hatrongjit and Packdibamrung. "A Novel NADP$^+$-dependent Formate Dehydrogenase from Burkholderia stabilis 15516: Screening, Purification and Characterization," Enzyme and Microbial Technology. 46(7):557-561 (2010).
Hawkley and McClure. "Compilation and Analysis of *Escherichia coli* Promoter DNA Sequences," Nucleic Acids Research. 11(8): 2237-2255 (1983).
Hayes, John M. "Fractionation of Carbon and Hydrogem Isotopes in Biosynthetic Processes," Rev. Mineral. Geochem. 43(1):225-277 (2001).
Helling and Kukora. "Nalidixic Acid-Resistant Mutants of *Escherichia coli* Deficient in Isocitrate Dehydrogenase," Journal of Bacteriology. 105(3): 1224-1226 (1971).
Henry et al., "Genome-Scale Thermodynamic Analysis of *Escherichia coli* Metabolism," Biophysical Journal. 90(4):1453-1461 (2006).
Henstra et al., "Microbiology of Synthesis Gas Fermentation for Biofuel Production," Current Opinion in Biotechnology. 18(3): 200-206 (2007).
Herter et al., "A Bicyclic Autotrophic $CO_2$ Fixation Pathway in Chloroflexus aurantiacus," Journal of Bacteriology. 277(23): 20277-20283 (2002).
Herter et al., "L-Malyl-Coenzyme A Lyases/β-Methylmalyl-Coenzyme A Lyase from Chloroflexus aurantiacus, a Biofunctional Enzyme Involved in Autotrophic $CO_2$ Fixation," Journal of Bacteriology. 184(21): 5999-6006 (2002).
Hirt, W. et al., Formaldehyde incorporation by a new methylotroph (L3), Applied and Environmental Microbiology, 36(1): 56-62 (1978).
Ho et al., "Genetically Engineered *Saccharomyces* Yeast Capable of Effective Cofermentation of Glucose and Xylose," Applied and Environmental Microbiology. 64(5): 1852-1859 (1998).
Hoffmeister et al., "Mitochondrial trans-2-Enoyl-CoA Reductase of Wax Ester Fermentation from Euglena gracilis Defines a New Family of Enzymes Involved in Lipid Synthesis," The Journal of Biological Chemistry. 280(6): 4329-4338 (2005).
Holo, Helge. "Chloroflexus aurantiacus Secretes 3-Hydroxypropionate, A Possible Intermediate in the Assimilation of $CO_2$ and Acetate," Archives of Microbiology. 151(3): 252-256 (1989).
Hou et al., "Metabolic Impact of Increased NADH Availability in *Saccharomyces cerevisiae*," Applied and Environmental Microbiology. 76(3): 851-859 (2010).
Huan-Hsu et al., "Addition of Autotrophic Carbon Fixation Pathways to Increase the Theoretical Heterotrophic Yield of Acetate", The Fourth International Conference on Computational Systems Biology (ISB2010), Suzhou, China, Sep. 9-11, 2010, pp. 314-322.
Hugler et al., "Autotrophic $CO_2$ Fixation via the Reductive Tricarboxylic Acid Cycle in Different Lineages Within the Phylum Aquificae: Evidence for Two Ways of Citrate Cleavage," Environmental Microbiology. 9(1): 81-92 (2007).
Hugler et al., "Beyond the Calvin Cycle: Autotrophic Carbon Fixation in the Ocean," Annu. Rev. Marine. Sci. 3:261-289 (2011).
Hugler et al., "Malonyl-Coenzyme A Reductase from Chloroflexus aurantiacus, a Key Enzyme of the 3-Hydroxypropionate Cycle for Autotrophic $CO_2$ Fixation," Journal of Bacteriology. 184(9):2404-2410 (2002).
Hugler et al., "Pathways of Carbon and Energy Metabolism of the Epibiotic Community Associated with the Deep-Sea Hydrothermal Vent Shrimp *Rimicaris exoculata*," PLoS One. 6(1):e16018 (2011).
Huisman and Gray, "Towards Novel Processes for the Fine-Chemical and Pharmaceutical Industries," Curr. Opin. Biotechnol. 13(4):352-358 (2002).
Ikeda et al., "Two Tandemly Arranged Ferredoxin Genes in the Hydrogenobacter thermophiles Genome: Comparative Characterization of the Recombinant [4FE-4S] Ferredoxins," Biosci. Biotechnol. Biochem. 69(6):1172-1177 (2005).
Inokuma et al., "Characterization of Enzymes Involved in the Ethanol Production of *Moorella* sp. HUC22-1," Arch. Microbiol. 188(1):37-45 (2007).

(56) References Cited

OTHER PUBLICATIONS

International Preliminary Report on Patentability for PCT/US2012/062540, 9 pages (dated May 15, 2014).
International Search Report for PCT/US2012/062540, 5 pages (dated Apr. 10, 2013).
International Search Report for PCT/US2013/073582, 5 pages (dated Mar. 20, 2015).
Janausch et al., "C$_4$-Dicarboxylate Carriers and Sensors in Bacteria," Biochemica et Biophysica Acta. 1553(1-2): 39-56 (2002).
Jukes and Osawa. "Mini Review: Evolutionary Changes in the Genetic Code," Comp. Biochem. Physiol. 106B(3): 489-494 (1993).
Kalscheuer and Steinbuchel. "A Novel Bifunctional Wax Ester Synthase/Acyl-CoA:Diacylglycerol Acyltransferases Mediates Wax Ester and Triacylglycerol Biosynthesis in Acinetobactor calcoaceticus ADP1," The Journal of Biological Chemistry.278(10):8075-8082 (2003).
Kalscheuer et al., "Microdiesel: *Escherichia coli* engineered for Fuel Production," Microbiology. 152:2529-2536 (2006).
Kanao et al., "Characterization of Isocitrate Dehydrogenase from the Green Sulfur Bacterium *Chlorobium limicola*," Eur. J. Biochem. 269(7): 1926-1931 (2002).
Kanao et al., "Kinetic and Biochemical Analyses on the Reaction Mechanism of a Bacterial ATP-Citrate Lyase," Eur. J. Biochem. 269(14): 3409-3416 (2002).
Kaneda, T. "Iso- and Antesio-Fatty Acids in Bacteria: Biosynthesis, Function, and Taxonomic Significance," Microbiological Reviews. 55(2): 288-302 (1991).
Kapust and Waugh. "*Escherichia coli* Maltose-Binding Protein is Uncommonly Effective at Promoting the Solubility of Polypeptides to Which it is Fused," Protein Science. 8:1668-1674 (1999).
Keasling, Jay D. "Gene-Expression Tools for the Metabolic Engineering of Bacteria," Trends in Biotechnol. 17(11):452-460 (1999).
Kelly et al., "Methodology: Measuring the Activity of BioBrick Promoters Using an in vivo Reference Standard," Journal of Biological Engineering. 3(4): 1-13 (2009).
Kelly et al., Autotrophic Metabolism of Formate by Thiobacillus Strain A2, Journal of General Microbiology. 144:1-13 (1979).
Kelly, D.P. et al., Proposal for the reclassification of Thiobaccillus novellus as *Starkeya novella* gen. nov., comb, nov., in the a-subclass of the Proteobacteria, International Journal of Systematic and Evolutionary Microbiology, 50: 1797-1802 (2000).
Kemp, M.B. "Hexose Phosphate Synthetase from Methylococcus capsulatus Makes a Darabino-3-Hexulose Phosphate," Biochem J. 139(1):129-134 (1974).
Kemp, M.B. "The Hexose Phosphate Synthetase of Methylococcus capsulatus," Biochem J. 127(3):64P-65P (1972).
Kiely, P.D. et al., Anodic biofilms in microbial fuel cells harbor low numbers of higher-powerproducing bacteria than abundant genera, Appl. Microbiol. Biotechnol., 88: 371-380 (2010).
Kim and Unden, "The I-Tartrate/Succinate AntiporterTtdT (YgjE) of I-Tartrate Fermentation in *Escherichia coli*," Journal of Bacteriology. 189(5): 1597-1603 (2007).
Kim et al., "Production of Biohydrogen by Heterologous Expression of Oxygen-Tolerant Hydrogenovibrio marinus [NiFe]-Hydrogenase in *Escherichia coli*," Journal of Biotechnology. 1155(3):312-319 (2011).
Klimke et al., "The National Center for Biotechnology Information's Protein Clusters Database," Nucleic Acids Research. 37:D216-D223 (2009).
Knight, T., "Draft Standard for Biobrick Biological Parts," http://hdl.handle.net/172.1/45138 (2007).
Knight, T., "Idempotent Vector Design for Standard Assembly of Biobricks," http://hdl.handle.net/172.1/21168 (2003).
Knothe et al., "Biodiesel: The Use of Vegetable Oils and Their Derivatives as Alternative Diesel Fuels," Am. Chem. Soc. Symp. Series, vol. 666, Fuels and Chemicals from Biomass, Chapter 10, pp. 172-208 (1997).
Knothe, Gerhard. "Dependence of Biodiesel Fuel Properties on the Structure of Fatty Acid Alkyl Esters," Fuel Processing Technology. 86:1059-1070 (2005).

Knothe, Gerhard. "Rapid Monitoring of Transesterification and Assessing Biodiesel Fuel Quality by Near-Infrared Spectroscopy Using a Fiber-Optic Probe," J. Am. Oil Chem. Soc. 76(7): 795-800 (1999).
Kolkman et al., "Directed Evolution of Proteins by Exon Shuffling," Nat. Biotechnol. 19(5):423-428 (2001).
Larkum, AWD. "Limitation and Prospects of Natural Photosynthesis for Bioenergy Production," Current Opinion in Biotechnology. 21(3):271-276 (2010).
LaRue and Kurz. "Estimation of Nitrogenase Using a Colorimetric Determination for Ethylene," Plant Physiol. 51(6):1074-1075 (1973).
Li et al., "Alteration of the Fatty Acid Profile of Streptomyces coelicolor by Replacement of the Initial Enzyme 3-Ketoacyl Carrier Protein Synthase III (FabH)," Journal of Bacteriology. 187(11): 3795-3799 (2005).
Liu et al., "Formate Dehydrogenase of Clostridium pasteurianum," Journal of Bacteriology. 159(1):375-380 (1984).
Marcia et al., "A New Structure-Based Classification of Sulfide: Quinone Oxidoreductases," Proteins. 78(5):1073-1083 (2010).
Marrakchi et al., "A New Mechanism for Anaerobic Unsaturated Fatty Acid Formation in *Streptococcus pneumoniae*," The Journal of Biological Chemistry. 277(47):44809-44816 (2002).
Marrakchi et al., "Mechanistic Diversity and Regulation of Type II Fatty Acids Synthesis," Biochem. Soc. Trans. 30(6): 1050-1055 (2002).
Martin et al., "Redesigning Cells for Production of Complex Organic Molecules," ASM News. 68(7): 336-343 (2002).
Martinez-Alonso et al., "Rehosting of Bacterial Chaperones for High-Quality Protein Production," Applied and Environmental Microbiology, 75(24): 7850-7854 (2009).
Martinez-Alonso et al., "Side Effects of Chaperone Gene Co-Expression in Recombinant Protein Production," Microbial Cell Factories. 9(64):1-6 (2010).
Marty and Planas. "A Comparison of Methods to Determine Algal $\Delta^{13}C$ in Freshwater," Limnol Oceanogr Methods. 6:51-63 (2008).
Mendoza et al., "Thermal Regulation of Membrane Fluidity in *Escherichia coli*," The Journal of Biological Chemistry. 258(4):2098-2101 (1983).
Menendez et al., "Presences of Acetyl Coenzyme A (CoA) Carboxylase and Propionyl-COA Carboxylase in Autotrophic Crenarchaeota and Indication for Operation of a 3-Hydroxypropionate Cycle in Autotrophic Carbon Fixation," Journal of Bacteriology.181(4):1088-1098 (1999).
Minshull and Stemmer. "Protein Evolution by Molecular Breeding," Curr. Opin. Chem. Biol. 3(3):284-290 (1999).
Miroshnichenko et al., "*Nautilia lithotrophica* gen. nov., sp. nov., a Thermophilic Sulfuro- Reducing ε-Proteobacterium Isolated from a Deep-Sea Hydrothermal Vent," International Journal of Systematic and Evolutionary Microbiology.52:1299-1304 (2002).
Mitsui et al., "A Novel Operon Encoding Formaldehyde Fixation: the Ribulose Monophosphate Pathway in the Gram-Positive Facultative Methylotrophic Bacterium *Mycobacterium gastri* MB 19," Journal of Bacteriology. 182(4):944-948 (2000).
Monson and Hayes. "Biosynthetic Control of the Natural Abundance of Carbon 13 at Specific Positions within Fatty Acids in *Escherichia coli*," The Journal of Biological Chemistry. 255(23):11435-11441 (1980).
Moriya et al., "KAAS: An Automatic Genome Annotation and Pathway Reconstruction Server," Nucleic Acids Research. 35:W182-W185 (2007).
Morweiser et al., "Developments and Perspectives of Photobioreactors for Biofuel Production," Appl. Microbiol. Biotechnol. 87:1291-1301 (2010).
Murli et al., "A Role for the umuDC Gene Products of *Escherichia coli* in Increasing Resistance to DNA Damage in Stationary Phase by Inhibiting the Transition to Exponential Growth," Journal of Bacteriology. 182(4):1127-1135 (2000).
Murtagh, F. "Complexities of Hierarchic Clustering Algorithms: State of the Art," Computational Statistics Quarterly. 1(2):101-113 (1984).
Ober, Joyce A. "Sulfur," U.S. Geological Survey Minerals Yearbook. U.S. Department of the Interior U.S. Geological Survey. 74.1-74.17 (2010).

(56) References Cited

OTHER PUBLICATIONS

Orita et al., "Bifunctional Enzyme Fusion of 3-Hexulose-6-Phosphate Synthase and 6-Phospho-3-Hexuloisomerase," Appl. Microbiol. Biotechnol. 76:439-445 (2007).
Orita et al., "The Archaeon Pyrococcus horikoshii Possesses a Bifunctional Enzyme for Formaldehyde Fixation via the Ribulose Monophosphate Pathway," Journal of Bacteriology. 187(11):3636-3642 (2005).
Orita et al., "The Ribulose Monophosphate Pathway Substitutes for the Missing Pentose Phosphate Pathway in the Archaeon Thermococcus kodakaraensis," Journal of Bacteriology. 188(13):4698-4704 (2006).
Palaniappan et al., "Enhancement and Selective Production of Phoslactomycin B, a Protein Phosphatase IIa Inhibitor, Through Identification and Engineering of the Corresponding Biosynthetic Gene Cluster," The Journal of Biological Chemistry. 278(37):35552-35557 (2003).
Pant, D. et al., A review of the substrates used in microbial fuel cells (MFCs) for substainable energy production, Bioresource Technology, 101: 1533-1543 (2010).
Parikh et al., "Directed Evolution of RuBisCO Hypermorphs Through Genetic Selection in Engineered *E. coli*," Protein Engineering, Design & Selection. 19(3): 113-119 (2006).
Park, Myong-Ok. "New Pathway for Long-Chain n-Alkane Synthesis via 1-Alcohol in Vibrio furnissii M1," Journal of Bacteriology. 187(4):1426-1429 (2005).
Patton et al., "A Novel $\Delta^3$, $\Delta^2$-Enoyl-CoA Isomerase Involved in the Biosynthesis of the Cyclohexanecarboxylic Acid-Derived Moiety of the Polyketide Anastrienin A," Biochemistry. 39:7595-7604 (2000).
Pinske et al., "Metabolic Deficiences Revealed in the Biotechnologically Important Model Bacterium *Escherichia coli* BL21 (DE3)," PLoS One. 6(8): e22830 (2011).
Portis and Parry. "Discoveries in Rubisco (Ribulose 1,5-Biophosphate Carboxylase/Oxygenase): A Historical Perspective," Photosynth Res. 94:121-143 (2007).
Pramanik and Keasling. "Effect of *Escherichia coli* Biomass Composition on Central Metabolic Fluxes Predicted by a Stoichiometric Model," Biotechnol. Bioeng. 60(2): 230-238 (1998).
Pramanik and Keasling. "Stoichiometric Model of *Escherichia coli* Metabolism: Incorporation of Growth-Rate Dependent Biomass Composition and Mechanistic Energy Requirements," Biotechnol. Bioeng. 56(4): 398-421 (1997).
Rathnasingh et al., "Production of 3-Hydroxypropionic Acid via Malonyl-CoA Pathway Using Recombinant *Escherichia coli* Strains," Journal of Biotechnology. 157(4):633-640 (2012).
Reading and Sperandio. "Quorum Sensing: The Many Languages of Bacteria," FEMS Microbiol. Left. 254(1):1-11 (2006).
Rock et al., "Increased Unsaturated Fatty Acid Production Associated with a Suppressor of the fabA6(Ts) Mutation in *Escherichia coli*," Journal of Bacteriology. 178(18):5382-5387 (1996).
Roessner et al., "Overexpression in *Escherichia coli* of 12 Vitamin $B_{12}$ Biosynthetic Enzymes," Protein Expression and Purification. 6(2):155-163 (1995).
Sachdev and Chirgwin. "Fusions to Maltose-Binding Protein: Control of Folding and Solubility in Protein Purification," Methods Enzymol. 326:312-321 (2000).
Sachdev and Chirgwin. "Solubility of Proteins Isolated from Inclusion Bodies is Enhanced by Fusion to Maltose-Binding Protein or Theoredoxin," Protein Expression and Purification. 12(1):122-132 (1998).
Saitou and Nei. "The Neighbor-joining Method: A New Method for Reconstructing Phylogenetic Trees," Mol. Biol. Evol. 4(4):406-425 (1987).
Sakata et al., "Carbon Isotopic Fractionation Associated with Lipid Biosynthesis by a Cyanobacterium: Relevance for Interpretation of Biomarker Records," Geochim. Cosmochim Acta. 61(24):5379-5389 (1997).
San et al., "Metabolic Engineering Through Cofactor Manipulation and its Effects on Metabolic Flux Redistribution in *Escherichia coli*," Metabolic Engineering. 4(2):182-192 (2002).

Sauer et al., "The Soluble and Membrane-Bound Transhydrogenases UdhA and PntAB Have Divergent Functions in NADPH Metabolism of Escherichia coli," The Journal of Biological Chemistry. 279(8):6613-6619 (2004).
Schendel, F.J. et al., L-lysine production at 50 degrees C by mutants of a newly isolated and characterized methylotrophic *Bacillus* sp, Applied and Environmental Microbiology, 56(4):963-970 (1990).
Schrader, Jens et al., Methanol-based industrial biotechnology: current status and future perspectives of methylotrophic bacteria, Trends in Biotechnology, 27(2): 107-115 (2009).
Schutz et al., "Sulfide-Quinone Reductase from Rhodobacter capsulates," The Journal of Biological Chemistry. 272(15):9890-9894 (1997).
Self et al., "Expression and Regulation of a Silent Operon, hyf, Coding for Hydrogenase 4 Isoenzyme in *Escherichia coli*," Journal of Bacteriology. 186(2):580-587 (2004).
Sen, S. et al., Developments in Directed Evolution for Improving Enzyme Functions, Appl. Biochem. Biotechnol., 143: 212-223 (2007).
Serov et al., "Engineering of Coenzyme Specificity of Formate Dehydrogenase from *Saccharomyces cerevisiae*," Biochem. J. 367:841-847 (2002).
Shetty et al., "Assembly of BioBrick Standard Biological Parts Using Three Antibiotic Assembly," Methods in Enzymology. 498: 311-326 (2011).
Shetty et al., "Methodology: Engineering BioBrick Vectors from BioBrick Parts," Journal of Biological Engineering. 2(5):1-12 (2008).
Shibata and Kobayashi. "Sulfide Oxidation in Gram-Negative Bacteria by Expression of the Sulfide-Quinone Reductase Gene of Rhodobacter capsulates and by Electron Transport to Ubiquinone," Can. J. Microbiol. 47(9):855-860 (2001).
Shpaer, Eugene G. "GeneAssist: Smith-Waterman and Other Database Similarity Searches and Identification of Motifs," Methods Mol. Biol. 70:173-187 (1997).
Singh et al., Bioengineering for Microbial Inulinases: Trends and Applications. Curr Protein Pept Sci. 2017;18(9):966-972. doi: 10.2174/1389203718666161122112251.
Smith et al., "*Nautilia profundicola* sp. nov., a Thermophilic Sulfur-Reducing Epsilonproteobacterium from Deep-Sea Hydrothermal Vents," Int. j. Syst. Evol. Microbiol. 58:1598-1602 (2008).
Smolke and Keasling. "Effect of Copy Number and mRNA Processing and Stabilization on Transcript and Protein Levels from an Engineered Dual-Gene Operon," Biotechnol. Bioeng. 78(4):412-424 (2002).
Smolke and Keasling. "Effect of Gene Location, mRNA Secondary Structures, and RNase Sites of Expression of Two Genes in an Engineered Operon," Biotechnol. Bioeng. 80(7): 762-776 (2002).
Smolke et al., "Controlling the Metabolic Flux Through the Carotenoid Pathway Using Directed mRNA Processing and Stabilization," Metabolic Engineering. 3(4):313-321 (2001).
Smolke et al., "Coordinated, Differential Expression of Two Genes Through Directed mRNA Cleavage and Stabilization by Secondary Structures," Appl. Environ. Microbiol. 66(12):5399-5405 (2000).
Sokal and Michener. "A Statistical method for Evaluating Systematic Relationships," The University of Kansas Science Bulletin. 38(22): 1409-1438 (1958).
Strauss and Fuchs. "Enzymes of a Novel Autotrophic $CO_2$ Fixation Pathway in the Phototrophic Bacterium *Chloroflexus aurantiacus*, the 3-Hydroxypropionate Cycle," Eur. J. Biochem. 215(3):633-643 (1993).
Strom et al., "The Carbon Assimilation Pathways of Methylococcus capsulatus, Pseudomonas methanica and Methylosinus trichosporium (OB3B) During Growth on Methane," Biochem. J. 144(3):465-476 (1974).
Sun et al., "Heterologous Expression and Maturation of an NADP-Dependent [NiFe]⁻ Hydrogenase: A Key Enzyme in Biofuel Production," PLoS One. 5(5): e10526 (2010).
Tabita et al., "Expression and Assembly of Active Cyanobacterial Ribulose-1,5-Bisphosphate Carboxylase/Oxygenase in *Escherichia coli* Containing Stoichiometric Amounts of Large and Small Subunits," Proc. Natl. Acad. Sci. 82(18):6100-6103 (1985).
Tatusov et al., "A Genomic Perspective on Protein Families," Science. 248(5338):631-637 (1997).

(56) References Cited

OTHER PUBLICATIONS

Tatusov et al., "The COG Database: An Updated Version Includes Eukaryotes," BMC Bioinformatics. 4:1-14(2003).
Theissen et al., Sulfide: quinone oxidoreductase (SQR) from the lugworm *Arenicola marina* shows cyanide and thioredoxin-dependent activity, FEBS Journal 275: 1131-1139 (2008).
Van Wezel et al., "GlcP Constitutes the Major Glucose Uptake System of Streptomyces Coelicolor A3(2)," Molecular Microbiology. 55(2):624-636 (2005).
Venturi, Vittorio. "Regulation of Quorum Sensing in Pseudomonas," FEMS Microbiol. Rev. 30(2):274-291 (2006).
Vignais and Billoud. "Occurrence, Classification, and Biological Function of Hydrogenases: An Overview," Chem. Rev. 107(10):4206-4272 (2007).
Vignais and Colbeau. "Molecular Biology of Microbial Hydrogenases," Curr. Issues Mol. Biol. 6(2):159-188 (2004).
Wells et al., "Engineering a Non-Native Hydrogen Production Pathway into *Escherichia coli* via a Cyanobacterial [NiFe] Hydrogenase," Metabolic Engineering. 13(4):445-453 (2011).
Whisstock, J.C. et al., Prediction of protein function from protein sequence and structure, Quarterly Reviews of Biophysics, 36(3): 307-340 (2003).
Written Opinion for PCT/U2012/062540, 13 pages (dated Apr. 10, 2013).
Written Opinion for PCT/US2013/073582 9 pages, (dated Mar. 20, 2015).
Wubbolts et al., "Variation of Cofactor Levels in *Escherichia coli*: Sequence Analysis and Expression of the pncB Gene Encoding Nicotinic Acid Phosphoribosyktrabsferase," The Journal of Biological Chemistry. 265(29): 17665-17672 (1990).
Yamamoto et al., "Carboxylation Reaction Catalyzed by 2-Oxoglutarate:Ferredoxin Oxidoreductases from Hydrogenobacter thremophilus," Extremeophiles. 14(1):79-85 (2010).
Yamane et al., Annals New York Academy of Science, 364-381 (1986).
Yoon et al., "Purification and Characterization of Pyruvate:Ferredoxin Oxidoreductase from Hydrogenobacter thermophilus TK-6," Arch. Microbiol. 167(5):275-279 (1997).
Yurimoto, H. et al., The ribulose monophosphate pathway operon encoding formaldehyde fixation in a thermotolerant methylotroph, Bacillus brevis S1, FEMS Microbiology, Letters, 214: 189-193 (2002).
Zarzycki and Fuchs. "Co-Assimilation of Organic Substrates via the Autotrophic 3-Hydroxypropionate Bi-Cycle in Chloroflexus auranticus," Appl. Environ. Microbio. 77(17):6181-6188 (2011).
Zarzycki et al., "Identifying the Missing Steps of the Autotrophic 3-Hydroxypropionate $CO_2$ Fixation Cycle in Chloroflexus aurantiacus," Proc. Natl. Acad. Sci. USA. 106(50):21317-21322 (2009).
Zdobnov and Apweiler. "InterProScan—An Integration Platform for the Signature-Recognition Methods in InterPro," Bioinformatics. 17(9):847-848 (2001).
Zhang et al., "Molecular and Genetical Analysis of the Fructose-Glucose Transport System in the Cyanobacterium Synechocystis PCC6803," Molecular Microbiology. 3(9):1221-1229 (1989).
Zhang et al., "The FabR (YijC) Transcription Factor Regulates Unsaturated Fatty Acid Biosynthesis in *Escherichia coli*," The Journal of Biological Chemistry. 277(18):15558-15565 (2002).
Zhu et al., "Production of Ubiquinone in *Escherichia coli* by Expression of Various Genes Responsible for Ubiquinone Biosynthesis," Journal of Fermentation and Bioengineering. 79(5):493-495 (1995).
Zweiger, Gary. "Knowledge Discovery in Gene-Expression-Microarray Data: Mining the Information Output of the Genome," Trends Biotechnol. 17(11):429-436 (1999).
PCT/US2012/062540, Apr. 10, 2013, International Search Report and Written Opinion.
PCT/US2012/062540, May 15, 2014, International Preliminary Report on Patentability.
PCT/US2013/073582, Mar. 20, 2015, International Search Report and Written Opinion.

[No Author Listed], hexulose-6-phosphate synthase/SIS domain-containing protein [*Methylococcus capsulatus* str. Bath]. NCBI Ref Seq ID No. YP_115138. Dec. 16, 2014. Retrieved from https://www.ncbi.nlm.nih.gov/protein/YP_115138.1?report=genpept. 2 pages.
[No Author Listed], hexulose-6-phosphate synthase [*Methylococcus capsulatus* str. Bath]. NCBI Ref Seq ID No. YP_115430. Dec. 16, 2014. Retrieved from https://www.ncbi.nlm.nih.gov/protein/YP_115430.1 ?report=genpept. 2 pages.
[No Author Listed], 3-hexulose-6-phosphate synthase. UniProt Acc. No. A0A089JE64. Nov. 26, 2014, sequence version 1, entry version 1. Accessible at https://rest.UniProt.org/unisave/A0A089JE64?format=txt&versions=1. 1 page.
[No Author Listed], 3-hexulose-6-phosphate synthase. UniProt Acc. No. A0A0J5SIS5. Oct. 14, 2015, sequence version 1, entry version 1. Accessible at https://rest.UniProt.org/unisave/A0A0J5SIS5?format=txt&versions=1. 1 page.
[No Author Listed], 3-hexulose-6-phosphate synthase. UniProt Acc. No. A0A0K9H4Z2. Nov. 11, 2015, sequence version 1, entry version 1. Accessible at https://rest.UniProt.org/unisave/A0A0K9H4Z2?format=txt&versions=1. 1 page.
[No Author Listed], 3-hexulose-6-phosphate synthase. UniProt Accession No. A0A0M4M0F0_9MICC. Dec. 9, 2015, sequence version 1, entry version 1. Accessible at https://rest.UniProt.org/unisave/A0A0M4M0F0?format=txt&versions=16. 1 page.
[No Author Listed], 3-hexulose-6-phosphate synthase. UniProt Acc. No. A0A0N1M834. Dec. 9, 2015, sequence version 1, entry version 1. Accessible at https://rest.UniProt.org/unisave/A0A0N1M834?format=txt&versions=1. 1 page.
[No Author Listed], 3-hexulose-6-phosphate synthase. UniProt Acc. No. A0A0Q4RLM0. Jan. 20, 2016, sequence version 1, entry version 1. https://rest.UniProt.org/unisave/A0A0Q4RLM0?format=txt&versions=1. 1 page.
[No Author Listed], 3-hexulose-6-phosphate synthase. UniProt Acc. No. A0A0R2DL35. Jan. 20, 2016, sequence version 1, entry version 1. Accessible at https://rest.UniProt.org/unisave/A0A0R2DL35?format=txt&versions=1. 1 page.
[No Author Listed], 3-hexulose-6-phosphate synthase. UniProt Acc. No. A0A0R2KRX5. Jan. 20, 2016, sequence version 1, entry version 1. Accessible at https://rest.UniProt.org/unisave/A0A0R2KRX5?format=txt&versions=1. 1 page.
[No Author Listed], 3-hexulose-6-phosphate synthase. UniProt Acc. No. A0K1B3. Oct. 9, 2011, entry version 31; Dec. 12, 2006, sequence version 1. Accessible at https://rest.UniProt.org/unisave/A0K1B3?format=txt&versions=31. 1 page.
[No Author Listed], 3-hexulose-6-phosphate synthase. UniProt Acc. No. B9E933. Jul. 27, 2011, entry version 13; Mar. 24, 2009, sequence version 1. Accessible at https://rest.UniProt.org/unisave/B9E933?format=txt&versions=13. 1 page.
[No Author Listed], 3-hexulose-6-phosphate synthase. UniProt Acc. No. E1CPX1. May 31, 2011, entry version 5; Nov. 30, 2010, sequence version 1. Accessible at https://rest.UniProt.org/unisave/E1CPX1?format=txt&versions=5. 1 page.
[No Author Listed], 3-hexulose-6-phosphate synthase. UniProt Acc. No. F8FIZ2. Oct. 9, 2011, entry version 2; Sep. 21, 2011, sequence version 1. Accessible at https://rest.UniProt.org/unisave/F8FIZ2?format=txt&versions=2. 1 page.
[No Author Listed], 3-hexulose-6-phosphate synthase. UniProt Acc. No. Q602L4_METCA. Oct. 9, 2011, entry version 47; Nov. 23, 2004, sequence version 1. https://rest.UniProt.org/unisave/Q602L4?format=txt&versions=47. 2 pages.
[No Author Listed], 3-hexulose-6-phosphate synthase. UniProt Acc. No. W4QWA4. Mar. 19, 2014, sequence version 1, entry version 1. Accessible at https://rest.UniProt.org/unisave/W4QWA4?format=txt&versions=1. 1 page.
[No Author Listed], 6-phospho-3-hexuloisomerase. UniProt Acc. No. A0A0E3SGF7. Jun. 24, 2015, sequence version 1, entry version 1. Accessible at https://rest.uniprot.org/unisave/A0A0E3SGF7?format=txt&versions=15. 1 page.
[No Author Listed], 6-phospho-3-hexuloisomerase. UniProt Acc. No. B0RAL7. Sep. 21, 2011, entry version 22; Apr. 8, 2008, sequence version 1. Accessible at https://rest.uniprot.org/unisave/B0RAL7?format=txt&versions=22. 1 page.

(56) References Cited

OTHER PUBLICATIONS

[No Author Listed], 6-phospho-3-hexuloisomerase. UniProt Acc. No. Q8TR01. Sep. 21, 2011, entry version 50; Jun. 1, 2002, sequence version 1. Accessible at https://rest.uniprot.org/unisave/Q8TR01?format=txt&versions=50. 1 page.

[No Author Listed], hexulose-6-phosphate synthase [Methylococcus capsulatus str. Bath]. NCBI Ref Seq ID No. YP_115430. Oct. 19, 2011. Retrieved from https://www.ncbi.nlm.nih.gov/protein/53802837?sat=15&satkey=1326712. 2 pages.

[No Author Listed], hexulose-6-phosphate synthase/SIS domain-containing protein [Methylococcus capsulatus str. Bath]. NCBI Ref Seq ID No. YP_115138. Oct. 19, 2011. Retrieved from https://www.ncbi.nlm.nih.gov/protein/53803128?sat=15&satkey=1326712. 2 pages.

Altschul et al., Basic local alignment search tool. J Mol Biol. Oct. 5, 1990;215(3):403-10. doi: 10.1016/S0022-2836(05)80360-2.

Altschul et al., Gapped BLAST and PSI-BLAST: a new generation of protein database search programs. Nucleic Acids Res. Sep. 1, 1997;25(17):3389-402. doi: 10.1093/nar/25.17.3389.

Goldenzweig et al., Automated Structure- and Sequence-Based Design of Proteins for High Bacterial Expression and Stability. Mol Cell. Jul. 21, 2016;63(2):337-346. doi: 10.1016/j.molcel.2016.06.012. Epub Jul. 14, 2016. Erratum in: Mol Cell. Apr. 19, 2018;70(2):380.

Hektor et al., Identification of a magnesium-dependent NAD(P)(H)-binding domain in the nicotinoprotein methanol dehydrogenase from Bacillus methanolicus. J Biol Chem. Dec. 6, 2002;277(49):46966-73. doi: 10.1074/jbc.M207547200. Epub Sep. 25, 2002.

Hirayama et al., *Methylothermus subterraneus* sp. nov., a moderately thermophilic methanotroph isolated from a terrestrial subsurface hot aquifer. Int J Syst Evol Microbiol. Nov. 2011;61(Pt 11):2646-2653. doi: 10.1099/ijs.0.028092-0. Epub Dec. 10, 2010.

Karlin et al., Applications and statistics for multiple high-scoring segments in molecular sequences. Proc Natl Acad Sci U S A. Jun. 15, 1993;90(12):5873-7. doi: 10.1073/pnas.90.12.5873.

Karlin et al., Methods for assessing the statistical significance of molecular sequence features by using general scoring schemes. Proc Natl Acad Sci U S A. Mar. 1990;87(6):2264-8. doi: 10.1073/pnas.87.6.2264.

Kolb et al., Prerequisites for amplicon pyrosequencing of microbial methanol utilizers in the environment. Front Microbiol. Sep. 5, 2013;4:268. doi: 10.3389/fmicb.2013.00268.

Krog et al., Methylotrophic Bacillus methanolicus encodes two chromosomal and one plasmid born NAD+ dependent methanol dehydrogenase paralogs with different catalytic and biochemical properties. PLoS One. 2013;8(3):e59188. doi: 10.1371/journal.pone.0059188. Epub Mar. 19, 2013.

Kunkel et al., Rapid and efficient site-specific mutagenesis without phenotypic selection. Proc Natl Acad Sci U S A. Jan. 1985;82(2):488-92. doi: 10.1073/pnas.82.2.488.

Martinez-Cruz et al., Crystal structure of MJ1247 protein from M. jannaschii at 2.0 A resolution infers a molecular function of 3-hexulose-6-phosphate isomerase. Structure. Feb. 2002;10(2):195-204. doi: 10.1016/s0969-2126(02)00701-3.

Müller et al., Engineering *Escherichia coli* for methanol conversion. Metab Eng. Mar. 2015;28:190-201. doi: 10.1016/j.ymben.2014.12.008. Epub Jan. 14, 2015.

Needleman et al., A general method applicable to the search for similarities in the amino acid sequence of two proteins. J Mol Biol. Mar. 1970;48(3):443-53. doi: 10.1016/0022-2836(70)90057-4.

Price et al., Scaffoldless engineered enzyme assembly for enhanced methanol utilization. Proc Natl Acad Sci U S A. Nov. 8, 2016;113(45):12691-12696. doi: 10.1073/pnas.1601797113. Epub Oct. 24, 2016.

Sievers et al., Fast, scalable generation of high-quality protein multiple sequence alignments using Clustal Omega. Mol Syst Biol. Oct. 11, 2011;7:539. doi: 10.1038/msb.2011.75.

Smith et al., Identification of common molecular subsequences. J Mol Biol. Mar. 25, 1981;147(1):195-7. doi: 10.1016/0022-2836(81)90087-5.

Sonnhammer et al., Pfam: a comprehensive database of protein domain families based on seed alignments. Proteins. Jul. 1997;28(3):405-20. doi: 10.1002/(sici)1097-0134(199707)28:3<405::aid-prot10>3.0.co;2-I.

Stormo et al., Use of the 'Perceptron' algorithm to distinguish translational initiation sites in *E. coli*. Nucleic Acids Res. May 11, 1982;10(9):2997-3011. doi: 10.1093/nar/10.9.2997.

Vogl et al., Orthologous promoters from related methylotrophic yeasts surpass expression of endogenous promoters of Pichia pastoris. AMB Express. Feb. 25, 2020;10(1):38. doi: 10.1186/s13568-020-00972-1.

Whitaker et al., Engineering the biological conversion of methanol to specialty chemicals in *Escherichia coli*. Metab Eng. Jan. 2017;39:49-59. doi: 10.1016/j.ymben.2016.10.015. Epub Nov. 1, 2016.

Whitthoff et al., Metabolic engineering of Corynebacterium glutamicum for methanol metabolism. Appl Environ Microbiol. Mar. 2015;81(6):2215-25. doi: 10.1128/AEM.03110-14. Epub Jan. 16, 2015.

Wu et al., Characterization and evolution of an activator-independent methanol dehydrogenase from Cupriavidus necator N-1. Appl Microbiol Biotechnol. Jun. 2016;100(11):4969-83. doi: 10.1007/s00253-016-7320-3. Epub Feb. 5, 2016.

Yu et al., Circular permutation: a different way to engineer enzyme structure and function. Trends Biotechnol. Jan. 2011;29(1):18-25. doi: 10.1016/j.tibtech.2010.10.004. Epub Nov. 17, 2010.

Yurimoto et al., Genomic organization and biochemistry of the ribulose monophosphate pathway and its application in biotechnology. Appl Microbiol Biotechnol. Sep. 2009;84(3):407-16. doi: 10.1007/s00253-009-2120-7. Epub Jul. 11, 2009.

\* cited by examiner

CHEMOAUTOTROPHIC CELLS COMPRISING AN ENGINEERED CARBON FIXATION PATHWAY

CROSS REFERENCE TO RELATED APPLICATIONS

This application is a continuation application of U.S. application Ser. No. 15/867,209, filed Jan. 10, 2018, which is a continuation application of U.S. application Ser. No. 14/354,354, filed Apr. 25, 2014, which is a national stage filing under 35 U.S.C. § 371 of International Application No. PCT/US2012/062540, filed Oct. 30, 2012, which was published under PCT Article 21(2) in English, and which claims priority to and the benefit of U.S. patent application Ser. No. 13/285,919, filed on Oct. 31, 2011, each of which is incorporated herein by reference in its entirety.

STATEMENT REGARDING GOVERNMENT LICENSE RIGHTS

This invention was made with government support under contract number DE-AR0000091 awarded by U.S. Department of Energy, Office of ARPA-E. The government has certain rights in the invention.

SEQUENCE LISTING

The instant application contains a sequence listing (.txt file named Sequence Listing, generated on May 27, 2014 and is 180 kilobytes) which has been submitted in ASCII format via EFS-Web and is incorporated by reference herein.

TECHNICAL FIELD

The invention relates to systems, mechanisms and methods to confer chemoautotrophic production of carbon-based products to a heterotrophic organism to efficiently convert inorganic carbon into various carbon-based products using chemical energy, and in particular the use of such organism for the commercial production of various carbon-based products of interest. The invention also relates to systems, mechanisms and methods to confer additional and/or alternative pathways for chemoautotrophic production of carbon-based products to an organism that is already autotrophic or mixotrophic.

BACKGROUND

Heterotrophs are biological organisms that utilize energy from organic compounds for growth and reproduction. Commercial production of various carbon-based products of interest generally relies on heterotrophic organisms that ferment sugar from crop biomass such as corn or sugarcane as their energy and carbon source [Bai, 2008]. An alternative to fermentation-based bio-production is the production of carbon-based products of interest from photosynthetic organisms, such as plants, algae and cyanobacteria, that derive their energy from sunlight and their carbon from carbon dioxide to support growth [U.S. Pat. No. 7,981,647]. However, the algae-based production of carbon-based products of interest relies on the relatively inefficient process of photosynthesis to supply the reducing power needed for production of organic compounds from carbon dioxide [Larkum, 2010]. Moreover, commercial production of carbon-based products of interest using photosynthetic organisms relies on reliable and consistent exposure to light to achieve the high productivities needed for economic feasibility; hence, photobioreactor design remains a significant technical challenge [Morweiser, 2010].

Chemoautotrophs are biological organisms that utilize energy from inorganic energy sources such as molecular hydrogen, hydrogen sulfide, ammonia or ferrous iron, and carbon dioxide to produce all organic compounds necessary for growth and reproduction. Existing, naturally-occurring chemoautotrophs are poorly suited for industrial bio-processing and have therefore not demonstrated commercial viability for this purpose. Such organisms have long doubling times (minimum of approximately one hour for *Thiomicrospira crunogena* but generally much longer) relative to industrialized heterotrophic organisms such as *Escherichia coli* (twenty minutes), reflective of low total productivities. In addition, techniques for genetic manipulation (homologous recombination, transformation or transfection of nucleic acid molecules, and recombinant gene expression) are inefficient, time-consuming, laborious or non-existent.

Accordingly, the ability to endow an otherwise heterotrophic organism with chemoautotrophic capability would significantly enable more energy- and carbon-coefficient production of carbon-based products of interest. Alternatively, the ability to add one or more additional or alternative pathways for chemoautotrophic capability to an autotrophic or mixotrophic organism would enhance its ability to produce carbon-based products on interest.

SUMMARY

Systems and methods of the present invention provide for efficient production of renewable energy and other carbon-based products of interest (e.g., fuels, sugars, chemicals) from inorganic carbon (e.g., greenhouse gas) using inorganic energy. As such, the present invention materially contributes to the development of renewable energy and/or energy conservation, as well as greenhouse gas emission reduction. Furthermore, systems and methods of the present invention can be used in the place of traditional methods of producing chemicals such as olefins (e.g., ethylene, propylene), which are traditionally derived from petroleum in a process that generates toxic by-products that are recognized as hazardous waste pollutants and harmful to the environment. As such, the present invention can additionally avoid the use of petroleum and the generation of such toxic by-products, and thus materially enhances the quality of the environment by contributing to the maintenance of basic life-sustaining natural elements such as air, water and/or soil by avoiding the generation of hazardous waste pollutants in the form of petroleum-derived by-products in the production of various chemicals.

In certain aspect, the invention described herein provides an organism engineered to confer chemoautotrophic production of various carbon-based products of interest from inorganic carbon and inorganic energy. The engineered organism comprises a modular metabolic architecture encompassing three metabolic modules. The first module comprises one or more energy conversion pathways that use energy from an inorganic energy source, such as formate, formic acid, methane, carbon monoxide, carbonyl sulfide, carbon disulfide, hydrogen sulfide, bisulfide anion, thiosulfate, elemental sulfur, molecular hydrogen, ferrous iron, ammonia, cyanide ion, and/or hydrocyanic acid, to produce reduced cofactors inside the cell, such as NADH, NADPH, ubiquinol, menaquinol, cytochromes, flavins and/or ferredoxin. The second module comprises one or more carbon fixation pathways that use energy from reduced cofactors to convert inorganic carbon, such as carbon dioxide, carbon monoxide, formate, formic acid, carbonic acid, bicarbonate, carbon monoxide, carbonyl sulfide, carbon disulfide, cyanide ion and/or hydrocyanic acid, to central metabolites, such as acetyl-coA, pyruvate, pyruvic acid, 3-hydropropionate, 3-hydroxypropionic acid, glycolate, glycolic acid, glyoxylate, glyoxylic acid, dihydroxyacetone phosphate, glyceraldehyde-3-phosphate, malate, malic acid, lactate, lactic acid, acetate, acetic acid, citrate and/or citric acid. Optionally, the third module comprises one or more carbon product biosynthetic pathways that convert central metabolites into desired products, such as carbon-based products of interest. Carbon-based products of interest include but are not limited to alcohols, fatty acids, fatty acid derivatives, fatty alcohols, fatty acid esters, wax esters, hydrocarbons, alkanes, polymers, fuels, commodity chemicals, specialty chemicals, carotenoids, isoprenoids, sugars, sugar phosphates, central metabolites, pharmaceuticals and pharmaceutical intermediates.

The resulting engineered chemoautotroph of the invention is capable of efficiently synthesizing carbon-based products of interest from inorganic carbon using inorganic energy. The invention also provides energy conversion pathways, carbon fixation pathways and carbon product biosynthetic pathways for conferring chemoautotrophic production of the carbon-based product of interest upon the host organism where the organism lacks the ability to efficiently produce carbon-based products of interest from inorganic carbon using inorganic energy. The invention also provides methods for culturing the engineered chemoautotroph to support efficient chemoautotrophic production of carbon-based products of interest.

In one aspect, the present invention provides an engineered cell for producing a carbon-based product of interest. The engineered cell includes an at least partially engineered energy conversion pathway having at least one of a recombinant formate dehydrogenase and a recombinant sulfide-quinone oxidoreductase introduced into a host cell, wherein said energy conversion pathway is capable of using energy from oxidation to produce a reduced cofactor. The engineered cell also includes a carbon fixation pathway that is capable of converting inorganic carbon to a central metabolite using energy from the reduced cofactor. The engineered cell further includes, optionally, a carbon product biosynthetic pathway that is capable of converting the central metabolite into a carbon-based product of interest.

In certain embodiments, the recombinant formate dehydrogenase reduces $NADP^+$. For example, the recombinant formate dehydrogenase can be encoded by SEQ ID NO:1, or a homolog thereof having at least 80% sequence identity thereto. In some embodiments, the recombinant formate dehydrogenase reduces $NAD^+$. In an example, the recombinant formate dehydrogenase can be encoded by any one of SEQ ID NOs:2-4, or a homolog thereof having at least 80% sequence identity thereto. In other embodiments, the recombinant formate dehydrogenase reduces ferredoxin. As an example, the recombinant formate dehydrogenase can be encoded by one or more of SEQ ID NOs:5-8, or a homolog thereof having at least 80% sequence identity thereto.

In certain embodiments, the recombinant sulfide-quinone oxidoreductase reduces quinone. For example, the recombinant sulfide-quinone oxidoreductase can be encoded by any one of SEQ ID NOs:9-16, or a homolog thereof having at least 80% sequence identity thereto.

In some embodiments, the energy conversion pathway includes the recombinant formate dehydrogenase and and the energy from oxidation is from formate oxidation. The energy conversion pathway can also include the recombinant sulfide-quinone oxidoreductase and the energy from oxidation can be from hydrogen sulfide oxidation.

In various embodiments, the inorganic carbon is one or more of formate and carbon dioxide.

In certain embodiments, the carbon fixation pathway can be at least partially engineered and can be derived from the 3-hydroxypropionate (3-HPA) bicycle. The carbon fixation pathway can include one or more of: acetyl-CoA carboxylase, malonyl-CoA reductase, propionyl-CoA synthase, propionyl-CoA carboxylase, methylmalonyl-CoA epimerase, methylmalonyl-CoA mutase, succinyl-CoA:(S)-malate CoA transferase, succinate dehydrogenase, fumarat hydratase, (S)-malyl-CoA/β-methylmalyl-CoA/(S)-citramalyl-CoA lyase, mesaconyl-C1-CoA hydratase or β-methylmalyl-CoA dehyratase, mesaconyl-CoA C1-C4 CoA transferase and mesaconyl-C4-CoA hydratase.

In some embodiments, the carbon fixation pathway can be at least partially engineered and can be derived from the ribulose monophosphate (RuMP) cycle. In one embodiment, said carbon fixation pathway can include one or more of: hexulose-6-phosphate synthase, 6-phospho-3-hexuloisomerase, hexulose-6-phosphate synthase/6-phospho-3-hexuloisomerase fusion enzyme, phosphofructokinase, fructose bisphosphate aldolase, transketolase, transaldolase, transketolase, ribose 5-phosphate isomerase and ribulose-5-phosphate-3-epimrase.

In some embodiments, said carbon fixation pathway can be at least partially engineered and can be derived from the Calvin-Benson-Bassham cycle or the reductive pentose phosphate (RPP) cycle. For example, the carbon fixation pathway can include one or more of: ribulose bisphosphate carboxylase, phosphoglycerate kinase, glyceraldehyde-3P dehydrogenase (phosphorylating), triose-phosphate isomerase, fructose-bisphosphate aldolase, fructose-bisphosphatase, transketolase, sedoheptulose-1,7-bisphosphate aldolase, sedoheptulose bisphosphatase, transketolase, ribose-5-phosphate isomerase, ribulose-5-phosphate-3-epimerase and phosphoribulokinase.

In certain embodiments, said carbon fixation pathway can be at least partially engineered and can be derived from the reductive tricarboxylic acid (rTCA) cycle. In some embodiments, the carbon fixation pathway can include one or more of: ATP citrate lyase, citryl-CoA synthetase, citryl-CoA lyase, malate dehydrogenase, fumarate dehydratase, fumarate reductase, succinyl-CoA synthetase, 2-oxoglutarate:ferredoxin oxidoreductase, isocitrate dehydrogenase, 2-oxoglutarate carboxylase, oxalosuccinate reductase, aconitate hydratrase, pyruvate:ferredoxin oxidoreductase, phosphoenolpyruvate synthetase and phosphoenolpyruvate carboxylase.

DETAILED DESCRIPTION

Figure 1:
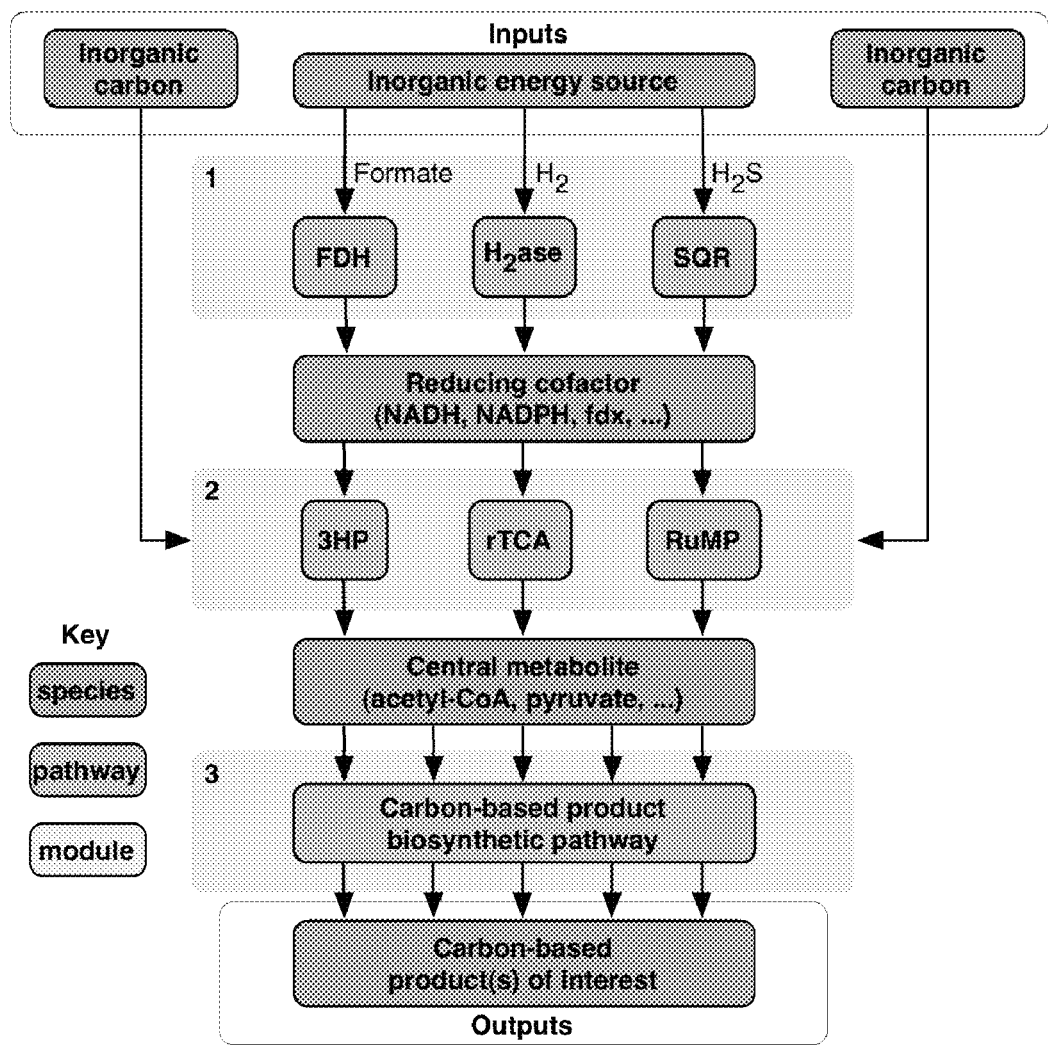
FIG. 1 is an overview of modular architecture of an engineered chemoautotroph. An engineered chemoautotroph comprises three metabolic modules. (1) In Module 1, one or more energy conversion pathways that use energy from an extracellular inorganic energy source, such as formate, hydrogen sulfide, molecular hydrogen, or ferrous iron, to produce reduced cofactors inside the cell, such as NADII, NADPII, reduced ferredoxin and/or reduced quinones or cytochromes. Depicted examples of energy conversion pathways include formate dehydrogenase (FDH), hydrogenase ($H_2$ase), and sulfide-quinone oxidoreductase (SQR). (2) In Module 2, one or more carbon fixation pathways that use energy from reduced cofactors to reduce and convert inorganic carbon, such as carbon dioxide, formate and formaldehyde, to central metabolites, such as acetyl-coA, pyruvate, glycolate, glyoxylate, and dihydroxyacetone phosphate. Depicted examples of carbon fixation pathways include the 3-hydroxypropionate cycle (3-HPA), the reverse or reductive tricarboxylic acid cycle (rTCA), and the ribulose monophosphate pathway (RuMP). (3) Optionally, in Module 3, one or more carbon product biosynthetic pathways that convert central metabolites into desired products, such as carbon-based products of interest. Since there are many possible carbon-based products of interest, no individual pathways are depicted.

The present invention relates to developing and using engineered chemoautotrophs capable of utilizing energy from inorganic energy sources and inorganic carbon to produce a desired product. The invention provides for the engineering of a heterotrophic organism, for example, *Escherichia coli* or other organism suitable for commercial large-scale production of fuels and chemicals, that can efficiently utilize inorganic energy sources and inorganic carbon as a substrate for growth (a chemoautotroph) and for chemical production provides cost-advantaged processes for manufacturing of carbon based products of interest. The organisms can be optimized and tested rapidly and at reasonable costs. The invention further provides for the engineering of an autotrophic organism to include one or more additional or alternative pathways for utilization of inorganic energy sources and inorganic carbon to produce central metabolites for growth and/or other desired products.

Inorganic energy sources together with inorganic carbon represent an alternative feedstock to sugar or light plus carbon dioxide for the production of carbon-based products of interest. There exist non-biological routes to convert inorganic energy sources and inorganic carbon to chemicals and fuels of interest. For example, the Fischer-Tropsch process consumes carbon monoxide and hydrogen gas generated from gasification of coal or biomass to produce methanol or mixed hydrocarbons as fuels [U.S. Pat. No. 1,746,464]. The drawbacks of Fischer-Tropsch processes are: 1) a lack of product selectivity, which results in difficulties separating desired products; 2) catalyst sensitivity to poisoning: 3) high energy costs due to high temperatures and pressures required; and 4) the limited range of products available at commercially competitive costs. Without the advent of carbon sequestration technologies that can operate at scale, the Fischer-Tropsch process is widely considered to be an environmentally costly method for generating liquid fuels. Alternatively, processes that rely on naturally occurring microbes that convert synthesis gas or syngas, a mixture of primarily molecular hydrogen and carbon monoxide that can be obtained via gasification of any organic feedstock, such as coal, coal oil, natural gas, biomass, or waste organic matter, to products such as ethanol, acetate, methane, or molecular hydrogen are available [Henstra, 2007]. However, these naturally occurring microbes can produce only a very restricted set of products, are limited in their efficiencies, lack established tools for genetic manipulation, and are sensitive to their end products at high concentrations. Finally, there is some work to introduce syngas utilization into industrial microbial hosts [U.S. Pat. No. 7,803,589]; however, these processes have yet to be demonstrated at commercial scale and are limited to using syngas as the feedstock.

In some embodiments, the invention provides for the use of an inorganic energy source, such as molecular hydrogen or formate, derived from electrolysis. There is tremendous commercial activity towards the goal of renewable and/or carbon-neutral energy from solar voltaic, geothermal, wind, nuclear, hydroelectric and more. However, most of these technologies produce electricity and are thus limited in use to the electrical grid [Whipple, 2010]. Furthermore, at least some of these renewable energy sources such as solar and wind suffer from being intermittent and unreliable. The lack of practical, large scale electricity storage technologies limits how much of the electricity demand can be shifted to renewable sources. The ability to store electrical energy in chemical form, such as in carbon-based products of interest, would both offer a means for large-scale electricity storage and allow renewable electricity to meet energy demand from the transportation sector. Renewable electricity combined with electrolysis, such as the electrochemical production of hydrogen from water [for example, WO/2009/154753, WO/2010/042197, WO/2010/028262 and WO/2011/028264] or formate/formic acid from carbon dioxide [for example, WO/2007/041872], opens the possibility of a sustainable, renewable supply of the inorganic energy source as one aspect of the present invention.

In some embodiments, the invention provides for the use of an inorganic energy source, such as hydrogen sulfide or molecular hydrogen, derived from waste streams. For example, hydrogen sulfide is present in waste streams arising from both hydrodesulfurization processes used during oil recovery and desulfurization of natural gas. Indeed, currently many oil companies stockpile elemental sulfur (the oxidation product of hydrogen sulfide) since worldwide production exceeds demand [Ober, 2010]. As lower quality oil deposits with higher sulfur contents (5% w/w) open up to drilling, the expectation is that global sulfur supply will continue to grow. As a second example, hydrogen and carbon dioxide are off-gas by-products of clostridial acetone-butanol-ethanol fermentations.

In some embodiments, the invention provides for the use of an inorganic carbon source, such as carbon dioxide, derived from waste streams. For example, carbon dioxide is a component of synthesis gas, the major product of gasification of coal, coal oil, natural gas, and of carbonaceous materials such as biomass materials, including agricultural crops and residues, and waste organic matter. Additional sources include, but are not limited to, production of carbon dioxide as a byproduct in ammonia and hydrogen plants, where methane is converted to carbon dioxide; combustion of wood and fossil fuels; production of carbon dioxide as a byproduct of fermentation of sugar in the brewing of beer, whisky and other alcoholic beverages, or other fermentative processes; thermal decomposition of limestone, $CaCO_3$, in the manufacture of lime, CaO; production of carbon dioxide as byproduct of sodium phosphate manufacture; and directly from natural carbon dioxide springs, where it is produced by the action of acidified water on limestone or dolomite. As a second example, formaldehyde is an oxidation product of methanol or methane. Methanol can be prepared from synthesis gas or reductive conversion of carbon dioxide and hydrogen by chemical synthetic processes. Methane is a major component of natural gas and can also be obtained from renewable biomass.

In one embodiment, the invention provides for the inorganic energy source and the inorganic carbon coming from the same chemical species, such as formate or formic acid. Formate is oxidized by an energy conversion pathway to generate reduced cofactor and carbon dioxide. The carbon dioxide can then be used as the inorganic carbon source.

The invention provides for the expression of one or more exogenous proteins or enzymes in the host cell, thereby conferring biosynthetic pathway(s) to utilize inorganic energy sources and inorganic carbon to produce reduced organic compounds. In a preferred embodiment, the present invention provides for a modular architecture for the metabolism of the engineered chemoautotroph comprising the following three metabolic modules (FIG. 1).

In Module 1, one or more energy conversion pathways that us energy from an extracellular inorganic energy source, such as formate, hydrogen sulfide, molecular hydrogen, or ferrous iron, to produce reduced cofactors inside the cell, such as NADH. NADPH, reduced ferredoxin and/or reduced quinones or cytochromes.

In Module 2, one or more carbon fixation pathways that use energy from reduced cofactors to reduce and convert inorganic carbon, such as carbon dioxide or formate, to central metabolites, such as acetyl-coA, pyruvate, glycolate, glyoxylate, and dihydroxyacetone phosphate.

Optionally, in Module 3, one or more carbon product biosynthetic pathways that convert central metabolites into desired products, such as carbon-based products of interest.

A key advantage of a modular architecture for the metabolism of an engineered chemoautotroph is that each module may be instantiated via one or more possible biosynthetic pathways. For example, in Module 1, there are several possible energy conversion pathways, such as those based on format dehydrogenase (e.g., E.C. 1.2.1.2, E.C. 1.2.1.43, E.C. 1.1.5.6, E.C. 1.2.2.1 or E.C. 1.2.2.3), ferredoxin-dependent formate dehydrogenase, hydrogenase (e.g., E.C. 1.12.1.2, E.C. 1.12.1.3, or E.C. 1.12.7.2), sulfide-quinone oxidoreductase (e.g., E.C. 1.8.5.4), flavocytochrome c sulfide dehydrogenase (e.g., E.C. 1.8.2.3), ferredoxin-NADP+ reductase (e.g., E.C. 1.18.1.2), ferredoxin-NAD$^+$ reductase (e.g., E.C. 1.18.1.3), NAD(P)+ transhydrogenase (e.g., E.C. 1.6.1.1 or E.C. 1.6.1.2), NADH:ubiquinone oxidoreductase I (e.g., E.C. 1.6.5.3). As a second example, in Module 2, there are several possible naturally occurring carbon fixation pathways, such as the Calvin-Benson-Bassham cycle or reductive pentose phosphate cycle, the reductive tricarboxylic acid cycle, the Wood-Ljungdhal or reductive acetyl-coA pathway, the 3-hydroxypropionate bicycle or 3-hydroxypropionate/malyl-CoA cycle, 3-hydroxypropionate/4-hydroxybutyrate cycle and the dicarboxylate/4-hydroxybutyrate cycle [Hügler, 2011] as well as many possible synthetic carbon fixation pathways [Bar-Even, 2010]. As a final example, in Module 3, there are numerous possible carbon-based products of interest, each of which has one or more corresponding biosynthetic pathways. Every combination of energy conversion pathway, carbon fixation pathway and, optionally, carbon product biosynthetic pathway, when expressed in a heterotrophic or autotrophic host cell or organism, represents a different embodiment of the present invention. It should be noted, however, that only certain embodiments of Module 1 may be paired with a particular embodiment of Module 2. For example, the reductive tricarboxylic acid cycle likely requires a low potential ferredoxin for particular carbon dioxide fixation steps in the pathway. Thus, the energy conversion pathway paired with the reductive tricarboxylic acid cycle must be capable of generating reduced low potential ferredoxin, such as using a ferredoxin-reducing formate dehydrogenase or a ferredoxin-reducing hydrogenase (E.C. 1.12.7.2). Similarly, only certain embodiments of carbon fixation pathways produce the necessary precursors for a particular carbon product biosynthetic pathway. For example, fatty acid biosynthetic pathways require acetyl-coA and malonyl-coA to be generated products from the carbon fixation pathway.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art would understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well-known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

Definitions

As used herein, the terms "nucleic acids," "nucleic acid molecule" and "polynucleotide" may be used interchangeably and include both single-stranded (ss) and double-stranded (ds) RNA, DNA and RNA:DNA hybrids. As used herein the terms "nucleic acid", "nucleic acid molecule", "polynucleotide", "oligonucleotide", "oligomer" and "oligo" are used interchangeably and are intended to include, but are not limited to, a polymeric form of nucleotides that may have various lengths, including either deoxyribonucleotides or ribonucleotides, or analogs thereof. For example, oligos may be from 5 to about 200 nucleotides, from 10 to about 100 nucleotides, or from 30 to about 50 nucleotides long. However, shorter or longer oligonucleotides may be used. Oligos for use in the present invention can be fully designed. A nucleic acid molecule may encode a full-length polypeptide or a fragment of any length thereof, or may be non-coding.

Nucleic acids can refer to naturally-occurring or synthetic polymeric forms of nucleotides. The oligos and nucleic acid molecules of the present invention may be formed from naturally-occurring nucleotides, for example forming deoxyribonucleic acid (DNA) or ribonucleic acid (RNA) molecules. Alternatively, the naturally-occurring oligonucleotides may include structural modifications to alter their properties, such as in peptide nucleic acids (PNA) or in locked nucleic acids (LNA). The terms should be understood to include equivalents, analogs of either RNA or DNA made from nucleotide analogs and as applicable to the embodiment being described, single-stranded or double-stranded polynucleotides. Nucleotides useful in the invention include, for example, naturally-occurring nucleotides (for example, ribonucleotides or deoxyribonucleotides), or natural or synthetic modifications of nucleotides, or artificial bases. Modifications can also include phosphorothioated bases for increased stability.

Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the nucleotide comparison methods and algorithms set forth below, or as defined as being capable of hybridizing to the polynucleotides that encode the protein sequences.

As used herein, the term "gene" refers to a nucleic acid that contains information necessary for expression of a polypeptide, protein, or untranslated RNA (e.g., rRNA, tRNA, anti-sense RNA). When the gene encodes a protein, it includes the promoter and the structural gene open reading frame sequence (ORF), as well as other sequences involved in expression of the protein. When the gene encodes an untranslated RNA, it includes the promoter and the nucleic acid that encodes the untranslated RNA.

The term "gene of interest" (GOI) refers to any nucleotide sequence (e.g., RNA or DNA), the manipulation of which may be deemed desirable for any reason (e.g., has the relevant activity for a biosynthetic pathway, confer improved qualities and/or yields, expression of a protein of interest in a host cell, expression of a ribozyme, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding sequences which do not encode an mRNA or protein product (e.g., promoter sequence, polyadenylation sequence, termination sequence, enhancer sequence, etc.). For example, genes involved in the cis,cis-muconic acid biosynthesis pathway can be genes of interest. It should be noted that non-coding regions are generally untranslated but can be involved in the regulation of transcription and/or translation.

As used herein, the term "genome" refers to the whole hereditary information of an organism that is encoded in the DNA (or RNA for certain viral species) including both coding and non-coding sequences. In various embodiments, the term may include the chromosomal DNA of an organism and/or DNA that is contained in an organelle such as, for example, the mitochondria or chloroplasts and/or extrachromosomal plasmid and/or artificial chromosome. A "native gene" or "endogenous gene" refers to a gene that is native to the host cell with its own regulatory sequences whereas an "exogenous gene" or "heterologous gene" refers to any gene that is not a native gene, comprising regulatory and/or coding sequences that are not native to the host cell. In some embodiments, a heterologous gene may comprise mutated sequences or part of regulatory and/or coding sequences. In some embodiments, the regulatory sequences may be heterologous or homologous to a gene of interest. A heterologous regulatory sequence does not function in nature to regulate the same gene(s) it is regulating in the transformed host cell. "Coding sequence" refers to a DNA sequence coding for a specific amino acid sequence. As used herein, "regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, ribosome binding sites, translation leader sequences, RNA processing site, effector (e.g., activator, repressor) binding sites, stem-loop structures, and so on.

As described herein, a genetic element may be any coding or non-coding nucleic acid sequence. In some embodiments, a genetic element is a nucleic acid that codes for an amino acid, a peptide or a protein. Genetic elements may be operons, genes, gene fragments, promoters, exons, introns, regulatory sequences, or any combination thereof. Genetic elements can be as short as one or a few codons or may be longer including functional components (e.g. encoding proteins) and/or regulatory components. In some embodiments, a genetic element includes an entire open reading frame of a protein, or the entire open reading frame and one or more (or all) regulatory sequences associated therewith. One skilled in the art would appreciate that the genetic elements can be viewed as modular genetic elements or genetic modules. For example, a genetic module can comprise a regulatory sequence or a promoter or a coding sequence or any combination thereof. In some embodiments, the genetic element includes at least two different genetic modules and at least two recombination sites. In eukaryotes, the genetic element can comprise at least three modules. For example, a genetic module can be a regulator sequence or a promoter, a coding sequence, and a polyadenlylation tail or any combination thereof. In addition to the promoter and the coding sequences, the nucleic acid sequence may comprises control modules including, but not limited to a leader, a signal sequence and a transcription terminator. The leader sequence is a non-translated region operably linked to the 5' terminus of the coding nucleic acid sequence. The signal peptide sequence codes for an amino acid sequence linked to the amino terminus of the polypeptide which directs the polypeptide into the cell's secretion pathway.

As generally understood, a codon is a series of three nucleotides (triplets) that encodes a specific amino acid residue in a polypeptide chain or for the termination of translation (stop codons). There are 64 different codons (61 codons encoding for amino acids plus 3 stop codons) but only 20 different translated amino acids. The overabundance in the number of codons allows many amino acids to be encoded by more than one codon. Different organisms (and organelles) often show particular preferences or biases for one of the several codons that encode the same amino acid. The relative frequency of codon usage thus varies depending on the organism and organelle. In some instances, when expressing a heterologous gene in a host organism, it is desirable to modify the gene sequence so as to adapt to the codons used and codon usage frequency in the host. In particular, for reliable expression of heterologous genes it may be preferred to use codons that correlate with the host's tRNA level, especially the tRNA's that remain charged during starvation. In addition, codons having rare cognate tRNA's may affect protein folding and translation rate, and thus, may also be used. Genes designed in accordance with codon usage bias and relative tRNA abundance of the host are often referred to as being "optimized" for codon usage, which has been shown to increase expression level. Optimal codons also help to achieve faster translation rates and high accuracy. In general, codon optimization involves silent mutations that do not result in a change to the amino acid sequence of a protein.

Genetic elements or genetic modules may derive from the genome of natural organisms or from synthetic polynucleotides or from a combination thereof. In some embodiments, the genetic elements modules derive from different organisms. Genetic elements or modules useful for the methods described herein may be obtained from a variety of sources such as, for example, DNA libraries, BAC (bacterial artificial chromosome) libraries, de novo chemical synthesis, or excision and modification of a genomic segment. The sequences obtained from such sources may then be modified using standard molecular biology and/or recombinant DNA technology to produce polynucleotide constructs having desired modifications for reintroduction into, or construction of, a large product nucleic acid, including a modified, partially synthetic or fully synthetic genome. Exemplary methods for modification of polynucleotide sequences obtained from a genome or library include, for example, site directed mutagenesis; PCR mutagenesis; inserting, deleting or swapping portions of a sequence using restriction enzymes optionally in combination with ligation; in vitro or in vivo homologous recombination; and site-specific recombination; or various combinations thereof. In other embodiments, the genetic sequences useful in accordance with the methods described herein may be synthetic oligonucleotides or polynucleotides. Synthetic oligonucleotides or polynucleotides may be produced using a variety of methods known in the art.

In some embodiments, genetic elements share less than 99%, less than 95%, less than 90%, less than 80%, less than 70% sequence identity with a native or natural nucleic acid sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Expression as a percentage of homology, similarity, or identity refers to a function of the number of identical or similar amino acids at positions shared by the compared sequences. Various alignment algorithms and/or programs may be used, including FASTA, BLAST, or ENTREZ FASTA and BLAST are available as a part of the GCG sequence analysis package (University of Wisconsin, Madison. Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences. Other techniques for alignment are described [Doolittle, 1996]. Preferably, an alignment program that permits gaps in the sequence is utilized to align the sequences. The Smith-Waterman is one type of algorithm that permits gaps in sequence alignments [Shpaer, 1997]. Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer.

As used herein, an "ortholog" is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor. Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art would understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of *mycoplasma* 5'-3' exonuclease and *Drosophila* DNA polymerase III activity. The DNA polymerase from the first species can be considered an ortholog to either or both of the exonuclease or the polymerase from the second species and vice versa.

In contrast, as used herein, "paralogs" are homologs related by, for example, duplication followed by evolutionary divergenee and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

As used herein, a "nonorthologous gene displacement" is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement may be identifiable as structurally related to a known gene encoding the referenced function, less structurally related but functionally similar genes and their corresponding gene products nevertheless still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Orthologs, paralogs and nonorthologous gene displacements can be determined by methods well known to those skilled in the art. For example, inspection of nucleic acid or amino acid sequences for two polypeptides can reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences. Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: I; mismatch: −2; gap open: 5; gap extension: 2; x_dropoff: 50; expect: 10.0; wordsize: 11; filter: off. Those skilled in the art would know what modifications can be made to the above parameters to either increase or decrease the stringency of the comparison, for example, and determine the relatedness of two or more sequences.

As used herein, the term "homolog" refers to any ortholog, paralog, nonorthologous gene, or similar gene encoding an enzyme catalyzing a similar or substantially similar metabolic reaction, whether from the same or different species.

As used herein, the phrase "homologous recombination" refers to the process in which nucleic acid molecules with similar nucleotide sequences associate and exchange nucleotide strands. A nucleotide sequence of a first nucleic acid molecule that is effective for engaging in homologous recombination at a predefined position of a second nucleic acid molecule can therefore have a nucleotide sequence that facilitates the exchange of nucleotide strands between the first nucleic acid molecule and a defined position of the second nucleic acid molecule. Thus, the first nucleic acid can generally have a nucleotide sequence that is sufficiently complementary to a portion of the second nucleic acid molecule to promote nucleotide base pairing. Homologous recombination requires homologous sequences in the two recombining partner nucleic acids but does not require any specific sequences. Homologous recombination can be used to introduce a heterologous nucleic acid and/or mutations into the host genome. Such systems typically rely on sequence flanking the heterologous nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

It should be appreciated that the nucleic acid sequence of interest or the gene of interest may be derived from the genome of natural organisms. In some embodiments, genes of interest may be excised from the genome of a natural organism or from the host genome, for example E. coli. It has been shown that it is possible to excise large genomic fragments by in vitro enzymatic excision and in vivo excision and amplification. For example, the FLP/FRT site specific recombination system and the Cre/loxP site specific recombination systems have been efficiently used for excision large genomic fragments for the purpose of sequencing [Yoon, 1998]. In some embodiments, excision and amplification techniques can be used to facilitate artificial genome or chromosome assembly. Genomic fragments may be excised from the chromosome of a chemoautotrophic organism and altered before being inserted into the host cell artificial genome or chromosome. In some embodiments, the excised genomic fragments can be assembled with engineered promoters and/or other gene expression elements and inserted into the genome of the host cell.

As used herein, the term "polypeptide" refers to a sequence of contiguous amino acids of any length. The terms "peptide," "oligopeptide," "protein" or "enzyme" may be used interchangeably herein with the term "polypeptide". In certain instances, "enzyme" refers to a protein having catalytic activities. As used herein, the terms "protein of interest," "POI," and "desired protein" refer to a polypeptide under study, or whose expression is desired by one practicing the methods disclosed herein. A protein of interest is encoded by its cognate gene of interest (GO). The identity of a POI can be known or not known. A POI can be a polypeptide encoded by an open reading frame.

A "proteome" is the entire set of proteins expressed by a genome, cell, tissue or organism. More specifically, it is the set of expressed proteins in a given type of cells or an organism at a given time under defined conditions. Transcriptome is the set of all RNA molecules, including mRNA rRNA, tRNA, and other non-coding RNA produced in one or a population of cells. Metabolome refers to the complete set of small-molecule metabolites (such as metabolic intermediates, hormones and other signaling molecules, and secondary metabolites) to be found within a biological sample, such as a single organism.

The term "fuse," "fused" or "link" refers to the covalent linkage between two polypeptides in a fusion protein. The polypeptides are typically joined via a peptide bond, either directly to each other or via an amino acid linker. Optionally, the peptides can be joined via non-peptide covalent linkages known to those of skill in the art.

As used herein, unless otherwise stated, the term "transcription" refers to the synthesis of RNA from a DNA template; the term "translation" refers to the synthesis of a polypeptide from an mRNA template. Translation in general is regulated by the sequence and structure of the 5' untranslated region (5'-UTR) of the mRNA transcript. One regulatory sequence is the ribosome binding site (RBS), which promotes efficient and accurate translation of mRNA. The prokaryotic RBS is the Shine-Dalgarno sequence, a purine-rich sequence of 5'-UTR that is complementary to the UCCU core sequence of the 3'-end of 16S rRNA (located within the 30S small ribosomal subunit). Various Shine-Dalgarno sequences have been found in prokaryotic mRNAs and generally lie about 10 nucleotides upstream from the AUG start codon. Activity of a RBS can be influenced by the length and nucleotide composition of the spacer separating the RBS and the initiator AUG. In eukaryotes, the Kozak sequence A/GCCACCAUGG, which lies within a short 5' untranslated region, directs translation of mRNA. An mRNA lacking the Kozak consensus sequence may also be translated efficiently in an in vitro systems if it possesses a moderately long 5'-UTR that lacks stable secondary structure. While E. coli ribosome preferentially recognizes the Shine-Dalgarno sequence, eukaryotic ribosomes (such as those found in retic lysate) can efficiently use either the Shine-Dalgarno or the Kozak ribosomal binding sites.

As used herein, the terms "promoter," "promoter element," or "promoter sequence" refer to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription.

One should appreciate that promoters have modular architecture and that the modular architecture may be altered. Bacterial promoters typically include a core promoter element and additional promoter elements. The core promoter refers to the minimal portion of the promoter required to initiate transcription. A core promoter includes a Transcription Start Site, a binding site for RNA polymerases and general transcription factor binding sites. The "transcription start site" refers to the first nucleotide to be transcribed and is designated +1. Nucleotides downstream the start site are numbered +1, +2, etc., and nucleotides upstream the start site are numbered −1, −2, etc. Additional promoter elements are located 5' (i.e., typically 30-250 bp upstream of the start site) of the core promoter and regulate the frequency of the transcription. The proximal promoter elements and the distal promoter elements constitute specific transcription factor site. In prokaryotes, a core promoter usually includes two consensus sequences, a −10 sequence or a −35 sequence, which are recognized by sigma factors (see, for example, [Hawley, 1983]). The −10 sequence (10 bp upstream from the first transcribed nucleotide) is typically about 6 nucleotides in length and is typically made up of the nucleotides adenosine and thymidine (also known as the Pribnow box). In some embodiments, the nucleotide sequence of the −10 sequence is 5'-TATAAT or may comprise 3 to 6 bases pairs of the consensus sequence. The presence of this box is essential to the start of the transcription. The −35 sequence of a core promoter is typically about 6 nucleotides in length. The nucleotide sequence of the −35 sequence is typically made up of the each of the four nucleosides. The presence of this sequence allows a very high transcription rate. In some embodiments, the nucleotide sequence of the −35 sequence is 5'-TTGACA or may comprise 3 to 6 bases pairs of the consensus sequence. In some embodiments, the −10 and the −35 sequences are spaced by about 17 nucleotides. Eukaryotic promoters are more diverse than prokaryotic promoters and may be located several kilobases upstream of the transcription starting site. Some eukaryotic promoters contain a TATA box (e.g. containing the consensus sequence TATAAA or part thereof), which is located typically within 40 to 120 bases of the transcriptional start site. One or more upstream activation sequences (UAS), which are recognized by specific binding proteins can act as activators of the transcription. Theses UAS sequences are typically found upstream of the transcription initiation site. The distance between the UAS sequences and the TATA box is highly variable and may be up to 1 kb.

As used herein, the term "vector" refers to any genetic element, such as a plasmid, phage, transposon, cosmid, chromosome, artificial chromosome, episome, virus, virion, etc., capable of replication when associated with the proper control elements and which can transfer gene sequences into or between cells. The vector may contain a marker suitable for use in the identification of transformed or transfected cells. For example, markers may provide antibiotic resistant, fluorescent, enzymatic, as well as other traits. As a second example, markers may complement auxotrophic deficiencies or supply critical nutrients not in the culture media. Types of vectors include cloning and expression vectors. As used herein, the term "cloning vector" refers to a plasmid or phage DNA or other DNA sequence which is able to replicate autonomously in a host cell and which is characterized by one or a small number of restriction endonuclease recognition sites and/or sites for site-specific recombination. A foreign DNA fragment may be spliced into the vector at these sites in order to bring about the replication and cloning of the fragment. The term "expression vector" refers to a vector which is capable of expressing of a gene that has been cloned into it. Such expression can occur after transformation into a host cell, or in IVPS systems. The cloned DNA is usually operably linked to one or more regulatory sequences, such as promoters, activator/repressor binding sites, terminators, enhancers and the like. The promoter sequences can be constitutive, inducible and/or repressible.

As used herein, the term "host" refers to any prokaryotic or eukaryotic (e.g., mammalian, insect, yeast, plant, bacterial, archaeal, avian, animal, etc.) cell or organism. The host cell can be a recipient of a replicable expression vector, cloning vector or any heterologous nucleic acid molecule. Host cells may be prokaryotic cells such as M. florum and E. coli, or eukaryotic cells such as yeast, insect, amphibian, or mammalian cells or cell lines. Cell lines refer to specific cells that can grow indefinitely given the appropriate medium and conditions. Cell lines can be mammalian cell lines, insect cell lines or plant cell lines. Exemplary cell lines can include tumor cell lines and stem cell lines. The heterologous nucleic acid molecule may contain, but is not limited to, a sequence of interest, a transcriptional regulatory sequence (such as a promoter, enhancer, repressor, and the like) and/or an origin of replication. As used herein, the terms "host," "host cell," "recombinant host" and "recombinant host cell" may be used interchangeably. For examples of such hosts, see [Sambrook, 2001].

One or more nucleic acid sequences can be targeted for delivery to target prokaryotic or eukaryotic cells via conventional transformation or transfection techniques. As used herein, the terms "transformation" and "transfection" are intended to refer to a variety of art-recognized techniques for introducing an exogenous nucleic acid sequence (e.g., DNA) into a target cell, including calcium phosphate or calcium chloride co-precipitation, DEAE-dextran-mediated transfection, lipofection, electroporation, optoporation, injection and the like. Suitable transformation or transfection media include, but are not limited to, water, $CaCl_2$, cationic polymers, lipids, and the like. Suitable materials and methods for transforming or transfecting target cells can be found in [Sambrook, 2001], and other laboratory manuals. In certain instances, oligo concentrations of about 0.1 to about 0.5 micromolar (per oligo) can be used for transformation or transfection.

As used herein, the term "marker" or "reporter" refers to a gene or protein that can be attached to a regulatory sequence of another gene or protein of interest, so that upon expression in a host cell or organism, the reporter can confer certain characteristics that can be relatively easily selected, identified and/or measured. Reporter genes are often used as an indication of whether a certain gene has been introduced into or expressed in the host cell or organism. Examples of commonly used reporters include: antibiotic resistance genes, auxotropic markers, β-galactosidase (encoded by the bacterial gene lacZ), luciferase (from lightning bugs), chloramphenicol acetyltransferase (CAT; from bacteria), GUS (β-glucuronidase: commonly used in plants) and green fluorescent protein (GFP: from jelly fish). Reporters or markers can be selectable or screenable. A selectable marker (e.g., antibiotic resistance gene, auxotropic marker) is a gene confers a trait suitable for artificial selection; typically host cells expressing the selectable marker is protected from a selective agent that is toxic or inhibitory to cell growth. A screenable marker (e.g., gfp, lacZ) generally allows researchers to distinguish between wanted cells (expressing the marker) and unwanted cells (not expressing the marker or expressing at insufficient level).

As used herein, the term "chemotroph" or "chemotrophic organism" refers to organisms that obtain energy from the oxidation of electron donors in their environment. As used herein, the term "chemoautotroph" or "chemoautotrophic organism" refers to organisms that produce complex organic compounds from simple inorganic carbon molecules using oxidation of inorganic compounds as an external source of energy. In contrast, "heterotrophs" or "heterotrophic organisms" refers to organisms that must use organic carbon for growth because they cannot convert inorganic carbon into organic carbon. Instead, heterotrophs obtain energy by breaking down the organic molecules they consume. Organisms that can use a mix of different sources of energy and carbon are mixotrophs or mixotrophic organisms which can alternate, e.g., between autotrophy and heterotrophy, between phototrophy and chemotrophy, between lithotrophy and organotrophy, or a combination thereof, depending on environmental conditions.

As used herein, the term "inorganic energy source", "electron donor", "source of reducing power" or "source of reducing equivalents" refers to chemical species, such as formate, formic acid, methane, carbon monoxide, carbonyl sulfide, carbon disulfide, hydrogen sulfide, bisulfide anion, thiosulfate, elemental sulfur, molecular hydrogen, ferrous iron, ammonia, cyanide ion, and/or hydrocyanic acid, with high potential electron(s) that can be donated to another chemical species with a concomitant release of energy (a process by which the electron donor undergoes "oxidation" and the other, recipient chemical species or "electron acceptor" undergoes "reduction"). Inorganic energy sources are generally but not always present external to the cell or biological organism. The term "reducing cofactor" refers to intracellular redox and energy carriers, such as NADH, NADPH, ubiquinol, menaquinol, cytochromes, flavins and/or ferredoxin, that can donate high energy electrons in reduction-oxidation reactions. The terms "reducing cofacor", "reduced cofactor" and "redox cofactor" can be used interchangeably.

As used herein, the term "inorganic carbon" or "inorganic carbon compound" refers to chemical species, such as carbon dioxide, carbon monoxide, formate, formic acid, carbonic acid, bicarbonate, carbon monoxide, carbonyl sulfide, carbon disulfide, cyanide ion and/or hydrocyanic acid, that contains carbon but lacks the carbon-carbon bounds characteristic of organic carbon compounds. Inorganic carbon may be present in a gaseous form, such as carbon monoxide or carbon dioxide, or may be present in a liquid form, such as formate.

As used herein, the term "central metabolite" refers to organic carbon compounds, such as acetyl-coA, pyruvate, pyruvic acid, 3-hydropropionate, 3-hydroxypropionic acid, glycolate, glycolic acid, glyoxylate, glyoxylic acid, dihydroxyacetone phosphate, glyceraldehyde-3-phosphate, malate, malic acid, lactate, lactic acid, acetate, acetic acid, citrate and/or citric acid, that can be converted into carbon-based products of interest by a host cell or organism. Central metabolites are generally restricted to those reduced organic compounds from which all or most cell mass components can be derived in a given host cell or organism. In some embodiments, the central metabolite is also the carbon product of interest in which case no additional chemical conversion is necessary.

Reference to a particular chemical species includes not only that species but also water-solvated forms of the species, unless otherwise stated. For example, carbon dioxide includes not only the gaseous form ($CO_2$) but also water-solvated forms, such as bicarbonate ion.

As used herein, the term "biosynthetic pathway" or "metabolic pathway" refers to a set of anabolic or catabolic biochemical reactions for converting (transmuting) one chemical species into another. Anabolic pathways involve constructing a larger molecule from smaller molecules, a process requiring energy. Catabolic pathways involve breaking down of larger molecules, often releasing energy. As used herein, the term "energy conversion pathway" refers to a metabolic pathway that transfers energy from an inorganic energy source to a reducing cofactor. The term "carbon fixation pathway" refers to a biosynthetic pathway that converts inorganic carbon, such as carbon dioxide, bicarbonate or formate, to reduced organic carbon, such as one or more carbon product precursors. The term "carbon product biosynthetic pathway" refers to a biosynthetic pathway that converts one or more carbon product precursors to one or more carbon based products of interest.

As used herein, the term "engineered chemoautotroph" or "engineered chemoautotrophic organism" refers to organisms that have been genetically engineered to convert inorganic carbon compounds, such as carbon dioxide or formate, to organic carbon compounds using energy derived from inorganic energy sources. The genetic modifications necessary to produce an engineered chemoautotroph comprise the introduction of heterologous energy conversion pathway(s) and/or carbon fixation pathway(s) into the host organism. The host organism can be originally heterotrophic organism. As used herein, an engineered chemoautotroph need not derive its organic carbon compounds solely from inorganic carbon and need not derive its energy solely from inorganic energy sources. The term engineered chemoautotroph may also be used to refer to originally autotrophic or mixotrophic organisms that have been genetically engineered to include one or more energy conversion, carbon fixation and/or carbon product biosynthetic pathways in addition or instead of its endogenous autotrophic capability. The term "engineer," "engineering" or "engineered," as used herein, refers to genetic manipulation or modification of biomolecules such as DNA, RNA and/or protein, or like technique commonly known in the biotechnology art.

As used herein, the term "carbon based products of interest" refers to include alcohols such as ethanol, propanol, isopropanol, butanol, octanol, fatty alcohols, fatty acid esters, wax esters; hydrocarbons and alkanes such as propane, octane, diesel, Jet Propellant 8, polymers such as terephthalate, 1,3-propanediol, 1,4-butanediol, polyols, polyhydroxyalkanoates (PHAs), polyhydroxybutyrates (PHBs), acrylate, adipic acid, epsilon-caprolactone, isoprene, caprolactam, rubber; commodity chemicals such as lactate, docosahexaenoic acid (DHA), 3-hydroxypropionate, γ-valerolactone, lysine, serine, aspartate, aspartic acid, sorbitol, ascorbate, ascorbic acid, isopentenol, lanosterol, omega-3 DHA, lycopene, itaconate, 1,3-butadiene, ethylene, propylene, succinate, citrate, citric acid, glutamate, malate, 3-hydroxyprionic acid (HPA), lactic acid, THF, gamma butyrolactone, pyrrolidones, hydroxybutyrate, glutamic acid, levulinic acid, acrylic acid, malonic acid; specialty chemicals such as carotenoids, isoprenoids, itaconic acid; biological sugars such as glucose, fructose, lactose, sucrose, starch, cellulose, hemicellulose, glycogen, xylose, dextrose, galactose, uronic acid, maltose, polyketides, or glycerol; central metabolites, such as acetyl-coA, pyruvate, pyruvic acid, 3-hydropropionate, 3-hydroxypropionic acid, glycolate, glycolic acid, glyoxylate, glyoxylic acid, dihydroxyacetone phosphate, glyceraldehyde-3-phosphate, malate, malic acid, lactate, lactic acid, acetate, acetic acid, citrate and/or citric acid, from which other carbon products can be made; pharmaceuticals and pharmaceutical intermediates such as 7-aminodesacetoxycephalosporonic acid, cephalosporin, erythromycin, polyketides, statins, paclitaxel, docetaxel, terpenes, peptides, steroids, omega fatty acids and other such suitable products of interest. Such products are useful in the context of biofuels, industrial and specialty chemicals, as intermediates used to make additional products, such as nutritional supplements, nutraceuticals, polymers, paraffin replacements, personal care products and pharmaceuticals.

As used herein, the term "hydrocarbon" refers a chemical compound that consists of the elements carbon, hydrogen and optionally, oxygen. "Surfactants" are substances capable of reducing the surface tension of a liquid in which they are dissolved. They are typically composed of a water-soluble head and a hydrocarbon chain or tail. The water soluble group is hydrophilic and can either be ionic or nonionic, and the hydrocarbon chain is hydrophobic. The term "biofuel" is any fuel that derives from a biological source.

The accession numbers provided throughout this description are derived from the NCBI database (National Ceter for Biotechnology Information) maintained by the National Institute of Health, USA. The accession numbers are provided in the database on Aug. 1, 2011. The Enzyme Classification Numbers (E.C.) provided throughout this description are derived from the KEGG Ligand database, maintained by the Kyoto Encyclopedia of Genes and Genomics, sponsored in part by the University of Tokyo. The E.C. numbers are provided in the database on Aug. 1, 2011.

Other terms used in the fields of recombinant nucleic acid technology, microbiology, metabolic engineering, and molecular and cell biology as used herein will be generally understood by one of ordinary skill in the applicable arts.

Electrolytic/Electrochemical Production of Hydrogen and Formate

Hydrogen gas and formate can be produced via the electrolysis of $H_2O$ and the electrochemical conversion $CO_2$, respectively [Whipple, 2010]. Each has advantages and disadvantages as inorganic energy sources for the engineered chemoautotroph of the present invention.

Hydrogen gas mixtures with air are explosive across a wide range of hydrogen compositions. Hence, use of hydrogen gas as an inorganic energy source and oxygen gas as the terminal electron acceptor of an engineered chemoautotroph must necessarily be set up to cope with the resulting safety risk. To address this challenge, the reactor or fermentation conditions may be kept substantially anaerobic and alternative electron acceptors, such as nitrate, may be used.

Hydrogen is a gas with low water solubility which creates mass transfer limitations when using hydrogen as an inorganic energy source for engineered chemoautotrophs (biological systems are aqueous). At large reactor or fermentor scales, high rates of mass transfer from the gas to liquid phases is challenging (Example 11). There are new technologies being developed to address this issue [U.S. Pat. No. 7,923,227]. Formate, due to its higher solubility in $H_2O$, does not have this problem (Example 11).

The energy efficiency of electrolysis for production of hydrogen or electrochemical conversion of carbon dioxide impacts the overall energy efficiency of a bio-manufacturing process using an engineered chemoautotroph of the present invention. Electrolyzers achieve overall energy efficiencies of 56-73% at current densities of 110-300 $mA/cm^2$ (alkaline Electrolyzers) or 800-1600 $mA/cm^2$ (PEM electrolyzers) [Whipple, 2010]. In contrast, electrochemical systems to date have achieved moderate energy efficiencies or high current densities but not at the same time. Hence, additional technology improvements are needed for electrochemical production of formate.

Organisms or Host Cells for Engineering

The host cell or organism, as disclosed herein, may be chosen from eukaryotic or prokaryotic systems, such as bacterial cells (Gram-negative or Gram-positive), archaea, yeast cells (for example, *Saccharomyces cereviseae* or *Pichia pastoris*), animal cells and cell lines (such as Chinese hamster ovary (CHO) cells), plant cells and cell lines (such as *Arabidopsis* T87 cells and Tabacco BY-2 cells), and/or insect cells and cell lines. Suitable cells and cell lines can also include those commonly used in laboratories and/or industrial applications. In some embodiments, host cells/organisms can be selected from *Escherichia coli, Glucono-* bacter oxydans, Gluconobacter Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus Brevibacterium ammoniagenes, divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Mesoplasma florum, Micrococcus sp. CCM825, Morganella morganii, Nocardia opaca, Nocardia rugosa, Planococcus eucinatus, Proteus rettgeri, Propionibactetium shermanii, Pseudomonas synxantha, Pseudomonas azotoformans, Pseudomonas fluorescens, Pseudomonas Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus sp. ATCC 15592, Rhodococcus sp. ATCC 19070, Sporosarina ureae, Staphylococcus aureus, Vibrio metschnikovii, Vibrio tyrogenes, Actinomadura madurae, Actinomyces violacechromogenes, Kitasatosporia parulosa, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus subtilis, Bacillus pumilus, Bacillus circulans, Bacillus thiaminolyticus, Escherichia freundii, Microbacterium ammoniaphilum, Serratia marcescens, Salmonella enterica, Salmonella typhimurium, Salmonella schottmulleri, Xanthonmonas citri, Saccharomyces spp. (e.g., Saccharomyces cerevisiae, Saccharomyces bayanus, Saccharomyces boulardii, Schizosaccharomyces pombe), Arabidopsis thaliana, Nicotiana tabacum, CHO cells, 3T3 cells, COS-7 cells, DuCaP cells, HeLa cells, LNCap cells, THP1 cells, 293-T cells, Baby Hamster Kidney (BHK) cells, HKB cells, hybridoma cells, as well as bacteriophage, baculovirus, adenovirus, or any modifications and/or derivatives thereof. In certain embodiments, the genetically modified host cell is a Mesoplasma florum, E. coli, yeast, archaea, mammalian cells and cell lines, green plant cells and cell lines, or algae. Non-limiting examples of algae that can be used in this aspect of the invention include: Botryococcus braunii; Neochloris oleoabundans; Scenedesmus dimorphus; Euglena gracilis; Nannochloropsis salina; Dunaliella tertiolecta; Tetraselmis chui: Isochrysis galbana; Phaeodactylum tricornutum; Pleurochrysis carterae: Prymnesium parvum; Tetraselmis suecica; or Spirulina species. Those skilled in the art would understand that the genetic modifications, including metabolic alterations exemplified herein, are described with reference to a suitable host organism such as E. coli and their corresponding metabolic reactions or a suitable source organism for desired nucleic acids such as genes for a desired metabolic pathway. However, given the complete genome sequencing of a wide variety of organisms and the high level of skill in the area of genomics, those skilled in the art would readily be able to apply the teachings and guidance provided herein to essentially all other host cells and organisms. For example, the E. coli metabolic modifications exemplified herein can readily be applied to other species by incorporating the same or analogous encoding nucleic acid from species other than the referenced species. Such genetic modifications include, for example, genetic alterations of species homologs, in general, and in particular, orthologs, paralogs or nonorthologous gene displacements.

In certain embodiments, the host cell or organism is a microorganism which includes prokaryotic and eukaryotic microbial species from the Domains Archaea, Bacteria and Eucarya, the latter including yeast and filamentous fungi, protozoa, algae, or higher Protista. The terms "microbial organisms", "microbial cells" and "microbes" are used interchangeably with the term microorganism.

In certain embodiments, host microbial organisms can be selected from, and the engineered microbial organisms generated in, for example, bacteria, yeast, fungus or any of a variety of other microorganisms applicable to fermentation processes. Exemplary bacteria include species selected from Escherichia coli, Klebsiella oxytoca, Anaerobiopirillum succiniciproducens, Acetobacter aceti, Actinobacillus succinogenes, Mannheimia succiniciproducens, Mesoplasma florum, Rhizobium etli, Bacillus subtilis, Corynebacterium glutamicum, Gluconobacter oxydans, Zymomonas mobilis, Lactococcus lactis, Lactobacillus plantarum, Cupriavidus necator (formerly Ralstonia eutropha), Streptomyces coelicolor, Clostridium ljungdahlii, Clostridium thermocellum, Clostridium acetobutylicum, Pseudomonas fluorescens, and Pseudomonas putida. Exemplary yeasts or fungi include species selected from Saccharomyces cerevisiae, Schizosaccharomyces pombe, Kluyveromyces lactis, Kluyveromyces marxianus, Aspergillus terreus, Aspergillus niger, Penicillium chrysogenum and Pichia pastoris. E. coli is a particularly useful host organisms since it is a well characterized microbial organism suitable for genetic engineering. Other particularly useful host organisms include yeast such as Saccharomyces cerevisiae.

In various aspects of the invention, the cells are genetically engineered or metabolically evolved, for example, for the purposes of optimized energy conversion and/or carbon fixation. The terms "metabolically evolved" or "metabolic evolution" relates to growth-based selection (metabolic evolution) of host cells that demonstrate improved growth (cell yield). Yet other suitable organisms include synthetic cells or cells produced by synthetic genomes [US Patent Publication Number 2007/0264688] and cell-like systems or synthetic cells [US Patent Publication Number 2007/0269862].

Exemplary genomes and nucleic acids include full and partial genomes of a number of organisms for which genome sequences are publicly available and can be used with the disclosed methods, such as, but not limited to, Aeropyrum pernix; Agrobacterium tumefaciens; Anabaena; Anopheles gambiae; Apis mellifera; Aquifex aeolicus; Arabidopsis thaliana; Archaeoglobus fulgidus; Ashbya gossypii; Bacillus anthracis; Bacillus cereus: Bacillus halodurans; Bacillus lichenformis; Bacillus subtilis; Bacteroides fragilis; Bacteroides thetaiotaomicron; Bartonella henselae; Bartonella quintana; Bdellovibrio bacteriovirus; Bifidobacterium longum; Blochmannia floridanus; Bordetella bronchiseptica; Bordetella parapertussis; Bordetella pertussis; Borrelia burgdorferi; Bradyrhizoium japonicum; Brucella melitensis; Brucella suis; Buchnera aphidicola; Burkholderia mallei; Burkholderia pseudomallei; Caenorhabditis briggsae; Caenorhabditis elegans; Campylobacter jejuni; Candida glabrata; Canis familiaris; Caulobacter crescentus; Chlamydia muridarum; Chlamydia trachomatis; Chlamydophila caviae; Chlamydophila pneumoniae; Chlorobium tepidum; Chromobacterium violaceum; Ciona intestinalis; Clostridium acetobuylicum; Clostidium perfringens; Clostridium tetania Corynebacterium diphtheriae; Corynebacterium efficiens; Coxiella burnetii; Cryptosporidium hominis; Cryptospordium parvum; Cyanidiaoschyzon merolae; Debaryomyces hansenii; Deinococcus radiodurans; Desulfotalea psychrophila; Desulfovibrio vulgaris; Drosophila melanogaster; Encephalitozoon cuniculi; Enterococcus faecalis; Erwinia carotovora; Escherichia coli; Fusobacterium nucleatum; Gallus gallus; Geobacter sufurreducens; Gloeobacter violaceus; Guillardia theta; Haemophilus ducreyi; Haemophilus influenzae; Halobacterium; Helicobacter hepaticus; Helicobacter pylori; Homo sapiens; Kluyveromyces waltii; Lactobacillus johnsonii; Lactobacillus plantarum; Legionella pneumophila; Leifsonia xyli; Lactococcus lactis; Leptospira interrogans; Listeria innocua; Listeria monocytogenes; Magnaporthe grisea; Mannheimia succiniciproducens; Mesoplasma florum; Mesorhizobium loti; Methanobacterium thermoautotrophicum: Melhanococcoides burtonii; Methanococcus jannaschii; Methanococcus maripaludis; Methanogenium frigidum; Methanopyrus kandleri; Methanosarcina acetivorans; Methanosarcina mazei; Methylococcus capsulatus; Mus musculus; Mycobacterium Bovis; Mycobacterium leprae; Mycobacterium paratuberculosis; Mycobacterium tuberculosis; Mycoplasma gallisepticum; Mycoplasma genitalium; Mycoplasma mycoides; Mycoplasma penetrans; Mycoplasma pneumoniae; Mycoplasma pulmonis; Mycoplasma mobile; Nanoarchaeum equitans; Neisseria meningitidis; Neurospora crassa; Nitrosomonas europaea; Nocardia farcinica; Oceanobacillus iheyensis; Onions yellows phytoplasma; Oryza sativa; Pan troglodytes; Pasteurella multocida; Phanerochaete chrysosporium; Photorhabdus luminescens; Picrophilus torridus; Plasmodium falciparum; Plasmodium yoelii yoelii; Populus trichocarpa; Porphyromonas gingivalis Prochlorococcus marinus; Propionibacterium acnes; Protochlamydia amoebophila; Pseudomonas aeruginosa; Pseudomonas putida; Pseudomonas syringae; Pyrobaculum aerophilum; Pyrococcus abyssi; Pyrococcus furiosus; Pyrococcus horikoshii; Pyrolobus fumarii; Ralstonia solanacearum; Rattus norvegicus; Rhodpirellula baltica; Rhodopseudomonas palustris; Rickettsia conorii; Rickettsia typhi; Rickettsia prowazekii; Rickettsia sibirica; Saccharomyces cerevisiae; Saccharomyces bayanus; Saccharomyces boulardii; Saccharopolyspora erythraea; Schizosaccharomyces pombe; Salmonella enterica; Salmonella typhimurium; Schizosaccharomyces pombe; Shewanella oneidensis; Shigella flexneria; Sinorhizobium meliloti; Staphylococcus aureus; Staphylococcus epidermidis; Streptococcus agalactiae; Streptococcus mutans; Streptococcus pneumoniae Streptococcus pyogenes; Streptococcus thermophilus; Streptomyces avermitilis; Streptomyces coelicolor, Sulfolobus solfataricus; Sulfolobus tokodaii; Synechococcus; Synechoccous elongates; Synechocystis; Takifugu rubripes; Tetraodon nigroviridis; Thalassiosira pseudonana; Thermoanaerobacter tengcongensis; Thermoplasma acidophilum; Thermoplasma volcanium; Thermosynechococcus elongatus; Thermotagoa maritima; Thermus thermophilus; Treponema denticola; Treponema pallidum; Tropheryma whipplei; Ureaplasma urealyticum; Vibrio cholerae; Vibrio parahaemolyticus; Vibrio vulnficus; Wigglesworthia glossinidia; Wolbachia pipientis; Wolinella succinogenes; Xanthomonas axonopodis; Xanthomonas campestris; Xylella fastidiosa; Yarrowia lipolytica; Yersinia pseudotuberculosis; and Yersinia pestis nucleic acids.

In certain embodiments, sources of encoding nucleic acids for enzymes for an energy conversion pathway, carbon fixation pathway or carbon product biosynthetic pathway can include, for example, any species where the encoded gene product is capable of catalyzing the referenced reaction. Exemplary species for such sources include, for example, Aeropyrum pernix; Aquifex aeolicus; Aquifex pyrophilus; Candidatus Arcobacter sulfidicus; Candidatus Endoriftia persephone; Candidatus Nitrospira defluvii; Chlorobium limicola: Chlorobium tepidum; Clostridium pasteurianum; Desulfobacter hydrogenophilus; Desulfurobacterium thermolithotrophum; Geobacter metallireducens; Halobacterium sp. NRC-1; Hydrogenimonas thermophila; Hydrogenivirga strain 128-5-R1; Hydrogenobacter thermophilus; Hydrogenobaculum sp. Y04AAS1; Lebetimonas acidiphila Pd55$^T$; Leptospirillum ferriphilum: Leptospirillum ferrodiazotrophum; Leptospirillum rubarum; Magnetococcus marinus; Magnetospirillum magneticum; Mycobacterium bovis; Mycobacterium tuberculosis; Methylobacterium nodulans; Nautilia lithotrophica; Nautilia profundicola; Nautilua sp. strain AmN; Nitratifractor salsuginis; Nitratiruptor sp. strain SB155-2; Persephonella marina; Rimcaris exoculata episymbiont; Streptomyces avermitilis; Streptomyces coelicolor; Sufolobus avermitilis; Sufolobus solfataricus; Sulfolobus tokodaii; Sulfurihydrogenibium azorense; Sulfurihydrogenibium sp. Y03AOP1; Sulfurihydrogenibium yellowstonense; Sulfurihydrogenibium subterraneum; Sulfurimonas autotrophica; Sulfurimonas denitrifecans; Sulfurimonas paralvinella; Sulfurovum lithotrophicum; Sulfurovum sp. strain NBC37-1; Thermocrinis ruber; Thermovibrio ammonificans; Thermovibrio ruber; Thioreductor micatisoli; Nostoc sp. PCC 7120; Acidithiobacillus ferrooxidans; Allochromatium vinosum; Aphanothece halophytica; Oscillatoria limnetica: Rhodobacter capsulatus; Thiobacillus denitrificans; Cupriavidus necator (formerly Ralstonia eutropha), Methanosarcina barkeri; Methanosarcia mazei; Methanococcus maripaludis; Mycobacterium smegmatis: Burkholderia stabilis; Candida boidinii; Candida methylica; Pseudomonas sp. 101; Methylcoccus capsulatus; Mycobacterium gastri; Cenarchaeum synbiosum; Chloroflexus aurantiacus; Erythrobacter sp. NAP1; Metallosphaera sedula; gamma protcobacterium NOR51-B; marine gamma proteobacterium HTCC2080; Nitrosopumilus maritimus; Roseiflexus castenholzii; Synechococcus elongatus; and the like, as well as other exemplary species disclosed herein or available as source organisms for corresponding genes. However, with the complete genome sequence publicly available for now more than 4400 species (including viruses), including 1701 microbial genomes and a variety of yeast, fungi, plant, and mammalian genomes, the identification of genes encoding the requisite energy conversion, carbon fixation or carbon product biosynthetic activity for one or more genes in related or distant species. including for example, homologs, orthologs, paralogs and nonorthologous gene displacements of known genes, and the replacement of gene homolog either within an particular engineered chemosutotroph or between different host cells for the engineered chemoautotroph is routine and well known in the art. Accordingly, the metabolic modifications enabling chemoautotrophic growth and production of carbon-based products described herein with reference to a particular organism such as E. coli can be readily applied to other microorganisms, including prokaryotic and eukaryotic organisms alike. Given the teachings and guidance provided herein, those skilled in the art would know that a metabolic modification exemplified in one organism can be applied equally to other organisms.

In some instances, such as when an alternative energy conversion, carbon fixation or carbon product biosynthetic pathway exists in an unrelated species, chemoautotrophic growth and production of carbon-based products can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art would understand that the actual gene usage between different organisms may differ. However, given the teachings and guidance provided herein, those skilled in the art also would understand that the teachings and methods of the invention can be applied to all microbial organisms using the cognate metabolic modifications to those exemplified herein to construct a microbial organism in a species of interest that would produce carbon-based products of interest from inorganic energy and inorganic carbon.

It should be noted that various engineered strains and/or mutations of the organisms or cell lines discussed herein can also be used.

Methods for Identification and Selection of Candidate Enzymes for a Metabolic Activity of Interest In one aspect, the present invention provides a method for identifying candidate proteins or enzymes of interest capable of performing a desired metabolic activity. Leveraging the exponential growth of gene and genome sequence databases and the availability of commercial gene synthesis at reasonable cost, Bayer and colleagues adopted a synthetic metagenomics approach to bioinformatically search sequence databases for homologous or similar enzymes, computationally optimize their encoding gene sequences for heterologous expression, synthesize the designed gene sequence, clone the synthetic gene into an expression vector and screen the resulting enzyme for a desired function in E. coli or yeast [Bayer, 2009]. However, depending on the metabolic activity or protein of interest, there can be thousands of putative homologs in the publicly available sequence databases. Thus, it can be experimentally challenging or in some cases infeasible to synthesize and screen all possible homologs at reasonable cost and within a reasonable timeframe. To address this challenge, in one aspect, this invention provides an alternate method for identifying and selecting candidate protein sequences for a metabolic activity of interest. The method comprises the following steps. First, for a desired metabolic activity, such as an enzyme-catalyzed step in an energy conversion, carbon fixation or carbon product biosynthetic pathway, one or more enzymes of interest are identified. Typically, the enzyme(s) of interest have been previously experimentally validated to perform the desired activity, for example in the published scientific literature. In some embodiments, one or more of the enzymes of interest has been heterologously expressed and experimentally demonstrated to be functional. Second, a bioinformatic search is performed on protein classification or grouping databases, such as Clusters of Orthologous Groups (COGs) [Tatusov, 1997; Tatusov, 2003], Entrez Protein Clusters (ProtClustDB) [Klimke, 2009] and/or InterPro [Zdobnov, 2001], to identify protein groupings that contain one or more of the enzyme(s) of interest (or closely related enzymes). If the enzyme(s) of interest contain multiple subunits, then the protein corresponding to a single subunit, for example the catalytic subunit or the largest subunit, is selected as being representative of the enzyme(s) of interest for the purposes of bioinformatic analysis. Third, a systematic, expert-guided search is then performed to identify which database groupings are likely to contain a majority of members whose metabolic activity is the same or similar as the protein(s) of interest. Fourth, the list of NCBI Protein accession numbers corresponding to every members of each selected database grouping is then compiled and the corresponding protein sequences are downloaded from the sequence databases. Protein sequences available from sources other than the public sequence databases may be added to this set. Fifth, optionally, one or more outgroup protein sequences are identified and added to the set. Outgroup proteins are proteins which may share some functional, structural, or sequence similarities to the model enzyme(s) but lack an essential feature of the enzyme(s) of interest or desired metabolic activity. For example, the enzyme flavocytochrome c (E.C. 1.8.2.3) is similar to sulfide-quinone oxidoreductase (E.C. 1.8.5.4) in that it oxidizes hydrogen sulfide but it reduces cytochrome c instead of ubiquinone and thus offers a useful outgroup during bioinformatic analysis of sulfide-quinone oxidoreductases. Sixth, the complete set of protein sequences are aligned with an sequence alignment program capable of aligning large numbers of sequences, such as MUSCLE [Edgar, 2004a; Edgar, 2004b]. Seventh, a tree is drawn based on the resulting MUSCLE alignment via methods known to those skilled in the art, such as neighbor joining [Saitou, 1987] or UPGMA [Sokal, 1958; Murtagh, 1984]. Eighth, different clades are selected from the tree so that the number of clades equals the desired number of proteins for screening. Finally, one protein from each clade is selected for gene synthesis and functional screening based on the following heuristics Preference is given to proteins that have been heterologously expressed and experimentally demonstrated to have the desired metabolic activity.

Preference is given to proteins that have been biochemically characterized to have the desired metabolic activity previously.

Preference is given to proteins from source organisms for which there is strong experimental or genomic evidence that the organism has the desired metabolic activity.

Preference is given to proteins in which the key catalytic, binding and/or other signature residues are conserved with respect to the protein(s) of interest.

Preference is given to protein from source organisms whose optimal growth temperature is similar to that of the host cell or organism. For example, if the host cell is a mesophile, then the source organism is also a mesophile.

Therefore, in constructing the engineered chemoautotroph of the invention, those skilled in the art would understand that by applying the teaching and guidance provided herein, it is possible to replace or augment particular genes within a metabolic pathway, such as an energy conversion pathway, a carbon fixation pathway, and/or a carbon product biosynthetic pathway, with homologs identified using the methods described here, whose gene products catalyze a similar or substantially similar metabolic reaction. Such modifications can be done, for example, to increase flux through a metabolic pathway (for example, flux of energy or carbon), to reduce accumulation of toxic intermediates, to improve the kinetic properties of the pathway, and/or to otherwise optimize the engineered chemoautotroph. Indeed, gene homologs for a particular metabolic activity may be preferable when conferring chemoautrotrophic capability on a different host cell or organism.

Methods for Design of Nucleic Acids Encoding Enzymes for Heterologous Expression In one aspect, the present invention provides a computer program product for designing a nucleic acid that encodes a protein or enzyme of interest that is codon optimized for the host cell or organism (the target species). The program can reside on a hardware computer readable storage medium and having a plurality of instructions which, when executed by a processor, cause the processor to perform operations. The program comprises the following operations. At each amino acid position of the protein of interest, the codon is selected in which the rank order codon usage frequency of that codon in the target species is the same as the rank order codon usage frequency of the codon that occurs at that position in the source species gene. To select the desired codon at each amino acid position, both the genetic code (the mapping of codons to amino acids [Jukes, 1993]) and codon frequency table (the frequency with which each synonymous codon occurs in a genome or genome [Grantham, 1980]) for both the source and target species are needed. For source species for which a complete genome sequence is available, the usage frequency for each codon may be calculate simply by summing the number of instances of that codon in all annotated coding sequences, dividing by the total number of codons in that genome, and then multiplying by 1000. For source species for which no complete genome is available, the usage frequency can be computed based on any available coding sequences or by using the codon frequency table of a closely related organism. The program then preferably standardizes the start codon to ATG, the stop codon to TAA, and the second and second last codons to one of twenty possible codons (one per amino acid). The program then subjects the codon optimized nucleic acid sequence to a series of checks to improve the likelihood that the sequence can be synthesized via commercial gene synthesis and subsequently manipulated via molecular biology [Sambrook, 2001] and DNA assembly methods [Knight, 2003; Knight, 2007; WO/2010/070295]. These checks comprise identifying if key restriction enzyme recognition sites used in a DNA assembly standard or DNA assembly method are present; if hairpins whose GC content exceeds a threshold percentage, such as 60%, and whose length exceeds a threshold number of base pairs, such as 10, are present; if sequence repeats are present; if any subsequence between 100 and 150 nucleotides in length exceeds a threshold GC content, such as 65%; if G or C homopolymers greater than 5 nucleotides in length are present; and, optionally, if any sequence motifs are present that might give rise to spurious transposon insertion sites, transcriptional or translational initiation or termination, mRNA secondary structure, RNase cleavage, and/or transcription factor binding. If the codon optimized nucleic acid sequence fails any of these checks, the program then iterates through all possible synonymous mutations and designs a new nucleic acid sequence that both passes all checks and minimizes the difference in codon frequencies between the original and new nucleic acid sequence.

Various implementations of the systems and techniques described here can be realized in digital electronic circuitry, integrated circuitry, specially designed ASICs (application-specific integrated circuits), computer hardware, firmware, software, and/or combinations thereof. These various implementations can include one or more computer programs that are executable and/or interpretable on a programmable system including at least one programmable processor, which may be special or general purpose, coupled to receive data and instructions from, and to transmit data and instructions to, a storage system, at least one input device, and at least one output device. Such computer programs (also known as programs, software, software applications or code) may include machine instructions for a programmable processor, and may be implemented in any form of programming language, including high-level procedural and/or object-oriented programming languages, and/or in assembly/machine languages. A computer program may be deployed in any form, including as a stand-alone program, or as a module, component, subroutine, or other unit suitable for use in a computing environment. A computer program may be deployed to be executed or interpreted on one computer or on multiple computers at one site, or distributed across multiple sites and interconnected by a communication network.

A computer program may, in an embodiment, be stored on a computer readable storage medium. A computer readable storage medium stores computer data, which data can include computer program code that is executed and/or interpreted by a computer system or processor. By way of example, and not limitation, a computer readable medium may comprise computer readable storage media, for tangible or fixed storage of data, or communication media for transient interpretation of code-containing signals. Computer readable storage media, may refer to physical or tangible storage (as opposed to signals) and may include without limitation volatile and non-volatile, removable and non-removable media implemented in any method or technology for the tangible storage of information such as computer-readable instructions, data structures, program modules or other data. Computer readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor.

Figure 2:
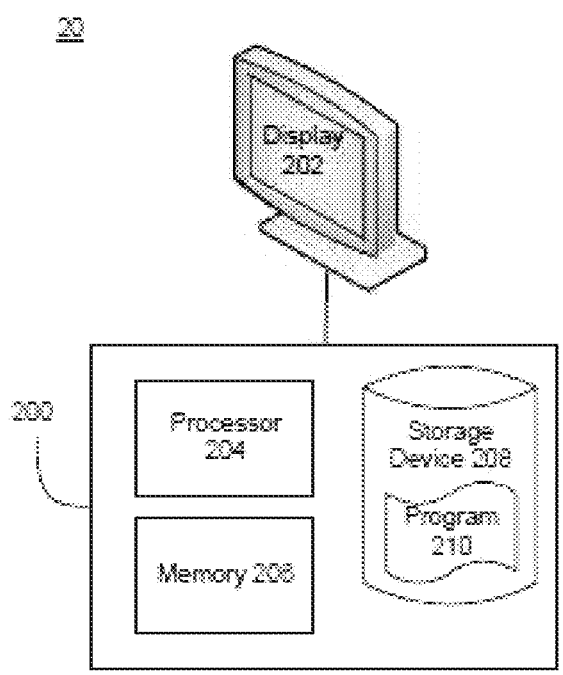
FIG. 2 is a block diagram of a computing architecture.

FIG. 2 shows a block diagram of a generic processing architecture, which may execute software applications and processes. Computer processing device 200 may be coupled to display 202 for graphical output. Processor 204 may be a computer processor capable of executing software. Typical examples of processor 204 are general-purpose computer processors (such as Intel® or AMD® processors), ASICs, microprocessors, any other type of processor, or the like. Processor 204 may be coupled to memory 206, which may be a volatile memory (e.g. RAM) storage medium for storing instructions and/or data while processor 204 executes. Processor 204 may also be coupled to storage device 208, which may be a non-volatile storage medium such as a hard drive, FLASH drive, tape drive, DVDROM, or similar device. Program 210 may be a computer program containing instructions and/or data, and may be stored on storage device 208 and/or in memory 206, for example. In a typical scenario, processor 204 may load some or all of the instructions and/or data of program 210 into memory 206 for execution.

Program 210 may be a computer program capable of performing the processes and functions described above. Program 210 may include various instructions and subroutines, which, when loaded into memory 206 and executed by processor 204 cause processor 204 to perform various operations, some or all of which may effectuate the methods, processes, and/or functions associated with the presently disclosed embodiments.

Although not shown, computer processing device 200 may include various forms of input and output. The I/O may include network adapters, USB adapters, Bluetooth radios, mice, keyboards, touchpads, displays, touch screens, LED, vibration devices, speakers, microphones, sensors, or any other input or output device for use with computer processing device 200.

Methods for Expression of Heterologous Enzymes

Composite nucleic acids can be constructed to include one or more energy conversion, carbon fixation and optionally carbon product biosynthetic pathway encoding nucleic acids as exemplified herein. The composite nucleic acids can subsequently be transformed or transfected into a suitable host organism for expression of one or more proteins of interest. Composite nucleic acids can be constructed by operably linking nucleic acids encoding one or more standardized genetic parts with protein(s) of interest encoding nucleic acids that have also been standardized. Standardized genetic parts are nucleic acid sequences that have been refined to conform to one or more defined technical standards, such as an assembly standard [Knight, 2003; Shetty, 2008; Shetty, 2011]. Standardized genetic parts can encode transcriptional initiation elements, transcriptional termination elements, translational initiation elements, translational termination elements, protein affinity tags. protein degradation tags, protein localization tags, selectable markers, replication elements, recombination sites for integration onto the genome, and more. Standardized genetic parts have the advantage that their function can be independently validated and characterized [Kelly, 2009] and then readily combined with other standardized parts to produce functional nucleic acids [Canton, 2008]. By mixing and matching standardized genetic parts encoding different expression control elements with nucleic acids encoding proteins of interest, transforming the resulting nucleic acid into a suitable host cell and functionally screening the resulting engineered cell, the process of both achieving soluble expression of proteins of interest and validing the function of those proteins is made dramatically faster. For example, the set of standardized parts might comprise constitutive promoters of varying strengths [Davis, 2011], ribosome binding sites of varying strengths [Anderson, 2007] and protein degradation of tags of varying strengths [Andersen, 1998].

For exogenous expression in *E. coli* or other prokaryotic cells, some nucleic acids encoding proteins of interest can be modified to introduce solubility tags onto the protein of interest to ensure soluble expression of the protein of interest. For example, addition of the maltose binding protein to a protein of interest has been shown to enhance soluble expression in *E. coli* [Sachdev, 1998; Kapust, 1999; Sachdev, 2000]. Either alternatively or in addition, chaperone proteins, such as DnaK, DnaJ, GroES and GroEL may be either co-expressed or overexpressed with the proteins of interest, such as RuBisCO [Greene. 2007], to promote correct folding and assembly [Martinez-Alonso, 2009; Martinez-Alonso, 2010].

For exogenous expression in *E. coli* or other prokaryotic cells, some nucleic acid sequences in the genes or cDNAs of eukaryolic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* [Hoffmeister, 2005]. For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties.

Energy Conversion from Inorganic Energy Sources to Reduced Cofactors

In certain aspects, the engineered chemoautotroph of the present invention comprises one or more energy conversion pathways to convert energy from one or more inorganic energy sources, such as formate, formic acid, carbon monoxide, methane, molecular hydrogen, hydrogen sulfide, bisulfide anion, thiosulfate, elemental sulfur, ferrous iron, and/or ammonia, to one or more reduced cofactors, such as NADH. NADPH reduced ferredoxins, quinols, reduced flavins, and reduced cytochromes. An energy conversion pathway comprises the following enzymes (only some of which may be exogenous depending on the host organism). Together, the enzymes confer an energy conversion capability on the host cell or organism that the natural organism lacks.

one or more redox enzymes to oxidize the inorganic energy source and transfer the electrons to a reducing cofactor optionally, one or more proteins that serve as a reducing cofactor and/or enzymes that can alter intracellular pools of reducing cofactors optionally, one or more oxidoreductases or transhydrogenases that can transfer electrons from high to lower energy redox cofactors (or between redox cofactors with similar redox potentials)

optionally, one or more transporters or channels to facilitate uptake of extracellular inorganic energy sources by the engineered chemoautotroph.

In certain embodiments, the nucleic acids encoding the proteins and enzymes of a energy conversion pathway are introduced into a host cell or organism that does not naturally contain all the energy conversion pathway enzymes. A particularly useful organism for genetically engineering energy conversion pathways is *E. coli*, which is well characterized in terms of available genetic manipulation tools as well as fermentation conditions. Following the teaching and guidance provided herein for introducing a sufficient number of encoding nucleic acids to generate a particular energy conversion pathway, those skilled in the art would understand that the same engineering design also can be performed with respect to introducing at least the nucleic acids encoding the energy conversion pathway enzymes or proteins absent in the host organism. Therefore, the introduction of one or more encoding nucleic acids into the host organisms of the invention such that the modified organism contains an energy conversion pathway can confer the ability to use inorganic energy to make reducing cofactors, provided the modified organism has a suitable inorganic energy source.

In certain embodiments, the invention provides an engineered chemoautroph that can utilize formate and/or formic acid as an inorganic energy source. To engineer a host cell for the utilization of formate and/or formic acid as the inorganic energy source, one or more formate dehydrogenases (FDH) can be expressed. In a preferred embodiment, the formate dehydrogenase reduces $NADP^+$. Some naturally occurring carbon fixation pathways use NADPH as the redox cofactor rather than NADH, such as the reductive pentose phosphate pathway and several variants of the 3-hydroxypropionate cycle. Accordingly, in certain aspects of the invention, the engineered chemoautotroph expresses a *Burkholderia stabilis* NADP$^+$-dependent formate dehydrogenase (E.C. 1.2.1.43, ACF35003) or a homolog thereof. The homologs can be selected by any suitable methods known in the art or by the methods described herein. This enzyme has been previously shown to preferentially use NADP$^+$ as a cofactor [Hatrongjit, 2010]. SEQ ID NO:1 represents the *E. coli* codon optimized coding sequence for the fdh gene of the present invention. In one aspect, the invention provides a nucleic acid molecule and homologs, variants and derivatives of SEQ ID NO:1. The nucleic acid sequence can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO:1. The present invention also provides nucleic acids comprising or consisting of a sequence which is a codon optimized version of the wild-type fdh gene. In another embodiment, the invention provides a nucleic acid encoding a polypeptide having the amino acid sequence of Genbank accession ACF35003, or homologs thereof having 70%, 71%, 72%, 73%, 74%, 75%, 76%, 77%, 78%, 79%, 80%, 81-85%, 90-95%, 96-98%, 99%, 99.9% or even higher identity thereto. Alternatively, enzymes that naturally use NAD$^+$ can be engineered using established protein engineering techniques to require NADP$^+$ instead of NAD$^+$ [Serov, 2002; Gul-Karaguler, 2001].

In another embodiment, the formate dehydrogenase reduces NAD$^+$. For example, formate dehydrogenase (E.C. 1.2.1.2) can couple the oxidation of formate to carbon dioxide with the reduction of NAD$^+$ to NADH. Exemplary FDH enzymes include Genbank accession numbers CAA57036, AAC49766 and NP_015033 or homologs thereof. SEQ ID NO:2, SEQ ID NO:3 and SEQ ID NO:4 represent *E. coli* codon optimized coding sequence for each of these three FDHs, respectively, of the present invention. In one aspect, the invention provides nucleic acid molecules and homologs, variants and derivatives of SEQ ID NO:2, SEQ ID NO:3 and SEQ ID NO:4. The nucleic acid sequences can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO:2, SEQ ID NO:3 and SEQ ID NO:4. The present invention also provides nucleic acids each comprising or consisting of a sequence which is a codon optimized version of one of the wild-type fdh genes. In another embodiment, the invention provides nucleic acids each encoding a polypeptide having the amino acid sequence of one of Genbank accession numbers CAA57036, AAC49766 and NP_015033, or homologs thereof having 70%, 71%, 72%, 73%, 74%, 75%, 76%, 77%, 78%, 79%, 80%, 81-85%, 90-95%, 96-98%, 99%, 99.9% or even higher identity thereto.

In certain embodiments, the invention provides an engineered chemoautroph that can utilize formate and/or formic acid as an inorganic energy source and produce reduced, low potential ferredoxin as the reducing cofactor. The reductive tricarboxylic acid cycle carbon fixation pathway is believed to require a low potential ferredoxin for particular carboxylation steps [Brugna-Guiral, 2003, Yoon, 1997: Ikeda, 2005]. The organisms *Nautilia* sp. strain AmN, *Nautilia profundicola, Nautilia lithotrophica* 525$^T$ and *Thermocrinis ruber* are reported to grow on formate as the sole electron donor and use the reductive tricarboxylic acid cycle as their carbon fixation pathway [Campbell, 2001; Smith, 2008; Campbell, 2009; Miroshnichenko, 2002; Hügler, 2007], thus implying that each of these organisms have an energy conversion pathway from formate to reduced ferredoxin. To engineer a host cell for the utilization of formate and/or formic acid as the inorganic energy source and production of reduced ferredoxin as the reducing cofactor, in certain embodiments the present invention provides for the expression of formate dehydrogenase capable of reducing low potential ferredoxin in the engineered chemoautotroph. Such an enzyme would facilitate the combination of an energy conversion pathway that utilizes formate with a carbon fixation pathway based on the reductive tricarboxylic acid cycle as an embodiment of the engineered chemoautotroph of the present invention. Exemplary putative ferredoxin-dependent formate dehydrogenases include (with Genbank accession numbers of the FDH subunits listed in parentheses) *Nautilia profundicola* AmH (YP_002607699, YP_002607700, YP_002607701 and YP_002607702), *Sulfurimonas denitrificans* DSM 1251 (YP_394410 and YP_394411), *Caminibacter mediatlanticus* TB-2 (ZP_01871216, ZP_01871217, ZP_01871218 and ZP_01871219) and *Methanococcus maripaludis* strain S2 (NP_988417 and NP_988418) or homologs thereof. In another embodiment, the invention provides nucleic acids each encoding a polypeptide having the amino acid sequence of one of Genbank accession numbers YP_002607699, YP_002607700, YP_002607701, YP_002607702, YP_394410, YP_394411, ZP_01871216, ZP_01871217, ZP_01871218, ZP_01871219, NP_988417 and NP_988418, or homologs thereof having 70%, 71%, 72%, 73%, 74%, 75%, 76%, 77%, 78%, 79%, 80%, 81-85%, 90-95%, 96-98%, 99%, 99.9% or even higher identity thereto.

A ferredoxin-reducing formate dehydrogenase (FDH) has been previously purified from *Clostridium pasteurianum* W5 [Liu, 1984]; however, no protein or nucleic acid sequence information is available on the enzyme nor is there a publicly available genome sequence for *Clostridium pasteurianum* as of Aug. 1, 2011. Based on the sequencing and bioinformatic analysis of the *Clostridium pasteurianum* genome, the sequence of a two putative subunits of a ferredoxin-dependent FDH (FdhF and FdhD) as well as two associated putative ferredoxin domain-containing proteins were identified (Example 7). In one aspect, the invention provides nucleic acids each encoding a polypeptide having the amino acid sequence of one of SEQ ID NO:5, SEQ TD NO:6. SEQ ID NO:7 and SEQ ID NO:8. In another embodiment, the invention provides nucleic acids each encoding a polypeptide having the amino acid sequence of one of SEQ ID NO:5, SEQ ID NO:6, SEQ ID NO:7 and SEQ ID NO:8 which have been codon optimized for the host organism, such as *E. coli*. Based on the *Clostridium pasteurianum* putative FDH subunits, additional putative ferredoxin-dependent FDH were identified. Exemplary ferredoxin-dependent FDH include (with Genbank accession numbers of the FDH subunits listed in parentheses) *Clostridium beijerincki* NCIMB 8052 (YP_001310874 and YP_001310871), *Clostridium difficile* 630 (YP_001089834 and YP_001089833), *Clostridium difficile* CD196 (YP_003216147 and YP_003216146), *Clostridium difficile* R20291 (YP_003219654 and YP_003219653) or homologs thereof. In another embodiment. the invention provides nucleic acids each encoding a polypeptide having the amino acid sequence of one of Genbank accession numbers YP_001310874, YP_001310871, YP_001089834, YP_001089833, YP_003216147, YP_003216146, YP_003219654 and YP_003219653, or homologs thereof having 70%, 71%, 72%, 73%, 74%, 75%, 76%, 77%, 78%, 79%, 80, 81-85%, 90-95%, 96-98%, 99%, 99.9% or even higher identity thereto.

In certain embodiments, the invention provides an engineered chemoautotroph that can utilize molecular hydrogen as an inorganic energy source. To engineer a host cell for the utilization of molecular hydrogen as an inorganic energy source, one or more hydrogenases can be expressed. For example, [NiFe]-hydrogenases are typically associated with the coupling of hydrogen oxidation to cofactor reduction [Vignais, 2004]. These hydrogenases tend to be composed of at least a large and small subunit and require several accesssory genes for maturation including a peptidase [Vignais, 2004]. Recently, there have been several published examples of heterologous expression of [NiFe]-hydrogenases in *E. coli* [Sun, 2010; Wells, 2011; Kim, 2011]. Taken together, these results demonstrate that particular maturation proteins, in particular the peptidase that cleaves the C-terminal end of the large subunit, tend to be very specific for their cognate hydrogenase and can not be substituted by homologous hydrogenase maturation factors endogenous to the host cell. Hence, functional heterologous expression of a [NiFe]-hydrogenase requires expression of not only the subunit proteins, such as the large and small subunit, but also one or more of the associated maturation factors, such as the peptidase. In a preferred embodiment, the hydrogenase reduces ferredoxin (E.C. 1.12.7.2) and in particular a low potential ferredoxin capable of being used as the reducing cofactor for the carboxylation steps of the reductive tricarboxylic acid cycle [Yoon, 1997; Ikeda, 2005]. The group 2a [NiFe]-hydrogenases are associated with reducing the ferredoxin needed for the reductive tricarboxylic acid cycle [Brugna-Guiral, 2003; Vignais, 2007]. Exemplary hydrogenases include (with Genbank accession numbers of the hydrogenase subunits listed in parentheses) *Aquifex aeolicus* Hydrogenase 3 (NP_213549 and NP_213548); *Hydrogenobacter thermophilus* TK-6 Hup2 (YP_003432664 and YP_003432663); *Hydrogenobaculum* sp. Y04AAS1 HY044AAS1_1400/HY044AAS1_1399 (YP_002122063 and YP_002122062); *Magnetococcus marinus* Mmc1_2493/Mmc1_2494 (YP_866399 and YP_866400); *Magneospirillum magneticum* AMB-1 amb114/amb1115 (YP_420477 and YP_420478); *Methanococcus maripaludis* S2 Hydrogenase B (NP_988273 and NP_988742); *Methanosarcina barkeri* str. fusaro Ech (YP_303717, YP_303716, YP_303715, YP_303714, YP_303713 and YP_303712); *Methanosarcina mazei* Go1 Ech (NP_634344, NP_634345, NP_634346, NP_634347, NP_634348 and NP_634349); *Mycobacterium smegmatis* str. MC2 155 Hydrogenase-2 (YP_886615 and YP_886614), *Nautilia profundicola* AmH NAMH_0573/NAMH_0572 (YP_002606989 and YP_002606988), *Nitratiruptor* sp. SB155-2 Hup (YP_001356429 and YP_001356428); *Persephonella marina* EX-H1 PERMA_0914/PERMA_0915 (YP_002730701 and YP_002730702); *Sulfurihydrogenibium azorense* Az-Fu1 SULAZ_0749/SULAZ_0748 (YP_002728734 and YP_002728733); *Sulfurimonas denitrificans* DSM 1251 Suden_1437/Suden_1436 (YP_393949 and YP_393948); *Sulfurovum* sp NBC37-1 Hup (YP_001358971 and YP_001358972); *Thermocrinis albus* DSM 14484 Thal_1414/Thal_1413 (YP_003474170 and YP_003474169); and homologs thereof. In an alternate embodiment, the hydrogenase reduces NADP$^+$ (E.C. 1.12.1.3). The group 3b and 3d [NiFe]-hydrogenases are typically NAD(P)$^+$ reducing hydrogenases from bacteria [Vignais, 2007]. Exemplary hydrogenases include (with Genbank accession numbers of the hydrogenase subunits listed in parentheses) *Cupriavidus necator* SH (NP_942732, NP_942730, NP_942729, NP_942728 and NP_942727) and *Synechocystis* sp PCC6803 bidirectional hydrogenase (NP_441418, NP_441417, NP_441415, NP_441414 and NP_441411), and homologs thereof. In an alternate embodiment, the hydrogenase reduces NAD$^+$ (E.C. 1.12.1.2). Exemplary hydrogenases include (with the Genbank accession numbers of the hydrogenase subunits listed in parentheses) *Cupriavidus necator* SH without the HoxI subunit (NP_942730, NP_942729, NP_942728 and NP_942727) and homologs thereof [Burgdorf, 2005].

In certain embodiments, the invention provides an engineered chemoautotroph that can utilize hydrogen sulfide as an inorganic energy source. To engineer a host cell for the utilization of hydrogen sulfide as the inorganic energy source, one or more sulfide-quinone oxidoreductases (SQR) can be expressed. Sulfide-quinone oxidoreductase couples the oxidation of hydrogen sulfide to the reduction of a quinone to the corresponding quinol (E.C. 1.8.5.4). The *Rhodobacter capsulatus* SQR has been functionally expressed in the heterologous host *E. coli* [Schütz, 1997] and demonstrated to reduce ubiquinone [Shibata, 2001]. Exemplary SQR enzymes include NP_214500, NP_488552, NP_661023, YP_002426210, YP_003444098, YP_003576957, YP_315983, YP_866354, and homologs thereof. SEQ ID NO:9, SEQ ID NO:10, SEQ ID NO:11, SEQ ID NO:12, SEQ ID NO:13, SEQ ID NO:14, SEQ ID NO:15 and SEQ ID NO:16 represent *E. coli* codon optimized coding sequence for each of these eight SQRs, respectively, of the present invention. In one aspect, the invention provides nucleic acid molecules and homologs, variants and derivatives of SEQ ID NO:9, SEQ ID NO:10, SEQ ID NO:11, SEQ ID NO:12, SEQ ID NO:13, SEQ ID NO:14, SEQ ID NO:15 and SEQ ID NO:16. The nucleic acid sequences can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO:9, SEQ ID NO:10, SEQ ID NO:11, SEQ ID NO:12, SEQ ID NO:13, SEQ ID NO:14, SEQ ID NO:15 and SEQ ID NO:16. The present invention provides nucleic acids each comprising or consisting of a sequence which is a codon optimized version of one of the wild-type sqr genes. In another embodiment, the invention provides nucleic acids each encoding a polypeptide having the amino acid sequence of one of Genbank accession numbers NP_214500, NP_488552, NP_661023, YP_002426210, YP_003444098, YP_003576957, YP_315983, YP_866354, or homologs thereof having 70%, 71%, 72%, 73%, 74%, 75%, 76%, 77%, 78%, 79%, 80%, 81-85%, 90-95%, 96-98%, 99%, 99.9% or even higher identity thereto. Alternatively, to engineer a host cell for the utilization of hydrogen sulfide, one or more flavocytochrome c sulfide dehydrogenases can be expressed. Flavocytochrome c sulfide dehydrogenase is similar in structure to SQR but couples the oxidation of hydrogen sulfide to the reduction of a cytochrome (E.C. 1.8.2.3) [Marcia, 2010].

In certain embodiments, the invention provides an engineered chemoautotroph that expresses a protein that can serve as a reducing cofactor, such as preferably ferredoxin or alternatively cytochrome c. In one embodiment, the ferredoxin is a low potential ferredoxin that can donate electrons to the carboxylation steps in the reductive tricarboxylic acid cycle [Yoon, 1997; Ikeda, 2005]. Exemplary ferredoxins include AAA83524, YP_003433536, YP_003433535, YP_304316, and homologs thereof. SEQ ID NO:17, SEQ ID NO:18, SEQ ID NO:19, SEQ ID NO:20 represent *E. coli* codon optimized coding sequence for each of these four ferredoxins, respectively, of the present invention. In one aspect, the invention provides nucleic acid molecules and homologs, variants and derivatives of SEQ ID NO:17, SEQ ID NO:18, SEQ ID NO:19, SEQ ID NO:20. The nucleic acid sequences can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO:17, SEQ ID NO:18, SEQ ID NO:19, SEQ ID NO:20. The present invention also provides nucleic acids each comprising or consisting of a sequence which is a codon optimized version of one of the wild-type ferredoxin genes. In another embodiment, the invention provides nucleic acids each encoding a polypeptide having the amino acid sequence of one of Genbank accession numbers AAA83524, YP_003433536, YP_003433535 and YP_304316, or homologs thereof having 70%, 71%, 72%, 73%, 74%, 75%, 76%, 77%, 78%, 79%, 80%, 81-85%, 90-95%, 96-98%, 99%, 99.9% or even higher identity thereto. Two additional exemplary ferredoxins for which no Genbank accession number has been assigned include SEQ ID NO:22 and SEQ ID NO:24, SEQ ID NO:21 and SEQ ID NO:23 represent *E. coli* codon optimized coding sequence for each of these two unannotated ferredoxins, respectively, of the present invention. In one aspect, the invention provides nucleic acid molecules and homologs, variants and derivatives of SEQ ID NO:21 and SEQ ID NO:23. The nucleic acid sequences can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO:21 and SEQ ID NO:23. The present invention also provides nucleic acids each comprising or consisting of a sequence which is a codon optimized version of one of these two wild-type ferredoxin genes. In another embodiment, the invention provides nucleic acids each encoding a polypeptide having the amino acid sequence of one of SEQ ID NO:22 and SEQ ID NO:24, or homologs thereof having 70%, 71%, 72%, 73%, 74%, 75%, 76%, 77%, 78%, 79%, 80%, 81-85%, 90-95%, 96-98%, 99%, 99.9% or even higher identity thereto.

In certain embodiments, the invention provides an engineered chemoautotroph that can transfer energy from one reduced cofactor to another. In one embodiment, a ferredoxin-NADP$^+$ reductase (FNR) is expressed. FNR can catalyze reversible electron transfer between the two-electron carrier NADPH and the one-electron carrier ferredoxin (E.C 1.18.1.2). Exemplary FNR enzymes include the *Hydrogenobacter thermophilus* Fpr (Genbank accession BAH29712) and homologs thereof [Ikeda, 2009]. In another embodiment, a ferredoxin-NAD$^+$ reductase (E.C. 1.18.1.3) and/or a NAD(P) transhydrogenase (E.C. 1.6.1.1 or E.C. 1.6.1.2) is expressed.

Carbon Fixation of Inorganic Carbon to Central Metabolites

In certain aspects, the engineered chemoautotroph of the present invention comprises one or more carbon fixation pathways to use energy from one or more reduced cofactors, such as NADH, NADPH, reduced ferredoxins, quinols, reduced flavins, and reduced cytochromes, to convert inorganic carbon, such as carbon dioxide, formate, or formic acid, into central metabolites, such as acetyl-coA, pyruvate, glyoxylate, glycolate and dihydroxyacetone phosphate. One or more of the carbon fixation pathways can be derived from naturally occurring carbon fixation pathways, such as the Calvin-Benson-Bassham cycle or reductive pentose phosphate cycle, the reductive tricarboxylic acid cycle, the Wood-Ljungdhal or reductive acetyl-coA pathway, the 3-hydroxypropionate bicycle, 3-hydroxypropionate/4-hydroxybutyrate cycle and the dicarboxylate/4-hydroxybutyrate cycle [Hügler, 2011]. Alternatively, one or more of the carbon fixation pathways can be derived from synthetic metabolic pathways not found in nature such as those enumerated by Bar-Even et al. [Bar-Even, 2010]. In certain embodiments, the nucleic acids encoding the proteins and enzymes of a carbon fixation pathway are introduced into a host cell or organism that does not naturally contain all the carbon fixation pathway enzymes. A particularly useful organism for genetically engineering carbon fixation pathways is *E. coli*, which is well characterized in terms of available genetic manipulation tools as well as fermentation conditions. Following the teaching and guidance provided herein for introducing a sufficient number of encoding nucleic acids to generate a particular carbon fixation pathway, those skilled in the art would understand that the same engineering design also can be performed with respect to introducing at least the nucleic acids encoding the carbon fixation pathway enzymes or proteins absent in the host organism. Therefore, the introduction of one or more encoding nucleic acids into the host organisms of the invention such that the modified organism contains a carbon fixation pathway can confer the ability to use inorganic carbon to make central metabolites, provided the modified organism has a suitable inorganic energy source and energy conversion pathway.

Figure 3:
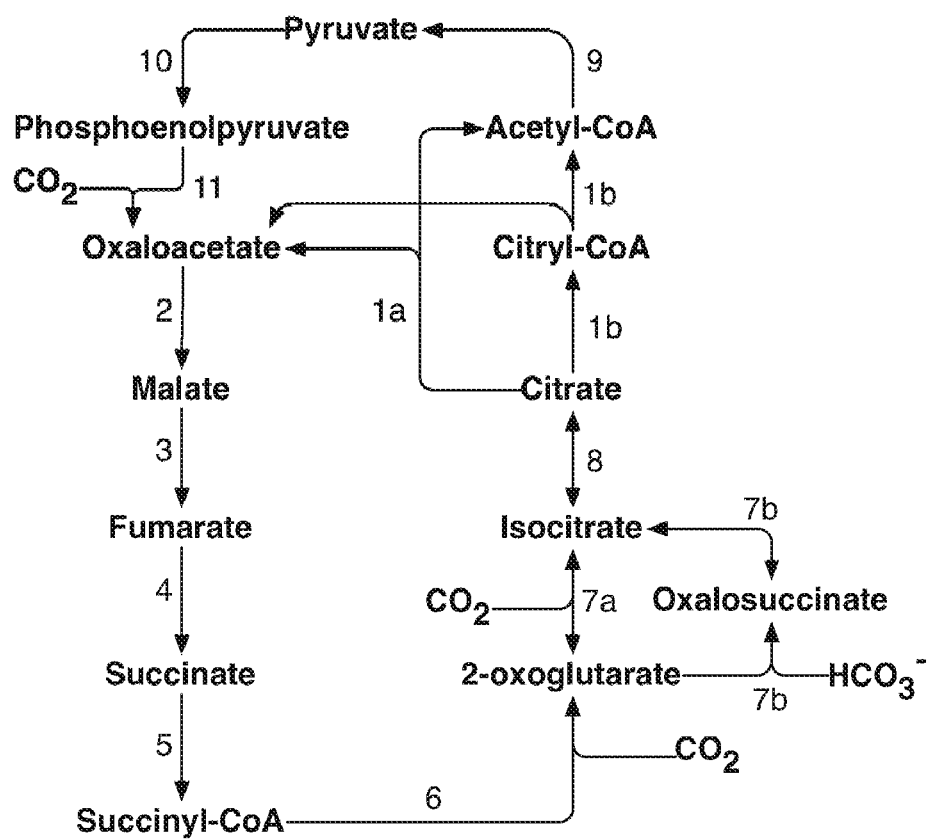
FIG. 3 depicts the metabolic reactions of the reductive tricarboxylic acid cycle [Evans, 1966; Buchanan, 1990; Hügler, 2011]. Each reaction is numbered. For certain reactions, such as reaction 1 and 7, there are two possible routes denoted by a and b, each of which is catalyzed by different enzyme(s). Enzymes catalyzing each reaction are as follows: 1a, ATP citrate lyase (E.C. 2.3.3.8); 1b, citryl-CoA synthetase (E.C. 6.2.1.18) and citryl-CoA lyase (E.C. 4.1.3.34); 2, malate dehydrogenase (E.C. 1.1.1.37); 3, fumarate dehydratase or fumarase (E.C. 4.2.1.2); 4, fumarate reductase (E.C. 1.3.99.1); 5, succinyl-CoA synthetase (E.C. 6.2.1.5); 6, 2-oxoglutarate synthase or 2-oxoglutarate:ferredoxin oxidoreductase (E.C. 1.2.7.3); 7a, isocitrate dehydrogenase (E.C. 1.1.1.41 or E.C. 1.1.1.42); 7b, 2-oxoglutarate carboxylase (E.C. 6.4.1.7) and oxalosuccinate reductase (E.C. 1.1.1.41); 8, aconitate hydratrase (E.C. 4.2.1.3); 9, pyruvate synthase or pyruvate:ferredoxin oxidoreductase (E.C. 1.2.7.1); 10, phosphoenolpyruvate synthetase (E.C. 2.7.9.2); 11, phosphoenolpyruvate carboxylase (E.C. 4.1.1.31).
Figure 4:
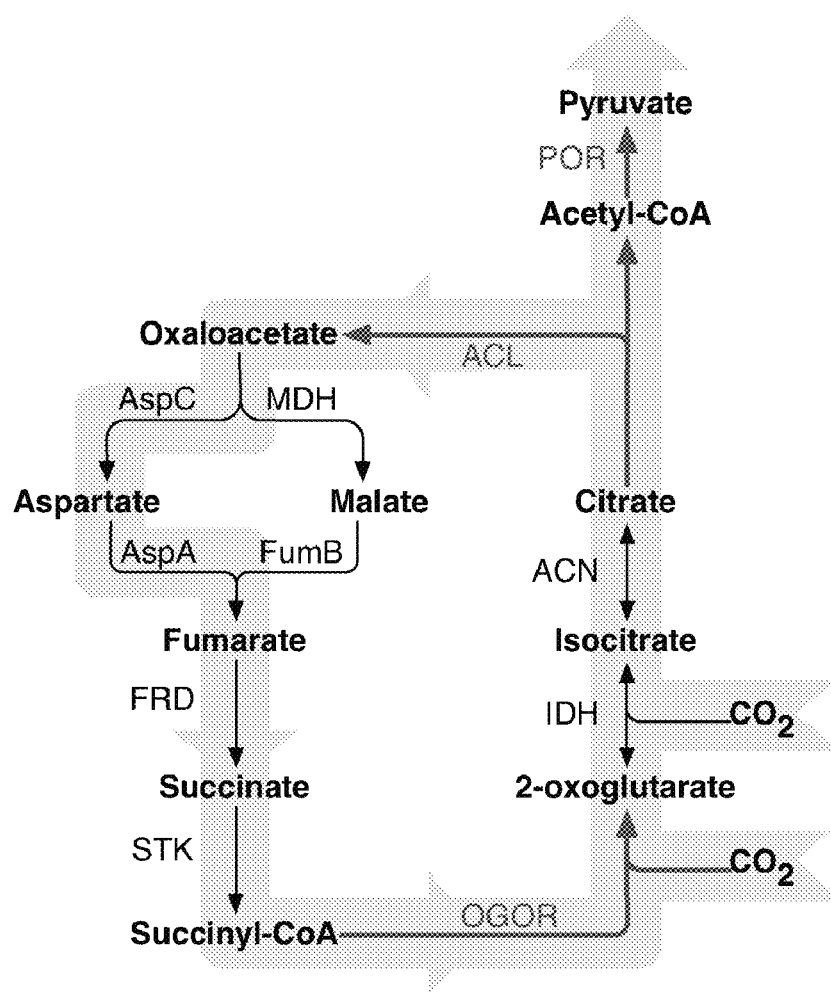
FIG. 4 depicts example metabolic reactions and enzymes needed to engineer a carbon fixation pathway derived from the reductive tricarboxylic acid (rTCA) cycle into the heterotroph *Escherichia coli*. Reactions in black are are known to occur in the wildtype host cell *E. coli* when grown in microaerobic or anaerobic conditions [Cronan, 2010]. Reactions in dark gray must be added to complete the rTCA-derived carbon fixation cycle in *E. coli*. The carbon input to the pathway is carbon dioxide ($CO_2$) and the carbon outputs of the pathway are acetylcoA and/or pyruvate. The desired net flow of carbon is indicated by the wide, light gray arrow. Metabolites are shown in bold and enzyme abbreviations are as follows: AspC, aspartate aminotransferase; MDH, malate dehydrogenase: AspA, aspartate ammonia-lyase; FumB, fumarase B; FRD, fumarate reductase; STK, succinate thiokinase; OGOR, 2-oxoglutarate:ferredoxin oxidoreductase; IDH, isocitrate dehydrogenase; ACN, aconitase; ACL, ATP-citrate lyase; POR, pyruvate:ferredoxin oxidoreductase.

In certain embodiments, the invention provides an engineered chemoautotroph with a carbon fixation pathway derived from the reductive tricarboxylic acid (rTCA) cycle. The rTCA cycle is well known in the art and consists of approximately 1 reactions (FIG. 3) [Evans, 1966; Buchanan. 1990]. For two of the reactions (reaction 1 and 7), there are two known routes between the substrate and product and each route is catalyzed by different enzyme(s). The reactions in the rTCA cycle are catalyzed by the following enzymes: ATP citrate lyase (E.C. 2.3.3.8) [Sintsov, 1980; Kanao, 2002b]; citryl-CoA synthetase (E.C. 6.2.1.18) [Aoshima, 2004a]; citryl-CoA lyase (E.C. 4.1.3.34) [Aoshima, 2004b]; malate dehydrogenase (E.C. 1.1.1.37); fumarate dehydratase or fumarase (E.C. 4.2.1.2); fumarate reductase (E.C. 1.3.99.1); succinyl-CoA synthetase (E.C. 6.2.1.5); 2-oxoglutarate synthase or 2-oxoglutarate:ferredoxin oxidoreductase (E.C. 1.2.7.3) [Gehring, 1972; Yamamoto, 2010]; isocitrate dehydrogenase (E.C. 1.1.1.41 or E.C. 1.1.1.42) [Kanao. 2002a]; 2-oxoglutarate carboxylase (E.C. 6.4.1.7) [Aushima, 2004c; Aoshima, 2006]; oxalosuccinate reductase (E.C. 1.1.1.41) [Aoshima, 2004c; Aushima, 2006]; aconitate hydratase (E.C. 4.2.1.3); pyruvate synthase or pyruvate:ferredoxin oxidoreductase (E.C. 1.2.7.1); phosphoenolpyruvate synthetase (E.C. 2.7.9.2); phosphoenolpyruvate carboxylase (E.C. 4.1.1.31). In one embodiment, the invention provides an engineered chemoautotroph comprising one or more exogenous proteins from the rTCA cycle conferring to the organism the ability to produce central metabolites from inorganic carbon, wherein the organism lacks the ability to fix carbon via the rTCA cycle (for example, see FIG. 4). For example, the one or more exogenous proteins can be selected from ATP citrate lyase, citryl-CoA synthetase, citryl-CoA lyase, malate dehydrogenase, fumarate dehydratase, fumarate reductase, succinyl-CoA synthetase, 2-oxoglutarate synthase, isocitrate dehydrogenase, 2-oxoglutarate carboxylase, oxalosuccinate reductase, aconitate hydratase, pyruvate synthase, phosphoenolpyruvate synthetase, and phosphoenolpyruvate carboxylase. The host organism can also express two or more, three or more, four or more, five or more, and the like, including up to all the protein and enzymes that confer the rTCA pathway. For example, in the host organism *E. coli*, the exogenous enzymes comprise 2-oxoglutarate synthase and ATP citrate lyase. As a second example, in the host organism *E. coli*, the exogenous enzymes comprise 2-oxoglutarate synthase, ATP citrate lyase and pyruvate synthase. Finally, as a third example, in the host organism *E. coli*, the exogenous enzymes comprise 2-oxoglutarate synthase, ATP citrate lyase, pyruvate synthase, 2-oxoglutarate carboxylase and oxalosuccinate reductase. In another embodiment, alternate enzymes can be used that result in the same overall carbon fixation pathway. For example, the enzyme malate dehydrogenase (E.C. 1.1.1.39) can substitute for malate dehydrogenase and phosphoenolpyruvate carboxylase. The enzymes 2-oxoglutarate synthase and pyruvate synthase can be difficult to distinguish from sequence data alone. Both enzymes comprise 1-5 protein subunits depending on the species. Exemplary pyruvate/2-oxoglutarate synthases include NP_213793, NP_213794, and NP_213795; NP_213818, NP_213819 and NP_213820; AAD07654, AAD07655, AAD07656 and AAD07653; ABK44257, ABK44258 and ABK44249; ACD90193 and ACD90192; YP_001942282 and YP_001942281; and homologs thereof. Exemplary 2-oxoglutarate synthases include BAI69550 and BAI69551; YP_003432753, YP_003432754, YP_003432755, YP_003432756 and YP_003432757; YP_393565, YP_393566, YP_393567 and YP_393568; BAF71539. BAF71540, BAF71541 and BAF71538; BAF69954, BAF69955, BAF69956 and BAF69953; AAM71411 and AAM71410; YP_002607621, YP_002607620, YP_002607619 and YP_002607622; CAA12243 and CAD27440; and homologs thereof. Exemplary pyruvate synthases include YP_392614, YP_392615, YP_392612 and YP_392613; YP_001357517, YP_001357518; YP_001357515 and YP_001357515; YP_001357066, YP_001357065, YP_001357068 and YP_001357067; and homologs thereof. ATP citrate lyases comprise 1-4 protein subunits depending on the species. Exemplary ATP citrate lyases include AAC06486; YP_393085 and YP_393084; BAF71501 and BAF71502; BAF69766 and BAF69767; ACX98447; AAM72322 and AAM72321; YP_002607124 and YP_002607125; BAB21376 and BAB21375; and homologs thereof. Exemplary citryl-coA synthetases include BAD17846 and BAD17844. Exemplary citryl-coA lyases include BAD17841.

Figure 5:
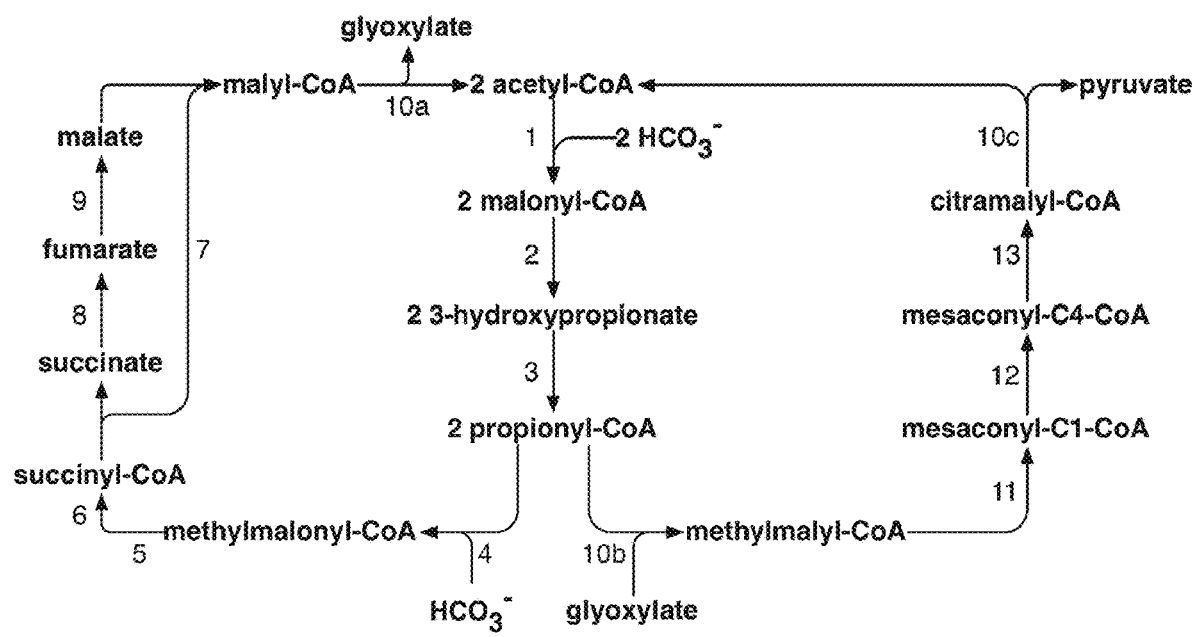
FIG. 5 depicts the metabolic reactions of the 3-hydroxypropionate bicycle [Holo, 1989; Strauss, 1993; Eisenreich, 1993; Herter, 2002a; Zarzycki, 2009; Zarzycki, 2011]. Each reaction is numbered. In some cases, multiple different reactions, such as reactions 10a, 10b and 10c, are catalyzed by the same multi-functional enzyme. Enzymes catalyzing each reaction are as follows: 1, acetyl-CoA carboxylase (E.C. 6.4.1.2); 2, malonyl-CoA reductase (E.C. 1.2.1.75 and E.C. 1.1.1.298); 3, propionyl-CoA synthase (E.C. 6.2.1.-, E.C. 4.2.1.- and E.C. 1.3.1.-); 4, propionyl-CoA carboxylase (E.C. 6.4.1.3); 5, methylmalonyl-CoA epimerase (E.C. 5.1.99.1); 6, methylmalonyl-CoA mutase (E.C. 5.4.99.2); 7, succinyl-CoA:(S)-malate CoA transferase (E.C. 2.8.3.-); 8, succinate dehydrogenase (E.C. 1.3.5.1); 9, fumarate hydratase (E.C. 4.2.1.2); 10abc, (S)-malyl-CoA/β-methylmalyl-CoA/(S)-citramalyl-CoA lyase (E.C. 4.1.3.24 and E.C. 4.1.3.25); 11, mesaconyl-C1-CoA hydratase or β-methylmalyl-CoA dehyratase (E.C. 4.2.1.-); 12, mesaconyl-CoA C1-C4 CoA transferase (E.C. 2.8.3.-); 13, mesaconyl-C4-CoA hydratase (E.C. 4.2.1.-).
Figure 6:
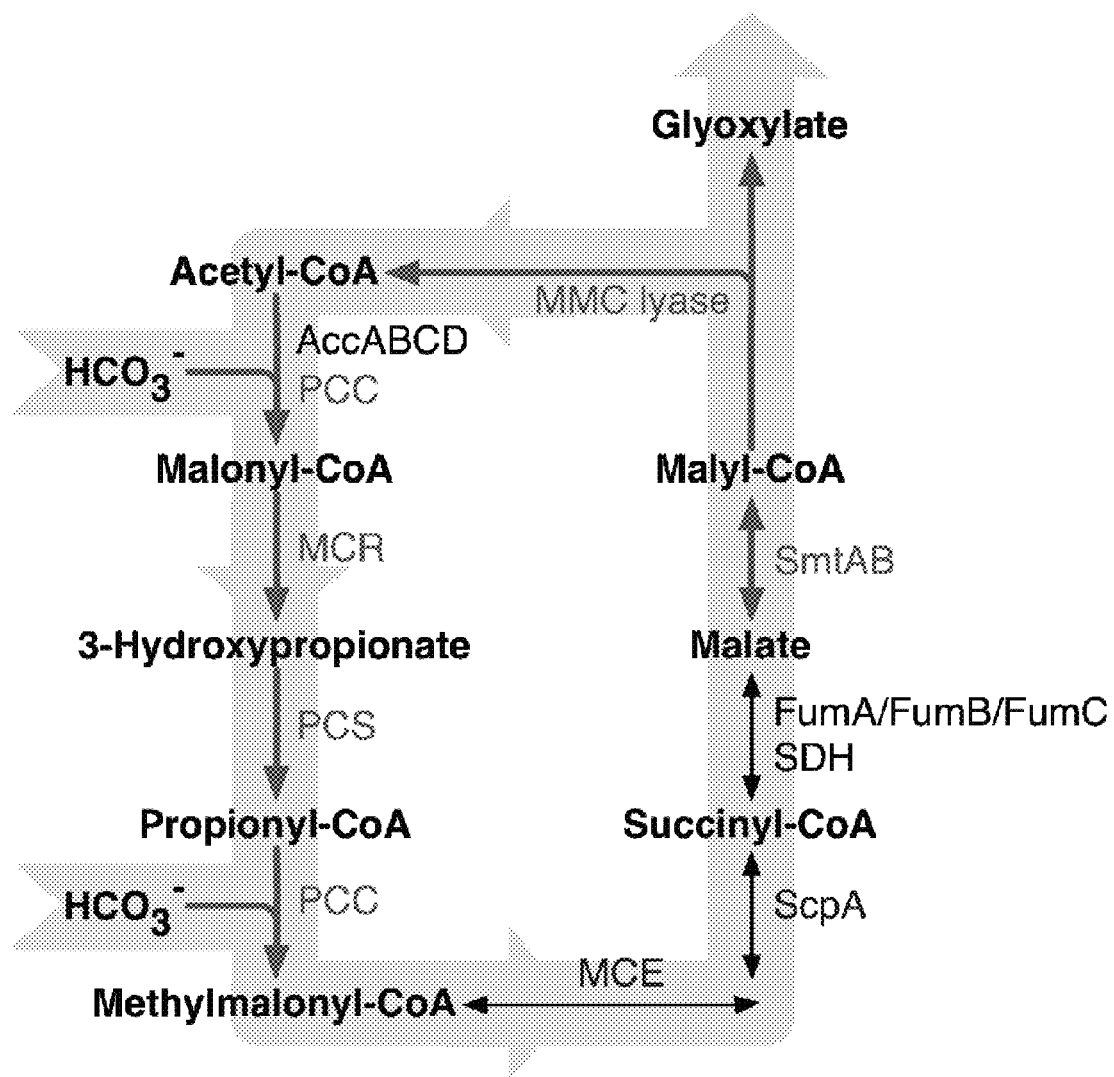
FIG. 6 depicts example metabolic reactions and enzymes needed to engineer a carbon fixation pathway derived from the 3-hydroxypropionate (3-HPA) bicycle into the heterotroph *Escherichia coli*. Reactions in black are reported to occur in the wildtype host cell *E. coli*. Reactions in dark gray must be added to complete the 3-HPA bicycle-derived carbon fixation cycle in *E. coli*. The carbon input to the pathway is bicarbonate ($HCO_3^-$) and the carbon output of the pathway is glyoxylate. The desired net flow of carbon is indicated by the wide, light gray arrow. Metabolites are shown in bold and enzyme abbreviations are as follows: PCC, propionyl-CoA carboxylase; MCR, malonyl-CoA reductase; PCS, propionyl-CoA synthase; MCE, methylmalonyl-CoA epimerase; ScpA, *E. coli* methylmalonyl-CoA mutase; SDH, *E. coli* succinate dehydrogenase; FumA/FumB/FumC, three *E. coli* fumarate hydratases; SmtAB, succinyl-CoA:(S)-malate CoA transferase; MMC lyase, (S)-malyl-CoA/β-methylmalyl-CoA/(S)-citramalyl-CoA lyase. Note that methylmalonyl-CoA epimerase activity has been reported in *E. coli* although no corresponding gene or gene product has been identified [Evans, 1993].

In certain embodiments, the invention provides an engineered chemoautotroph with a carbon fixation pathway derived from the 3-hydroxypropionate (3-HPA) bicycle. The 3-HPA bicycle is well known in the art and consists of 19 reactions catalyzed by 13 enzymes (FIG. 5) [Holo, 1989; Strauss, 1993; Eisenrich, 1993; Herter, 2002a; Zarzycki, 2009; Zarzycki. 2011]. The number of reactions in the metabolic pathway exceeds the number of enzymes because particular enzymes, such as malonyl-CoA reductase, propionyl-CoA synthase, and malyl-CoA/β-methylmalyl-CoA/ citramalyl-CoA lyase, are multi-functional enzymes that catalyze more than one reaction. Also, in some species, such as *Metallosphaera sedula*, the same enzyme can carboxylate acetyl-CoA and propionyl-CoA. The reactions in the 3-HPA bicycle are catalyzed by the following enzymes: acetyl-CoA carboxylase (E.C. 6.4.1.2) [Menendez, 1999; Hügler, 2003]; malonyl-CoA reductase (E.C. 1.2.1.75 and E.C. 1.1.1.298) [Hügler, 2002; Alber, 2006; Rathnasingh, 2011]; propionyl-CoA synthase (E.C. 6.2.1.-, E.C. 4.2.1.- and E.C. 1.3.1.-) [Alber, 2002]; propionyl-CoA carboxylase (E.C. 6.4.1.3) [Menendez, 1999; Hügler, 2003]; methylmalonyl-CoA epimerase (E.C. 5.1.99.1); methylmalonyl-CoA mutase (E.C. 5.4.99.2); succinyl-CoA:(S)-malate CoA transferase (E.C. 2.8.3.-) [Friedmann, 2006]; succinate dehydrogenase (E.C. 1.3.5.1); fumarate hydratase (E.C. 4.2.1.2); (S)-malyl-CoA/ β-methylmalyl-CoA/(S)-citramalyl-CoA lyase (MMC lyase, E.C. 4.1.3.24 and E.C. 4.1.3.25) [Herter, 2002b; Friedmann, 2007]; mesaconyl-C1-CoA hydratase or β-methylmalyl-CoA dehyratase (E.C. 4.2.1.-) [Zarzycki, 2008]; mesaconyl-CoA C1-C4 CoA transferase (E.C. 2.8.3.-) [Zarzycki, 2009]; mesaconyl-C4-CoA hydratase (E.C. 4.2.1.-) [Zarcycki, 2009]. In one embodiment, the invention provides an engineered chemoautotroph comprising one or more exogenous proteins from the 3-HPA bicycle conferring to the organism the ability to produce central metabolites from inorganic carbon, wherein the organism lacks the ability to fix carbon via the 3-HPA bicycle (for example, see FIG. 6). Methylmalonyl-CoA epimerase activity has been reported in *E. coli* although no corresponding gene or gene product has been identified [Evans. 1993]. For *E. coli* ScpA to be active, vitamin B12 must be present in culture medium or produced intracellularly. For example, the one or more exogenous proteins can be selected from acetyl-CoA carboxylase, malonyl-CoA reductase, propionyl-CoA synthase, propionyl-CoA carboxylase, methylmalonyl-CoA epimerase, methylmalonyl-CoA mutase, succinyl-CoA:(S)-malate CoA transferase, succinate dehydrogenase, fumarate hydratase, (S)-malyl-CoA/β-methylmalyl-CoA/(S)-citramalyl-CoA lyase, mesaconyl-C1-CoA hydratase, mesaconyl-CoA C1-C4 CoA transferase, and mesaconyl-C4-CoA hydratase. The host organism can also express two or more, three or more, four or more, five or more, six or more, seven or more, and the like, including up to all the protein and enzymes that confer the 3-HPA pathway. For example, in the host organism *E. coli*, the exogenous enzymes comprise malonyl-CoA reductase, propionyl-CoA synthase, acetyl-CoA/propionyl-CoA carboxylase, succinyl-CoA:(S)-malate CoA transferase, and MMC lyase. As a second example, in the host organism *E. coli*, the exogenous enzymes comprise malonyl-CoA reductase, propionyl-CoA synthase, acetyl-CoA/propionyl-CoA carboxylase, succinyl-CoA:(S)-malate CoA transferase, MMC lyase, and methylmalonyl-CoA epimerase. Finally, as a third example, in the host organism *E. coli*, the exogenous enzymes comprise malonyl-CoA reductase, propionyl-CoA synthase, propionyl-CoA carboxylase, succinyl-CoA:(S)-malate CoA transferase, MMC lyase, methylmalonyl-CoA epimerase and methylmalonyl-CoA mutase. Exemplary malonyl-coA reductases include ZP_04957196, YP_001433009, ZP_01626393, ZP_01039179 and YP_001636209, and homologs thereof. SEQ ID NO:25, SEQ ID NO:26, SEQ ID NO:27, SEQ ID NO:28 and SEQ ID NO:29 represent *E. coli* codon optimized coding sequence for each of these five malonyl-CoA reductases, respectively, of the present invention. In one aspect, the invention provides nucleic acid molecules and homologs, variants and derivatives of SEQ ID NO:25, SEQ ID NO:26, SEQ ID NO:27, SEQ ID NO:28 and SEQ ID NO:29. The nucleic acid sequences can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO:25, SEQ ID NO:26, SEQ ID NO:27, SEQ ID NO:28 and SEQ ID NO:29. The present invention also provides nucleic acids each comprising or consisting of a sequence which is a codon optimized version of one of the wild-type malonyl-CoA reductase genes. In another embodiment, the invention provides nucleic acids each encoding a polypeptide having the amino acid sequence of one of Genbank accession numbers ZP_04957196, YP_001433009, ZP_01626393, ZP_01039179 and YP_001636209, or homologs thereof having 70%, 71%, 72%, 73%, 74%, 75%, 76%, 77%, 78%, 79n, 80%, 81-85%, 90-95%, 96-98%, 99%, 99.9% or even higher identity thereto. Exemplary propionyl-CoA synthases include AAL47820, and homologs thereof. SEQ ID NO:30 represents the *E. coli* codon optimized coding sequence for this propionyl-CoA synthase of the present invention. In one aspect, the invention provides nucleic acid molecule and homologs, variants and derivatives of SEQ ID NO:30. The nucleic acid sequence can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO:30. The present invention provides nucleic acids each comprising or consisting of a sequence which is a codon optimized version of the wild-type propionyl-CoA synthase gene. In another embodiment, the invention provides a nucleic acid encoding a polypeptide having the amino acid sequence of SEQ ID NO:31, or homologs thereof having 70%, 71%, 72%, 73%, 74%, 75%, 76%, 77%, 78%, 79%, 80%, 81-85%, 90-95%, 96-98%, 99%, 99.9% or even higher identity thereto. The enzyme acetyl-CoA/propionyl-CoA carboxylase is composed of three subunits: PccB, AccC and AccB. Exemplary acetyl-CoA/propionyl-CoA carboxylases include those from *Metallosphaera sedula* DSM 5348 (YP_001191457, YP_001190248, YP_001190249); Nitrosopumilus maritimus SCM1 (YP_00158606, YP_001581607, YP_001581608); *Cenarchaeum symbiosum* A (YP_876582, YP_876583, YP_876584); *Halobacterium* sp. NRC-1 (NP_280337 or NP_279647; NP_280339 or NP_280547; NP_280866), and homologs thereof. SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44 and SEQ ID NO:45 represent *E. coli* codon optimized coding sequence for each of these acetyl-CoA/propionyl-CoA carboxylase subunits, respectively, of the present invention. In one aspect, the invention provides nucleic acid molecules and homologs, variants and derivatives of SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44 and SEQ ID NO:45. The nucleic acid sequences can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44 and SEQ ID NO:45. The present invention provides nucleic acids each comprising or consisting of a sequence which is a codon optimized version of one of the wild-type acetyl-CoA/propionyl-CoA carboxylase genes. In another embodiment, the invention provides nucleic acids each encoding a polypeptide having the amino acid sequence of one of Genbank accession numbers YP_001191457, YP_001190248, YP_001190249, YP_00158606, YP_001581607, YP_001581608, YP_876582, YP_876583, YP_876584, NP_280337, NP_279647, NP_280339, NP_280547 and NP_280866, or homologs thereof having 70%, 71%, 72%, 73%, 74%, 75%, 76%, 77%, 78%, 79%, 80%, 81-85%, 90-95%, 96-98%, 99%, 99.9% or even higher identity thereto. The enzyme succinyl-CoA:malate-CoA transferase is composed of two subunits, such as SmtA and SmtB in *Chloroflexus aurantiacus*. Exemplary succinyl-CoA:malate-CoA transferase subunits include ABF14399 and ABF14400, and homologs thereof. Exemplary MMC lyases include YP_0017633817, and homologs thereof.

Figure 7:
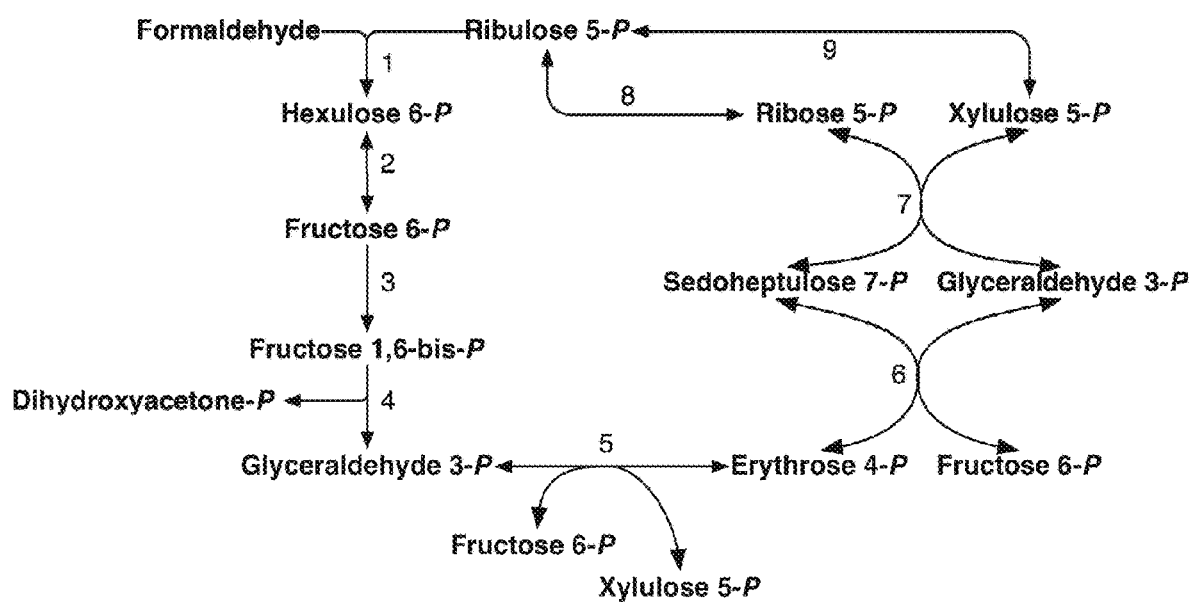
FIG. 7 depicts the metabolic reactions of the ribulose monophosphate cycle [Strom, 1974]. In metabolite names, —P denotes phosphate. Each reaction is numbered. Enzymes catalyzing each reaction are as follows: 1, hexulose-6-phosphate synthase (E.C. 4.1.2.43); 2, 6-phospho-3-hexuloisomerase (E.C. 5.3.1.27); 3, phosphofructokinase (E.C. 2.7.1.11); 4, fructose bisphosphate aldolase (E.C. 4.1.2.13); 5, transketolase (E.C. 2.2.1.1); 6, transaldolase (E.C. 2.2.1.2); 7, transketolase (E.C. 2.2.1.1); 8, ribose 5-phosphate isomerase (E.C. 5.3.1.6); 9, ribulose-5-phosphate-3-epimerase (E.C. 5.1.3.1).
Figure 8:
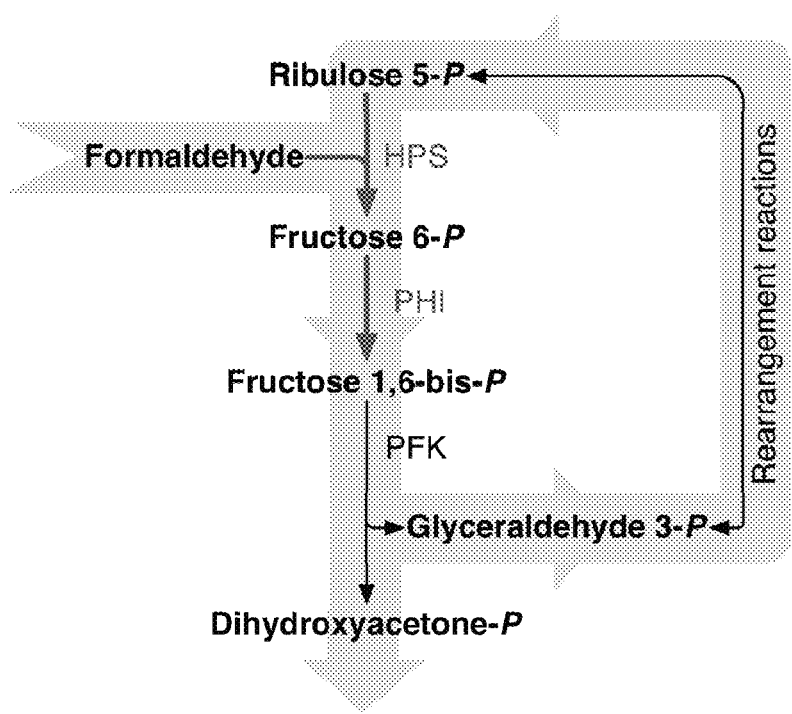
FIG. 8 depicts example metabolic reactions and enzymes needed to engineer a carbon fixation pathway derived from the ribulose monophosphate (RuMP) cycle into the heterotroph *Escherichia coli*. Reactions in black occur in the wildtype host cell *E. coli*. Reactions in dark gray must be added to complete the RuMP cycle-derived carbon fixation cycle in *E. coli*. The carbon input to the pathway is formaldehyde and the carbon output of the pathway is dihydroxyacetone-phosphate. The desired net flow of carbon is indicated by the wide, light gray arrow. For simplicity, a series of rearrangement reactions that regenerate ribulose-5-phosphate and all occur natively in *E. coli* are denoted by a single arrow. Metabolites are shown in bold with —P denoting phosphate. Enzyme abbreviations are as follows: HPS, hexulose-6-phosphate synthase; PHI, 6-phospho-3-hexuloisomerase; PFK, phosphofructokinase.

In certain embodiments, the invention provides an engineered chemoautotroph with a carbon fixation pathway derived from the ribulose monophosphate (RuMP) cycle. The RuMP cycle is well known in the art and consists of 9 reactions (FIG. 7) [Strom, 1974]. Reactions 1 and 2 (FIG. 7) are catalyzed by two separate enzymes in some organisms and by a bifunctional fusion enzyme in other organisms [Yurimoto, 2009]. The reactions in the RuMP cycle are catalyzed by the following enzymes: hexulose-6-phosphate synthase (HPS, E.C. 4.1.2.43) [Kemp, 1972; Kemp, 1974]; 6-phospho-3-hexuloisomerase (PHI, E.C. 5.3.1.27) [Strom, 1974; Ferenci, 1974]; phosphofructokinase (PFK, E.C. 2.7.1.11); fructose bisphosphate aldolase (FBA, E.C. 4.1.2.13); transketolase (TK, E.C. 2.2.1.1); transaldolase (TA, E.C. 2.2.1.2); 7, transketolase (TK, E.C. 2.2.1.1); ribose 5-phosphate isomerase (RPI, E.C. 5.3.1.6); ribulose-5-phosphate-3-epimerase (RPE, E.C. 5.1.3.1). In one embodiment, the invention provides an engineered chemoautotroph comprising one or more exogenous proteins from the RuMP cycle conferring to the organism the ability to produce central metabolites from inorganic carbon, wherein the organism lacks the ability to fix carbon via the RuMP cycle (for example, see FIG. 8). For example, the one or more exogenous proteins can be selected from hexulose-6-phosphate synthase, 6-phospho-3-hexuloisomerase, hexulose-6-phosphate synthase/6-phospho-3-hexuloisomerase fusion enzyme [Orita, 2005; Orita, 2006; Orita, 2007], phosphofructokinase, fructose bisphosphate aldolase, transketolase, transaldolase, transketolase, ribose 5-phosphate isomerase, and ribulose-5-phosphate-3-epimerase. The host organism can also express one or more, two or more, three or more, and the like, including up to all the protein and enzymes that confer the RuMP pathway. For example, in the host organism *E. coli*, the exogenous enzymes comprise hexulose-6-phosphate synthase and 6-phospho-3-hexuloisomerase. As a second example, in the host organism *E. coli*, the exogenous enzymes comprise the bifunctional fusion enzyme hexulose-6-phosphate synthase/6-phospho-3-hexuloisomerase. Exemplary HPS enzymes include YP_115138, YP_115430 and BAA90546, and homologs theroof. SEQ ID NO:46 and SEQ ID NO:47 represent *E. coli* codon optimized coding sequence for HPS enzymes YP_115138 and YP_115430, respectively, of the present invention. In one aspect, the invention provides nucleic acid molecules and homologs, variants and derivatives of SEQ ID NO:46 and SEQ ID NO:47. The nucleic acid sequences can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO:46 and SEQ ID NO:47. The present invention provides nucleic acids each comprising or consisting of a sequence which is a codon optimized version of one of the wild-type HPS genes. In another embodiment, the invention provides nucleic acids each encoding a polypeptide having the amino acid sequence of one of YP_115138 and YP_115430, or homologs thereof having 70%, 71%, 72%, 73%, 74%, 75%, 76%, 77%, 78%, 79%, 80%, 81-85%, 90-95%, 96-98%, 99%, 99.9% or even higher identity thereto. Exemplary PHI enzymes include YP_115431 and BAA90545, and homologs thereof. SEQ ID NO:48 represent *E. coli* codon optimized coding sequence for PHI enzyme YP_115431 of the present invention. In one aspect, the invention provides nucleic acid molecule and homologs, variants and derivatives of SEQ ID NO:48. The nucleic acid sequence can have preferably 78%, 79%, 80%, 81-85%, 90-95%, 96-98%, 99%, 99.9% or even higher identity to SEQ ID NO:48. The present invention provides nucleic acids each comprising or consisting of a sequence which is a codon optimized version of one of the wild-type PHI genes. In another embodiment, the invention provides nucleic acids each encoding a polypeptide having the amino acid sequence of YP_115431, or homologs thereof having 70%, 71%, 72%, 73%, 74%, 75%, 76%, 77%, 78%, 79%, 80%, 81-85%, 90-95%, 96-98%, 99%, 99.9% or even higher identity thereto. Exemplary HPS-PHI enzymes include NP_143767 and YP_182888, and homologs thereof. SEQ ID NO:49 represents an *E. coli* codon optimized coding sequence for a fusion of the *Mycobacterium gastri* MB19 HPS enzyme (BAA90546) and PHI enzyme (BAA90545) of the present invention. In one aspect, the invention provides nucleic acid molecule and homologs, variants and derivatives of SEQ ID NO:49. The nucleic acid sequence can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO:49. The present invention provides nucleic acids each comprising or consisting of a sequence which is a codon optimized version of one of the wild-type HPS and one of the wild-type PHI genes. In another embodiment, the invention provides nucleic acids each encoding a polypeptide having the amino acid sequence of SEQ ID NO:50, or homologs thereof having 70%, 71%, 72%, 73%, 74%, 75%, 76%, 77%, 78%, 79%, 80%, 81-85%, 90-95%, 96-98%, 99%, 99.9% or even higher identity thereto.

In certain embodiments, the invention provides an engineered chemoautotroph comprising a carbon fixation pathway derived from the RuMP cycle, as described above, and in which formaldehyde is produced from formate. The conversion of formate to formyl-coenzyme A (formyl-CoA) can be catalyzed by the enzyme acetyl-CoA synthetase (ACS) operating on a non-cognate substrate [see, e.g., WO 2012/037413]. The conversion of formyl-CoA to formaldehyde can be catalyzed by the enzyme (acylating) acetaldehyde dehydrogenase (ADH), operating on a non-cognate substrate. Exemplary ACS enzymes include AAC77039, and homologs thereof. SEQ ID NO:61 represents recoded coding sequence for ACS enzyme AAC77039 of the present invention. In one aspect, the invention provides nucleic acid molecules and homologs, variants and derivatives of SEQ ID NO:61. The nucleic acid sequences can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO:61. The present invention provides nucleic acids each comprising or consisting of a sequence which is a codon optimized version of one of the wild-type ACS genes. In another embodiment, the invention provides nucleic acids each encoding a polypeptide having the amino acid sequence of AAC77039, or homologs thereof having 70%, 71%, 72%, 73%, 74%, 75%, 76%, 77%, 78%, 79%, 80%, 81-85%, 90-95%, 96-98%, 99%, 99.9% or even higher identity thereto. Exemplary ADH enzymes include NP_464704, NP_415757, AAD31841, CAA43226, and homologs thereof. SEQ ID NO:62 represents an *E. coli* codon optimized coding sequence for ADH enzyme AAC77039 of the present invention. In one aspect, the invention provides nucleic acid molecules and homologs, variants and derivatives of SEQ ID NO:62. The nucleic acid sequences can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO:62. The present invention provides nucleic acids each comprising or consisting of a sequence which is a codon optimized version of one of the wild-type ADH genes. In another embodiment, the invention provides nucleic acids each encoding a polypeptide having the amino acid sequence of NP_464704, NP_415757, AAD31841 or CAA43226, or homologs thereof having 70%, 71%, 72%, 73%, 74%, 75%, 76%, 77%, 78%, 79%, 80%, 81-85%, 90-95%, 96-98%, 99%, 99.9% or even higher identity thereto.

Figure 9:
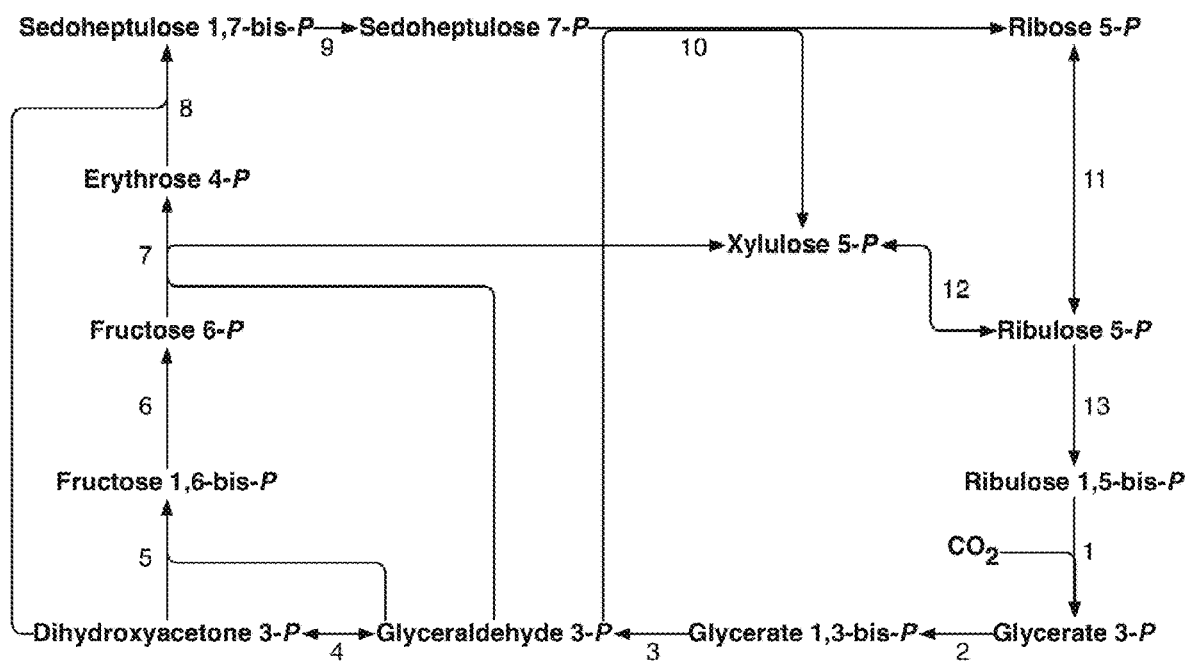
FIG. 9 depicts the metabolic reactions of the Calvin-Benson-Bassham cycle or the reductive pentose phosphate (RPP) cycle [Bassham, 1954]. In metabolite names, —P denotes phosphate. Each reaction is numbered. Enzymes catalyzing each reaction are as follows: 1, ribulose bisphosphate carboxylase (E.C. 4.1.1.39); 2, phosphoglycerate kinase (E.C. 2.7.2.3); 3, glyceraldehyde-3P dehydrogenase (phosphorylating) (E.C. 1.2.1.12 or E.C. 1.2.1.13); 4, triose-phosphate isomerase (E.C. 5.3.1.1); 5, fructose-bisphosphate aldolase (E.C. 4.1.2.13); 6, fructose-bisphosphatase (E.C. 3.1.3.11); 7, transketolase (E.C. 2.2.1.1); 8, sedoheptulose-1,7-bisphosphate aldolase (E.C. 4.1.2.-); 9, sedoheptulose bisphosphatase (E.C. 3.1.3.37); 10, transketolase (E.C. 2.2.1.1); 11, ribose-5-phosphate isomerase (E.C. 5.3.1.6); 12, ribulose-5-phosphate-3-epimerase (E.C. 5.1.3.1); 13, phosphoribulokinase (E.C. 2.7.1.19).
Figure 10:
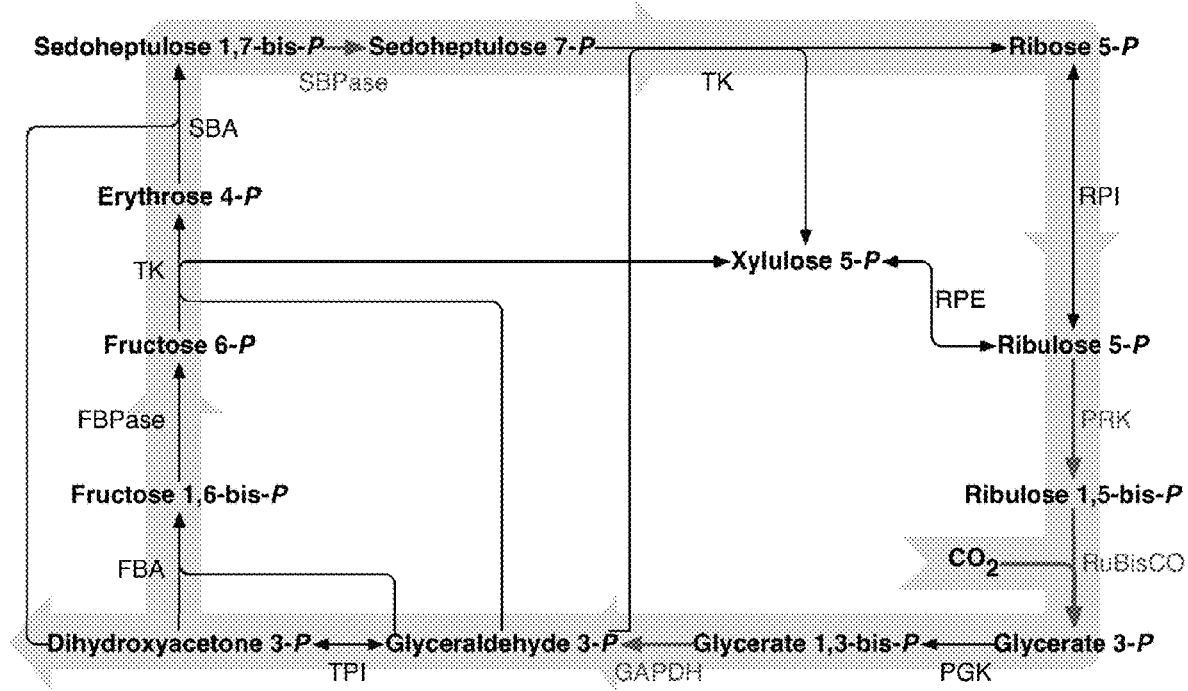
FIG. 10 depicts example metabolic reactions and enzymes needed to engineer a carbon fixation pathway derived from the Calvin-Benson-Bassham cycle or the reductive pentose phosphate (RPP) cycle into the heterotroph *Escherichia coli*. Reactions in black occur in the wildtype host cell *E. coli*. Reactions in dark gray must be added to complete the RPP cycle-derived carbon fixation cycle in *E. coli*. The carbon input to the pathway is carbon dioxide and the carbon output of the pathway is dihydroxyacetone-phosphate. The desired net flow of carbon is indicated by the wide, light gray arrow. Metabolites are shown in bold with —P denoting phosphate. Enzyme abbreviations are as follows: RuBisCO, ribulose bisphosphate carboxylase; PGK, phosphoglycerate kinase; GAPDH, NADPH-dependent glyceraldehyde-3P dehydrogenase (phosphorylating); TPI, triose-phosphate isomerase; FBA, fructose-bisphosphate aldolase; FBPase, fructose-bisphosphatase; TK, transketolase; SBA, sedoheptulose-1,7-bisphosphate aldolase; SBPase, sedoheptulose bisphosphatase; RPI, ribose-5-phosphate isomerase; RPE, ribulose-5-phosphate-3-epimerase; PRK, phosphoribulokinase.

In certain embodiments, the invention provides an engineered chemoautotroph whose carbon fixation pathway is the Calvin-Benson-Bassham cycle or reductive pentose phosphate (RPP) cycle. The Calvin cycle is well known in the art and consists of 13 reactions (FIG. 9) [Bassham, 1954]. The reactions in the RPP cycle are catalyzed by the following enzymes: ribulose bisphosphate carboxylase (RuBisCO, E.C. 4.1.1.39); phosphoglycerate kinase (PGK, E.C. 2.7.2.3); glyceraldehyde-3P dehydrogenase (phosphorylating) (GAPDH, E.C. 1.2.1.12 or E.C. 1.2.1.13); triosephosphate isomerase (TPI, E.C. 5.3.1.1); fructose-bisphosphate aldolase (FBA, E.C. 4.1.2.13); fructose-bisphosphatase (FBPase, E.C. 3.1.3.11); transketolase (TK, E.C. 2.2.1.1); sedoheptulose-1,7-bisphosphate aldolase (SBA, E.C. 4.1.2.-); sedoheptulose bisphosphatase (SBPase, E.C. 3.1.3.37); transketolase (TK, E.C. 2.2.1.1); ribose-5-phosphate isomerase (RPI, E.C. 5.3.1.6); ribulose-5-phosphate-3-epimerase (RPE, E.C. 5.1.3.1); phosphoribulokinase (PRK, E.C. 2.7.1.19). In one embodiment, the invention provides an engineered chemoautotroph comprising one or more exogenous proteins from the RPP cycle conferring to the organism the ability to produce central metabolites from inorganic carbon, wherein the organism lacks the ability to fix carbon via the RPP cycle (for example, see FIG. 10). For example, the one or more exogenous proteins can be selected from ribulose bisphosphate carboxylase, phosphoglycerate kinase, glyceraldehyde-3P dehydrogenase (phosphorylating), triose-phosphate isomerase, fructose-bisphosphate aldolase, fructose-bisphosphatase, transketolase, sedoheptulose-1,7-bisphosphate aldolase, sedoheptulose bisphosphatase, transketolase, ribose-5-phosphate isomerase, ribulose-5-phosphate-3-epimerase and phosphoribulokinase. The host organism can also express two or more, three or more, four or more, and the like, including up to all the protein and enzymes that confer the RPP pathway. For example, in the host organism *E. coli*, the exogenous enzymes comprise ribulose bisphosphate carboxylase, sedoheptulose bisphosphatase and phosphoribulokinase. As a second example, in the host organism *E. coli*, the exogenous enzymes comprise ribulose bisphosphate carboxylase, NADPH-dependent glyceraldehyde-3P dehydrogenase, sedoheptulose bisphosphatase and phosphoribulokinase. Ribulose bisphosphate carboxylase has two distinct forms: Form I and Form II [Portis, 2007]. Form I is composed of four large subunit dimers and eight small subunits ($L_8S_8$) and has been expressed previously in heterologous hosts, such as *Escherichia coli* [Gatenby, 1985: Tabita, 1985; Gutteridge, 1986]. Exemplary RuBisCO subunits include YP_170840 and YP_170839, and homologs thereof. Extensive work has been done to attempt to optimize the function of RuBisCO [Parikh, 2006; Greene, 2007], and thus engineered RuBisCO enzymes may also be used in the present invention. Exemplary NADPH-dependent GAPDH enzymes include YP_400759, and homologs thereof. SEQ ID NO:51 represents an *E. coli* codon optimized coding sequence for this GAPDH of the present invention. In one aspect, the invention provides nucleic acid molecule and homologs, variants and derivatives of SEQ ID NO:51. The nucleic acid sequence can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO:51. The present invention provides nucleic acids each comprising or consisting of a sequence which is a codon optimized version of one of the wild-type GAPDH genes. In another embodiment, the invention provides nucleic acids each encoding a polypeptide having the amino acid sequence of YP_400759, or homologs thereof having 70%, 71%, 72%, 73%, 74%, 75%, 76%, 77%, 78%, 79%, 80%, 81-85%, 90-95%, 96-98%, 99%, 99.9% or even higher identity thereto. Exemplary SBPase enzymes include YP_399524, and homologs thereof. SEQ ID NO:52 represents an E. coli codon optimized coding sequence for this SBPase of the present invention. In one aspect, the invention provides nucleic acid molecule and homologs, variants and derivatives of SEQ ID NO:52. The nucleic acid sequence can have preferably 70%, 71%, 72%, 73%, 74%, 75%, 76%, 77%, 78%, 79%, 80%, 81-85%, 90-95%, 96-98%, 990%, 99.9% or even higher identity to SEQ ID NO:52. The present invention provides nucleic acids each comprising or consisting of a sequence which is a codon optimized version of one of the wild-type SBPase genes. In another embodiment, the invention provides nucleic acids each encoding a polypeptide having the amino acid sequence of YP_399524, or homologs thereof having 70%, 71%, 72%, 73%, 74%, 75%, 76%, 77%, 78%, 79%, 80%, 81-85%, 90-95%, 96-98%, 99%, 99.9% or even higher identity thereto. Exemplary PRK enzymes include YP_399994, and homologs thereof. SEQ ID NO:53 represents an E. coli codon optimized coding sequence for this PRK of the present invention. In one aspect, the invention provides nucleic acid molecule and homologs, variants and derivatives of SEQ ID NO:53. The nucleic acid sequence can have preferably 70%, 71%, 72%, 73%, 74%, 75%, 76%, 77%, 78%, 79/, 80%, 81-85%, 90-95%, 96-98%, 99%, 99.9% or even higher identity to SEQ ID NO:53. The present invention provides nucleic acids each comprising or consisting of a sequence which is a codon optimized version of one of the wild-type PRK genes. In another embodiment, the invention provides nucleic acids each encoding a polypeptide having the amino acid sequence of YP_399994, or homologs thereof having 70%, 71%, 72%, 73%, 74%, 75%, 76%, 77%, 78%, 79%, 80%, 81-85%, 90-95%, 96-98%, 99%, 99.9% or even higher identity thereto.

Production of Central Metabolites as the Carbon-Based Products of Interest

Figure 11:
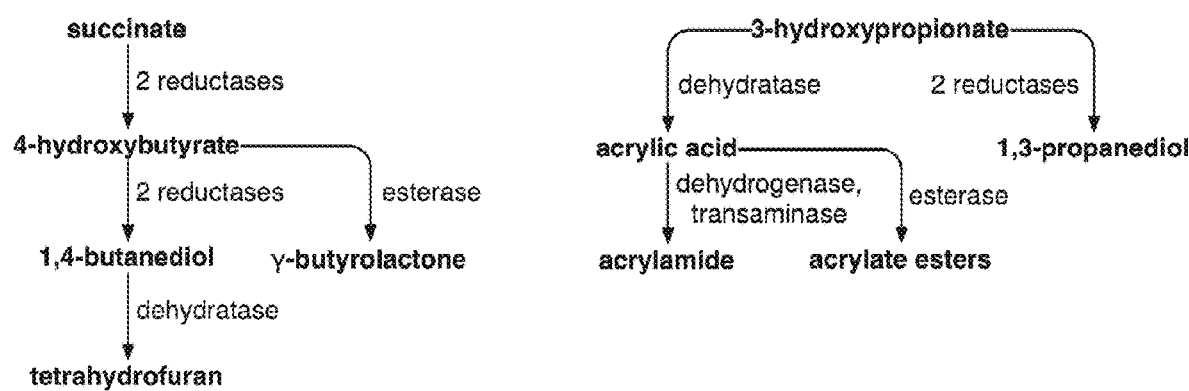
FIG. 11 provides a schematic to convert succinate or 3-hydroxypropionate to various chemicals.

In certain embodiments, the engineered chemoautotroph of the present invention produces the central metabolites, including but not limited to citrate, malate, succinate, fumarate, dihydroxyacetone, dihydroxyacetone phosphate, 3-hydroxypropionate, pyruvate, as the carbon-based products of interest. The engineered chemoautotroph produces central metabolites as an intermediate or product of the carbon fixation pathway or as a intermediate or product of host metabolism. In such cases, one or more transporters may be expressed in the engineered chemoautotroph to export the central metabolite from the cell. For example, one or more members of a family of enzymes known as C4-dicarboxylate carriers serve to export succinate from cells into the media [Janausch, 2002; Kim. 2007]. These central metabolites can be converted to other products (FIG. 11).

In some embodiments, the engineered chemoautotroph may interconvert between different central metabolites to produce alternate carbon-based products of interest. In one embodiment, the engineered chemoautotroph produces aspartate by expressing one or more aspartate aminotransferase (E.C. 2.6.1.1), such as Escherichia coli AspC, to convert oxaloacetate and L-glutamate to L-aspartate and 2-oxoglutarate.

In another embodiment, the engineered chemoautotroph produces dihydroxyacetone phosphate by expressing one or more dihydroxyacetone kinases (E.C. 2.7.1.29), such as C. freundii DhaK, to convert dihydroxyacetone and ATP to dihydroxyacetone phosphate.

In another embodiment, the engineered chemoautotroph produces serine as the carbon-based product of interest. The metabolic reactions necessary for serine biosynthesis include: phosphoglycerate dehydrogenase (E.C. 1.1.1.95), phosphoserine transaminase (E.C. 2.6.1.52), phosphoserine phosphatase (E.C. 3.1.3.3). Phosphoglycerate dehydrogenase, such as E. coli SerA, converts 3-phospho-D-glycerate and $NAD^+$ to 3-phosphonooxypyruvate and NADH. Phosphoserine transaminase, such as E. coli SerC, interconverts between 3-phosphonooxypyruvate+L-glutamate and O-phospho-L-serine+2-oxoglutarate. Phosphoserine phosphatase, such as E. coli SerB, converts O-phospho-L-serine to L-serine.

Figure 12:
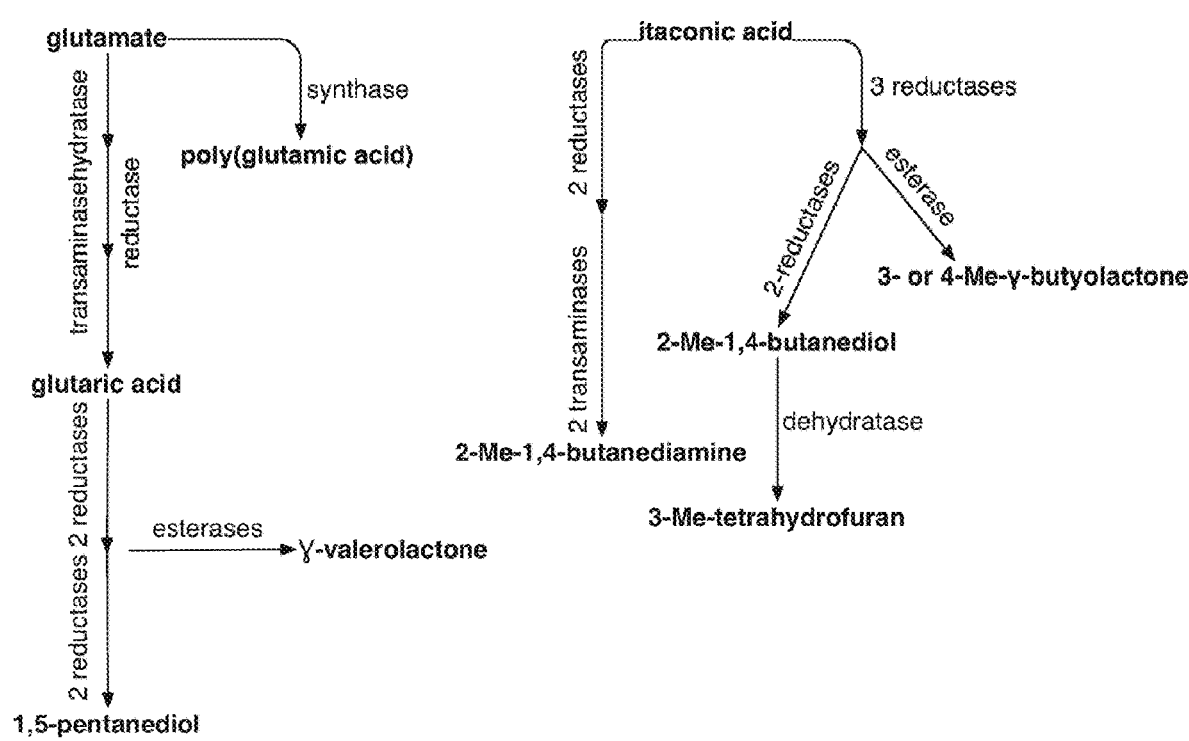
FIG. 12 provides a schematic of glutamate or itaconic acid conversion to various chemicals.

In another embodiment, the engineered chemoautotroph produces glutamate as the carbon-based product of interest. The metabolic reactions necessary for glutamate biosynthesis include glutamate dehydrogenase (E.C. 1.4.1.4; e.g., E. coli (GdhA) which converts α-ketoglutarate, $NH_3$ and NADPH to glutamate. Glutamate can subsequently be converted to various other carbon-based products of interest, e.g., according to the scheme presented in FIG. 12.

In another embodiment, the engineered chemoautotroph produces itaconate as the carbon-based product of interest. The metabolic reactions necessary for itaconate biosynthesis include aconitate decarboxylase (E.C. 4.1.1.6; such as that from A. terreus) which converts cis-aconitate to itaconate and $CO_2$. Itaconate can subsequently be converted to various other carbon-based products of interest, e.g., according to the scheme presented in FIG. 12.

Production of Sugars as the Carbon-Based Products of Interest

Industrial production of chemical products from biological organisms is often accomplished using a sugar source, such as glucose or fructose, as the feedstock. Hence, in certain embodiments, the engineered chemoautotroph of the present invention produces sugars including glucose and fructose or sugar phosphates including triose phosphates (such as 3-phosphoglyceraldehyde and dihydroxyacetone-phosphate) as the carbon-based products of interest. Sugars and sugar phosphates may also be interconverted. For example, glucose-6-phosphate isomrase (E.C. 5.3.1.9; e.g., E. coli Pgi) may interconvert between D-fructose 6-phosphate and D-glucose-6-phosphate. Phosphoglucomutase (E.C. 5.4.2.2; e.g., E. coli Pgm) converts D-α-glucose-6-P to D-α-glucose-1-P. Glucose-1-phosphatase (E.C. 3.1.3.10; e.g., E. coli Agp) converts D-α-glucose-1-P to D-α-glucose. Aldose 1-epimerase (E.C. 5.1.3.3; e.g., E. coli GalM) D-β-glucose to D-α-glucose. The sugars or sugar phosphates may optionally be exported from the engineered chemoautotroph into the culture medium.

Sugar phosphates may be converted to their corresponding sugars via dephosphorylation that occurs either intra- or extracellularly. For example, phosphatases such as a glucose-6-phosphatase (E.C. 3.1.3.9) or glucose-1-phosphatase (E.C. 3.1.3.10) can be introduced into the engineered chemoautotroph of the present invention. Exemplary phosphatases include Homo sapiens glucose-6-phosphatase G6PC (P35575), Escherichia coli glucose-1-phosphatase Agp (P19926). *E. cloacae* glucose-1-phosphatase AgpE (Q6EV19) and *Escherichia coli* acid phosphatase YihX (P0A8Y3).

Sugar phosphates can be exported from the engineered chemoautotroph into the culture media via transporters. Transporters for sugar phosphates generally act as antiporters with inorganic phosphate. An exemplary triose phosphate transporter includes *A. thaliana* triose-phosphate transporter APE2 (Genbank accession AT5G46110.4). Exemplary glucose-6-phosphate transporters include *E. coli* sugar phosphate transporter UhpT (NP_418122.1). *A. thaliana* glucose-6-phosphate transporter GPT (AT5G54800.1). *A. thaliana* glucose-6-phosphate transporter GPT2, or homologs thereof. Dephosphorylation of glucose-b-phosphate can also be coupled to glucose transport, such as Genbank accession numbers AAA16222, AAD19898, 043826.

Sugars can be diffusively effluxed from the engineered chemoautotroph into the culture media via permeases. Exemplary permeases include *H. sapiens* glucose transporter GLUT-1, -3, or -7 (P11166, P11169, Q6PXP3), *S. cerevisiae* hexose transporter HXT-1, -4, or -6 (P32465, P32467, P39003), *Z. mobilis* glucose uniporter Glf (P21906), *Synechocytis* sp. 1148 glucose/fructose:$H^+$ symporter GlcP (T.C. 2.A.1.1.32; P15729) [Zhang, 1989], *Streptomyces lividans* major glucose (or 2-deoxyglucose) uptake transporter GlcP (T.C. 2.A.1.1.35; Q7BEC4) [van Wezel, 2005], *Plasmodium falciparum* hexose (glucose and fructose) transporter PfHT1 (T.C. 2.A.1.1.24; 097467), or homologs thereof. Alternatively, to enable active efflux of sugars from the engineered chemoautotroph, one or more active transporters may be introduced to the cell. Exemplary transporters include mouse glucose transporter GLUT 1 (AAB20846) or homologs thereof.

Preferably, to prevent buildup of other storage polymers from sugars or sugar phosphates, the engineered chemoautotrophs of the present invention are attenuated in their ability to build other storage polymers such as glycogen, starch, sucrose, and cellulose using one or more of the following enzymes: cellulose synthase (UDP forming) (E.C. 2.4.1.12), glycogen synthase e.g. glgA1, glgA2 (E.C. 2.4.1.21), sucrose phosphate synthase (E.C. 2.4.1.14), sucrose phosphorylase (E.C. 3.1.3.24), alpha-1,4-glucan lyase (E.C. 4.2.2.13), glycogen synthase (E.C. 2.4.1.11), 1,4-alpha-glucan branching enzyme (E.C. 2.4.1.18).

Figure 13:
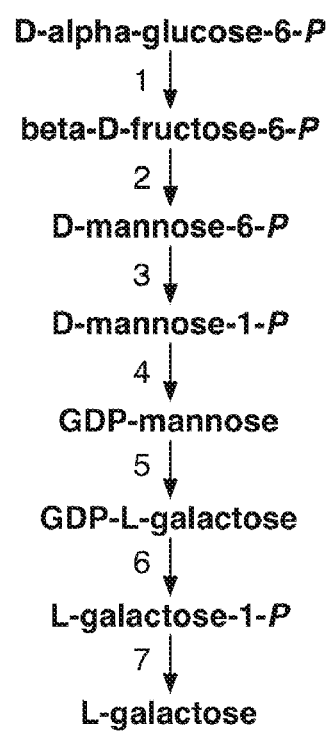
FIG. 13 depicts the metabolic reactions of a galactose biosynthetic pathway. In metabolite names, —P denotes phosphate. Each reaction is numbered. Enzymes catalyzing each reaction are as follows: 1, alpha-D-glucose-6-phosphate ketol-isomerase (E.C. 5.3.1.9); 2, D-mannose-6-phosphate ketol-isomerase (E.C. 5.3.1.8); 3, D-mannose 6-phosphate 1,6-phosphomutase (E.C. 5.4.2.8); 4, mannose-1-phosphate guanylyltransferase (E.C. 2.7.7.22); 5, GDP-mannose 3,5-epimerase (E.C. 5.1.3.18); 6, galactose-1-phosphate guanylyltransferase (E.C. 2.7.n.n); 7, L-galactose 1-phosphate phosphatase (E.C. 3.1.3.n).

The invention also provides engineered chemoautotrophs that produce other sugars such as sucrose, xylose, lactose, maltose, pentose, rhamnose, galactose and arabinose according to the same principles. A pathway for galactose biosynthesis is shown (FIG. 13). The metabolic reactions in the galactose biosynthetic pathway are catalyzed by the following enzymes: alpha-D-glucose-6-phosphate ketol-isomerase (E.C. 5.3.1.9; e.g., *Arabidopsis thaliana* PGI1), D-mannose-6-phosphate ketol-isomerase (E.C. 5.3.1.8 e.g., *Arabidopsis thaliana* DIN9), D-mannose 6-phosphate 1,6-phosphomutase (E.C. 5.4.2.8; e.g., *Arabidopsis thaliana* ATPMM), mannose-1-phosphate guanylyltransferase (E.C. 2.7.7.22; e.g., *Arabidopsis thaliana* CYT), GDP-mannose 3,5-epimerase (E.C. 5.1.3.18; e.g., *Arabidopsis thaliana* GME), galactose-1-phosphate guanylyltransferase (E.C. 2.7.n.n; e.g., *Arabidopsis thaliana* VTC2), L-galactose 1-phosphate phosphatase (E.C. 3.1.3.n; e.g., *Arabidopis thaliana* VTC4). In one embodiment, the invention provides an engineered chemoautotroph comprising one or more exogenous proteins from the galactose biosynthetic pathway.

The invention also provides engineered chemoautotrophs that produce sugar alcohols, such as sorbitol, as the carbon-based product of interest. In certain embodiments, the engineered chemoautotroph produces D-sorbitol from D-α-glucose and NADPH via the enzyme polyol dehydrogenase (E.C. 1.1.1.21; e.g., *Saccharomyces ceievisiae* GRE3).

The invention also provides engineered chemoautotrophs that produce sugar derivatives, such as ascorbate, as the carbon-based product of interest. In certain embodiments, the engineered chemoautotroph produces ascorbate from galactose via the enzymes L-galactose dehydrogenase (E.C. 1.1.1.122; e.g., *Arabidopsis thaliana* At4G33670) and L-galactonolactone oxidase (E.C. 1.3.3.12; e.g., *Saccharomyes cerevisiae* ATGLDH). Optionally, a catalase (E.C. 1.11.1.6; e.g., *E. coli* KatE) may be included to convert the waste produce hydrogen peroxide to molecular oxygen.

The fermentation products according to the above aspect of the invention are sugars, which are exported into the media as a result of carbon fixation during chemoautotrophy. The sugars can also be reabsorbed later and fermented, directly separated, or utilized by a co-cultured organism. This approach has several advantages. First, the total amount of sugars the cell can handle is not limited by maximum intracellular concentrations because the end-product is exported to the media. Second, by removing the sugars from the cell, the equilibria of carbon fixation reactions are pushed towards creating more sugar. Third, during chemoautotrophy, there is no need to push carbon flow towards glycolysis. Fourth, the sugars are potentially less toxic than the fermentation products that would be directly produced.

Chemoautotrophic fixation of carbon dioxide may be followed by flux of carbon compounds to the creation and maintenance of biomass and to the storage of retrievable carbon in the form of glycogen, cellulose and/or sucrose. Glycogen is a polymer of glucose composed of linear alpha 1,4-linkages and branched alpha 1,6-linkages. The polymer is insoluble at degree of polymerization (DP) greater than about 60,000 and forms intracellular granules. Glycogen in synthesized in vivo via a pathway originating from glucose 1-phosphate. Its hydrolysis can proceed through phosphorylation to glucose phosphates; via the internal cleavage of polymer to maltodextrins; via the successive exo-cleavage to maltose; or via the concerted hydrolysis of polymer and maltodextrins to maltose and glucose. Hence, an alternative biosynthetic route to glucose and/or maltose is via the hydrolysis of glycogen which can optionally be exported from the cell as described above. There are a number of potential enzyme candidates for glycogen hydrolysis (Table 1).

In addition to the above, another mechanism is described to produce glucose biosynthetically. In certain embodiments, the present invention provides for cloned genes for glycogen hydrolyzing enzymes to hydrolyze glycogen to glucose and/or maltose and transport maltose and glucose from the cell. Preferred enzymes are set forth below in Table 1. Glucose is transported from the engineered chemoautotroph by a glucose/hexose transporter. This alternative allows the cell to accumulate glycogen naturally but adds enzyme activities to continuously return it to maltose or glucose units that can be collected as a carbon-based product.

TABLE 1

Enzymes for hydrolysis of glycogen

| Enzyme | E.C. number | Function |
|---|---|---|
| α-amylase | 3.2.1.1 | endohydrolysis of 1,4-α-D-glucosidic linkages in polysaccharides |
| β-amylase | 3.2.1.2 | hydrolysis of 1,4-α-D-glucosidic linkages in polysaccharides so as to remove successive maltose units from the non-reducing ends of the chains |
| γ-amylase | 3.2.1.3 | hydrolysis of terminal 1,4-linked α-D-glucose residues successively from non-reducing ends of the chains with release of β-D-glucose |
| glucoamylase | 3.2.1.3 | hydrolysis of terminal 1,4-linked α-D-glucose residues successively from non-reducing ends of the chains with release of β-D-glucose |
| isoamylase | 3.2.1.68 | hydrolysis of (1->6)-α-D-glucosidic branch linkages in glycogen, amylopectin and their beta-limit dextrins |
| pullulanase | 3.2.1.41 | hydrolysis of (1->6)-α-D-glucosidic linkages in pullulan [a linear polymer of α-(1->6)-linked maltotriose units] and in amylopectin and glycogen, and the α- and β-limit dextrins of amylopectin and glycogen |
| amylomaltase | 2.4.1.25 | transfers a segment of a 1,4-α-D-glucan to a new position in an acceptor, which may be glucose or a 1,4-α-D-glucan (part of yeast debranching system) |
| amylo-α-1,6-glucosidase | 3.2.1.33 | debranching enzyme; hydrolysis of (1->6)-α-D-glucosidic branch linkages in glycogen phosphorylase limit dextrin |
| phosphorylase kinase | 2.7.11.19 | 2 ATP + phosphorylase b = 2 ADP + phosphorylase a |
| phosphorylase | 2.4.1.1 | $(1,4\text{-}\alpha\text{-D-glucosyl})_n$ + phosphate = $(1,4\text{-}\alpha\text{-D-glucosyl})_{n-1}$ + α-D-glucose-1-phosphate |

Production of Fermentative Products as the Carbon-Based Products of Interest

Figure 14:
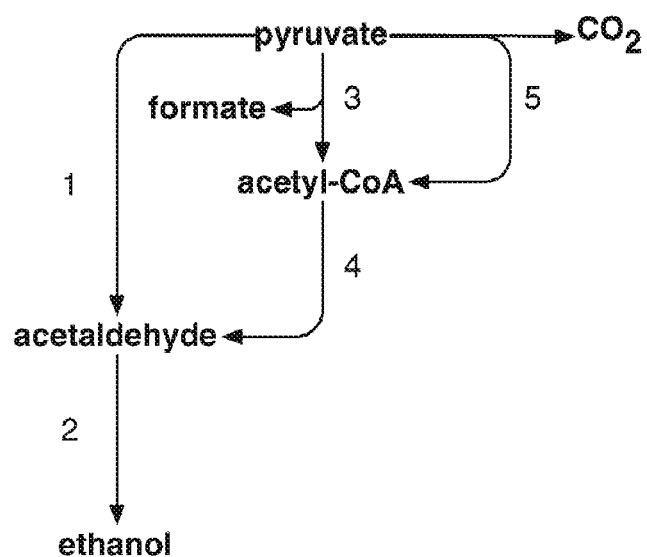
FIG. 14 depicts different fermentation pathways from pyruvate to ethanol. Each reaction is numbered. Enzymes catalyzing each reaction are as follows: 1, pyruvate decarboxylase (E.C. 4.1.1.1); 2, alcohol dehydrogenase (E.C. 1.1.1.1); 3, pyruvate-formate lyase (E.C. 2.3.1.54); 4, acetaldehyde dehydrogenase (E.C. 1.2.1.10); 5, pyruvate synthase (E.C. 1.2.7.1).

In certain embodiments, the engineered chemoautotroph of the present invention produces alcohols such as ethanol, propanol, isopropanol, butanol and fatty alcohols as the carbon-based products of interest. In some embodiments, the engineered chemoautotroph of the present invention is engineered to produce ethanol via pyruvate fermentation. Pyruvate fermentation to ethanol is well know to those in the art and there are several pathways including the pyruvate decarboxylase pathway, the pyruvate synthase pathway and the pyruvate formate-lyase pathway (FIG. 14). The reactions in the pyruvate decarboxylase pathway are catalyzed by the following enzymes: pyruvate decarboxylase (E.C. 4.1.1.1) and alcohol dehydrogenase (E.C. 1.1.1.1 or E.C. 1.1.1.2). The reactions in the pyruvate synthase pathway are catalyzed by the following enzymes: pyruvate synthase (E.C. 1.2.7.1), acetaldehyde dehydrogenase (E.C. 1.2.1.10 or E.C. 1.2.1.5), and alcohol dehydrogenase (E.C. 1.1.1.1 or E.C. 1.1.1.2). The reactions in the pyruvate formate-lyase pathway are catalyzed by the following enzymes: pyruvate formate-lyase (E.C. 2.3.1.54), acetaldehyde dehydrogenase (E.C. 1.2.1.10 or E.C. 1.2.1.5), and alcohol dehydrogenase (E.C. 1.1.1.1 or E.C. 1.1.1.2).

In some embodiments, the engineered chemoautotroph of the present invention is engineered to produce lactate via pyruvate fermentation. Lactate dehydrogenase (E.C. 1.1.1.28) converts NADH and pyruvate to D-lactate. Exemplary enzymes include E. coli ldhA.

Currently, fermentative products such as ethanol, butanol, lactic acid, formate, acetate produced in biological organisms employ a NADH-dependent processes. However, depending on the energy conversion pathways added to the engineered chemoautotroph, the cell may produce NADPH or reduced ferredoxin as the reducing cofactor. NADPH is used mostly for biosynthetic operations in biological organisms, e.g., cell for growth, division, and for building up chemical stores, such as glycogen, sucrose, and other macromolecules. Using natural or engineered enzymes that utilize NADPH or reduced ferredoxin as a source of reducing power instead of NADH would allow direct use of chemoautotrophic reducing power towards formation of normally fermentative byproducts. Accordingly, the present invention provides methods for producing fermentative products such as ethanol by expressing NADP⁺-dependent or ferredoxin-dependent enzymes. NADP⁺-dependent enzymes include alcohol dehydrogenase [NADP⁺] (E.C. 1.1.1.2) and acetaldehyde dehydrogenase [NAD(P)⁺](E.C. 1.2.1.5). Exemplary NADP⁺-dependent alcohol dehydrogenases include Moorella sp. HUC22-1 AdhA (YP_430754) [Inokuma, 2007], and homologs thereof.

In addition to providing exogenous genes or endogenous genes with novel regulation, the optimization of ethanol production in engineered chemoautotrophs preferably requires the elimination or attenuation of certain host enzyme activities. These include, but are not limited to, pyruvate oxidase (E.C. 1.2.2.2), D-lactate dehydrogenase (E.C. 1.1.1.28), acetate kinase (E.C. 2.7.2.1), phosphate acetyltransferase (E.C. 2.3.1.8), citrate synthase (E.C. 2.3.3.1), phosphoenolpyruvate carboxylase (E.C. 4.1.1.31). The extent to which these manipulations are necessary is determined by the observed byproducts found in the bioreactor or shake-flask. For instance, observation of acetate would suggest deletion of pyruvate oxidase, acetate kinase, and/or phosphotransacetylase enzyme activities. In another example, observation of D-lactate would suggest deletion of D-lactate dehydrogenase enzyme activities, whereas observation of succinate, malate, fumarate, oxaloacetate, or citrate would suggest deletion of citrate synthase and/or PEP carboxylase enzyme activities.

Production of Ethylene, Propylene, 1-Butene, 1,3-Butadiene, Acrylic Acid, Etc. As the Carbon-Based Products of Interest In certain embodiments, the engineered chemoautotroph of the present invention produces ethylene, propylene, 1-butene, 1,3-butadiene and acrylic acid as the carbon-based products of interest. Ethylene and/or propylene may be produced by either (1) the dehydration of ethanol or propanol (E.C. 4.2.1.-), respectively or (2) the decarboxylation of acrylate or crotonate (E.C. 4.1.1.-), respectively. While many dehydratases exist in nature, none has been shown to convert ethanol to ethylene (or propanol to propylene, propionic acid to acrylic acid, etc.) by dehydration. Genes encoding enzymes in the 4.2.1.x or 4.1.1.x group can be identified by searching databases such as GenBank using the methods described above, expressed in any desired host (such as *Escherichia coli*, for simplicity), and that host can be assayed for the the appropriate enzymatic activity. A high-throughput screen is especially useful for screening many genes and variants of genes generated by mutagenesis (i.e., error-prone PCR, synthetic libraries, chemical mutagenesis, etc.).

The ethanol dehydratase gene, after development to a suitable level of activity, can then be expressed in an ethanologenic organism to enable that organism to produce ethylene. For instance, coexpress native or evolved ethanol dehydratase gene into an organism that already produces ethanol, then test a culture by GC analysis of offgas for ethylene production that is significantly higher than without the added gene or via a high-throughput assay adapted from a colorimetric test [Larue, 1973]. It may be desirable to eliminate ethanol-export proteins from the production organism to prevent ethanol from being secreted into the medium and preventing its conversion to ethylene.

Alternatively, acryloyl-CoA can be produced as described above, and acryloyl-CoA hydrolases (E.C. 3.1.2.-), such as the acuN gene from *Halomonas* sp. HTNK1, can convert acryloyl-CoA into acrylate, which can be thermally decarboxylated to yield ethylene.

Alternatively, genes encoding ethylene-forming enzyme activities (EfE, E.C. 1.14.17.4) from various sources are expressed. Exemplary enzymes include *Pseudomonas syringae* pv. *Phaseolicola* (BAA02477), *P. syringae* pv. *Pisi* (AAD16443), *Ralstonia solanacearum* (CAD18680). Optimizing production may require further metabolic engineering (improving production of alpha-ketogluterate, recycling succinate as two examples).

In some embodiments, the engineered chemoautotroph of the present invention is engineered to produce ethylene from methionine. The reactions in the ethylene biosynthesis pathway are catalyzed by the following enzymes: methionine adenosyltransferase (E.C. 2.5.1.6), 1-aminocyclopropane-1-carboxylate synthase (E.C. 4.4.1.14) and 1-aminocyclopropane-1-carboxylate oxidase (E.C. 1.14.17.4).

In some embodiments, the engineered chemoautotroph of the present invention is engineered to produce propylene as the carbon-based product of interest. In one embodiment, the engineered chemoautotroph is engineered to express one or more of the following enzymes: propionyl-CoA synthase (E.C. 6.2.1.-, E.C. 4.2.1.- and E.C. 1.3.1.-), propionyl-CoA transferase (E.C. 2.8.3.1), aldehyde dehydrogenase (E.C. 1.2.1.3 or E.C. 1.2.1.4), alcohol dehydrogenase (E.C. 1.1.1.1 or E.C. 1.1.1.2), and alcohol dehydratase (E.C. 4.2.1.-). Propionyl-CoA synthase is a multi-functional enzyme that converts 3-hydroxypropionate, ATP and NADPH to propionyl-CoA. Exemplary propionyl-CoA synthases include AAL47820, and homologs thereof. SEQ ID NO:30 represents the *E. coli* codon optimized coding sequence for this propionyl-CoA synthase of the present invention. In one aspect, the invention provides nucleic acid molecule and homologs, variants and derivatives of SEQ ID NO:30. The nucleic acid sequence can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO:30. The present invention provides nucleic acids each comprising or consisting of a sequence which is a codon optimized version of the wild-type propionyl-CoA synthase gene. In another embodiment, the invention provides a nucleic acid encoding a polypeptide having the amino acid sequence of SEQ ID NO:31. Propionyl-CoA transferase converts propionyl-CoA and acetate to acetyl-CoA and propionate. Exemplary enzymes include *Ralstonia eutropha* pct and homologs thereof. Aldehyde dehydrogenase converts propionate and NADPH to propanal. Alcohol dehydrogenase converts propanal and NADPH to 1-propanol. Alcohol dehydratase converts 1-propanol to propylene.

In another embodiment. *E. coli* thiolase atoB (E.C. 2.3.1.9) converts 2 acetyl-CoA into acetoacetyl-CoA, and *C. acetobutylicum* hbd (E.C. 1.1.1.157) converts acetoacetyl-CoA and NADH into 3-hydroxybutyryl-CoA. *E. coli* tesB (EC 3.1.2.20) or *C. acetobutylicum* ptb and buk (E.C. 2.3.1.19 and 2.7.2.7 respectively) convert 3-hydroxybutyryl-CoA into 3-hydroxybutyrate, which can be simultaneously decarboxylated and dehydrated to yield propylene. Optionally, the 3-hydroxybutyryl-CoA is polymerized to form poly(3-hydroxybutyrate), a solid compound which can be extracted from the fermentation medium and simultaneously depolymerizied, hydrolyzed, dehydrated, and decarboxyated to yield propylene (U.S. patent application Ser. No. 12/527, 714, 2008).

Production of Fatty Acids, their Intermediates and Derivatives as the Carbon-Based Products of Interest In certain embodiments, the engineered chemoautotroph of the present invention produces fatty acids, their intermediates and their derivatives as the carbon-based products of interest. The engineered chemoautotrophs of the present invention can be modified to increase the production of acyl-ACP or acyl-CoA, to reduce the catabolism of fatty acid derivatives and intermediates, or to reduce feedback inhibition at specific points in the biosynthetic pathway used for fatty acid products. In addition to modifying the genes described herein, additional cellular resources can be diverted to over-produce fatty acids. For example the lactate, succinate and/or acetate pathways can be attenuated and the fatty acid biosynthetic pathway precursors acetyl-CoA and/or malonyl-CoA can be overproduced.

In one embodiment, the engineered chemoautotrophs of the present invention can be engineered to express certain fatty acid synthase activities (FAS), which is a group of peptides that catalyze the initiation and elongation of acyl chains [Marrakchi, 2002a]. The acyl carrier protein (ACP) and the enzymes in the FAS pathway control the length, degree of saturation and branching of the fatty acids produced, which can be attenuated or over-expressed. Such enzymes include accABCD, FabD, FabH, FabG, FabA, FabZ, FabI, FabK, FabL, FabM, FabB, FabF, and homologs thereof.

In another embodiment, the engineered chemoautotrophs of the present invention form fatty acid byproducts through ACP-independent pathways, for example, the pathway described recently by [Dellomonaco, 2011] involving reversal of beta oxidation. Enzymes involved in these pathways include such genes as atoB, fadA, fadB, fadD, fadE, fadI, fadK, fadJ, paaZ, ydiO, yfcY, JcZ, ydiD, and homologs thereof.

In one aspect, the fatty acid biosynthetic pathway precursors acetyl-CoA and malonyl-CoA can be overproduced in the engineered chemoautotroph of the present invention. Several different modifications can be made, either in combination or individually, to the host cell to obtain increased acetyl CoA/malonyl CoA/fatty acid and fatty acid derivative production. To modify acetyl-CoA and/or malonyl-CoA production, the expression of acetyl-CoA carboxylase (E.C. 6.4.1.2) can be modulated. Exemplary genes include accABCD (AAC73296) or homologs thereof. To increase acetyl CoA production, the expression of several genes may be altered including pdh, panK, aceEF, (encoding the E1p dehydrogenase component and the E2p dihydrolipoamide acyltransferase component of the pyruvate and 2-oxoglutarate dehydrogenase complexes), fabH/fabD/fabG/acpP/fabF, and in some examples additional nucleic acid encoding fatty-acyl-CoA reductases and aldehyde decarbonylases. Exemplary enzymes include pdh (BAB34380. AAC73227, AAC73226), panK (also known as coaA, AAC76952), aceEF (AAC73227, AAC73226), fabH (AAC74175), fabD (AAC74176), fabG (AAC74177), acpP (AAC74178), fabF (AAC74179).

Genes to be knocked-out or attenuated include fadE, gpsA, ldhA, pflb, adhE, pta, poxB, ackA, and/or ackB. Exemplary enzymes include fadE (AAC73325), gspA (AAC76632), ldhA (AAC74462), pflb (AAC73989), adhE (AAC74323), pta (AAC75357), poxB (AAC73958), ackA (AAC75356), ackB (BAB81430), and homologs thereof.

Additional potential modifications include the following. To achieve fatty acid overproduction, lipase (E.C. 3.1.1.3) which produce triacylglycerides from fatty acids and glycerol and in some cases serves as a suppressor of fabA can be included in the engineered chemoautotroph of the present invention. Exemplary enzymes include *Saccharomyces cerevisiae* LipA (CAA89087), *Saccharomyces cerevisiae* TGL2 CAA98876, and homologs thereof. To remove limitations on the pool of acyl-CoA, the D311E mutation in psB (AAC77011) can be introduced.

To engineer an engineered chemoautotroph for the production of a population of fatty acid derivatives with homogeneous chain length, one or more endogenous genes can be attenuated or functionally deleted and one or more thioesterases can be expressed. Thiosterases (E.C. 3.1.2.14) generate acyl-ACP from fatty acid and ACP. For example, C10 fatty acids can be produced by attenuating endogenous C18 thioesterases (for example, *E. coli* tesA AAC73596 and P0ADA1, and homologs thereof), which uses C18:1-ACP, and expressing a C10 thioesterase, which uses C10-ACP, thus, resulting in a relatively homogeneous population of fatty acids that have a carbon chain length of 10. In another example, C14 fatty acid derivatives can be produced by attenuating endogenous thiaesterases that produce non-C14 fatty acids and expressing the C14 thioesterase, which uses C14-ACP. In yet another example, C12 fatty acid derivatives can be produced by expressing thioesterases that use C12-ACP and attenuating thioesterases that produce non-C12 fatty acids. Exemplary C8:0 to C10:0 thioesterases include *Cuphea hookeriana* fatB2 (AAC49269) and homologs thereof. Exemplary C12:0 thioesterases include *Umbellularia california* fatB (Q41635) and homologs thereof. Exemplary C14:0 thioesterases include *Cinnamonum cumphorum* fatB (Q39473). Exemplary C14:0 to C16:0 thioesterases include *Cuphea hookeriana* fatB3 (AAC49269). Exemplary C16:0 thioesterases include *Arabidopsis thaliana* fatB (CAA85388), *Cuphea hookeriana* fatB1 (Q39513) and homologs thereof. Exemplary C18:1 thioesterases include *Arabidopsis thaliana* fatA (NP_189147, NP_193041), *Arabidopsis thaliana* fatB (CAA85388), *Bradyrhizobium japonicum* fatA (CAC39106), *Cuphea hookeriana* fatA (AAC72883), *Escherichia coli* tesA (NP_415027) and homologs thereof. Acetyl CoA, malonyl CoA, and fatty acid overproduction can be verified using methods known in the art, for example by using radioactive precursors, HPLC, and GC-MS subsequent to cell lysis.

In yet another aspect, fatty acids of various lengths can be produced in the engineered chemoautotroph by expressing or overexpressing acyl-CoA synthase peptides (E.C. 2.3.1.86), which catalyzes the conversion of fatty acids to acyl-CoA. Some acyl-CoA synthase peptides, which are non-specific, accept other substrates in addition to fatty acids.

In yet another aspect, branched chain fatty acids, their intermediates and their derivatives can be produced in the engineered chemoautotroph as the carbon-based products of interest. By controlling the expression of endogenous and heterologous enzymes associated with branched chain fatty acid biosynthesis, the production of branched chain fatty acid intermediates including branched chain fatty acids can be enhanced. Branched chain fatty acid production can be achieved through the expression of one or more of the following enzymes [Kaneda, 1991]: branched chain amino acid aminotransferase to produce α-ketoacids from branched chain amino acids such as isoleucine, leucine and valine (E.C. 2.6.1.42), branched chain α-ketoacid dehydrogenase complexes which catalyzes the oxidative decarboxylation of α-ketoacids to branched chain acyl-CoA (bkd, E.C. 1.2.4.4) [Denoya, 1995], dihydrolipoyl dehydrogenase (E.C. 1.8.1.4), beta-ketoacyl-ACP synthase with branched chain acyl CoA specificity (E.C. 2.3.1.41) [Li, 2005], crotonyl-CoA reductase (E.C. 1.3.1.8, 1.3.1.85 or 1.3.1.86) [Han, 1997], and isobutyryl-CoA mutase (large subunit E.C. 5.4.99.2 and small subunit E.C. 5.4.99.13). Exemplary branched chain amino acid aminotransferases include *E. coli* ilvE (YP_026247), *Lactococcus lactis* ilvE (AAF34406), *Pseudomonas putida* ilvE (NP_745648), *Streptomyces coelicolor* ilvE (NP_629657), and homologs thereof. Branched chain α-ketoacid dehydrogenase complexes consist of E1α/β (decarboxylase), E2 (dihydrolipoyl transacylase) and E3 (dihydrolipoyl dehydrogenase) subunits. The industrial host *E. coli* has only the E3 component as a part of its pyruvate dehydrogenase complex (lpd, E.C. 1.8.1.4, NP_414658) and so it requires the E1α/β and E2 bkd proteins. Exemplary α-ketoacid dehydrogenase complexes include *Streptomyces coelicolor* bkdA1 (NP_628006) E1α (decarboxylase component), *S. coelicolor* bkdB2 (NP_628005) E1β (decarboxylase component). *S. coelicolor* bkdA3 (NP_638004) E2 (dihydrolipoyl transacylase); or *S. coelicolor* bkdA2 (NP_733618) E1α (decarboxylase component), *S. coelicolor* bkdB2 (NP_628019) E1β (decarboxylase component), *S. coelicolor* bkdC2 (NP_628018) E2 (dihydrolipoyl transacylase); or *S. avermitilis* bkdA (BAC72074) E1α (decarboxylase component), *S. avermitilis* bkdB (BAC72075) E1β (decarboxylase component), *S. avermitilis* bkdC (BAC72076) E2 (dihydrolipoyl transacylase); *S. avermitilis* bkdF (E.C.1.2.4.4, BAC72088) E1α (decarboxylase component), *S. avermitilis* bkdG (BAC72089) E1β (decarboxylase component), *S. avermitilis* bkdH (BAC72090) E2 (dihydrolipoyl transacylase); *B. subtilis* bkdAA (NP_390288) E1α (decarboxylase component), *B. subtilis* bkdAB (NP_390288) E1β (decarboxylase component), *B. subtilis* bkdB (NP_390288) E2 (dihydrolipoyl transacylase); or *P. putida* bkdA 1 (AAA65614) E1α (decarboxylase component), *P. putida* bkdA2 (AAA65615) E1β (decarboxylase component), *P. putida* bkdC (AAA65617) E2 (dihydrolipoyl transacylase); and homologs thereof. An exemplary dihydrolipoyl dehydrogenase is *E. coli* lpd (NP_414658) E3 and homologs thereof. Exemplary beta-ketoacyl-ACP synthases with branched chain acyl CoA specificity include *Streptomyces coelicolor* fabH 1 (NP_626634), ACP (NP_626635) and fabF (NP_626636): *Streptomyces avermitilis* fabH3 (NP_823466), fbC3 (NP_823467), fabF (NP_823468); *Bacillus subtilis* fabH_A (NP_389015), fabH_B (NP_388898), ACP (NP_389474), fabF (NP_389016); *Stenotrophomonas maltophilia* SmalDRAFT_0818 (ZP_01643059), SmalDRAFT_0821

(ZP_01643063), SmalDRAFT_0822 (ZP_01643064); *Legionella pneumophila* fabH (YP_123672). ACP (YP_123675), fabF (YP_123676); and homologs thereof. Exemplary crotonyl-CoA reductases include *Streptomyces coelicolor* ccr (NP_630556), *Streptomyces cinnamonensis* ccr (AAD53915), and homologs thereof. Exemplary isobutyryl-CoA mutases include *Streptomyces coelicolor* icmA & icmB (NP_629554 and NP_630904), *Streptomyces cinnamonensis* icmA and icmB (AAC08713 and AJ246005), and homologs thereof. Additionally or alternatively, endogenous genes that normally lead to straight chain fatty acids, their intermediates, and derivatives may be attenuated or deleted to eliminate competing pathways. Enzymes that interfere with production of branched chain fatty acids include f-ketoacyl-ACP synthase II (E.C. 2.3.1.41) and α-ketoacyl-ACP synthase III (E.C. 2.3.1.41) with straight chain acyl CoA specificity. Exemplary enzymes for deletion include *E. coli* fabF (NP_415613) and fabH (NP_415609).

In yet another aspect, fatty acids, their intermediates and their derivatives with varying degrees of saturation can be produced in the engineered chemoautotroph as the carbon-based products of interest. In one aspect, hosts are engineered to produce unsaturated fatty acids by over-expressing β-ketoacyl-ACP synthase I (E.C. 2.3.1.41), or by growing the host at low temperatures (for example less than 37° C.). FabB has preference to cis-$\delta^3$decenoyl-ACP and results in unsaturated fatty acid production in *E. coli*. Over-expression of FabD results in the production of a significant percentage of unsaturated fatty acids [de Mendoza, 1983]. These unsaturated fatty acids can then be used as intermediates in hosts that are engineered to produce fatty acids derivatives, such as fatty alcohols, esters, waxes, olefins, alkanes, and the like. Alternatively, the repressor of fatty acid biosynthesis. *E. coli* FabR (NP_418398), can be deleted, which can also result in increased unsaturated fatty acid production in *E. coli* [Zhang, 2002]. Further increase in unsaturated fatty acids is achieved by over-expression of heterologous trans-2, cis-3-decenoyl-ACP isomerase and controlled expression of trans-2-enoyl-ACP reductase II [Marrakchi, 2002b], while deleting *E. coli* FabI (trans-2-enoyl-ACP reductase, E.C. 1.3.1.9, NP_415804) or homologs thereof in the host organism. Exemplary β-ketoacyl-ACP synthase I include *Escherichia coli* fabB (BAA16180) and homologs thereof. Exemplary trans-2, cis-3-decenoyl-ACP isomerase include *Streptococcus mutans* UA159 FabM (DAA05501) and homologs thereof. Exemplary trans-2-enoyl-ACP reductase II include *Streptococcus pneumoniae* R6 FabK (NP_357969) and homologs thereof. To increase production of monounsaturated fatty acids, the sfa gene, suppressor of FabA, can be over-expressed [Rock, 1996]. Exemplary proteins include AAN79592 and homologs thereof. One of ordinary skill in the art would appreciate that by attenuating fabA, or over-expressing fabB and expressing specific thioesterases (described above), unsaturated fatty acids, their derivatives, and products having a desired carbon chain length can be produced.

In some examples the fatty acid or intermediate is produced in the cytoplasm of the cell. The cytoplasmic concentration can be increased in a number of ways, including, but not limited to, binding of the fatty acid to coenzyme A to form an acyl-CoA thioester. Additionally, the concentration of acyl-CoAs can be increased by increasing the biosynthesis of CoA in the cell, such as by over-expressing genes associated with pantothenate biosynthesis (panD) or knocking out the genes associated with glutathione biosynthesis (glutathione synthase).

Production of Fatty Alcohols as the Carbon-Based Products of Interest

In yet further aspects, hosts cells are engineered to convert acyl-CoA to fatty alcohols by expressing or overexpressing a fatty alcohol forming acyl-CoA reductase (FAR, E.C. 1.1.1.*), or an acyl-CoA reductases (E.C. 1.2.1.50) and alcohol dehydrogenase (E.C. 1.1.1.1) or a combination of the foregoing to produce fatty alcohols from acyl-CoA. Hereinafter fatty alcohol forming acyl-CoA reductase (FAR, E.C. 1.1.1.*), acyl-CoA reductases (E.C. 1.2.1.50) and alcohol dehydrogenase (E.C. 1.1.1.1) are collectively referred to as fatty alcohol forming peptides. Some fatty alcohol forming peptides are non-specific and catalyze other reactions as well: for example, some acyl-CoA reductase peptides accept other substrates in addition to fatty acids. Exemplary fatty alcohol forming acyl-CoA reductases include *Acinetobacter baylyi* ADP1 acr1 (AAC45217), *Simmondsia chinensis* jjfar (AAD38039), *Mus musculus* mfar1 (AAH07178), *Mus musculus* mfar2 (AAH55759) *Acinetobacter* sp. M1 acrM1, *Homo sapiens* hfar (AAT42129), and homologs thereof. Fatty alcohols can be used as surfactants.

Many fatty alcohols are derived from the products of fatty acid biosynthesis. Hence, the production of fatty alcohols can be controlled by engineering fatty acid biosynthesis in the engineered chemoautotroph. The chain length, branching and degree of saturation of fatty acids and their intermediates can be altered using the methods described herein, thereby affecting the nature of the resulting fatty alcohols.

As mentioned above, through the combination of expressing genes that support brFA synthesis and alcohol synthesis, branched chain alcohols can be produced. For example, when an alcohol reductase such as Acr1 from *Acinetobacter baylyi* ADP1 is coexpressed with a bkd operon, *E. coli* can synthesize isopentanol, isobutanol or 2-methyl butanol. Similarly, when Acr1 is coexpressed with ccr/icm genes, *E. coli* can synthesize isobutanol.

Production of Fatty Esters as the Carbon-Based Products of Interest

In another aspect, engineered chemoautotrophs produce various lengths of fatty esters (biodiesel and waxes) as the carbon-based products of interest. Fatty esters can be produced from acyl-CoAs and alcohols. The alcohols can be provided in the fermentation media, produced by the engineered chemoautotroph itself or produced by a co-cultured organism.

In some embodiments, one or more alcohol O-acetyltransferases is expressed in the engineered chemoautotroph to produce fatty esters as the carbon-based product of interest. Alcohol O-acetyltransferase (E.C. 2.3.1.84) catalyzes the reaction of acetyl-CoA and an alcohol to produce CoA and an acetic ester. In some embodiments, the alcohol O-acetyltransferase peptides are co-expressed with selected thioesterase peptides. FAS peptides and fatty alcohol forming peptides to allow the carbon chain length, saturation and degree of branching to be controlled. In other embodiments, the bkd operon can be co-expressed to enable branched fatty acid precursors to be produced.

Alcohol O-acetyltransferase peptides catalyze other reactions such that the peptides accept other substrates in addition to fatty alcohols or acetyl-CoA thioester. Other substrates include other alcohols and other acyl-CoA thioesters. Modification of such enzymes and the development of assays for characterizing the activity of a particular alcohol O-acetyltransferase peptides are within the scope of a skilled artisan. Engineered 0-acetyltransferases and O-acyltransferases can be created that have new activities and specificities for the donor acyl group or acceptor alcohol moiety.

Alcohol acetyl transferases (AATs, E.C. 2.3.1.84), which are responsible for acyl acetate production in various plants, can be used to produce medium chain length waxes, such as octyl octanoate, decyl octanoate, decyl decanoate, and the like. Fatty esters, synthesized from medium chain alcohol (such as C6, C8) and medium chain acyl-CoA (or fatty acids, such as C6 or C8) have a relative low melting point. For example, hexyl hexanoate has a melting point of −55° C. and octyl octanoate has a melting point of −18 to −17° C. The low melting points of these compounds make them good candidates for use as biofuels. Exemplary alcohol acetyltransferases include Fragaria×ananassa SAAT (AAG13130) [Aharoni, 2000], Saccharomyces cerevisiae Atfp1 (NP_015022), and homologs thereof.

In some embodiments, one or more wax synthases (E.C. 2.3.1.75) is expressed in the engineered chemoautotroph to produce fatty esters including waxes from acyl-CoA and alcohols as the carbon-based product of interest. Wax synthase peptides are capable of catalyzing the conversion of an acyl-thioester to fatty esters. Some wax synthase peptides can catalyze other reactions, such as converting short chain acyl-CoAs and short chain alcohols to produce fatty esters. Methods to identify wax synthase activity are provided in U.S. Pat. No. 7,118,896, which is herein incorporated by reference. Medium-chain waxes that have low melting points, such as octyl octanoate and octyl decanoate, are good candidates for biofuel to replace triglyceride-based biodiesel. Exemplary wax synthases include Acinetobacter baylyi ADP1 wsadp1, Acinetobacter baylyi ADP1 waxdgaT (AA017391) [Kalscheuer. 2003], Saccharomyces cerevisiae Eeb1 (NP_015230), Saccharomyces cerevisiae YMR210w (NP_013937), Simmondsia chinensis acyltransferase (AAD38041), Mus musculus Dgat214 (Q6E1M8), and homologs thereof.

In other aspects, the engineered chemoautotrophs are modified to produce a fatty ester-based biofuel by expressing nucleic acids encoding one or more wax ester synthases in order to confer the ability to synthesize a saturated, unsaturated, or branched fatty ester. In some embodiments, the wax ester synthesis proteins include, but are not limited to: fatty acid elongases, acyl-CoA reductases, acyltransferases or wax synthases, fatty acyl transferases, diacylglycerol acyltransferases, acyl-coA wax alcohol acyltransferases, bifunctional wax ester synthase/acyl-CoA: diacylglycerol acyltransferase selected from a multienzyme complex from Simmondsia chinensis, Acinetobacter sp. strain ADP1 (formerly Acinetobacter calcoaceticus ADP1), Pseudomonas aeruginosa, Fundibacter jadensis, Arabidopsis thaliana, or Alkaligenes eutrophus. In one embodiment, the fatty acid elongases, acyl-CoA reductases or wax syntheses are from a multienzyme complex from Alkaligenes eutrophus and other organisms known in the literature to produce wax and fatty acid esters.

Many fatty esters are derived from the intermediates and products of fatty acid biosynthesis. Hence, the production of fatty esters can be controlled by engineering fatty acid biosynthesis in the engineered chemoautotroph. The chain length, branching and degree of saturation of fatty acids and their intermediates can be altered using the methods described herein, thereby affecting the nature of the resulting fatty esters.

Additionally, to increase the percentage of unsaturated fatty acid esters, the engineered chemoautotroph can also overexpress Sfa which encodes a suppressor of fabA (AAN79592, AAC44390), β-ketoacyl-ACP synthase 1 (E.C. 2.3.1.41, BAA16180), and secG null mutant suppressors (cold shock proteins) gnsA and gnsB (ABD18647 and AAC74076). In some examples, the endogenous fabF gene can be attenuated, thus, increasing the percentage of palmitoleate (C 16:1) produced.

Optionally a wax ester exporter such as a member of the FATP family is used to facilitate the release of waxes or esters into the extracellular environment from the engineered chemoautotroph. An exemplary wax ester exporter that can be used is fatty acid (long chain) transport protein CG7400-PA, isoform A from D. melanogaster (NP_524723), or homologs thereof.

The centane number (CN), viscosity, melting point, and heat of combustion for various fatty acid esters have been characterized in for example, [Knothe, 2005]. Using the teachings provided herein the engineered chemoautotroph can be engineered to produce any one of the fatty acid esters described in [Knothe, 2005].

Production of Alkanes as the Carbon-Based Products of Interest

In another aspect, engineered chemoautotrophs produce alkanes of various chain lengths (hydrocarbons) as the carbon-based products of interest. Many alkanes are derived from the products of fatty acid biosynthesis. Hence, the production of alkanes can be controlled by engineering fatty acid biosynthesis in the engineered chemoautotroph. The chain length, branching and degree of saturation of fatty acids and their intermediates can be altered using the methods described herein. The chain length, branching and degree of saturation of alkanes can be controlled through their fatty acid biosynthesis precursors.

In certain aspects, fatty aldehydes can be converted to alkanes and CO in the engineered chemoautotroph via the expression of decarbonylases [Cheesbrough, 1984; Dennis, 1991]. Exemplary enzymes include Arabidopsis thaliana cer1 (NP_171723), Oryza sativacer1 CER1 (AAD29719) and homologs thereof.

In another aspect, fatty alcohols can be converted to alkanes in the engineered chemoautotroph via the expression of terminal alcohol oxidoreductases as in Vibrio furnissii M1 [Park, 2005].

Production of Olefins as the Carbon-Based Products of Interest

In another aspect, engineered chemoautotrophs produce olefins (hydrocarbons) as the carbon-based products of interest. Olefins are derived from the intermediates and products of fatty acid biosynthesis. Hence, the production of olefins can be controlled by engineering fatty acid biosynthesis in the engineered chemoautotroph. Introduction of genes affecting the production of unsaturated fatty acids, as described above, can result in the production of olefins. Similarly, the chain length of olefins can be controlled by expressing, overexpressing or attenuating the expression of endogenous and heterologous thioesterases which control the chain length of the fatty acids that are precursors to olefin biosynthesis. Also, by controlling the expression of endogenous and heterologous enzymes associated with branched chain fatty acid biosynthesis, the production of branched chain olefins can be enhanced. Methods for controlling the chain length and branching of fatty acid biosynthesis intermediates and products are described above.

Production of ω-Cyclic Fatty Acids and their Derivatives as the Carbon-Based Products of Interest In another aspect, the engineered chemoautotroph of the present invention produces ω-cyclic fatty acids (cyFAs) as the carbon-based product of interest. To synthesize w-cyclic fatty acids (cyFAs), several genes need to be introduced and expressed that provide the cyclic precursor cyclohexylcarbonyl-CoA [Cropp. 2000]. The genes (fabH, ACP and fabF)

can then be expressed to allow initiation and elongation of ω-cyclic fatty acids. Alternatively, the homologous genes can be isolated from microorganisms that make cyFAs and expressed in *E. coli*. Relevant genes include bkdC, lpd, fabH, ACP, fabF, fabH1, ACP, fabF, fabH3, fabC3, fabF, fabH_A, fabH_B, ACP.

Expression of the following genes are sufficient to provide cyclohexylcarbonyl-CoA in *E. coli*: ansJ, ansK, ansL, chcA (1-cyclohexenylcarbonyl CoA reductase) and ansM from the ansatrienin gene cluster of *Streptomyces collinus* [Chen. 1999] or plmJK (5-enolpyruvylshikimate-3-phosphate synthase), plmL (acyl-CoA dehydrogenase), chcA (enoyl-(ACP) reductase) and plmM (2,4-dienoyl-CoA reductase) from the phoslactomycin B gene cluster of *Streptomyces* sp. HK803 [Palaniappan, 2003] together with the acyl-CoA isomerase (chcB gene) [Patton, 2000] from *S. collinus, S. avermitilis* or *S. coelicolor*. Exemplary ansatrienin gene cluster enzymes include AAC44655, AAF73478 and homologs thereof. Exemplary phoslactomycin B gene cluster enzymes include AAQ84158, AAQ84159, AAQ84160, AAQ84161 and homologs thereof. Exemplary chcB enzymes include NP_629292, AAF73478 and homologs thereof.

The genes (fabH, ACP and fabF) are sufficient to allow initiation and elongation of ω-cyclic fatty acids, because they can have broad substrate specificity. In the event that coexpression of any of these genes with the ansJKLM/chcAB or pmUKLM/chcAB genes does not yield cyFAs, fabH, ACP and/or fabF homologs from microorganisms that make cyFAs can be isolated (e.g., by using degenerate PCR primers or heterologous DNA probes) and coexpressed.

Production of Halogenated Derivatives of Fatty Acids

Genes are known that can produce fluoroacetyl-CoA from fluoride ion. In one embodiment, the present invention allows for production of fluorinated fatty acids by combining expression of fluoroacetate-involved genes (e.g., fluorinase, nucleotide phosphorylase, fluorometabolite-specific aldolases, fluoroacetaldehyde dehydrogenase, and fluoroacetyl-CoA synthase).

Transport/Efflux/Release of Fatty Acids and their Derivatives

Also disclosed herein is a system for continuously producing and exporting hydrocarbons out of recombinant host microorganisms via a transport protein. Many transport and efflux proteins serve to excrete a large variety of compounds and can be evolved to be selective for a particular type of fatty acid. Thus, in some embodiments an ABC transporter can be functionally expressed by the engineered chemoautotroph, so that the organism exports the fatty acid into the culture medium. In one example, the ABC transporter is an ABC transporter from *Caenorhabditis elegans, Arabidopsis thalania, Alkaligenes eutrophus* or *Rhodococcus erythropolis* or homologs thereof. Exemplary transporters include AAU44368, NP_188746, NP_175557, AAN73268 or homologs thereof.

The transport protein, for example, can also be an efflux protein selected from: AcrAB (NP_414996.1, NP_414995.1), TolC (NP_417507.2) and AcrEF (NP_417731.1, NP_417732.1) from *E. coli*, or tll1618 (NP_682408), tll1619 (NP_682409), tll0139 (NP_680930), H11619 and U10139 from *Thermosynechococcus elongatus* BP-I or homologs thereof.

In addition, the transport protein can be, for example, a fatty acid transport protein (FATP) selected from *Drosophila melanogaster, Caenorhabditis elegans, Mycobacterium tuberculosis* or *Saccharomyces cerevisiae, Acinetobacter* sp. H01-N, any one of the mammalian FATPs or homologs thereof. The FATPs can additionally be resynthesized with the membranous regions reversed in order to invert the direction of substrate flow. Specifically, the sequences of amino acids composing the hydrophilic domains (or membrane domains) of the protein can be inverted while maintaining the same codons for each particular amino acid. The identification of these regions is well known in the art.

Production of Isoprenoids as the Carbon-Based Products of Interest

Figure 15:
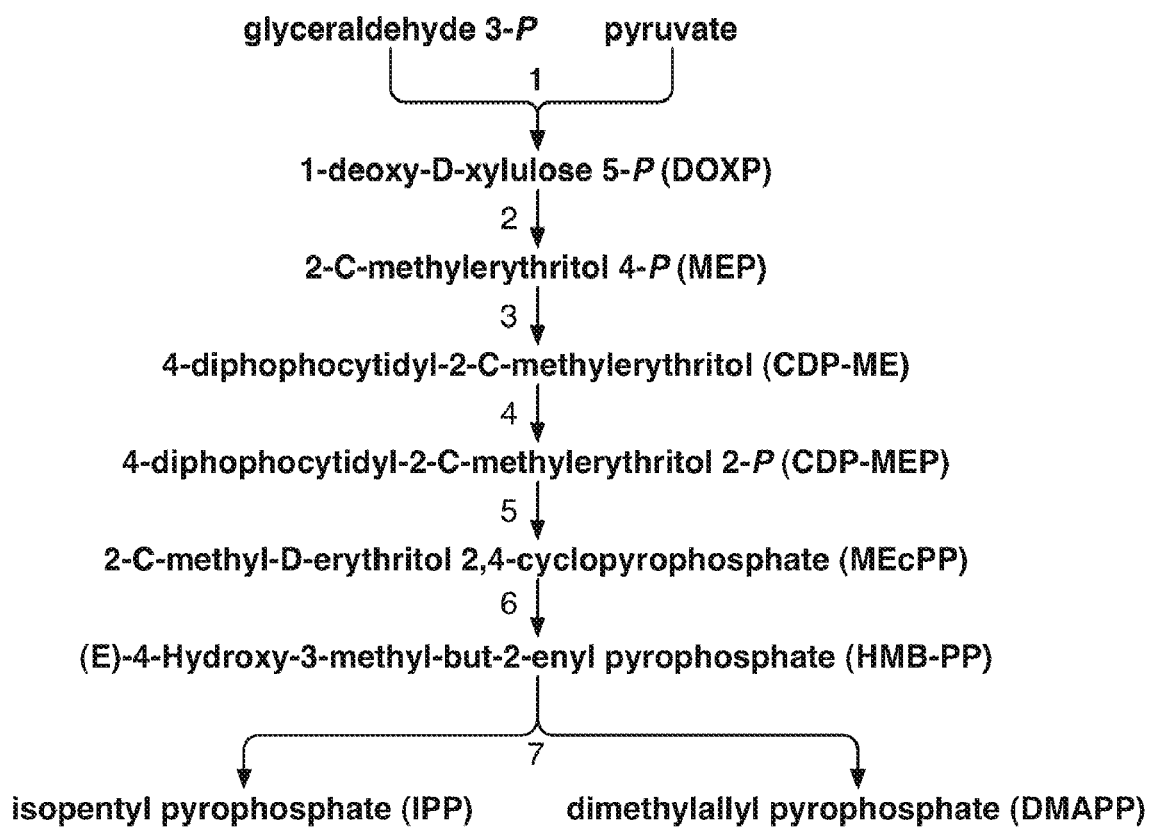
FIG. 15 depicts the metabolic reactions of the mevalonate-independent pathway (also known as the non-mevalonate pathway or deoxyxylulose 5-phosphate (DXP) pathway) for production of isopentenyl pyrophosphate (IPP) and its isomer dimethylallyl pyrophosphate (DMAPP). In metabolite names, —P denotes phosphate. Each reaction is numbered. Enzymes catalyzing each reaction are as follows: 1, 1-deoxy-D-xylulose-5-phosphate synthase (E.C. 2.2.1.7); 2, 1-deoxy-D-xylulose-5-phosphate reductoisomerase (E.C. 1.1.1.267); 3, 4-diphosphocytidyl-2C-methyl-D-erythritol synthase (E.C. 2.7.7.60); 4, 4-diphosphocytidyl-2C-methyl-D-erythritol kinase (E.C. 2.7.1.148); 5, 2C-methyl-D-erythritol 2,4-cyclodiphosphate synthase (E.C. 4.6.1.12); 6, (E)-4-hydroxy-3-methylbut-2-enyl diphosphate synthase (E.C. 1.17.7.1); 7, isopentyl/dimethylallyl diphosphate synthase or 4-hydroxy-3-methylbut-2-enyl diphosphate reductase (E.C. 1.17.1.2).
Figure 16:
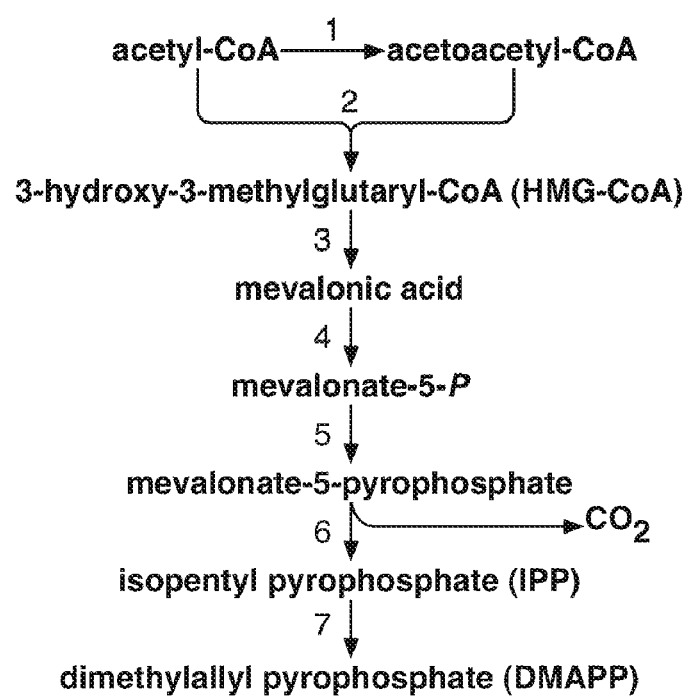
FIG. 16 depicts the metabolic reactions of the mevalonate pathway (also known as the HMG-CoA reductase pathway) for production of isopentenyl pyrophosphate (IPP) and its isomer dimethylallyl pyrophosphate (DMAPP). In metabolite names, —P denotes phosphate. Each reaction is numbered. Enzymes catalyzing each reaction are as follows: 1, acetyl-CoA thiolase; 2, HMG-CoA synthase (E.C. 2.3.3.10); 3, HMG-CoA reductase (E.C. 1.1.1.34); 4, mevalonate kinase (E.C. 2.7.1.36); 5, phosphomevalonate kinase (E.C. 2.7.4.2); 6, mevalonate pyrophosphate decarboxylase (E.C. 4.1.1.33); 7, isopentenyl pyrophosphate isomerase (E.C. 5.3.3.2).

In one aspect, the engineered chemoautotroph of the present invention produces isoprenoids or their precursors isopentenyl pyrophosphate (IPP) and its isomer, dimethylallyl pyrophosphate (DMAPP) as the carbon-based products of interest. There are two known biosynthetic pathways that synthesize IPP and DMAPP. Prokaryotes, with some exceptions, use the mevalonate-independent or deoxyxylulose 5-phosphate (DXP) pathway to produce IPP and DMAPP separately through a branch point (FIG. 15). Eukaryotes other than plants use the mevalonate-dependent (MEV) isoprenoid pathway exclusively to convert acetyl-coenzyme A (acetyl-CoA) to IPP, which is subsequently isomerized to DMAPP (FIG. 16). In general, plants use both the MEV and DXP pathways for IPP synthesis.

The reactions in the DXP pathway are catalyzed by the following enzymes: 1-deoxy-D-xylulose-5-phosphate synthase (E.C. 2.2.1.7), 1-deoxy-D-xylulose-5-phosphate reductoisomerase (E.C. 1.1.1.267), 4-diphosphocytidyl-2C-methyl-D-erythritol synthase (E.C. 2.7.7.60), 4-diphosphocytidyl-2C-methyl-D-erythritol kinase (E.C. 2.7.1.148), 2C-methyl-D-erythritol 2,4-cyclodiphosphate synthase (E.C. 4.6.1.12), (E)-4-hydroxy-3-methylbut-2-enyl diphosphate synthase (E.C. 1.17.7.1), isopentyl/dimethylallyl diphosphate synthase or 4-hydroxy-3-methylbut-2-enyl diphosphate reductase (E.C. 1.17.1.2). In one embodiment, the engineered chemoautotroph of the present invention expresses one or more enzymes from the DXP pathway. For example, one or more exogenous proteins can be selected from 1-deoxy-D-xylulose-5-phosphate reductoisomerase, 4-diphosphocytidyl-2C-methyl-D-erythritol synthase, 4-diphosphocytidyl-2C-methyl-D-erythritol kinase, 2C-methyl-D-erythritol 2,4-cyclodiphosphate synthase, (F)-4-hydroxy-3-methylbut-2-enyl diphosphate synthase, and 4-hydroxy-3-methylbut-2-enyl diphosphate reductase. The host organism can also express two or more, three or more, four or more, and the like, including up to all the protein and enzymes that confer the DXP pathway. Exemplary 1-deoxy-D-xylulose-5-phosphate synthases include *E. coli* Dxs (AAC46162); *P. putida* KT2440 Dxs (AAN66154); *Salmonella enterica* Paratyphi, see ATCC 9150 Dxs (AAV78186); *Rhodobacter sphaeroides* 2.4.1 Dxs (YP_353327); *Rhodopseudomonas palustris* CGA009 Dxs (NP_946305); *Xylella fastidiosa* Temecula1 Dxs (NP_779493); *Arabidopsis thaliana* Dxs (NP_001078570 and/or NP_196699); and homologs thereof. Exemplary 1-deoxy-D-xylulose-5-phosphate reductoisomerases include *E. coli* Dxr (BAA32426); *Arabidopsis thaliana* DXR (AA73140); *Pseudomonas putida* KT2440 Dxr (NP_743754 and/or Q88MH4); *Streptomyces coelicolor* A3(2) Dxr (NP_629822); *Rhodobacter sphaeroides* 2.4.1 Dxr (YP_352764); *Pseudomonas fluorescens* Pt-1 Dxr (YP_346389); and homologs thereof. Exemplary 4-diphosphocytidyl-2C-methyl-D-erythritol synthases include *E. coli* IspD (AAF43207); *Rhodobacter sphaeroides* 2.4.1 IspD (YP_352876); *Arabidopsis thaliana* ISPD (NP_565286); *P. putida* KT2440 IspD (NP_743771); and homologs thereof. Exemplary 4-diphosphocytidyl-2C-methyl-D-erythritol kinases include *E. coli* IspE (AAF29530); *Rhodobacter sphaeroides* 2.4.1 IspE (YP_351828); and homologs thereof. Exemplary 2C-methyl-D-erythritol 2,4-cyclodiphosphate synthases include *E. coli* IspF (AAF44656); *Rhodobacter sphaeroides* 2.4.1 IspF (YP_352877); *P. putida* KT2440 IspF (NP_743775); and homologs thereof. Exemplary (E)-4-hydroxy-3-methylbut-2-enyl diphosphate synthase include *E. coli* IspG (AAK53460); *P. putida* KT2440 IspG (NP_743014); *Rhodobacter sphaeroides* 2.4.1 IspG (YP_353044); and homologs thereof. Exemplary 4-hydroxy-3-methylbut-2-enyl diphosphate reductases include *E. coli* IspH (AAL38655); *P. putida* KT2440 IspH (NP_742768); and homologs thereof.

The reactions in the MEV pathway are catalyzed by the following enzymes: acetyl-CoA thiolase, HMG-CoA synthase (E.C. 2.3.3.10), HMG-CoA reductase (E.C. 1.1.1.34), mevalonate kinase (E.C. 2.7.1.36), phosphomevalonate kinase (E.C. 2.7.4.2), mevalonate pyrophosphate decarboxylase (E.C. 4.1.1.33), isopentenyl pyrophosphate isomerase (E.C. 5.3.3.2). In one embodiment, the engineered chemoautotroph of the present invention expresses one or more enzymes from the MEV pathway. For example, one or more exogenous proteins can be selected from acetyl-CoA thiolase, HMG-CoA synthase, HMG-CoA reductase, mevalonate kinase, phosphomevalonate kinase, mevalonate pyrophosphate decarboxylase and isopentenyl pyrophosphate isomerase. The host organism can also express two or more, three or more, four or more, and the like, including up to all the protein and enzymes that confer the MEV pathway. Exemplary acetyl-CoA thiolases include NC_000913 REGION: 232413 L.2325315, *E. coli*; D49362, *Paracoccus denitrificans*; L20428, *S. cerevisiae*; and homologs thereof. Exemplary HMG-CoA synthases include NC_001145 complement 19061 . . . 20536, *S. cerevisiae*; X96617, *S. cerevisiae*; X83882, *A. thaliana*; AB037907, *Kitasatospora griseola*; BT007302, *H. sapiens*; NC_002758, Locus lag SAV2546, GeneID 1 122571, *S. aureus*; and homlogs thereof. Exemplary HMG-CoA reductases include NM-206548, *D. melanogaster*: NC_002758, Locus tag SAV2545, GeneID 1122570, *S. aureus*; NM 204485, *Gallus gallus*; AB015627, *Streptomyces* sp. KO 3988; AF542543, *Nicotiana attenuata*; AR037907, *Kitasatospora griseola*; AX128213, providing the sequence encoding a truncated HMGR, *S. cerevisiae*; NC_001145: complement 115734 . . . 1 18898, *S. cerevisiae*; and homologs thereof. Exemplary mevalonate kinases include L77688, *A. thaliana*; X55875, *S. cerevisiae*; and homologs thereof. Exemplary phosphomevalonate kinases include AF429385, *Hevea brasiliensis*; NM_006556, *H. sapiens*: NC_001145 complement 712315 . . . 713670, *S. cerevisiae*; and homologs thereof. Exemplary mevalonate pyrophosphate decarboxylase include include X97557, *S. cerevisiae*: AF290095, *E. faecium*; U49260, *H. sapiens*; and homologs thereof. Exemplary isopentenyl pyrophosphate isomerases include NC_000913, 3031087 . . . 3031635, *E. coli*; AF082326, *Haematococcus pluvialis*; and homologs thereof.

In some embodiments, the host cell produces IPP via the MEV pathway, either exclusively or in combination with the DXP pathway. In other embodiments, a host cell's DXP pathway is functionally disabled so that the host cell produces IPP exclusively through a heterologously introduced MEV pathway. The DXP pathway can be functionally disabled by disabling gene expression or inactivating the function of one or more of the DXP pathway enzymes.

In some embodiments, the host cell produces IPP via the DXP pathway, either exclusively or in combination with the MEV pathway. In other embodiments, a host cell's MEV pathway is functionally disabled so that the host cell produces IPP exclusively through a heterologously introduced DXP pathway. The MEV pathway can be functionally disabled by disabling gene expression or inactivating the function of one or more of the MEV pathway enzymes.

Provided herein is a method to produce isoprenoids in engineered chemoautotrophs engineered with the isopentenyl pyrophosphate pathway enzymes. Some examples of isoprenoids include: hemiterpenes (derived from 1 isoprene unit) such as isoprene; monoterpenes (derived from 2 isoprene units) such as myrcene or limonene; sesquiterpenes (derived from 3 isoprene units) such as *amorpha*-4,11-diene, bisabolene or farnesene; diterpenes (derived from four isoprene units) such as taxadiene; sesterterpenes (derived from 5 isoprene units); triterpenes (derived from 6 isoprene units) such as squalene; sesquarterpenes (derived from 7 isoprene units); tetraterpenes (derived from 8 isoprene units) such as 0-carotene or lycopene; and polyterpenes (derived from more than 8 isoprene units) such as polyisoprene. The production of isoprenoids is also described in some detail in the published PCT applications WO2007/139925 and WO/2007/140339.

In another embodiment, the engineered chemoautotroph of the present invention produces rubber as the carbon-based product of interest via the isopentenyl pyrophosphate pathway enzymes and cis-polyprenyleistransferase (E.C. 2.5.1.20) which converts isopentenyl pyrophosphate to rubber. The enzyme cis-polyprenyleistransferase may come from, for example, *Hevea brasilensis*.

In another embodiment, the engineered chemoautotroph of the present invention produce isopentanol as the carbon-based product of interest via the isopentenyl pyrophosphate pathway enzymes and isopentanol dikinase.

In another embodiment, the engineered chemoautotroph produces squalene as the carbon-based product of interest via the isopentenyl pyrophosphate pathway enzymes, geranyl diphosphate synthase (E.C. 2.5.1.1), farnesyl diphosphate synthase (E.C. 2.5.1.10) and squalene synthase (E.C. 2.5.1.21). Geranyl diphosphate synthase converts dimethylallyl pyrophosphate and isopentenyl pyrophosphate to geranyl diphosphate. Farnesyl diphosphate synthase converts geranyl diphosphate and isopentenyl diphosphate to farnesyl diphosphate. A bifunctional enzyme carries out the conversion of dimethylallyl pyrophosphate and two isopentenyl pyrophosphate to farnesyl pyrophosphate. Exemplary enzymes include *Escherichia coli* IspA (NP_414955) and homologs thereof. Squalene synthase converts two farnesyl pyrophosphate and NADPH to squalene. In another embodiment, the engineered chemoautotroph produces lanosterol as the carbon-based product of interest via the above enzymes, squalene monooxygenase (E.C. 1.14.99.7) and lanosterol synthase (E.C. 5.4.99.7). Squalene monooxygenase converts squalene, NADPH and $O_2$ to (S)-squalene-2,3-epoxide. Exemplary enzymes include *Saccharomyces cerevisiae* Erg1 (NP_011691) and homologs thereof. Lanosterol synthase converts (S)-squalene-2,3-epoxide to lanosterol. Exemplary enzymes include *Saccharomyces cerevisiae* Erg7 (NP_011939) and homologs thereof.

In another embodiment, the engineered chemoautotroph of the present invention produces lycopene as the carbon-based product of interest via the isopentenyl pyrophosphate pathway enzymes, geranyl diphosphate synthase (E.C. 2.5.1.21, described above), farnesyl diphosphate synthase (E.C. 2.5.1.10, described above), geranylgeranyl pyrophosphate synthase (E.C. 2.5.1.29), phytoene synthase (E.C. 2.5.1.32), phytoene oxidoreductase (E.C. 1.14.99.n) and ζ-carotene oxidoreductase (E.C. 1.14.99.30). Geranylgeranyl pyrophosphate synthase converts isopentenyl pyrophosphate and farnesyl pyrophosphate to (all trans)-geranylgeranyl pyrophosphate. Exemplary geranylgeranyl pyrophosphate synthases include *Synechocystis* sp. PCC6803 crtE (NP_440010) and homologs thereof. Phytoene synthase converts 2 geranylgeranyl-PP to phytoene. Exemplary enzymes include *Synechocystis* sp. PCC6803 crtB (P37294). Phytoene oxidoreductase converts phytoene, 2 NADPH and 2 $O_2$ to ζ-carotene. Exemplary enzymes include *Synechocystis* sp. PCC6803 crtI and *Synechocystis* sp. PCC6714 crtI (P21134). ζ-carotene oxidoreductase converts ζ-carotene, 2 NADPH and 2 $O_2$ to lycopene. Exemplary enzymes include *Synechocystis* sp. PCC6803 crtQ-2 (NP_441720).

In another embodiment, the engineered chemoautotroph of the present invention produces limonene as the carbon-based product of interest via the isopentenyl pyrophosphate pathway enzymes, geranyl diphosphate synthase (E.C. 2.5.1.21, described above) and one of (R)-limonene synthase (E.C. 4.2.3.20) and (4S)-limonene synthase (E.C. 4.2.3.16) which convert geranyl diphosphate to a limonene enantiomer. Exemplary (R)-limonene synthases include that from *Citrus limon* (AAM53946) and homologs thereof. Exemplary (4S)-limonene synthases include that from *Mentha spicata* (AAC37366) and homologs thereof.

Figure 17:
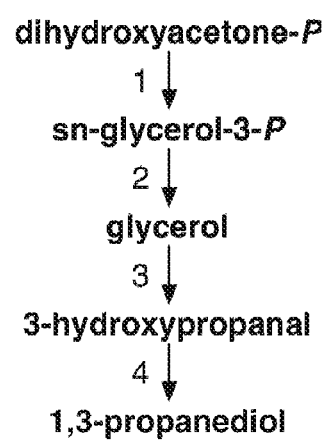
FIG. 17 depicts the metabolic reactions of the glycerol/1,3-propanediol biosynthetic pathway for production of glycerol or 1,3-propanediol. In metabolite names. —P denotes phosphate. Each reaction is numbered. Enzymes catalyzing each reaction are as follows: 1, sn-glycerol-3-P dehydrogenase (E.C. 1.1.1.8 or 1.1.1.94); 2, sn-glycerol-3-phosphatase (E.C. 3.1.3.21); 3, sn-glycerol-3-P. glycerol dehydratase (E.C. 4.2.1.30); 4, 1,3-propanediol oxidoreductase (E.C. 1.1.1.202).

Production of Glycerol or 1,3-Propanediol as the Carbon-Based Products of Interest In one aspect, the engineered chemoautotroph of the present invention produces glycerol or 1,3-propandiol as the carbon-based products of interest (FIG. 17). The reactions in the glycerol pathway are catalyzed by the following enzymes: sn-glycerol-3-P dehydrogenase (E.C. 1.1.1.8 or E.C. 1.1.1.94) and sn-glycerol-3-phosphatase (E.C. 3.1.3.21). To produce 1,3,-propanediol, the following enzymes are also included: sn-glycerol-3-P. glycerol dehydratase (E.C. 4.2.1.30) and 1,3-propanediol oxidoreductase (E.C. 1.1.1.202). Exemplary sn-glycerol-3-P dehydrogenases include *Saccharomyces cerevisiae* dar1 and homologs thereof. Exemplary sn-glycerol-3-phosphatases include *Saccharomyces cerevisiae* gpp2 and homologs thereof. Exemplary sn-glycerol-3-P. glycerol dehydratases include *K. pneumoniae* dhaB1-3. Exemplary 1,3-propanediol oxidoreductase include *K. pneumoniae* dhaT.

Production of 1,4-Butanediol or 1,3-Butadiene as the Carbon-Based Products of Interest In one aspect, the engineered chemoautotroph of the present invention produces 1,4-butanediol or 1,3-butanediene as the carbon-based products of interest. The metabolic reactions in the 1,4-butanediol or 1,3-butadiene pathway are catalyzed by the following enzymes: succinyl-CoA dehydrogenase (E.C. 1.2.1.n; e.g., *C. kluyveri* SucD) 4-hydroxybutyrate dehydrogenase (E.C. 1.1.1.2; e.g., *Arabidopsis thaliana* GHBDH), aldehyde dehydrogenase (E.C. 1.1.1.n; e.g., *E. coli* AldH), 1,3-propanediol oxidoreductase (E.C. 1.1.1.202; e.g., *K. pneumoniae* DhaT), and optionally alcohol dehydratase (E.C. 4.2.1.-). Succinyl-CoA dehydrogenase converts succinyl-CoA and NADPH to succinic semialdehyde and CoA. 4-hydroxybutyrate dehydrogenase converts succinic semialdehyde and NADPH to 4-hydroxybutyrate. Aldehyde dehydrogenase converts 4-hydroxybutyrate and NADH to 4-hydroxybutanal. 1,3-propanediol oxidoreductase converts 4-hydroxybutanal and NADH to 1,4-butanediol. Alcohol dehydratase converts 1,4-butanediol to 1,3-butadiene.

Figure 18:
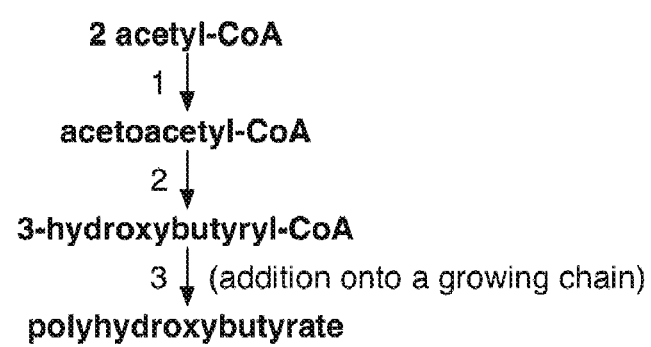
FIG. 18 depicts the metabolic reactions of the polyhydroxybutyrate biosynthetic pathway. Each reaction is numbered. Enzymes catalyzing each reaction are as follows: 1, acetyl-CoA:acetyl-CoA C-acetyltransferase (E.C. 2.3.1.9); 2, (R)-3-hydroxyacyl-CoA:NADP+ oxidoreductase (E.C. 1.1.1.36); 3, polyhydroxyalkanoate synthase (E.C. 2.3.1.-).

Production of Polyhydroxybutyrate as the Carbon-Based Products of Interest in one aspect, the engineered chemoautotroph of the present invention produces polyhydroxybutyrate as the carbon-based products of interest (FIG. 18). The reactions in the polyhydroxybutyrate pathway are catalyzed by the following enzymes: acetyl-CoA:acetyl-CoA C-acetyltransferase (E.C. 2.3.1.9), (R)-3-hydroxyacyl-CoA:NADP+ oxidoreductase (E.C. 1.1.1.36) and polyhydroxyalkanoate synthase (E.C. 2.3.1.-). Exemplary acetyl-CoA:acetyl-CoA C-acetyltransferases include *Ralstonia eutropha* phaA. Exemplary (R)-3-hydroxyacyl-CoA:NADP+ oxidoreductases include *Ralstonia eutropha* phaB. Exemplary polyhydroxyalkanoate synthase include *Ralstonia eutropha* phaC. In the event that the host organism also has the capacity to degrade polyhydroxybutyrate, the corresponding degradation enzymes, such s poly[(R)-3-hydroxybutanoate] hydrolase (E.C. 3.1.1.75), may be inactivated. Hosts that lack the ability to naturally synthesize polyhydroxybutyrate generally also lack the capacity to degrade it, thus leading to irreversible accumuation of polyhydroxybutyrate if the biosynthetic pathway is introduced.

Intracellular polyhydroxybutyrate can be measured by solvent extraction and esterification of the polymer from whole cells. Typically, lyophilized biomass is extracted with methanol-chloroform with 10/o HCl as a catalyst. The chloroform dissolves the polymer, and the methanol esterifies it in the presence of HCl. The resulting mixture is extracted with water to remove hydrophilic substances and the organic phase is analyzed by GC.

Production of Lysine as the Carbon-Based Products of Interest

Figure 19:
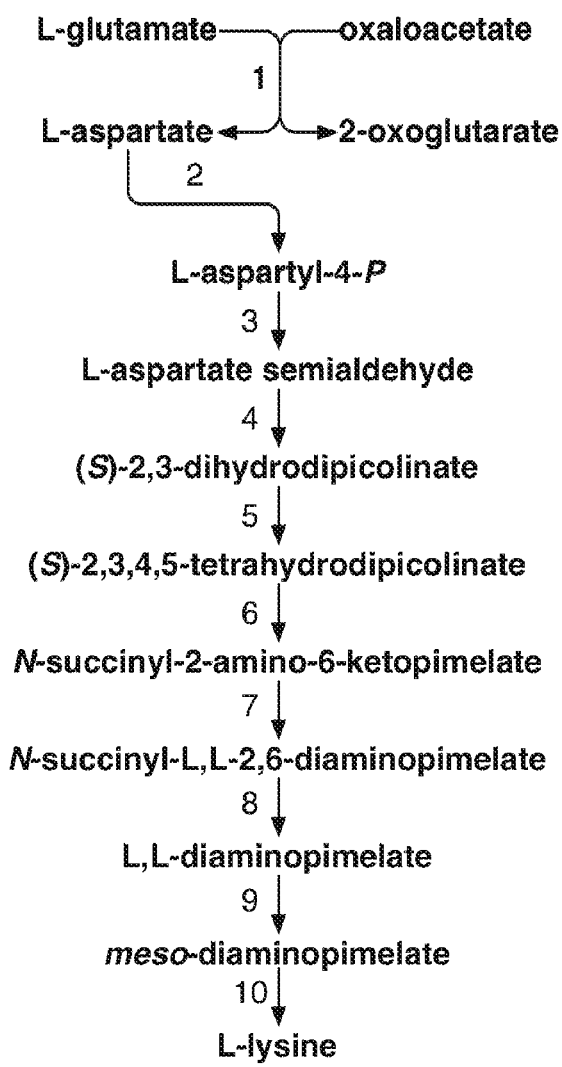
FIG. 19 depicts the metabolic reactions of one lysine biosynthesis pathway. In metabolite names, —P denotes phosphate. Each reaction is numbered. Enzymes catalyzing each reaction are as follows: 1, aspartate aminotransferase (E.C. 2.6.1.1); 2, aspartate kinase (E.C. 2.7.2.4); 3, aspartate semialdehyde dehydrogenase (E.C. 1.2.1.11); 4, dihydrodipicolinate synthase (E.C. 4.2.1.52); 5, dihydrodipicolinate reductase (E.C. 1.3.1.26); 6, tetrahydrodipicolinate succinylase (E.C. 2.3.1.117); 7, N-succinyldiaminopimelate-aminotransferase (E.C. 2.6.1.17); 8, N-succinyl-L-diaminopimelate desuccinylase (E.C. 3.5.1.18); 9, diaminopimelate epimerase (E.C. 5.1.1.7); 10, diaminopimelate decarboxylase (E.C. 4.1.1.20).

In one aspect, the engineered chemoautotroph of the present invention produces lysine as the carbon-based product of interest. There are several known lysine biosynthetic pathways. One lysine biosynthesis pathway is depicted in FIG. 19. The reactions in one lysine biosynthetic pathway are catalyzed by the following enzymes: aspartate aminotransferase (E.C. 2.6.1.1; e.g. *E. coli* AspC), aspartate kinase (E.C. 2.7.2.4: e.g., *E. coli* LysC), aspartate semialdehyde dehydrogenase (E.C. 1.2.1.11; e.g., *E. coli* Asd), dihydrodipicolinate synthase (E.C. 4.2.1.52; e.g., *E. coli* DapA), dihydrodipicolinate reductase (E.C. 1.3.1.26; e.g., *E. coli* DapB), tetrahydrodipicolinate succinylase (E.C. 2.3.1.117; e.g., *E. coli* DapD), N-succinyldiaminopimelate-aminotransferase (E.C. 2.6.1.17; e.g., *E. coli* ArgD), N-succinyl-L-diaminopimelate desuccinylase (E.C. 3.5.1.18; e.g., *E. coli* DapE), diaminopimelate epimerase (E.C. 5.1.1.7; *E. coli* DapF), diaminopimelate decarboxylase (E.C. 4.1.1.20; e.g., *E. coli* LysA). In one embodiment, the engineered chemoautotroph of the present invention expresses one or more enzymes from a lysine biosynthetic pathway. For example, one or more exogenous proteins can be selected from aspartate aminotransferase, aspartate kinase, aspartate semialdehyde dehydrogenase, dihydrodipicolinate synthase, dihydrodipicolinate reductase, tetrahydrodipicolinate succinylase, N-succinyldiaminopimelate-aminotransferase, N-succinyl-L-diaminopimelate desuccinylase, diaminopimelate epimerase, diaminopimelate decarboxylase, L,L-diaminopimelate aminotransferase (E.C. 2.6.1.83; e.g., *Arabidopsis thaliana* At4g33680), homocitrate synthase (E.C. 2.3.3.14; e.g., *Saccharomyces cerevisiae* LYS21), homoaconitase (E.C. 4.2.1.36; e.g., *Saccharomyces cerevisiae* LYS4, LYS3), homoisocitrate dehydrogenase (E.C. 1.1.1.87; e.g., *Saccharomyces cerevisiae* LYS12, LYS11, LYS10), 2-aminoadipate transaminase (E.C. 2.6.1.39; e.g., *Saccharomyces cerevisiae* ARO8), 2-aminoadipate reductase (E.C. 1.2.1.31; e.g., *Saccharomyces cerevisiae* LYS2, LYS5), aminoadipate semialdehyde-glutamate reductase (E.C. 1.5.1.10; e.g., *Saccharomyces cerevisiae* LYS9, LYS13), lysine-2-oxoglutarate reductase (E.C.

1.5.1.7; e.g., *Saccharomyces cerevisiae* LYS1). The host organism can also express two or more, three or more, four or more, and the like, including up to all the protein and enzymes that confer lysine biosynthesis.

Production of γ-Valerolactone as the Carbon-Based Product of Interest

Figure 20:
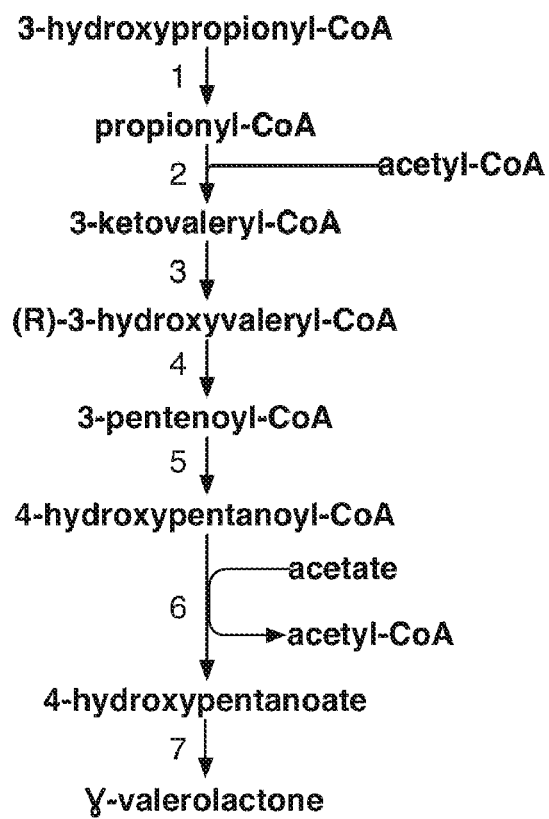
FIG. 20 depicts the metabolic reactions of the γ-valerolactone biosynthetic pathway. Each reaction is numbered. Enzymes catalyzing each reaction are as follows: 1, propionyl-CoA synthase (E.C. 6.2.1.-, E.C. 4.2.1.- and E.C. 1.3.1.-); 2, beta-ketothiolase (E.C. 2.3.1.16); 3, acetoacetyl-CoA reductase (E.C. 1.1.1.36); 4, 3-hydroxybutyryl-CoA dehydratase (E.C. 4.2.1.55); 5, vinylacetyl-CoA Δ-isomerase (E.C. 5.3.3.3); 6, 4-hydroxybutyryl-CoA transferase (E.C. 2.8.3.-); 7, 1,4-lactonase (E.C. 3.1.1.25).

In some embodiments, the engineered chemoautotroph of the present invention is engineered to produce γ-valerolactone as the carbon-based product of interest. One example γ-valerolactone biosynthetic pathway is shown in FIG. 20. In one embodiment, the engineered chemoautotroph is engineered to express one or more of the following enzymes: propionyl-CoA synthase (E.C. 6.2.1.-, E.C. 4.2.1.- and E.C. 1.3.1.-), beta-ketothiolase (E.C. 2.3.1.16; e.g., *Ralstonia eutropha* BktB), acetoacetyl-CoA reductase (E.C. 1.1.1.36; e.g., *Ralstonia eutropha* PhaB), 3-hydroxybutyryl-CoA dehydratase (E.C. 4.2.1.55; e.g., *X. axonopodis* Crt), vinylacetyl-CoA Δ-isomerase (E.C. 5.3.3.3; e.g., *C. difficile* AbfD), 4-hydroxybutyryl-CoA transferase (E.C. 2.8.3.-; e.g., *C. kluyveri* OrfZ), 1,4-lactonase (E.C. 3.1.1.25; e.g., that from *R. norvegicus*). Propionyl-CoA synthase is a multi-functional enzyme that converts 3-hydroxypropionate, ATP and NADPH to propionyl-CoA. Exemplary propionyl-CoA synthases include AAL47820, and homologs thereof. SEQ ID NO:30 represents the *E. coli* codon optimized coding sequence for this propionyl-CoA synthase of the present invention. In one aspect, the invention provides nucleic acid molecule and homologs, variants and derivatives of SEQ ID NO:30. The nucleic acid sequence can have preferably 70%, 71%, 72%, 73%, 74%, 75%, 76%, 77%, 78%, 79%, 80%, 81-85%, 90-95%, 96-98%, 99%, 99.9% or even higher identity to SEQ ID NO:30. The present invention provides nucleic acids each comprising or consisting of a sequence which is a codon optimized version of the wild-type propionyl-CoA synthase gene. In another embodiment, the invention provides a nucleic acid encoding a polypeptide having the amino acid sequence of SEQ ID NO:31.

Integration of Metabolic Pathways into Host Metabolism

The engineered chemoautotrophs of the invention can be produced by introducing expressible nucleic acids encoding one or more of the enzymes or proteins participating in one or more energy conversion, carbon fixation and, optionally, carbon product biosynthetic pathways. Depending on the host organism chosen for conferring a chemoautotrophic capability, nucleic acids for some or all of particular metabolic pathways can be expressed. For example, if a chosen host is deficient in one or more enzymes or proteins for desired metabolic pathways, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve production of desired carbon products from inorganic energy and inorganic carbon. Thus, an engineered chemosutotroph of the invention can be produced by introducing exogenous enzyme or protein activities to obtain desired metabolic pathways or desired metabolic pathways can be obtained by introducing one or more exogenous enzyme or protein activities that, together with one or more endogenous enzymes or proteins, produces a desired product such as reduced cofactors, central metabolites and/or carbon-based products of interest.

Depending on the metabolic pathway constituents of a selected host microbial organism, the engineered chemoautotrophs of the invention can include at least one exogenously expressed metabolic pathway-encoding nucleic acid and up to all encoding nucleic acids for one or more energy conversion, carbon fixation and, optionally, carbon-based product pathways. For example, a RuMP-derived carbon fixation pathway can be established in a host deficient in a pathway enzyme or protein through exogenous expression of the corresponding encoding nucleic acid. In a host deficient in all enzymes or proteins of a metabolic pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a carbon fixation pathway derived from the 3-HPA bicycle can be included, such as the acetyl-CoA carboxylase, malonyl-CoA reductase, propionyl-CoA synthase, propionyl-CoA carboxylase, methylmalonyl-CoA epimerase, methylmalonyl-CoA mutase, succinyl-CoA:(S)-malate CoA transferase, succinate dehydrogenase, fumarate hydratase, (S)-malyl-CoA/β-methylmalyl-CoA/(S)-citramalyl-CoA lyase, mesaconyl-C1-CoA hydratase, mesaconyl-CoA C1-C4 CoA transferase, and mesaconyl-C4-CoA hydratase. Given the teachings and guidance provided herein, those skilled in the art would understand that the number of encoding nucleic acids to introduce in an expressible form can, at least, parallel the metabolic pathway deficiencies of the selected host microbial organism.

Genetic Engineering Methods for Optimization of Metabolic Pathways

In some embodiments, the engineered chemoautotrophs of the invention also can include other genetic modifications that facilitate or optimize production of a carbon-based product from an inorganic energy source and inorganic carbon or that confer other useful functions onto the host organism.

In one aspect, the expression levels of the proteins of interest of the energy conversion pathways, carbon fixation pathways and, optionally, carbon product biosynthetic pathways can be either increased or decreased by, for example, replacing or altering the expression control sequences with alternate expression control sequences encoded by standardized genetic parts. The exogenous standardized genetic parts can regulate the expression of either heterologous or endogenous genes of the metabolic pathway. Altered expression of the enzyme or enzymes and/or protein or proteins of a metabolic pathway can occur, for example, through changing gene position or gene order [Smolke, 2002b], altered gene copy number [Smolke, 2002a], replacement of a endogenous, naturally occurring regulated promoters with constitutive or inducible synthetic promoters, mutation of the ribosome binding sites [Wang. 2009], or introduction of RNA secondary structural elements and/or cleavage sites [Smolke, 2000; Smolke, 2001].

In another aspect, some engineered chemoautotrophs of the present invention may require specific transporters to facilitate uptake of inorganic energy sources and/or inorganic carbon sources. In some embodiments, the engineered chemoautotrophs use formate as an inorganic energy source, inorganic carbon source or both. If formate uptake is limiting for either growth or production of carbon-based products of interest, then expression of one or more formate transporters in the engineered chemoautotroph of the present invention can alleviate this bottleneck. The formate transporters may be heterologous or endogenous to the host organism. Exemplary formate transporters include NP_415424 and NP_416987, and homologs thereof. SEQ ID NO:54 and SEQ ID NO:55 represent *E. coli* codon optimized coding sequence each of these two formate transporters, respectively, of the present invention. The present invention provides nucleic acids each comprising or consisting of a sequence which is a codon optimized version of one of the wild-type malonyl-CoA reductase genes. In another embodiment, the invention provides nucleic acids each encoding a polypeptide having the amino acid sequence of one of NP_415424 and NP_416987.

In addition, the invention provides an engineered chemoautotroph comprising a genetic modification conferring to the engineered chemoautotrophic microorganism an increased efficiency of using inorganic energy and inorganic carbon to produce carbon-based products of interest relative to the microorganism in the absence of the genetic modification. The genetic modification comprises one or more gene disruptions, whereby the one or more gene disruptions increase the efficiency of producing carbon-based products of interest from inorganic energy and inorganic carbon. In one aspect, the one or more gene disruptions target genes encoding competing reactions for inorganic energy, reduced cofactors, inorganic carbon, and/or central metabolites. In another aspect, the one or more gene disruptions target genes encoding competing reactions for intermediates or products of the energy conversion, carbon fixation, and/or carbon product biosynthetic pathways of interest. The competing reactions usually, but not exclusively, arise from metabolism endogenous to the host cell or organism.

A combination of different approaches may be used to identify candidate genetic modifications. Such approaches include, for example, metabolomics (which may be used to identify undesirable products and metabolic intermediates that accumulate inside the cell), metabolic modeling and isotopic labeling (for determining the flux through metabolic reactions contributing to hydrocarbon production), and conventional genetic techniques (for eliminating or substantially disabling unwanted metabolic reactions). For example, metabolic modeling provides a means to quantify fluxes through the cell's metabolic pathways and determine the effect of elimination of key metabolic steps. In addition, metabolomics and metabolic modeling enable better understanding of the effect of eliminating key metabolic steps on production of desired products.

To predict how a particular manipulation of metabolism affects cellular metabolism and synthesis of the desired product, a theoretical framework was developed to describe the molar fluxes through all of the known metabolic pathways of the cell. Several important aspects of this theoretical framework include: (i) a relatively complete database of known pathways, (ii) incorporation of the growth-rate dependence of cell composition and energy requirements, (iii) experimental measurements of the amino acid composition of proteins and the fatty acid composition of membranes at different growth rates and dilution rates and (iv) experimental measurements of side reactions which are known to occur as a result of metabolism manipulation. These new developments allow significantly more accurate prediction of fluxes in key metabolic pathways and regulation of enzyme activity [Keasling, 1999a; Keasling, 1999b; Martin. 2002; Henry, 2006].

Such types of models have been applied, for example, to analyze metabolic fluxes in organisms responsible for enhanced biological phosphorus removal in wastewater treatment reactors and in filamentous fungi producing polyketides [Pramanik, 1997; Pramanik, 1998a; Pramanik, 1998b; Pramanik, 1998c].

In some embodiments, the host organism may have native formate dehydrogenases or other enzymes that consume formate thereby competing with either energy conversion pathways that use formate as an inorganic energy source or carbon fixation pathways that use formate as an inorganic carbon source; hence, these competing formate consumption reactions may be disrupted to increase the efficiency of energy conversion and/or carbon fixation in the engineered chemoautotroph of the present invention. For example, in the host organism $E.$ $coli$, there are three native formate dehydrogenases. Exemplary $E.$ $coli$ formate dehydrogenase genes for disruption include fdnG, fdnH, ftnI, fdoI, fdoH, fdoG and/or fdhF. Alternatively, since all three native formate dehydrogenases in $E.$ $coli$ require selenium and only those three enzymes require selenium, in a preferred embodiment, genes for selenium uptake and/or biosynthesis of selenocysteine, such as selA, selB, selC, and/or selD, are disrupted.

In other embodiments, the host organism may have native hydrogenases or other enzymes that consume molecular hydrogen thereby competing with energy conversion pathways that use hydrogen as an inorganic energy source. For example, in the host organism $E.$ $coli$, there are four native hydrogenases although the fourth is not expressed to significant levels [Self, 2004]. Exemplary $E.$ $coli$ formate hydrogenase genes for disruption include hyaB, hybC, hycE, hyfG and fhlA. In another embodiment, a particular strain of the host organism can be selected that specifically lacks the competing reactions typical found in the species. For example, $E.$ $coli$ B strain BL21(DE3) lacks formate and hydrogenase metabolism unlike $E.$ $coli$ K strains [Pinske, 2011].

In some embodiments, the host organism may have metabolic reactions that compete with reactions of the carbon fixation pathways in the engineered chemoautotroph of the present invention. For example, in the host organism $E.$ $coli$, the tricarboxylic acid cycle generally runs in the oxidative direction during aerobic growth and as a split reductive and oxidative branches during anaerobic growth. Hence, $E.$ $coli$ has several endogenous reactions that may compete with desired reactions of an rTCA-derived carbon fixation pathway. Exemplary $E.$ $coli$ enzymes whose function are candidates for disruption include citrate synthase (competes with reaction 1 in FIG. 3), 2-oxoglutarate dehydrogenase (competes with reaction 6), isocitrate dehydrogenase (may compete with desired flux for reaction 7), isocitrate dehydrogenase phosphatase (competes with reaction 8), pyruvate dehydrogenase (competes with reaction 9).

In another aspect, some engineered chemoautotrophs of the present invention may require alterations to the pool of intracellular reducing cofactors for efficient growth and/or production of the carbon-based product of interest from inorganic energy and inorganic carbon. In some embodiments, the total pool of NAD+/NADH in the engineered chemoautotroph is increased or decreased by adjusting the expression level of nicotinic acid phosphoribosyltransferase (E.C. 2.4.2.11). Over-expression of either the $E.$ $coli$ or $Salmonella$ gene pncB which encodes nicotinic acid phosphoribosyltransferase has been shown to increase total NAD+/NADH levels in $E.$ $coli$ [Wubbolts, 1990; Berrios-River, 2002; San, 2002]. In another embodiment, the availability of intracellular NADPH can be also altered by modifying the engineered chemoautotroph to express an NADH:NADPH transhydrogenase [Sauer, 2004; Chin, 2011]. In another embodiment, the total pool of ubiquinone in the engineered chemoautotroph is increased or decreased by adjusting the expression level of ubiquinone biosynthetic enzymes, such as p-hydroxybenzoate-polyprenyl pyrophosphate transferase and polyprenyl pyrophosphate synthetase.

Overexpression of the corresponding E. coli genes uhiA and ispB increased the ubiquinone pool in E. coli [Zhu, 1995]. In another embodiment, the level of the redox cofactor ferredoxin in the engineered chemoautotroph can be increased or decreased by changing the expression control sequences that regulate its expression.

In another aspect, in addition to an inorganic energy and carbon source, some engineered chemoautotrophs may require a specific nutrients or vitamin(s) for growth and/or production of carbon-based products of interest. For example, hydroxocobalamin, a vitamer of vitamin B12, is a cofactor for particular enzymes of the present invention, such as methylmalonyl-CoA mutase (E.C. 5.4.99.2). Required nutrients are generally supplemented to the growth media during bench scale propagation of such organisms. However, such nutrients can be prohibitively expensive in the context of industrial scale bio-processing. In one embodiment of the present invention, the host cell is selected from an organism that naturally produces the required nutrient(s), such as $Salmonella\ enterica$ or $Pseudomonas\ denitrificans$ which naturally produces hydroxocobalamin. In an alternate embodiment, the need for a vitamin is obviated by modifying the engineered chemoautotroph to express a vitamin biosynthesis pathway [Roessner, 1995]. An exemplary biosynthesis pathway for hydroxocobalamin comprises the following enzymes: uroporphyrin-III C-methyltransferase (E.C. 2.1.1.107), precorrin-2 cobaltochelatase (E.C. 4.99.1.3), cobalt-precorrin-2 ($C^{20}$)-methyltransferase (E.C. 2.1.1.151), cobalt-precorrin-3 ($C^{17}$)-methyltransferase (E.C. 2.1.1.131), cobalt precorrin-4 ($C^{11}$)-methyltransferase (E.C. 2.1.1.133), cobalt-precorrin 5A hydrolase (E.C. 3.7.1.12), cobalt-precorrin-5B ($C^{11}$)-methyltransferase (E.C. 2.1.1.195), cobalt-precorrin-6A reductase, cobalt-precorrin-6V ($C^5$)-methyltransferase (E.C. 2.1.1.-), cobalt-precorrin-7 ($C^{15}$)-methyltransferase (decarboxylating) (E.C. 2.1.1.196), cobalt-precorrin-8X methylmutase, cobyrinate A,C-diamide synthase (E.C. 6.3.5.11), cob(II)yrinate a,c-diamide reductase (E.C. 1.16.8.1), cob(I)yrinic acid a,c-diamide adenosyltransferase (E.C. 2.5.1.17), adenosylcobyrate synthase (E.C. 6.3.5.10), adenosylcobinamide phosphate synthase (E.C. 6.3.1.10), GTP:adenosylcobinamide-phosphate guanylyltransferase (E.C. 2.7.7.62), nicotinate-nucleotide dimethylbenzimidazole phosphoribosyltransferase (E.C. 2.4.2.21), adenosylcobinamide-GDP:α-ribazole-5-phosphate ribazoletransferase (E.C. 2.7.8.26) and adenosylcobalamine-5'-phosphate phosphatase (E.C. 3.1.3.73). In addition, to allow for cobalt uptake and incorporation into vitamin B12, the genes encoding the cobalt transporter are overexpressed. The exemplary cobalt transporter protein found in $Salmonella\ enterica$ is overexpressed and is encoded by proteins ABC-type $Co^{2+}$ transport system, permease component (CbiM, NP_460968), ABC-type cobalt transport system, periplasmic component (CbiN, NP_460967), and ABC-type cobalt transport system, permease component (CbiQ, NP_461989).

In some embodiments, the intracellular concentration (e.g., the concentration of the intermediate in the engineered chemosutotroph) of the metabolic pathway intermediate can be increased to further boost the yield of the final product. For example, by increasing the intracellular amount of a substrate (e.g., a primary substrate) for an enzyme that is active in the metabolic pathway, and the like.

In another aspect, the carbon-based products of interest are or are derived from the intermediates or products of fatty acid biosynthesis. To increase the production of waxes/fatty acid esters, and fatty alcohols, one or more of the enzymes of fatty acid biosynthesis can be over expressed or mutated to reduce feedback inhibition. Additionally, enzymes that metabolize the intermediates to make nonfatty-acid based products (side reactions) can be functionally deleted or attenuated to increase the flux of carbon through the fatty acid biosynthetic pathway thereby enhancing the production of carbon-based products of interest.

Growth-Based Selection Methods for Optimization of Engineered Carbon-Fixing Strains Selective pressure provides a valuable means for testing and optimizing the engineered chemoautotrophs of the present invention. In some embodiments, the engineered chemoautotrophs of the invention can be evolved under selective pressure to optimize production of a carbon-based product from an inorganic energy source and inorganic carbon or that confer other useful functions onto the host organism. The ability of an optimized engineered chemoautotroph to replicate more rapidly than unmodified counterparts confirms the utility of the optimization. Similarly, the ability to survive and replicate in media lacking a required nutrient, such as vitamin B12, confirms the successful implementation of a nutrient biosynthetic module. In some embodiments, the engineered chemoautotrophs can be cultured in the presence of inorganic energy source(s), inorganic carbon and a limiting amount of organic carbon. Over time, the amount of organic carbon present in the culture media is decreased in order to select for evolved strains that more efficiently utilize the inorganic energy and carbon.

Evolution can occur as a result of either spontaneous, natural mutation or by addition of mutagenic agents or conditions to live cells. If desired, additional genetic variation can be introduced prior to or during selective pressure by treatment with mutagens, such as ultra-violet light, alkylators [e.g., ethyl methanesulfonate (EMS), methyl methane sulfonate (MMS), diethylsulfate (DES), and nitrosoguanidine (NTG, NG, MMG)], DNA intercalcators (e.g., ethidium bromide), nitrous acid, base analogs, bromouracil, transposonsm and the like. The engineered chemoautotrophs can be propagated either in serial batch culture or in a turbidostat as a controlled growth rate.

Alternately or in addition to selective pressure, pathway activity can be monitored following growth under permissive (i.e., non-selective) conditions by measuring specific product output via various metabolic labeling studies (including radioactivity), biochemical analyses (Michaelis-Menten), gas chromatography-mass spectrometry (GC/MS), mass spectrometry, matrix assisted laser desorption ionization time-of-flight mass spectrometry (MALDI-TOF), capillary electrophoresis (CE), and high pressure liquid chromatography (HPLC).

To generate engineered chemoautrophs with improved yield of central metabolites and/or carbon-based products of interest, metabolic modeling can be utilized to guide strain optimization. Modeling analysis allows reliable predictions of the effects on cell growth of shifting the metabolism towards more efficient production of central metabolites or products derived from central metabolites. Modeling can also be used to design gene knockouts that additionally optimize utilization of the energy conversion, carbon fixation and carbon product biosynthetic pathways. In some embodiments, modeling is used to select growth conditions that create selective pressure towards uptake and utilization of inorganic energy and inorganic carbon. An in silico stoichiometric model of host organism metabolism and the metabolic pathway(s) of interest can be constructed (see, for example, a model of the E. coli metabolic network [Edwards, 2002]). The resulting model can be used to compute phenotypic phase planes for the engineered chemoautotrophs of the present invention. A phenotypic phase plane is a portrait of the accessible growth states of an engineered chemoautotroph as a function of imposed substrate uptake rates. A particular engineered chemoautotroph, at particular uptake rates for limiting nutrients, may not grow as well as the phenotypic phase plane predicts, but no strain should be able to grow better than indicated by the phenotypic phase plane. Under a variety of circumstances, it has been shown the modified *E. coli* strains evolve towards, and then along, the phenotypic phase plane, always in the direction of increasing growth rates [Fong, 2004]. Thus, a phenotypic phase plane can be viewed as a landscape of selective pressure. Strains in an environment where a given nutrient uptake is positively correlated with growth rate are predicted to evolve towards increased nutrient uptake. Conversely, strains in an environment where nutrient uptake are inversely correlated with growth rate are predicted to evolve away from nutrient uptake.

Fermentation Conditions

The engineered chemoautotrophs of the present invention are cultured in a medium comprising inorganic energy source(s), inorganic carbon source(s) and any required nutrients. The culture conditions can include, for example, liquid culture procedures as well as fermentation and other large scale culture procedures.

The production and isolation of carbon-based products of interest can be enhanced by employing specific fermentation techniques. One method for maximizing production while reducing costs is increasing the percentage of the carbon that is converted to carbon-based products of interest. During normal cellular lifecycles carbon is used in cellular functions including producing lipids, saccharides, proteins, organic acids, and nucleic acids. Reducing the amount of carbon necessary for growth-related activities can increase the efficiency of carbon source conversion to output. This can be achieved by first growing engineered chemoautotrophs to a desired density, such as a density achieved at the peak of the log phase of growth. At such a point, replication checkpoint genes can be harnessed to stop the growth of cells. Specifically, quorum sensing mechanisms [Camilli, 2006; Venturi, 2006; Reading, 2006] can be used to activate genes such as p53, p21, or other checkpoint genes. Genes that can be activated to stop cell replication and growth in *E. coli* include umuDC genes, the over-expression of which stops the progression from stationary phase to exponential growth [Murli, 2000]. UmuC is a DNA polymerase that can carry out translesion synthesis over non-coding lesions—the mechanistic basis of most UV and chemical mutagenesis. The umuDC gene products are used for the process of translesion synthesis and also serve as a DNA damage checkpoint. UmuDC gene products include UmuC, UmuD, umuD', UmuD'$_2$C, UmuD'$_2$ and UmUD$_2$. Simultaneously, the carbon product biosynthetic pathway genes are activated, thus minimizing the need for replication and maintenance pathways to be used while the carbon-based product of interest is being made.

Alternatively, cell growth and product production can be achieved simultaneously. In this method, cells are grown in bioreactors with a continuous supply of inputs and continuous removal of product. Batch, fed-batch, and continuous fermentations are common and well known in the art and examples can be found in [Brock, 1989; Deshpande, 1992].

In a preferred embodiment, the engineered chemoautotroph is engineered such that the final product is released from the cell. In embodiments where the final product is released from the cell, a continuous process can be employed. In this approach, a reactor with organisms producing desirable products can be assembled in multiple ways. In one embodiment, the reactor is operated in bulk continuously, with a portion of media removed and held in a less agitated environment such that an aqueous product can self-separate out with the product removed and the remainder returned to the fermentation chamber. In embodiments where the product does not separate into an aqueous phase, media is removed and appropriate separation techniques (e.g., chromatography, distillation, etc.) are employed.

In an alternate embodiment, the product is not secreted by the engineered chemoautotrophs. In this embodiment, a batch-fed fermentation approach is employed. In such cases, cells are grown under continued exposure to inputs (inorganic energy and inorganic carbon) as specified above until the reaction chamber is saturated with cells and product. A significant portion to the entirety of the culture is removed, the cells are lysed, and the products are isolated by appropriate separation techniques (e.g., chromatography, distillation, filtration. centrifugation, etc.).

In certain embodiments, the engineered chemoautotrophs of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. It is highly desirable to maintain anaerobic conditions in the fermenter to reduce the cost of the overall process.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

In another embodiment, the engineered chemoautotrophs can be cultured in the presence of an electron acceptor, for example, nitrate, in particular under substantially anaerobic conditions. It is understood that an appropriate amount of nitrate can be added to a culture to achieve a desired increase in biomass, for example, 1 mM to 100 mM nitrate, or lower or higher concentrations, as desired, so long as the amount added provides a sufficient amount of electron acceptor for the desired increase in biomass. Such amounts include, but are not limited to, 5 mM, 10 mM, 15 mM, 20 mM, 25 mM, 30 mM, 40 mM, 50 mM, as appropriate to achieve a desired increase in biomass.

In some embodiments, the engineered chemoautotrophs of the present invention are initially grown in culture conditions with a limiting amount of organic carbon to facilitate growth. Then, once the supply of organic carbon is exhausted, the engineered chemoautotrophs transition from heterotrophic to autotrophic growth relying on energy from an inorganic energy sources to fix inorganic carbon in order to produce carbon-based products of interest. The organic carbon can be, for example, a carbohydrate source. Such sources include, for example, sugars such as glucose, xylose, arabinose, galactose, mannose, fructose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art would understand that renewable feedstocks and biomass other than those exemplified above also can be used for culturing the engineered chemoautotrophs of the invention. In some embodiments, the engineered chemoautotrophs are optimized for a two stage fermentation by regulating the expression of the carbon product biosynthetic pathway.

In one aspect, the percentage of input carbon atoms converted to hydrocarbon products is an efficient and inexpensive process. Typical efficiencies in the literature are ~<5%. Engineered chemoautotrophs which produce hydrocarbon products can have greater than 1, 3, 5, 10, 15, 20, 25, and 30% efficiency. In one example engineered chemoautotrophs can exhibit an efficiency of about 10% to about 25%. In other examples, such microorganisms can exhibit an efficiency of about 25% to about 30%, and in other examples such engineered chemoautotrophs can exhibit >30% efficiency.

In some examples where the final product is released from the cell, a continuous process can be employed. In this approach, a reactor with engineered chemoautrophs producing for example, fatty acid derivatives, can be assembled in multiple ways. In one example, a portion of the media is removed and allowed to separate. Fatty acid derivatives are separated from the aqueous layer, which can in turn, be returned to the fermentation chamber.

In another example, the fermentation chamber can enclose a fermentation that is undergoing a continuous reduction. In this instance, a stable reductive environment can be created. The electron balance would be maintained by the release of oxygen. Efforts to augment the NAD/H and NADP/H balance can also facilitate in stabilizing the electron balance.

Consolidated Chemoautotrophic Fermentation

The above aspect of the invention is an alternative to directly producing final carbon-based product of interest as a result of chemoautotrophic metabolism. In this approach, carbon-based products of interest would be produced by leveraging other organisms that are more amenable to making any one particular product while culturing the engineered chemoautotroph for its carbon source. Consequently, fermentation and production of carbon-based products of interest can occur separately from carbon source production in a bioreactor.

In one aspect, the methods of producing such carbon-based products of interest include two steps. The first-step includes using engineered chemoautotrophs to convert inorganic carbon to central metabolites or sugars such as glucose. The second-step is to use the central metabolites or sugars as a carbon source for cells that produce carbon-based products of interest. In one embodiment, the two-stage approach comprises a bioreactor comprising engineered chemoautotrophs; a second reactor comprising cells capable of fermentation; wherein the engineered chemoautotrophs provides a carbon source such as glucose for cells capable of fermentation to produce a carbon-based product of interest. The second reactor may comprise more than one type of microorganism. The resulting carbon-based products of interest are subsequently separated and/or collected.

Preferably, the two steps are combined into a single-step process whereby the engineered chemoautotrophs convert inorganic energy and inorganic carbon and directly into central metabolites or sugars such as glucose and such organisms are capable of producing a variety of carbon-based products of interest.

The present invention also provides methods and compositions for sustained glucose production in engineered chemoautotrophs wherein these or other organisms that use the sugars are cultured using inorganic energy and inorganic carbon for use as a carbon source to produce carbon-based products of interest. In such embodiments, the host cells are capable of secreting the sugars, such as glucose from within the cell to the culture media in continuous or fed-batch in a bioreactor.

Certain changes in culture conditions of engineered chemoautotrophs for the production of sugars can be optimized for growth. For example, conditions are optimized for inorganic energy source(s) and their concentration(s), inorganic carbon source(s) and their concentration(s), electron acceptor(s) and their concentrations, addition of supplements and nutrients. As would be apparent to those skilled in the art, the conditions sufficient to achieve optimum growth can vary depending upon location, climate, and other environmental factors, such as the temperature, oxygen concentration and humidity. Other adjustments may be required, for example, an organism's ability for carbon uptake. Increased inorganic carbon, such as in the form of carbon dioxide, may be introduced into a bioreactor by a gas sparger or aeration devices.

Advantages of consolidated chemoautotrophic fermentation include a process where there is separation of chemical end products, e.g., glucose, spatial separation between end products (membranes) and time. Additionally, unlike traditional or cellulosic biomass to biofuels production, pretreatment, saccharification and crop plowing are obviated.

The consolidated chemoautrophic fermentation process produces continuous products. In preferred embodiments, the process involves direct conversion of inorganic energy and inorganic carbon to product from engineered front-end organisms to produce various products without the need to lyse the organisms. For instance, the organisms can utilize 3PGAL to make a desired fermentation product, e.g., ethanol. Such end products can be readily secreted as opposed to intracellular products such as oil and cellulose. In yet other embodiments, organisms produce sugars, which are secreted into the media and such sugars are used during fermentation with the same or different organisms or a combination of both.

Processing and Separation of Carbon-Based Products of Interest

The carbon-based products produced by the engineered chemoautotrophs during fermentation can be separated from the fermentation media. Known techniques for separating fatty acid derivatives from aqueous media can be employed. One exemplary separation process provided herein is a two-phase (bi-phasic) separation process. This process involves fermenting the genetically-engineered production hosts under conditions sufficient to produce for example, a fatty acid, allowing the fatty acid to collect in an organic phase and separating the organic phase from the aqueous fermentation media. This method can be practiced in both a batch and continuous fermentation setting.

Bi-phasic separation uses the relative immisciblity of fatty acid to facilitate separation. A skilled artisan would appreciate that by choosing a fermentation media and the organic phase such that the fatty acid derivative being produced has a high log P value, even at very low concentrations the fatty acid can separate into the organic phase in the fermentation vessel.

When producing fatty acids by the methods described herein, such products can be relatively immiscible in the fermentation media, as well as in the cytoplasm. Therefore, the fatty acid can collect in an organic phase either intracellularly or extracellularly. The collection of the products in an organic phase can lessen the impact of the fatty acid derivative on cellular function and allows the production host to produce more product.

The fatty alcohols, fatty acid esters, waxes, and hydrocarbons produced as described herein allow for the production of homogeneous compounds with respect to other compounds wherein at least 50%, 60%, 70%, 80%, 90%, or 95% of the fatty alcohols, fatty acid esters, waxes and hydrocarbons produced have carbon chain lengths that vary by less than 4 carbons, or less than 2 carbons. These compounds can also be produced so that they have a relatively uniform degree of saturation with respect to other compounds, for example at least 50%, 60%, 70%, 80%, 90%, or 95% of the fatty alcohols, fatty acid esters, hydrocarbons and waxes are mono-, di-, or tri-unsaturated.

Detection and Analysis

Generally, the carbon-based products of interest produced using the engineered chemoautotrophs described herein can be analyzed by any of the standard analytical methods, e.g., gas chromatography (GC), mass spectrometry (MS) gas chromatography-mass spectrometry (GCMS), and liquid chromatography-mass spectrometry (LCMS), high performance liquid chromatography (HPLC), capillary electrophoresis, Matrix-Assisted Laser Desorption Ionization time-of-flight mass spectrometry (MALDI-TOF MS), nuclear magnetic resonance (NMR), near-infrared (NIR) spectroscopy, viscometry [Knothe, 1997; Knothe, 1999], titration for determining free fatty acids [Komers, 1997], enzymatic methods [Bailer, 1991], physical property-based methods, wet chemical methods, etc.

Carbon Fingerprinting

Biologically-produced carbon-based products, e.g., ethanol, fatty acids, alkanes, isoprenoids, represent a new commodity for fuels, such as alcohols, diesel and gasoline. Such biofuels have not been produced using biomass but use carbon dioxide as its carbon source. These new fuels may be distinguishable from fuels derived form petrochemical carbon on the basis of carbon-isotopic fingerprinting. Such products, derivatives, and mixtures thereof may be completely distinguished from their petrochemical derived counterparts on the basis of $^{14}C$ (fM) and carbon-isotopic fingerprinting, indicating new compositions of matter.

There are three naturally occurring isotopes of carbon: $^{12}C$, $^{13}C$, and $^{14}C$. These isotopes occur in above-ground total carbon at fractions of 0.989, 0.011, and $10^{12}$, respectively. The isotopes $^{12}C$ and $^{13}C$ are stable, while $^{14}C$ decays naturally with a half-life of 5730 years to $^{14}N$, a beta particle, and an anti-neutrino. The isotope $^{14}C$ originates in the atmosphere, due primarily to neutron bombardment of $^{14}N$ caused ultimately by cosmic radiation. Because of its relatively short half-life (in geologic terms), $^{14}C$ occurs at extremely low levels in fossil carbon. Over the course of 1 million years without exposure to the atmosphere, just 1 part in $10^{50}$ will remain $^{14}C$.

The $^{13}C:^{12}C$ ratio varies slightly but measurably among natural carbon sources. Generally these differences are expressed as deviations from the $^{13}C:^{12}C$ ratio in a standard material. The international standard for carbon is Pee Dee Belemnite, a form of limestone found in South Carolina, with a $^{13}C$ fraction of 0.0112372. For a carbon source a, the deviation of the $^{13}C:^{12}C$ ratio from that of Pee Dee Belemnite is expressed as:

$\delta_a = (R_a/R_s) - 1$, where $R_a = {}^{13}C:^{12}C$ ratio in the natural source, and $R_z = {}^{13}C:^{12}C$ ratio in Pee Dee Belemnite, the standard.

For convenience, $\delta_a$ is expressed in parts per thousand, or ‰. A negative value of $\delta_a$ shows a bias toward $^{12}C$ over $^{13}C$ as compared to Pee Dee Belemnite. Table 2 shows $\delta_a$ and $^{13}C$ fraction for several natural sources of carbon.

TABLE 2

$^{13}C:^{12}C$ variations in natural carbon sources

| Source | $-\delta_a$ (‰) | References |
| --- | --- | --- |
| Underground coal | 32.5 | [Farquhar, 1989] |
| Fossil fuels | 26 | [Farquhar, 1989] |
| Ocean DIC* | 0-1.5 | [Goericke, 1994; Ivlev, 2010] |
| Atmospheric $CO_2$ | 6-8 | [Ivlev, 2010; Farquhar, 1989] |
| Freshwater DIC* | 6-14 | [Dettman, 1999] |
| Pee Dee Belemnite | 0 | [Ivlev, 2010] |

*DIC = dissolved inorganic carbon.

Biological processes often discriminate among carbon isotopes. The natural abundance of $^{14}C$ is very small, and hence discrimination for or against $^{14}C$ is difficult to measure. Biological discrimination between $^{13}C$ and $^{12}C$, however, is well-documented. For a biological product p, we can define similar quantities to those above:

$\delta_p = (R_p/R_s) - 1$, where $R_p = {}^{13}C:^{12}C$ ratio in the biological product, and $R_s = {}^{13}C:^{12}C$ ratio in Pee Dee Belemnite, the standard.

Table 3 shows measured deviations in the $^{13}C:^{12}C$ ratio for some biological products that arise from carbon fixation by the Calvin cycle. Other carbon fixation pathways provide different "fingerprint" $^{13}C:^{12}C$ ratios.

TABLE 3

$^{13}C:^{12}C$ variations in selected biological products.

| Product | $-\delta_p$ (‰) | $-$epsilon (‰)* | References |
| --- | --- | --- | --- |
| Plant sugar/starch from atmospheric $CO_2$ | 18-28 | 10-20 | [Ivlev, 2010] |
| Cyanobacterial biomass from marine DIC | 18-31 | 16.5-31 | [Goericke, 1994; Sakata, 1997] |
| Cyanobacterial lipid from marine DIC | 39-40 | 37.5-40 | [Sakata, 1997] |
| Algal lipid from marine DIC | 17-28 | 15.5-28 | [Goericke, 1994; Abelseon, 1961] |
| Algal biomass from freshwater DIC | 17-36 | 3-30 | [Marty, 2008] |
| E. coli lipid from plant sugar | 15-27 | near 0 | [Monson, 1980] |
| Cyanobacterial lipid from fossil carbon | 63.5-66 | 37.5-40 | — |
| Cyanobacterial biomass from fossil carbon | 42.5-57 | 16.5-31 | — |

*epsilon = fractionation by a biological process in its utilization of $^{12}C$ versus $^{13}C$ (see text)

Table 3 introduces a new quantity, epsilon. This is the discrimination by a biological process in its utilization of $^{12}C$ vs. $^{13}C$. We define epsilon as follows: epsilon= $(R_p/R_a)-1$.

This quantity is very similar to $\delta_a$ and $\delta_p$, except we now compare the biological product directly to the carbon source rather than to a standard. Using epsilon, we can combine the bias effects of a carbon source and a biological process to obtain the bias of the biological product as compared to the standard. Solving for $\delta_p$, we obtain: $\delta_p=($epsilon$)(\delta_a)+$epsilon$+\delta_a$, and, because (epsilon)$(\delta_a)$ is generally very small compared to the other terms, $\delta_p \approx \delta_a+$epsilon.

For a biological product having a production process with a known epsilon, we may therefore estimate $\delta_p$ by summing $\delta_a$ and epsilon. We assume that epsilon operates irrespective of the carbon source.

This has been done in Table 3 for cyanobacterial lipid and biomass produced from fossil carbon. As shown in the Tables above, cyanobacterial products made from fossil carbon (in the form of, for example, flue gas or other emissions) can have a higher $\delta_p$ than those of comparable biological products made from other sources, distinguishing them on the basis of composition of matter from these other biological products. In addition, any product derived solely from fossil carbon can have a negligible fraction of $^{14}C$, while products made from above-ground carbon can have a $^{14}C$ fraction of approximately $10^{-12}$.

Accordingly, in certain aspects, the invention provides various carbon-based products of interest characterized as $-\delta_p$(‰) of about 63.5 to about 66 and $-$epsilon(‰) of about 37.5 to about 40. For carbon-based products that are derived from engineered autotrophs that make use of carbon fixation pathways other than the Calvin cycle, epsilon, and thus $\delta_p$ can vary, as previously described [Hayes, 2001].

Sequences Provided by the Invention

Table 4 provides a summary of SEQ ID NOs:1-60 disclosed herein.

TABLE 4

Sequences

| SEQ ID NO | Sequence |
| --- | --- |
| 1 | Codon optimized *Burkholderia stabilis* NADP$^+$ FDH gene |
| 2 | Codon optimized *Candida methylica* NAD$^+$ FDH gene |
| 3 | Codon optimized *Candida boidinii* NAD$^+$ FDH gene |
| 4 | Codon optimized *Saccharomyces cerevisiae* S288c NAD$^+$ FDH gene |
| 5 | *Clostridium pasteurianum* putative ferredoxin-FDH FdhF subunit amino acid sequence |
| 6 | *Clostridium pasteurianum* putative ferredoxin-FDH FdhD subunit amino acid sequence |
| 7 | *Clostridium pasteurianum* putative FDH-associated ferredoxin domain containing protein 1 amino acid sequence |
| 8 | *Clostridium pasteurianum* putative FDH-associated ferredoxin domain containing protein 2 amino acid sequence |
| 9 | Codon optimized *Aquifex aeolicus* VF5 SQR gene |
| 10 | Codon optimized *Nostoc* sp. PCC 7120 SQR gene |
| 11 | Codon optimized *Chlorobium tepidum* TLS SQR gene |
| 12 | Codon optimized *Acidithiobacillus ferrooxidans* ATCC 23270 SQR gene |
| 13 | Codon optimized *Allochromatium vinosum* DSM 180 SQR gene |
| 14 | Codon optimized *Rhodobacter capsulatus* SB 1003 SQR gene |
| 15 | Codon optimized *Thiobacillus denitrificans* ATCC 25259 SQR gene |
| 16 | Codon optimized *Magnetococcus* sp. MC-1 SQR gene |
| 17 | Codon optimized *Clostridium pasteurianum* ferredoxin gene |
| 18 | Codon optimized *Hydrogenobacter thermophilus* TK-6 fdx1 gene |
| 19 | Codon optimized *Hydrogenobacter thermophilus* TK-6 fdx2 gene |
| 20 | Codon optimized *Methanosarcina barkeri* str. Fusaro ferredoxin gene |
| 21 | Codon optimized *Aquifex aeolicus* fdx7 gene |
| 22 | *Aquifex aeolicus* fdx7 amino acid sequence |
| 23 | Codon optimized *Aquifex aeolicus* fdx6 gene |
| 24 | *Aquifex aeolicus* fdx6 amino acid sequence |
| 25 | Codon optimized gamma-proteobacterium NOR51-B MCR gene |
| 26 | Codon optimized *Roseiflexus castenholzii* DSM 13941 MCR gene |
| 27 | Codon optimized marine gamme proteobacterium HTCC2080 MCR gene |
| 28 | Codon optimized *Erythrobacter* sp. NAP1 MCR gene |
| 29 | Codon optimized *Chloroflexus aurantiacus* J-10-fl MCR gene |
| 30 | Codon optimized *Chloroflexus aurantiacus* PCS gene |
| 31 | *Chloroflexus aurantiacus* PCS amino acid sequence |
| 32 | Codon optimized *Metallosphaera sedula* PccB gene |
| 33 | Codon optimized *Metallosphaera sedula* AccC gene |
| 34 | Codon optimized *Metallosphaera sedula* AccB gene |
| 35 | Codon optimized *Nitrosopumilus maritimus* SCM1 PccB gene |
| 36 | Codon optimized *Nitrosopumilus maritimus* SCM1 AccC gene |
| 37 | Codon optimized *Nitrosopumilus maritimus* SCM1 AccB gene |
| 38 | Codon optimized *Cenarchaeum symbiosum* A PccB gene |
| 39 | Codon optimized *Cenarchaeum symbiosum* A AccC gene |
| 40 | Codon optimized *Cenarchaeum symbiosum* A AccB gene |
| 41 | Codon optimized *Halobacterium* sp. NRC-1 PccB gene 1 |
| 42 | Codon optimized *Halobacterium* sp. NRC-1 PccB gene 2 |
| 43 | Codon optimized *Halobacterium* sp. NRC-1 AccC gene 1 |
| 44 | Codon optimized *Halobacterium* sp. NRC-1 AccC gene 2 |
| 45 | Codon optimized *Halobacterium* sp. NRC-1 AccB gene |
| 46 | Codon optimized *Methylococcus capsulatus* str. Bath HPS gene 1 |
| 47 | Codon optimized *Methylococcus capsulatus* str. Bath HPS gene 2 |
| 48 | Codon optimized *Methylococcus capsulatus* str. Bath PHI gene |
| 49 | Codon optimized *Mycobacterium gastri* MB19 HPS-PHI fusion gene |

TABLE 4-continued

Sequences

| SEQ ID NO | Sequence |
|---|---|
| 50 | *Mycobacterium gastri* MB19 HPS-PHI fusion amino acid sequence |
| 51 | Codon optimized *Synechococcus elongatus* PCC 7942 GAPDH gene |
| 52 | Codon optimized *Synechococcus elongatus* PCC 7942 SBPase gene |
| 53 | Codon optimized *Synechococcus elongatus* PCC 7942 PRK gene |
| 54 | Codon optimized *Escherichia coli* FocA gene |
| 55 | Codon optimized *Escherichia coli* FocB gene |
| 56 | Plasmid 2430 |
| 57 | Plasmid 2429 |
| 58 | Plasmid 4767 |
| 59 | Plasmid 4768 |
| 60 | Plasmid 4986 |
| 61 | Codon optimized *Escherichia coli* ACS gene |
| 62 | Codon optimized *Listeria monocytogenes* ADH gene |
| 63 | Plasmid 9463 |
| 64 | Plasmid 9462 |
| 65 | Plasmid 20566 |
| 66 | Plasmid 27439 |

EXAMPLES

The examples below are provided herein for illustrative purposes and are not intended to be restrictive.

Example 1: Identification and Selection of Candidate Sulfide:Quinone Oxidoreductase Enzymes To identify candidate sulfide-quinone oxidoreductases (SQR) for the energy conversion pathway that uses hydrogen sulfide as an inorganic energy source, the *Rhodobacter capsulatus* SQR was selected as the model enzyme. The *R. capsulatus* SQR has been functionally expressed in the heterologous host *E. coli* [Schtütz, 1997] and demonstrated to reduce ubiquinone [Shibata, 2001]. A search of the NCBI Protein Clusters database was performed using the search term "sulfide quinone reductase" and 17 different protein clusters were identified as of Feb. 1, 2011 (CLSK2755575, CLSK2397089, CLSK2336986, CLSK2302249, CLSK2299965, CLSK943035, CLSK940594, CLSK917086, CLSK903971. CLSK892907, CLSK884384, CLSK871744, CLSK871685, CLSK870501, CLSK785404, CLSK767599, CLSK724710). The 17 protein clusters comprised 203 putative SQRs which were subsequently aligned using MUSCLE 3.8.31 using sequence YP_003443063 as an outgroup. The resulting alignment was imported into Gencious Pro 5.3.6 and a tree was made using a neighbor-joining method. Based on the alignment, any sequences containing less than four of six conserved residues were eliminated from the set. The six conserved residues were three conserved cysteines, two conserved histidines thought to be involved n quinone binding and the absence of a conserved aspartate that is characteristic of all glutathion reductase family of flavoproteins with the exception of SQRs [Griesbeck, 2000]. The resulting sequences were realigned using MUSCLE and a new tree was made. Representative sequences from each clade were selected as candidate SQRs.

Example 2: Engineered *E. coli* that Transfer Electrons from Formate to NADH or NADPH Plasmids comprising a high copy number replication origin, chloramphenicol resistance marker and each of two different codon-optimized formate dehydrogenase (fdh) genes under the control of an rrnB-derived constitutive promoter were constructed using DNA assembly methods described in WO2010/070295. The resulting plasmids 2430 (SEQ ID NO:56) and 2429 (SEQ ID NO:57) and transformed into *E. coli* using standard plasmid transformation techniques. As a negative control, an expression plasmid without any fdh gene was also constructed. As a positive control, purified $NAD^+$-dependent FDH enzyme obtained from commercial sources was used.

Figure 21:
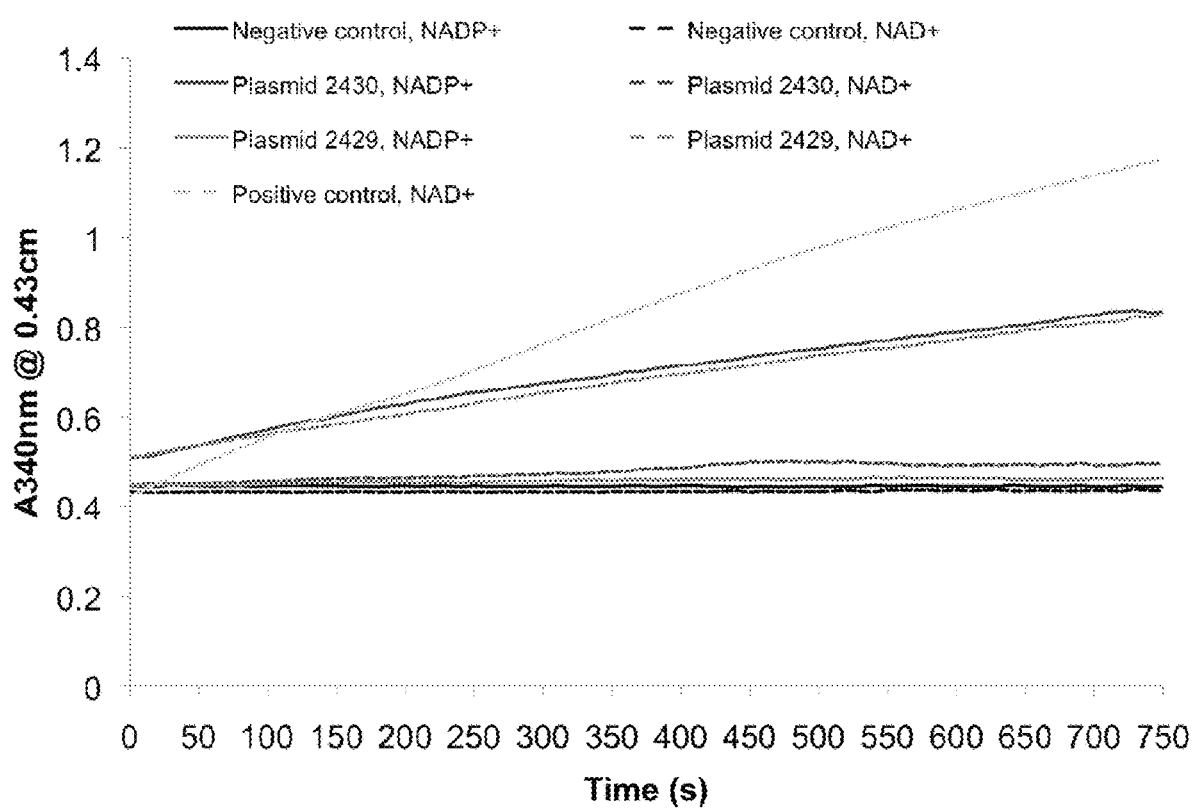
FIG. 21 depicts the spectrophotometric assay results of in vitro formate dehydrogenase (FDH) assays for strains propagating plasmid 2430, plasmid 2429 as well as positive and negative control. The positive control is commercially available purified $NAD^+$-dependent FDH enzyme. The negative control is a strain propagating a plasmid without an FDH-encoding gene. For each strain, assay results are shown with for both $NADP^+$ and $NAD^+$ as the cofactor, as indicated. The reduction of either $NADP^+$ or $NAD^+$ is monitored by measuring the absorbance at 340 nm.

Cultures propagating each of the plasmids were inoculated from glycerol stocks and grown overnight in a 24-well plate with fresh LB media supplemented with 34 pg/ml chloramphenicol at 37° C. The grown cultures were then diluted into 1 ml fresh media in a 96-well plate. Cells were pelleted by centrifugation for 10 minutes at 3000×g and the supernatant decanted. The cell pellets were resuspended in 100 µl complete B-PER (contains DNaseI and lysozyme). The assay reactions were prepared in a 96-well assay plate and contained the following: 100 of 200 mM potassium phosphate buffer, pH 7.0 (made by titering 200 mM dipotassium hydrogen phosphate into 200 mM potassium dihydrogen phosphate until the solution pH reached 7.0), 15 µl of 10 mM $NAD(P)^+$ as appropriate. 20 µl cell lysate, and 30 µl 0.5 M sodium formate. The absorbance at 340 nm of each sample was measured every 20 seconds in a Spectramax Gemini Plus plate reader in order to monitor the reduction of $NAD(P)^+$. The assay plate was maintained at a temperature of 37° C. The measured rates of $NAD(P)^+$ reduction were normalized to the number of cells used to prepare the cell lysates. The assay results are shown in FIG. 21. From the assay data, the quantitative activities of each FDH can be computed as well as their cofactor preference (Table 5).

TABLE 5

Quantitative, measured activities of FDH

| Plasmid | amol $NADP^+$ $min^{-1}$ $CFU^{-1}$ | amol $NADP^+$ $min^{-1}$ $CFU^{-1}$ | $ln(NADP^+/NAD^+)$ |
|---|---|---|---|
| negative control | −0.05 | 0.18 | — |
| 2430 | 21.37 | 3.06 | 1.9 |
| 2429 | 0.12 | 9.79 | −4.4 |

Example 3: Engineered *E. coli* that Oxidizes Hydrogen Sulfide

Plasmids comprising a high copy number replication origin, chloramphenicol resistance marker and a codon-optimized sulfide-quinone oxidoreductase from *Rhodobacter capsulatus* (sqr) gene under the control of two different rrnB-derived constitutive promoters were constructed using DNA assembly methods described in WO/2010/070295. The resulting plasmids 4767 (SEQ ID NO:58) and 4768 (SEQ ID NO:59) were transformed into *E. coli* using standard plasmid transformation techniques. As a negative control, an expression plasmid without a constitutive promoter but including the sqr gene was also constructed.

Figure 22:
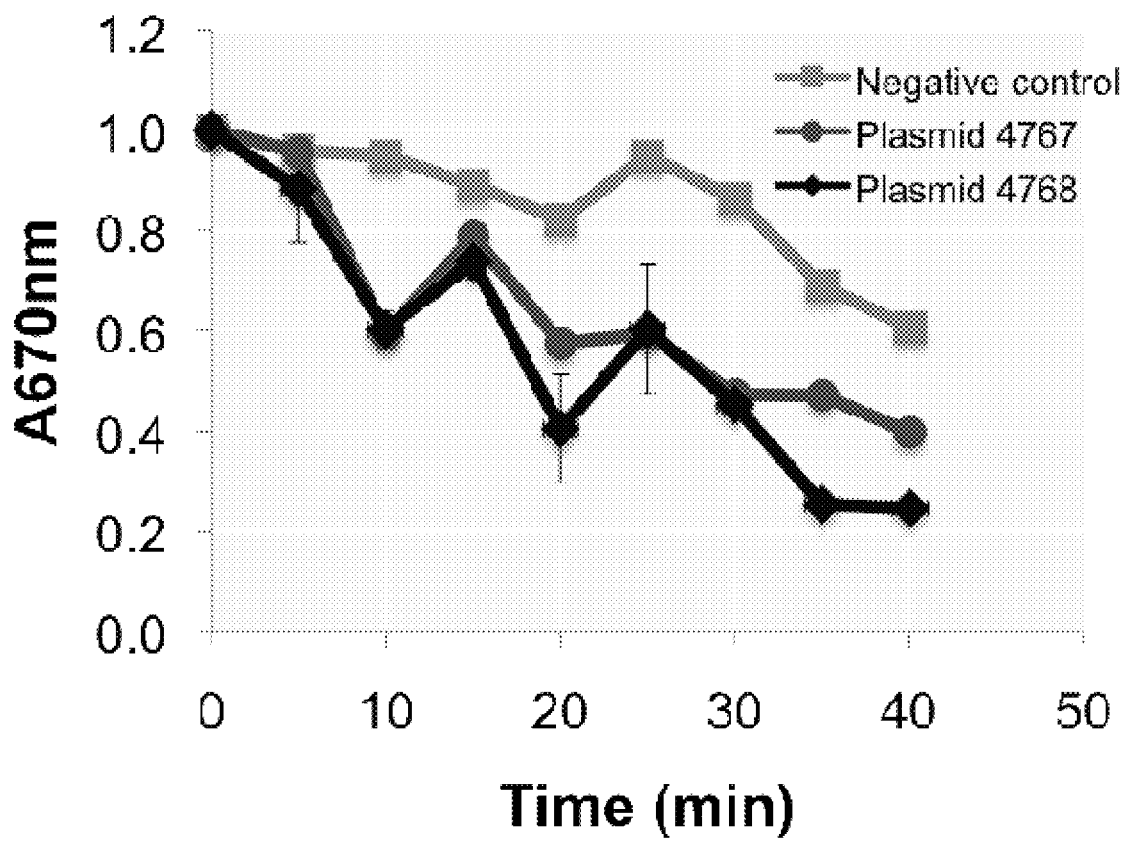
FIG. 22 depicts the spectrophotometric assay results of sulfide oxidation assays for strain propagating plasmid 4767, plasmid 4768 and a negative control plasmid (a plasmid without a constitutive promoter upstream of the sqr gene). Depletion of sulfide over time is monitored by measuring the absorbance at 670 nm after treatment of the samples with Cline reagent [Cline, 1969].

Cultures propagating each of the plasmids were inoculated from glycerol stocks and grown for two days in an 8-well plate with fresh LB media supplemented with 34 µg/ml chloramphenicol at 30° C. Cells were pelleted by centrifugation for 10 minutes at 2500 rpm and the supernatant decanted. The cell pellets were resuspended in 2 ml of SQR assay buffer (5 g/L sodium chloride, 5 mM magnesium chloride hexahydrate, 1 mM calcium chloride dihydrate, 20 mM Tris-HCl, pH 7.5). The absorbance at 600 nm of a 100 µl aliquot of each resuspended culture was measured to monitor the cell density. The assay reactions were prepared in a 96-well plate containing 0, 100, 150, 200 µl of SQR assay buffer; 10 g of 0.1M sodium sulfide: and 200, 100, 50, and 0 µl of resuspended cells. The absorbance at 600 nm of each assay reaction was measured to monitor the cell density. The sampling reactions were prepared in a 96-well assay plate and contained the following: 90 µl of Tris-HCl, pH 7.5; 8 µl aliquot from sampling plate; and 8 µl Cline reagent [Cline, 1969]. The absorbance at 670 nm of each sampling reaction was measured to monitor the sulfide concentration. The assay results are shown in FIG. 22. Based on this data, we estimate the sulfide oxidation rates in the cell resuspensions to be between 2-3.5 mM hour$^{-1}$ or roughly 0.5-2.0 mmol sulfide g DCW$^{-1}$ hour$^{-1}$.

Example 4: Engineered *E. coli* Producing Propionyl-coA from 3-Hydroxypropionate Plasmids comprising a high copy number replication origin, chloramphenicol resistance marker and a codon-optimized propionyl-coA synthase from *Chloroflexus aurantiacus* (pcs) gene under the control of two different rrnB-derived constitutive promoters were constructed using DNA assembly methods described in WO/2010/070295. The resulting plasmid 4986 (SEQ ID NO:60) was transformed into *E. coli* using standard plasmid transformation techniques. As a negative control, an expression plasmid without the pcs gene was also constructed.

Figure 23:
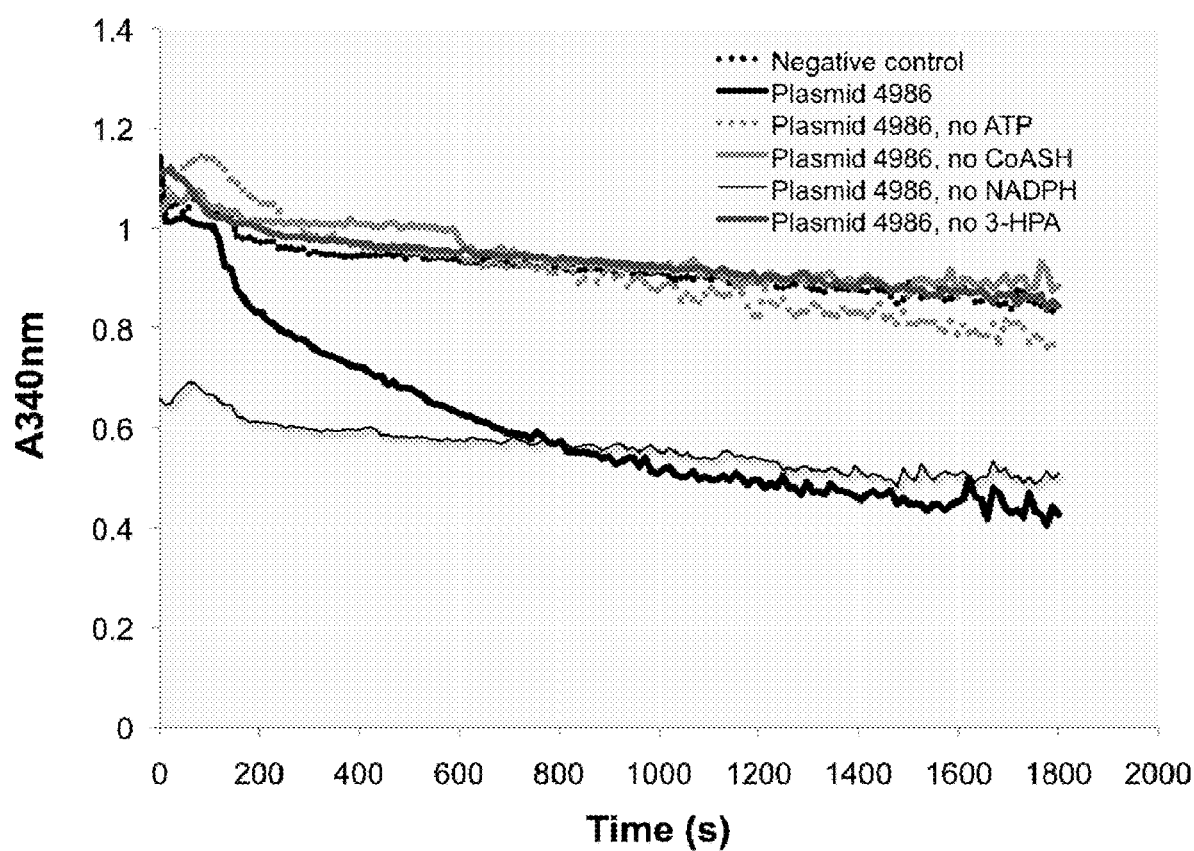
FIG. 23 depicts the spectrophotometric assay results of in vitro propionyl-CoA synthase (PCS) assays for strain propagating plasmid 4986 as well as a negative control plasmid containing no pcs gene. For the strain propagating plasmid 4986, assay results are shown with all required substrates as well as control reactions that omit one of the required substrates, as indicated. The oxidation of NADPH is monitored by measuring the absorbance at 340 nm.

Cultures propagating each of the plasmids were inoculated from glycerol stocks and grown overnight in a 24-well plate with fresh LB media supplemented with 34 g/ml chloramphenicol at 37° C. Cells were pelleted by centrifugation and the supernatant decanted. The cell pellets were resuspended in 600 µl complete B-PER (contains DNaseI and lysozyme) and incubated for 30 minutes at 37° C. The assay reactions were prepared in a 96-well assay plate and contained the following: 71 µl of reaction buffer (3 mM ATP, 0.5 mM CoASH, 0.4 mM NADPH, 1×PCS buffer), 20 µl of cell lysate and 9 µl of a ten-fold dilution of chemically synthesized 3-hydroxypropionate (see below). The 1×PCS buffer contained 100 mM Tris-HCl, pH 7.6, 10 mM potassium chloride, 5 mM magnesium chloride hexahydrate, 2 mM 1,4-dithioerythritol. The absorbance at 340 nm of each assay reaction was measured every 12 seconds to monitor the oxidation of NADPH. As controls, the assay reaction contain lysate from a strain propagating plasmid 4986 was also assayed in the absence of each required substrate (ATP, CoASH, NADPH, 3-hydroxypropionate or 3-HPAA). The assay results are shown in FIG. 23.

The chemical 3-hydroxypropionate is used a substrate in enzymatic assays of propionyl-coA synthase (PCS). 3-hydroxypropionate can be made via chemical synthesis from β-propiolactone via the following method. A solution is prepared containing 0.3 M technical grade β-propiolactone (Sigma Aldrich catalog number β-5648) and 2 M sodium hydroxide and incubated overnight at room temperature. The solution is then neutralized with either hydrochloric acid or phosphoric acid. The presence of the reaction product 3-hydroxypropionate can be confirmed via LC-MS. LC-MS can also reveal that no other measurable side-products are formed. Since the starting material, β-propiolactone, is highly bacteriocidal, but the product, 3-hydroxypropionate, is not, growth inhibition assays can also be used to demonstrate complete conversion of the starting material.

Example 5: Engineered *E. coli* with Reduced Competing Formate Uptake Activity The formate uptake of a series of gene deletion strains of *E. coli* were analyzed as to identify genes responsible for competing, endogenous formate uptake activity in *E. coli*. All deletion strains were obtained from the Keio collection [Baba, 2006]. The negative control was the absence of cells. Cultures were grown aerobically in LB medium supplemented with 50 mM formate overnight, harvested by centrifugation, resuspended in fresh LB medium with formate, and incubated for four hours to allow the cells to reenter growth phase. The cells were then resuspended in either M9 minimal medium with 50 mM formate as the sole carbon source (results shown in Table 6) or LB medium with 50 mM formate (results shown in Table 7). Assays for formate levels (as measured in mM of formate) were performed as described in Example 8 at different timepoints.

TABLE 6

Formate uptake by various deletion strains, minimal medium

| Strain genotype | 0 | 20 | 40 | 60 | 240 |
|---|---|---|---|---|---|
| negative control | 88 | 89 | 98 | 90 | 85 |
| ΔfdhF | 89 | 91 | 85 | 66 | 46 |
| ΔfdnG | 84 | 80 | 65 | 48 | 14 |
| ΔfdoG | 84 | 77 | 93 | 54 | 54 |
| ΔselA | 84 | 130 | 93 | 88 | 77 |
| ΔselB | 89 | 124 | 95 | 86 | 59 |

TABLE 7

Formate uptake by various deletion strains, rich medium

| Strain genotype | 0 | 20 | 40 | 60 | 240 |
|---|---|---|---|---|---|
| negative control | 68 | 74 | 74 | 64 | 70 |
| ΔfdhF | 81 | 76 | 74 | 66 | 62 |
| ΔfdnG | 73 | 74 | 66 | 57 | 28 |
| ΔfdoG | 77 | 74 | 69 | 63 | 64 |
| ΔselA | 77 | 78 | 76 | 72 | 78 |
| ΔselB | 72 | 46 | 67 | 60 | 76 |

Example 6: Assay Methods to Measure Hydrogenase Activity

Figure 24:
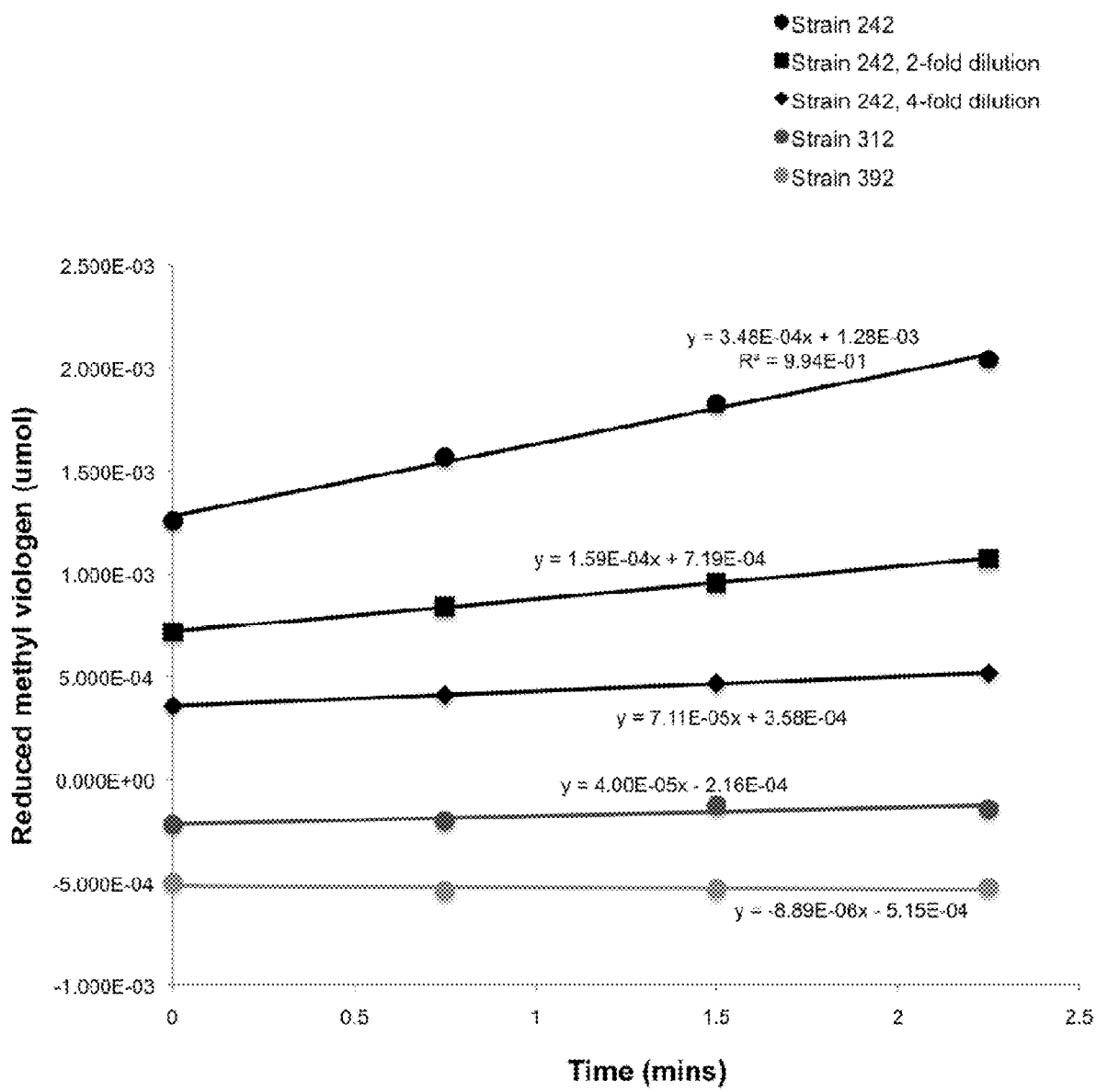
FIG. 24 depicts hydrogenase assay results for strains 242 (at three different dilutions), 312 and 392. Hydrogense activity is measured by monitoring the reduction of the electron acceptor methyl viologen; hence, the y axis is denoted in μmol of reduced methyl viologen.

The following assay can be used to measure hydrogenase enzyme activity in intact cells. All steps are performed in a Shel-labs Bactron IV anaerobic chamber containing anaerobic mixed gas (90% nitrogen gas, 5% hydrogen gas, 5% carbon dioxide). Cultures with and without hydrogenase activity are inoculated from single colonies on LB-agar plates and grown overnight in a 24-well plate with fresh LB media. An aliquot of each culture (1-2 ml) is pelleted by centrifugation and the supernatant decanted. The cells are then resuspended in 1-2 ml 50 mM Tris-HCl, pH 7.6. A very small amount of sodium dithionite is picked up with a pipette tip and dissolved into 100 µl of 50 mM Tris-HCl, pH 7.6. The assay reactions are prepared in a 96-well plate and contain the following: 100 µl resuspended cells and 100 µl 0.8 mM methyl viologen in 50 mM Tris-HCl, pH 7.6. The 96-well plate is then loaded into a Biochrom UVM340 spectrophotometric plate reader and the absorbance at 600 nm is measured at 45 second intervals. To validate the assay, we assayed E. coli strain 242 (K strain MG1655), strain 312 (B strain BL21 DE3 with pLysS plasmid) and strain 393 (B strain BL21 DE2 with genes tonA, hycE, hyaB and hybC deleted). E. coli K strains are known to have hydrogenase activity whereas B strains do not [Pinske, 2011]. Assay results are shown in FIG. 24.

Example 7: Identification and Sequencing of a Formate-Ferredoxin Oxidoreductase from Clostridium pasteurianum A culture sample of Clostridium pasteurianum W5 (ATCC 6013) was obtained from the ATCC (genome size is 3.9 Mbp) [Fogel, 1999]. The strain was cultured under anaerobic conditions in reinforced clostridial medium (Difco). Four aliquots of 1 ml of culture were pelleted by centrifugation at 6000×g for 5 minutes and the supernatant removed by aspiration. Genomic DNA was isolated with the Wizard genomic DNA purification kit (Promega) according to the manufacturer's instructions for Gram-positive bacteria with the following exceptions. In the lysis step, 10 mg/L lysozyme in 10 mM Tris, 0.5 mM EDTA, pH 8.2 was used without any additional lysis enzymes. Also, 10 mM Tris, 0.5 mM EDTA, pH 8.2 was used in lieu of DNA rehybridization solution. The DNA yield was approximate 26 µg of DNA from 4 ml of culture. The genomic DNA was sequenced at the Harvard/MGH sequencing facility. They prepared 160 bp inserts from the genomic DNA and obtained 300 MM 75 bp paired end reads on an 1llumina HiSeq sequencer. The resulting coverage was 5000×. De novo assembly of the reads using Velvet resulting in 170 contigs greater than 5 kb in length comprising 3.9 Mbp. The resulting contigs were analyzed by Glimmer resulting in 3474 identified ORFs comprising 3.6Mbp. A BLASTable database of amino acid sequences of all identified ORFs was produced using NCBI BLAST formatdb tool and subsequently a BLASTable contig database was generated. Based on inspection of the BLAST results, two putative FDH subunits were identified (SEQ ID NO:5 and SEQ ID NO:6) as well as two putative associated ferredoxin domain containing subunits (SEQ ID NO:7 and SEQ ID NO:8).

Example 8: Assay Methods to Measure Formate Uptake by Intact Cells

Figure 25:
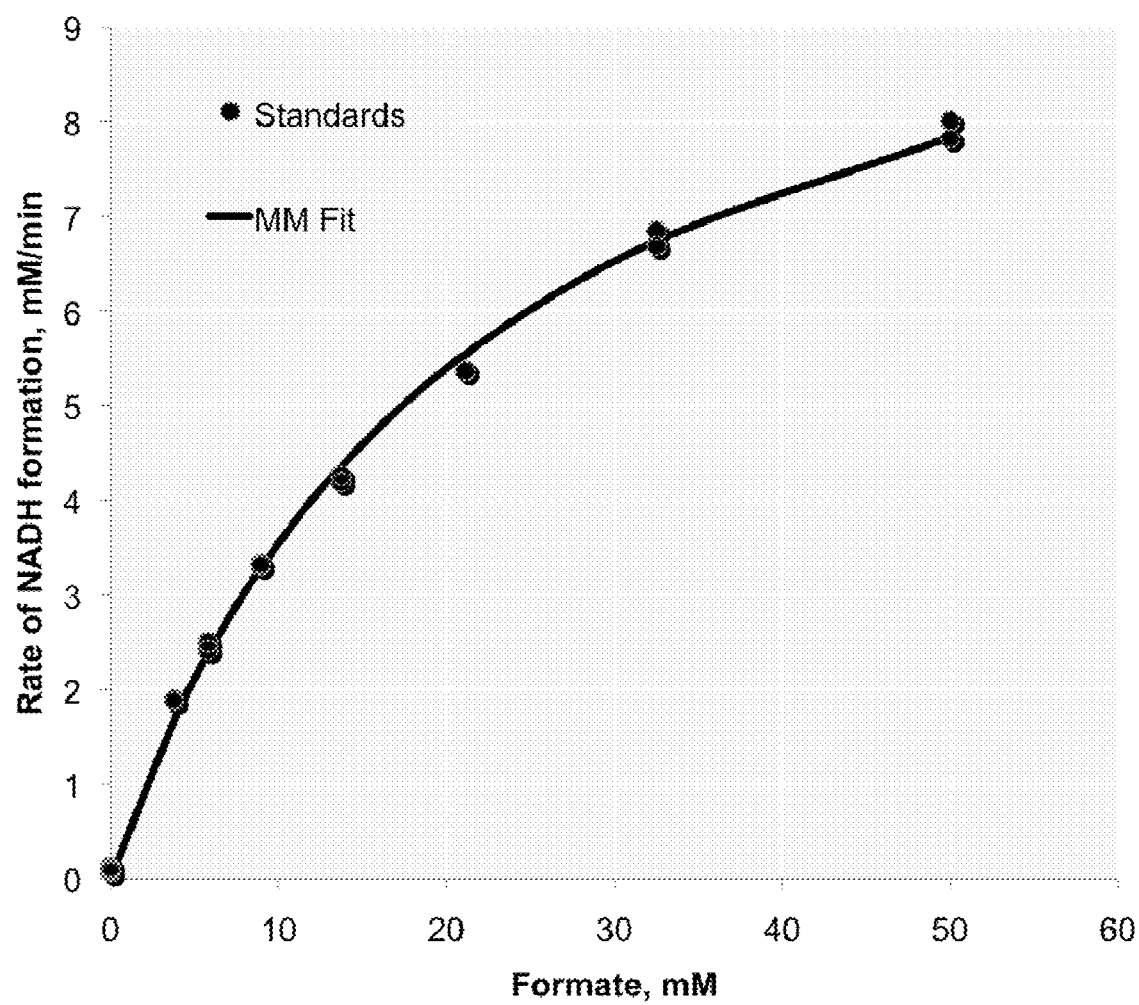
FIG. 25 depicts a standard curve correlating the rate of NADH formation by a commercially available formate dehydrogenase as a function of formate concentration in the sample.

The following assay can be used to measure formate levels in cultures thereby facilitating measurement of formate uptake by intact cells. Cultures are inoculated from glycerols and grown overnight in a 24-well plate with fresh LB media supplemented with the appropriate antibiotic as needed. The cultures are pelleted and an aliquot of the supernatant (300 µl) is saved. The assay reactions are prepared in a 96-well plate and contain the following: 80 µl of 200 mM potassium phosphate buffer pH 7.0, 15 of freshly prepared 100 mM NAD, 35 µl of culture supernant, 20 µl of 100× dilution of pure FDH enzyme purchased commercially. The 96-well plate is then loaded into a Spectramax spectrophotometric plate reader and the absorbance at 340 nm is measured at 12 second intervals preceded by 5 seconds of mixing. The rate of NADH formation can be calculated from the rate of change in the absorbance at 340 nm and varies with the level of formate in the sample (FIG. 25).

Example 9: Methods for Growth-Based Selections for 2-Oxoglutarate Synthase Activity To select for functional 2-oxoglutarate synthase activity in E. coli, the following growth-based selection can be used. A strain with the gene encoding isocitrate dehydrogenase rendered non-functional is used such that the strain cannot make 2-oxoglutarate (a precursor to glutamate synthesis in the cell). Such a strain can only grow in glucose minimal media that is supplemented with either glutamate or proline (proline degradation produces glutamate) [Helling, 1971]. Strain 149 (CGSC #4451) has the icd-3 mutation rendering isocitrate dehydrogenase non-functional. Table 8 shows the results of endpoint absorbance at 600 nm measurements of Strain 149 grown under different conditions for 36 hours at 37° C. The negative control is M9 media with glucose with no cells. All readings shown are an average of three measurement replicates of the same culture.

TABLE 8

| Endpoint A600 nm measurements of Strain 149 | | |
|---|---|---|
| Growth conditions | Average | Std Dev |
| Negative control | 0.0358 | 0.0003 |
| M9 media + glucose | 0.0363 | 0.0008 |
| M9 media + glucose + glutamate | 0.2155 | 0.0073 |
| M9 media + glucose + proline | 0.1913 | 0.0041 |
| M9 media + glucose + glutamate + proline | 0.2145 | 0.0049 |

Figure 26:
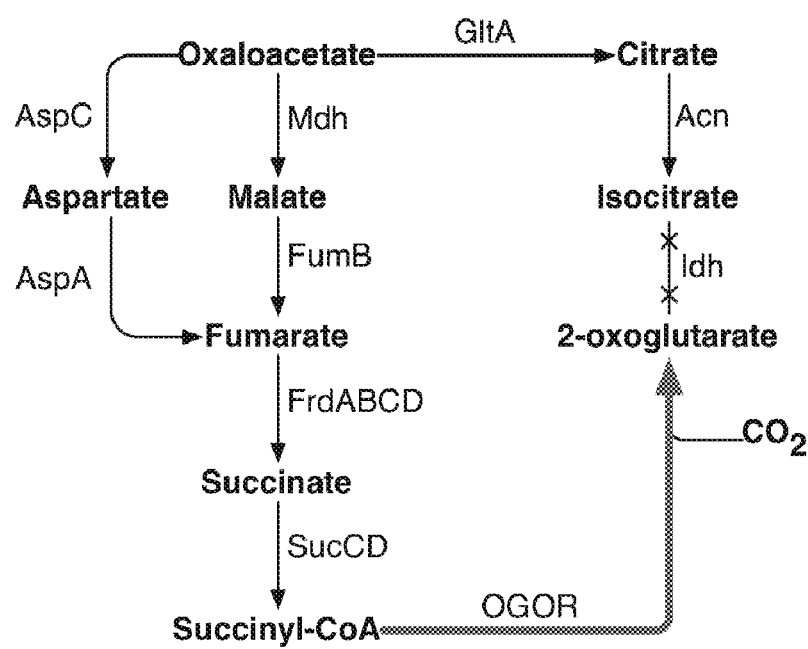
FIG. 26 depicts the branched tricarboxylic acid cycle run by *E. coli* when grown under anaerobic conditions. If the gene encoding isocitrate dehydrogenase (Icd) is rendered non-functional (denoted by Xs), then synthesis of 2-oxoglutarate is restored through introduction of a functional 2-oxoglutarate synthase (OGOR, bold gray arrow). Metabolite names are denoted in bold.

When grown under anaerobic conditions, E. coli runs a branched version of the tricarboxylic acid cycle. Hence, the glutamate/proline auxotrophy phenotype of strains such as Strain 149 in which the icd gene is rendered non-functional can be rescued by introduction of an exogenous, functional 2-oxoglutarate synthase (FIG. 26).

Example 10: Methods for Growth-Based Selections for Formate Utilization

Figure 27:
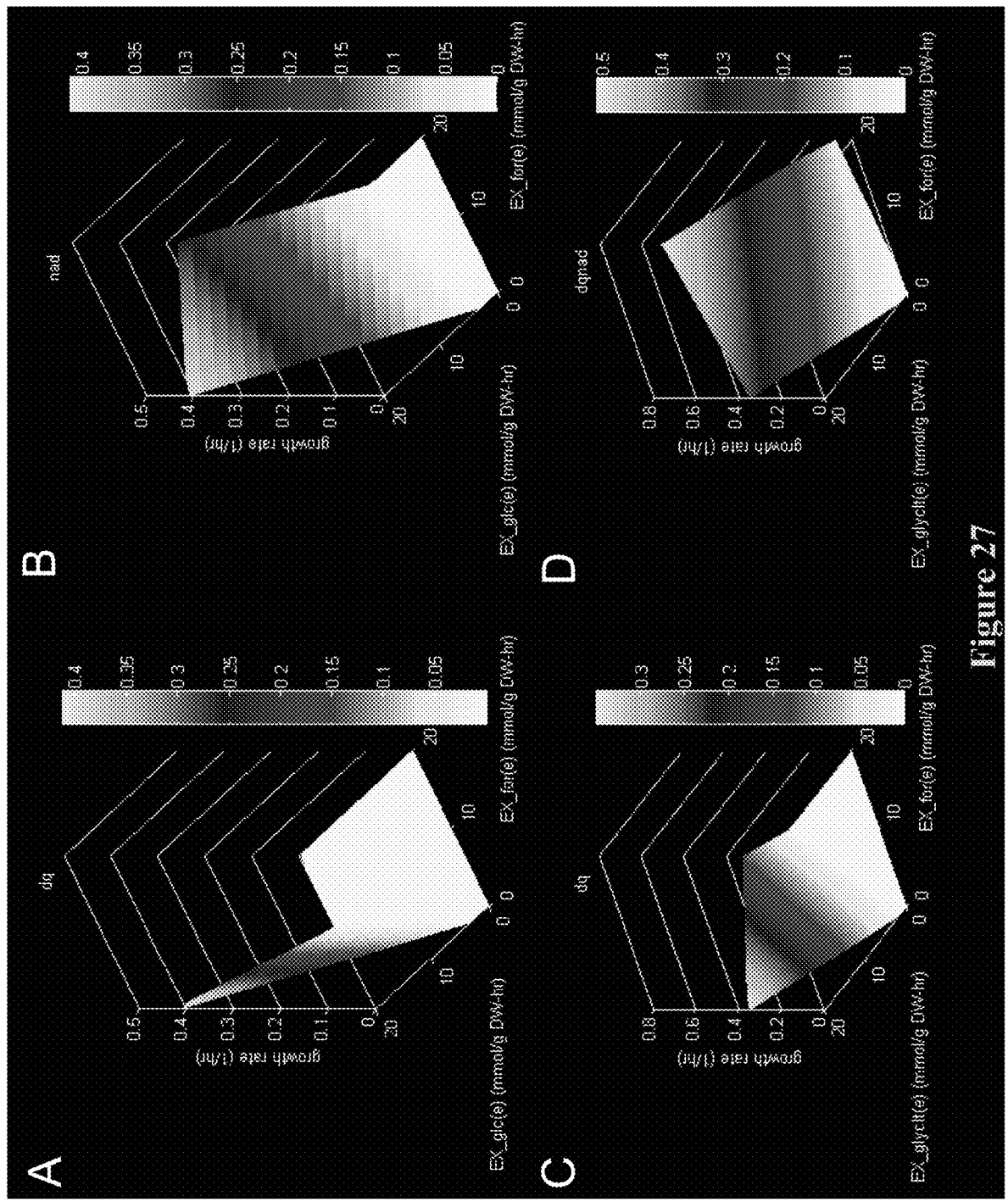
FIG. 27 depicts computed phenotypic phase planes for *E. coli* strains with the native formate dehydrogenases deleted in either the absence (A and C) or presence (B and D) of an exogenous $NAD^+$-dependent formate dehydrogenase. The growth conditions are aerobic with dual carbon sources of formate and either glucose (A and B) or glycolate (C and D).
Figure 28:
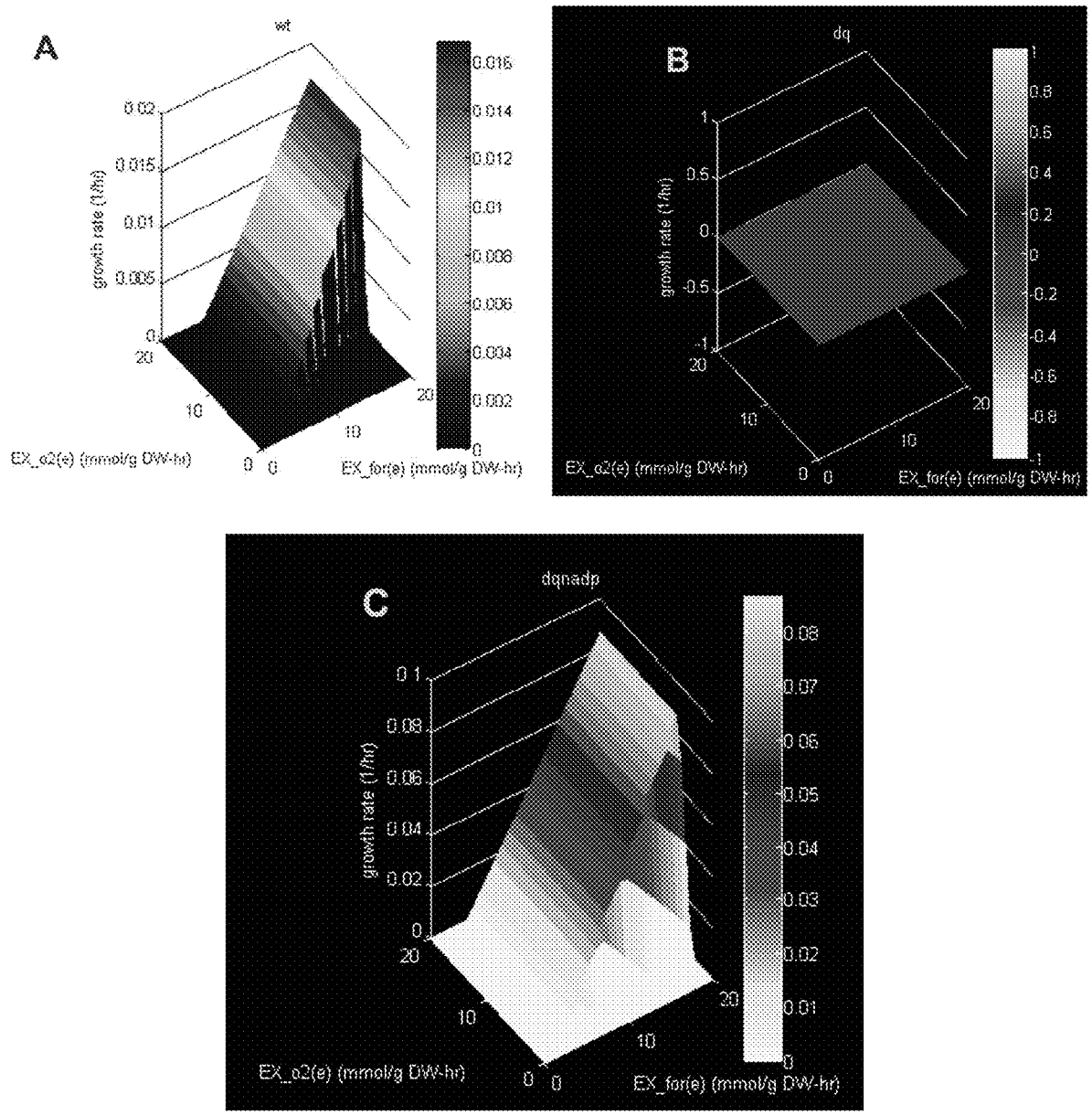
FIG. 28 depict computed phenotypic phase planes during growth on formate as a sole carbon source for wildtype *E. coli* (FIG. 28A), *E. coli* with native formate dehydrogenases deleted (FIG. 28B) and *E. coli* with native formate dehydrogenases deleted and an exogenous $NAD^+$-dependent formate dehydrogenase added (FIG. 28C).

Using a model of E. coli metabolism [Edwards. 2002], the phenotypic phase planes for E. coli under a variety of growth conditions were computed. The growth conditions examined included formate co-metabolism with a second, limiting organic carbon source under both anaerobic and aerobic (i.e., unlimited oxygen uptake) conditions. The organic carbon sources examined include glucose, glycerol, malate, succinate, acetate and glycolate. For each carbon source, several in silico genotypes were evaluated including (1) wild-type E. coli, (2) E. coli with its native formate dehydrogenases (FDH) enzymes removed, (3) wild-type E. coli with a heterologous NAD(P)+-dependent FDH and (4) *E. coli* with native FDHs removed and a heterologous NAD(P)-dependent FDH. The purpose of the analysis was to identify growth conditions that created selective pressure for increased formate uptake and utilization. Based on the computed phenotypic phase planes (FIG. 27), increased formate uptake correlated with increased growth rates under aerobic growth conditions with a non-fermentable inorganic carbon source (glycerol >succinate >malate=propionate >acetate >glycolate). Hence, this set of growth conditions is the preferred set of conditions for growth-based selections for formate utilization. The model analysis also suggests that wildtype *E. coli* is capable of growth on formate as a sole carbon source with a predicted doubling time of 1.4 days and that inclusion of an exogenous NAD+-dependent FDH reduces the doubling time (FIG. 28).

*E. coli* strains can be evolved for improved formate utilization either through repeated subculturing or through continuous culturing in a chemostat or turbidostat using the above culture conditions.

Example 11: Computing Mass Transfer Limitations of Hydrogen Versus Formate as an Inorganic Energy Source The mass transfer limitations of hydrogen from the gas to liquid phase is illustrated here. For the purpose of this analysis, an ideal engineered chemoautotroph that has an unlimited capacity to (i) metabolize dissolved aqueous-phase hydrogen and (ii) convert it and carbon dioxide to a desired fuel at 100% of the theoretical yield is assumed. Under these conditions, the rate of fuel production per unit of reactor volume can depend solely on the rate at which hydrogen can be transferred from the gas phase to the liquid phase.

Fuel productivity P in units of $g \cdot L^{-1} \cdot h^{-1}$ can be expressed as the product of fuel molecular weight $m_F$, fuel molar yield on hydrogen $Y_{F/H}$, the biomass concentration in a bioreactor X, and the specific cellular uptake rate of hydrogen $q_H$, as shown in the equation below.

$$P = m_F Y_{F/H} X q_H$$

At steady state, the bulk hydrogen uptake rate $Xq_H$ is equal to the rate of hydrogen transfer from gas to liquid, meaning the productivity can be expressed as in the equation below, where $C^*$ is the liquid-phase solubility of hydrogen, $C_L$ is the liquid-phase concentration of hydrogen, and $K_L a$ is the mass transfer coefficient for hydrogen transport from the gas phase (e.g., as bubbles sparged into the reactor) to the liquid. $K_L a$ is a complex function of reactor geometry, bubble size, superficial gas velocity, impeller speed, etc. and is best regarded as an empirical parameter that needs to be determined for a given bioreactor setup.

$$P = F_F Y_{F/H} K_L a (C^* - C_L)$$

Again, as a best-case scenario, an ideal engineered chemoautotroph capable of maintaining rapid hydrogen uptake rates even at vanishingly low hydrogen concentrations (i.e. that $q_H$ is not a function of $C_L$ even as $C_L$ tends to zero) is assumed. This assumption maximizes the fuel productivity at $P = m_F Y_{F/H} K_L a C^*$.

For a fixed production target t, say 0.5 t d$^{-1}$ (equivalent to 20800 g h$^{-1}$), the productivity P determines the required reactor volume V because V=t/P. Thus, both fuel productivity and reactor volumes, even assuming "perfect" organisms, are bounded by achievable $K_L a$ values, as shown in the equations below.

$$P = (m_F Y_{F/H} C^*) K_L a$$

$$V = \frac{t}{(m_F Y_{F/H} C^*) K_L a}$$

Figure 29:
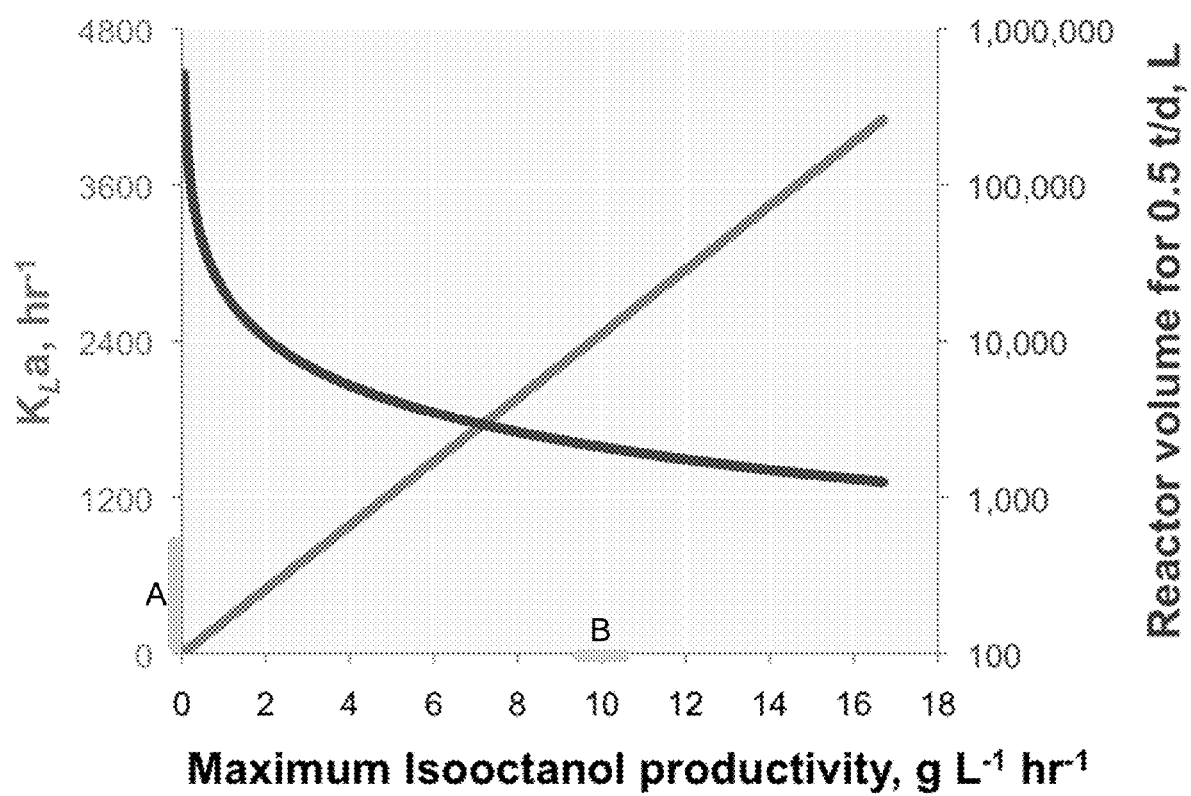
FIG. 29 depicts the required mass transfer coefficient ($K_L a$) and required reactor volume for 0.5 t/d of fuel production, as a function of maximum fuel productivity for isooctanol, assuming fuel production from inorganic energy source $H_2$ and inorganic carbon source $CO_2$ for an ideal engineered chemoautotroph. On the y axis, the typical range of $K_L a$ in large-scale stirred-tank bioreactors is denoted (A). On the x axis, reported natural formate uptake rates at industrially relevant culture densities is denoted (B).

Maximal productivity corresponds to minimal reaction volumes, and occurs at maximal values of $m_F Y_{F/H} C^* K_L a$. The fuel yield cannot exceed the stoichiometric maximal yield. For the fuel isooctanol, the stoichiometric maximal yield is determined from the balanced chemical equation 8 $CO_2 + 24 H_2 + C_8H_{18}O + 15 H_2O$, which shows that 24 moles of H2 are required for each mole of isooctanol produced. At atmospheric pressure, $C^*$ is unlikely to greatly exceed 0.75 mM, the solubility of H2 in pure water. Using these representative values for representative values for $m_F$, $Y_{F/H}$, $C^*$ and t, the relationships between $K_L a$ and P as well as between $K_L a$ and t are shown (FIG. 29).

Alternative electron donors have the potential to solve both the safety problem and the mass transfer problem presented by hydrogen. An ideal non-hydrogen vector for carrying electrical energy would share hydrogen's attractive characteristics, which include (a) a highly negative standard reduction potential, and (b) established high-efficiency technology to for converting electricity into the vector. Unlike hydrogen, however, it would (c) have a low propensity to explode when mixed with air, and (d) have high water solubility under bio-compatible conditions. Formic acid, HCOOH, or its salts, satisfies these conditions. Formic acid is stoichiometrically equivalent to $H_2 + CO_2$, and formate has as standard reduction potential nearly identical to that of hydrogen. Since both formic acid and formate salts are highly soluble in water, the mass transfer limitations discussed above for hydrogen do not apply. However, a modified form of the fuel productivity equation, written for formic acid (A) instead of hydrogen (H), still applies, as shown below.

$$P = m_F Y_{F/A} X q_A$$

Unlike hydrogen-powered electrofuels bioproduction, limits on formate-powered fuel productivity P stem only from the attainable yield, the biomass concentration in the reactor, and the specific uptake rate. We assume $Y_{F/A}$, the molar yield of fuel on formic acid, is the stoichiometric maximum, whose value is the same as for hydrogen, 0.0467 mol isooctanol (mol HCOOH)$^{-1}$. For high-cell density cultivations of *E. coli*, biomass concentrations of X=50 gDCW L$^{-1}$ are attainable, although these values have not been observed for growth on formate or in minimal medium. For *Thiobacillus* strain A2, naturally capable of growing on formate, observed values of were 0.0368 mol formate-gDCW$^{-1} \cdot h^{-1}$ [Kelly, 1979]. The representative values for $q_A$ and X imply a maximal isooctanol productivity on formate of about 10 $g \cdot L^{-1} \cdot h^{-1}$.

On the y-axis of FIG. 29, the range of reported $K_L a$ attainable in large-scale stirred-tank bioreactors is shown. Although there are many reports of higher $K_L a$ values in laboratory-scale reactors, during scale up the inevitable increase in volume-to-surface area ratios means that maintaining high $K_L a$ values is for practical purposes impossible. The maximum of the indicated range of 10-800 h$^{-1}$ translates to a best-case productivity of 4 $g \cdot L^{-1} \cdot h - 1$, which implies a best-case reactor volume of 6,400 L. The best-case productivity on formate is 10 $g \cdot L^{-1} \cdot h^{-1}$, implying a reactor volume less than half as large would be required to achieve the same production. Most sources that give $K_L a$ values for large scale reactors have values much closer to 100 h$^{-1}$,

Example 12: Engineered Organisms Producing Butanol

The enzyme beta-ketothiolase (*R. eutropha* PhaA or *E. coli* AtoB) (E.C. 2.3.1.16) converts 2 acetyl-CoA to acetoacetyl-CoA and CoA. Acetoacetyl-CoA reductase (*R. eutropha* PhaB) (E.C. 1.1.1.36) generates R-3-hydroxybutyryl-CoA from acetoacetyl-CoA and NADPH. Alternatively, 3-hydroxybutyryl-CoA dehydrogenase (*C. acetobutylicum* Hbd) (E.C. 1.1.1.30) generates S-3-hydroxybutyryl-CoA from acetoacetyl-CoA and NADH. Enoyl-CoA hydratase (*E. coli* MaoC or *C. acetobutylicum* Crt) (E.C. 4.2.1.17) generates crotonyl-CoA from 3-hydroxybutyryl-CoA. Butyryl-CoA dehydrogenase (*C. acetobutylicum* Bed) (E.C. 1.3.99.2) generates butyryl-CoA and NAD(P)H from crotonyl-CoA. Alternatively, trans-enoyl-coenzyme A reductase (*Treponema denticola* Ter) (E.C. 1.3.1.86) generates butyryl-CoA from crotonyl-CoA and NADH. Butyrate CoA-transferase (*R. eutropha* Pct) (E.C. 2.8.3.1) generates butyrate and acetyl-CoA from butyryl-CoA and acetate. Aldehyde dehydrogenase (*E. coli* AdhE) (E.C. 1.2.1.{3,4}) generates butanal from butyrate and NADH. Alcohol dehydrogenase (*E. coli* adhE) (E.C. 1.1.1.{1,2}) generates 1-butanol from butanal and NADH, NADPH. Production of 1-butanol is conferred by the engineered host cell by expression of the above enzyme activities.

To create butanol-producing cells, host cells can be further engineered to express acetyl-CoA acetyltransferase (atoB) from *E. coli* K12, β-hydroxybutyryl-CoA dehydrogenase from *Butyrivibrio fibrisolvens*, crotonase from *Clostridium beijernickii*, butyryl CoA dehydrogenase from *Clostridium beijerincki*, CoA-acylating aldehyde dehydrogenase (ALDH) from *Cladosporium fulvum*, and adhE encoding an aldehyde-alcohol dehydrogenase of *Clostridium acetobultyicum* (or homologs thereof).

Example 13: Engineered Organisms Producing Acrylate

Enoyl-CoA hydratase (*E. coli* paaF) (E.C. 4.2.1.17) converts 3-hydroxypropionyl-CoA to acryloyl-CoA. Propionyl-CoA synthase (E.C. 6.2.1.-, E.C. 4.2.1.- and E.C. 1.3.1.-) also converts 3-hydroxypropionyl-CoA to acryloyl-CoA (AAL47820, SEQ ID NO:30, SEQ ID NO:31). Acrylate CoA-transferase (*R. eutropha* pct) (E.C. 2.8.3.n) generates acrylate+acetyl-CoA from acryloyl-CoA and acetate.

Example 14: Conversion of Formaldehyde to Central Metabolic Intermediates by Lysates of Recombinant *E. coli* Cells The hexulose-6-phosphate isomerase (HPS) enzyme YP_115430 and 6-phospho-3-hexuloisomerase (PIH) enzyme YP_115431 were recoded for expression in *E. coli* using the algorithm described in [00109] above and/or elsewhere in the present application. Briefly, the algorithm attempts to (a) preserve codon rank order frequency in the source organism (*Methylococcus capsulatus*) and the target organism (*E. coli*); (b) eliminate undesired restriction endonuclease recognition sequences in the re-coded gene sequence; and (c) avoid undesired DNA or RNA secondary structure in the re-coded gene or its transcript. The resulting nucleotide sequences are provided as SEQ ID NO:47 and SEQ ID NO:48, respectively. The codon-optimized genes were obtained via commercial gene synthesis.

Plasmids encoding a high copy number replication origin, an antibiotic resistance marker and either a codon-optimized hexulose-6-phosphate isomerase from *M. capsulatus* under the control of a constitutive promoter or a codon-optimized 6-phospho-3-hexuloisomerase from *M. capsulatus* were constructed using DNA assembly methods described in WO/2010/07025. The resulting plasmids 9463 (SEQ ID NO:63) and 9462 (SEQ ID NO:64) were transformed into *E. coli* using standard plasmid transformation techniques.

*E. coli* NEB10β cells harboring plasmid 9463 were grown overnight with selection in Luria Broth (LB) medium containing 20 g L$^{-1}$ of xylose. In parallel, *E. coli* NEB10β cells harboring plasmid 9462 were grown overnight with selection in Luria Broth (LB) medium containing 20 g L$^{-1}$ of xylose.

Both *E. coli* cultures were harvested by centrifugation, and cell pellets were lysed by resuspension in 0.1 culture volumes of a buffer containing DNAse I (8 U mL$^{-1}$), lysozyme (>1 mg mL$^{-1}$), dithioerythritol (0.5 mM), and Tris buffer (20 mM, pH 7.5) followed by rapid freeze-thaw (3 cycles using liquid nitrogen and at warm water bath). Lysates were clarified by centrifugation for 5 min at >4000 g.

The lysates were mixed by combining 20 µL of each into the well of a standard 96-well flat-bottom assay plate. The plate was incubated at 30 C. In parallel, lysates from *E. coli* cultures expressing a metabolically inert gfp gene as a negative control were prepared in an identical fashion. "Blank" lysates made from the lysis reagent only—i.e. with no cells—were also included as a control.

A reaction mixture was added to the lysates or lysate mixtures at time zero so that the final volume in the well was 200 µL and the final concentration of (non-lysate derived) reactants was: coenzyme A, 0.5 mM; adenosine triphosphate (ATP), 10 mM; ribulose-5-phosphate (Ru5P), 1 mM; nicotine adenine dinucleotide (NAD$^+$), 1 mM; magnesium sulfate, 5 mM; potassium phosphate buffer pH 7.0, >150 mM; formaldehyde; 5 mM. The formaldehyde stock solution was previously prepared by autoclaving 240 mg of paraformaldehyde powder suspended in 8 mL of pure water at 121 C in a sealed septum vial until it was solubilized.

In parallel, a separate reaction mixture was prepared with an identical composition, except that $^{13}$C-enriched paraformaldehyde (>99% isotopic purity; Cambridge Isotope Laboratories, Massachusetts USA) was used as a formaldehyde source.

At 0 minutes, 30 minutes, and 120 minutes after the start of the enzyme reactions, 40 µL of the reaction mixture was withdrawn from the assay plate and mixed with 160 µL of a quenching solution consisting of 0.1 M formic acid in 40% v/v methanol, 40% v/v acetonitrile, and 20% v/v water. Samples were vacuum-aspirated to dryness in preparation for detection by liquid chromatography electrospray ionization mass spectrometry (LC-ESI-MS) of fructose-6-phosphate pool sizes and fructose-1,6-bisphosphate pool sizes.

LC-ESI-MS analysis was carried out on a Thermo Q-Exactive LC-ESI-MS system capable of mass determination to within 5 ppm. Metabolites were eluted from a 100-by-2.1 mm hybrid reverse-phase chromatography column with 2.6 m beads (Accucore aQ, Thermo Scientific) with a linear gradient consisting of 15 mM acetic acid in ultrapure water as the weak solvent and methanol as the strong solvent and introduced to the mass spectrometer via a HESI-III ESI source. Elution and column reequilibration was carried out under uPLC conditions at a flow rate of 500 μL/min and total run time of 7 minutes using an Accela 1250 uPLC pump and Accela Open AS autosampler. During autosampling, samples were maintained at 4 C, while the column was kept at 30 C. ESI source and mass spectrometer acquisition settings were optimized and operated in both negative and positive polarities, using a panel of pure standards of metabolites of interest. Full MS scans were performed at a resolution of 70,000 over a mass range of 70-900 m/z, allowing for a minimum of 15-20 scans across each extracted ion chromatogram for absolute and relative quantitation under uPLC conditions. When needed, tandem MS/MS scans were also performed in both targeted and data dependent schemes to obtain additional structural information via HCD-induced fragmentation of intact precursor ions. Metabolite feature identification and full scan quantitation were performed using integration and alignment algorithms in Xcalibur (Thermo) and XCMS (Scripps Research Institute).

Fructose-6-phosphate was detected in negative mode as the $C_6H_{12}O_9P^-$ anion at m/z=259.0224 Da+/−5 ppm. The M+1 $^{13}C$ isotopologue of fructose-6-phosphate (1-$^{13}$C-F6P) was detected at m/z=260.0258 Da+/−5 ppm. A time course showing incorporation of carbon derived from formaldehyde into fructose-6-phosphate (F6P) is shown in Table 9. The time is in units of minutes and the metabolites are in units of peak area (counts). $H^{12}CHO$ denotes formaldehyde and $H^{13}CHO$ denotes $^{13}$C-enriched paraformaldehyde. The results shows that carbon from formaldehyde is converted to the native E. coli metabolite fructose-6-phosphate in an HPS and PHI-dependent manner.

or its transcript. The resulting nucleotide sequences is provided as SEQ ID NO:61. The codon-optimized gene was obtained via commercial gene synthesis.

A plasmid encoding a medium copy number replication origin, an antibiotic resistance marker and the recoded acetyl-CoA synthetase from E. coli under the control of an rrnB-derived constitutive promoter was constructed using DNA assembly methods described in WO/2010/07025. The resulting plasmid 20566 (SEQ ID NO:65) was transformed into E. coli using standard plasmid transformation techniques.

E. coli cells harboring plasmid 20566 were grown in culture and lysed by the methods described in Example 14. Lysate-based enzyme reactions were started as described in Example 14, except that sodium formate 30 mM was used in place of formaldehyde and 30 mM of sodium $^{13}$C-formate (>99 atom % isotopic purity; Cambridge Isotope Laboratories) was used in place of $^{13}$C formaldehyde.

Samples were withdrawn for LC-ESI-MS analysis as described in Example 14.

Formyl-coenzyme A (formyl-CoA) was detected in negative mode as the $C_{22}H_{35}N_7O_7P_3S^-$ anion at m/z=794.1028 Da. The M+1 $^{13}C$ isotopologue of formyl-CoA (1-$^{13}$C-formyl-CoA) was detected at m/z=795.1062 Da. Total counts detected for the m/z=794.1028 ion increased sharply in a time in reaction mixtures to which sodium formate 30 mM ($H^{12}COO^-$) was added. Total counts detected for the m/z=795.1062 ion increased sharply in time only in reaction mixtures to which sodium 30 mM $^{13}$C-formate ($H^{13}COO^-$) was added. In control reactions using lysates from cells not expressing acs, no corresponding increases were observed.

TABLE 9

HPS- and PHI-dependent conversion of formaldehyde ($H^{12}CHO$) to fructose-6-phosphate (F6P)

| | | with $H^{12}CHO$ | | with $H^{13}CHO$ | | with no formaldehyde | |
|---|---|---|---|---|---|---|---|
| | Time | F6P | 1-$^{13}$C-F6P | F6P | 1-$^{13}$C-F6P | F6P | 1-$^{13}$C-F6P |
| HPS/PHI mixture | 0 | 2.6E+06 | NF | 1.0E+06 | 2.0E+06 | 6.1E+05 | NF |
| | 30 | 4.9E+07 | 4.1E+06 | 4.4E+06 | 4.7E+07 | 6.0E+06 | 2.9E+05 |
| | 120 | 3.1E+07 | 2.0E+06 | 5.3E+06 | 2.7E+07 | 2.5E+07 | 3.1E+06 |
| GFP control lysate | 0 | 3.4E+05 | NF | 4.0E+05 | NF | 4.5E+05 | NF |
| | 30 | 1.1E+06 | NF | 1.1E+06 | NF | 1.7E+06 | NF |
| | 120 | 2.9E+06 | NF | 2.8E+06 | 1.2E+04 | 5.2E+06 | NF |

Example 15: Conversion of Formate to Formyl-CoA in Lysates Derived from Recombinant E. coli Cells Expressing Acetyl-CoA Synthetase The E. coli acetyl-CoA synthetase (ACS) enzyme AAC77039 was recoded using the algorithm described in [00109] above, and/or elsewhere in the present application, to eliminate undesired restriction endonuclease recognition sequences in the re-coded gene sequence and avoid undesired DNA or RNA secondary structure in the re-coded gene In control reactions using lysis buffer and no cellular material, no corresponding increase was observed. The data are shown in Table 10. The time is in units of minutes and the metabolites are in units of peak area (counts). Formyl-CoA is denoted by f-CoA and the M+1 $^{13}C$ isotopologue of formyl-CoA is denoted by 1-$^{13}$C-f-CoA. The results demonstrate that formate was converted to formyl-CoA in a formate- and ACS-dependent manner.

TABLE 10

ACS-dependent conversion of formate to formyl-CoA

| | | with $H^{12}COO^-$ | | with $H^{13}COO^-$ | | with no formate | |
|---|---|---|---|---|---|---|---|
| | Time | f-CoA | 1-$^{13}$C-f-CoA | f-CoA | 1-$^{13}$C-f-CoA | f-CoA | 1-$^{13}$C-f-CoA |
| Plasmid 20566 lysate | 0 | 2.0E+08 | 5.9E+07 | 1.5E+08 | 4.5E+07 | 4.5E+07 | 1.0E+09 |
| | 30 | 2.6E+08 | 6.9E+07 | 5.5E+07 | 7.5E+07 | 1.7E+08 | 4.6E+07 |
| | 120 | 1.3E+09 | 3.7E+08 | 4.5E+07 | 1.0E+09 | 7.9E+07 | 2.1E+07 |

TABLE 10-continued

ACS-dependent conversion of formate to formyl-CoA

| | Time | with H$^{12}$COO$^-$ | | with H$^{13}$COO$^-$ | | with no formate | |
|---|---|---|---|---|---|---|---|
| | | f-CoA | 1-$^{13}$C-f-CoA | f-CoA | 1-$^{13}$C-f-CoA | f-CoA | 1-$^{13}$C-f-CoA |
| GFP control lysate | 0 | 2.0E+08 | 5.6E+07 | 1.5E+08 | 4.4E+07 | 1.7E+08 | 4.9E+07 |
| | 30 | 2.0E+08 | 5.6E+07 | 1.5E+08 | 4.5E+07 | 1.4E+08 | 3.9E+07 |
| | 120 | 1.8E+08 | 4.8E+07 | 1.4E+08 | 4.4E+07 | 1.5E+08 | 4.2E+07 |

Example 16: Interconversion of Formyl-CoA and Formaldehyde by Lysates Derived from Recombinant E. coli Cells Expressing an Acylating Aldehyde Dehydrogenase The *Listeria monocytogenes* acetaldehyde dehydrogenase, acylating (ADH) enzyme NP_464704 was recoded for expression in *E. coli* using the algorithm described in [00109] and Example 14 above, and/or elsewhere in the present application. The resulting nucleotide sequences is provided as SEQ ID NO:62.

A plasmid encoding a high copy number replication origin, an antibiotic resistance marker and the recoded ADH under the control of an isopropyl β-D-1-thiogalactopyranoside (IPTG)-inducible bacteriophage T7-based promoter was designed by us and synthesized via commercial gene synthesis. The resulting plasmid 27439 (SEQ ID NO:66) was transformed into *E. coli* using standard plasmid transformation techniques.

Cells were grown as described in Example 14, except that after 2 hr of incubation in the overnight growth medium, 1 mM of IPTG was added to induce gene expression.

Lysates were prepared and reactions were initiated as described in Example 14, except (i) that ATP and ribulose-5-phosphate were omitted from the reaction and (ii) time point samples were taken after 0, 3, and 10 minutes after starting the reactions.

Formyl-CoA was detected as described in Example 15. Total counts detected for the m/z=794.1028 ion increased sharply in time in reaction mixtures to which formaldehyde 5 mM was added. Total counts detected for the m/z=795.1062 ion increased sharply with time only in reaction mixtures to which $^{13}$C formaldehyde 5 mM was added. In control reactions using lysates from cells that were not induced to express ADH, no corresponding increases were observed. LC-ESI-MS detection of both NAD$^+$ and NADH (in negative mode using m/z=662.1018 and m/z=664.1175, respectively) confirmed that formyl-CoA formation was linked to NAD$^+$ depletion and NADH formation (data not shown). The data are shown in Table 11. The time is in units of minutes and the metabolites are in units of peak area (counts). Formyl-CoA is denoted by f-CoA, and the M+1 $^{13}$C isotopologue of formyl-CoA is denoted by 1-$^{13}$C-f-CoA. The results show that ADH expressed in *E. coli* lysates effects the interconversion of formaldehyde and NAD$^+$ with formyl-CoA and NADH.

TABLE 11

ADH-dependent interconversion of formaldehyde and formyl-CoA

| | Time | with H$^{12}$CHO | | with H$^{13}$CHO | | with no formaldehyde | |
|---|---|---|---|---|---|---|---|
| | | f-CoA | 1-$^{13}$C-f-CoA | f-CoA | 1-$^{13}$C-f-CoA | f-CoA | 1-$^{13}$C-f-CoA |
| induced | 0 | 5.3E+06 | NF | NF | NF | 4.5E+05 | NF |
| | 3 | 9.2E+07 | 2.3E+07 | NF | 4.4E+07 | 1.0E+06 | NF |
| | 10 | 1.7E+08 | 4.4E+07 | NF | 1.1E+08 | NF | NF |
| uninduced | 0 | NF | NF | | | | |
| | 3 | 2.9E+06 | NF | | | | |
| | 10 | NF | NF | | | | |

OTHER EMBODIMENTS

The examples have focused on *E. coli*. Nevertheless, the key concept of using genetically engineering to convert a heterotroph into an engineered chemoautotroph is extensible to other, more complex organisms such as other prokaryotic or eukaryotic single cell organisms such as *E. coli* or *S. cerevisiae*, hosts suitable for scale up during fermentation, archaea, plant cells or cell lines, mammalian cells or cell lines, or insect cells or cell lines. Alternatively, the same energy conversion, carbon fixation and/or carbon product biosynthetic pathways described here may be used to enhance or augment the autotrophic capability of an organism that is natively autotrophic.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EQUIVALENTS

The present invention provides among other things novel methods and systems for synthetic biology. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

All publications, patents and patent applications referenced in this specification are incorporated herein by reference in their entirety for all purposes to the same extent as if each individual publication, patent or patent application were specifically indicated to be so incorporated by reference.

REFERENCES CITED

Abelseon P H, Hoering T C. Carbon isotope fractionation in formation of amino acids by photosynthetic organisms. Proc Natl Acad Sci. 1961; 47:623-32.
Aharoni A, Keizer L C, Bouwmeester H J, Sun Z. Alvarez-Huerta M, Verhoeven H A, Blaas J, van Houwelingen A M, De Vos R C, van der Voet H, Jansen R C, Guis M, Mol J, Davis R W, Schena M, van Tunen A J, O'Connell A P. Identification of the SAAT gene involved in strawberry flavor biogenesis by use of DNA microarrays. Plant Cell. 2000 May; 12(5):647-62.
Alber B E, Fuchs G Prpionyl-coenzyme A synthase from *Chloroflexus aurantiacus*, a key enzyme of the 3-hydroxypropionate cycle for autotrophic $CO_2$ fixation. J Biol Chem. 2002 Apr. 5; 277(14):12137-43.
Alber B, Olinger M, Rieder A, Kockelkorn D, Jobst B, Hügler M, and Fuchs G Malonyl-coenzyme A reductase in the modified 3-hydroxypropionate cycle for autotrophic carbon fixation in archaeal Metallosphaera and *Sulfolobus* spp. J Bacteriol 2006 December; 188(24) 8551-9.
Andersen J B, Sternberg C. Poulsen L K, Bjorn S P, Givskov M. Molin S. New unstable variants of green fluorescent protein for studies of transient gene expression in bacteria. Appl Environ Microbiol. 1998 June; 64(6):2240-6.
Anderson J C, Voigt C A, Arkin A P. Environmental signal integration by a modular AND gate. Mol Syst Biol. 2007; 3:133.
Aoshima M, Ishii M, and Igarashi Y. A novel enzyme, citryl-CoA synthetase, catalysing the first step of the citrate cleavage reaction in *Hydrogenobacter thermophilus* TK-6. Mol Microbiol 2004 May; 52(3) 751-61. (a)
Aoshimna M Ishii M, and Igarashi Y. A novel enzyme, citryl-CoA lyase, catalysing the second step of the citrate cleavage reaction in *Hydrogenobacter thermophilus* TK-6. Mol Microbiol 2004 May; 52(3) 763-70. (b)
Aoshima M, Ishii M, and Igarashi Y. A novel biotin protein required for reductive carboxylation of 2-oxoglutarate by isocitrate dehydrogenase in *Hydrogenobacter thermophilus* TK-6.Mol Microbiol 2004 February; 51(3) 791-8. ©

Aoshima M and Igarashi Y. A novel oxalosuccinate-forming enzyme involved in the reductive carboxylation of 2-oxoglutarate in *Hydrogenobacter thermophilus* TK-6. Mol Microbiol 2006 November; 62(3) 748-59.
Baba T. Ara T. Hasegawa M. Takai Y. Okumura Y. Baba M. Datsenko K A, Tomita M. Wanner B L, Mori H. Construction of *Escherichia coli* K-12 in-frame, single-gene knockout mutants: the Keio collection. Mol Syst Biol. 2006:2:2006.0008.
Bai F W, Anderson W A, Moo-Young M. Ethanol fermentation technologies from sugar and starch feedstocks. Biotechnol Adv. 2008 January-February; 26(1):89-105.
Bailer J, de Hueber K. Determination of saponifiable glycerol in "bio-diesel." Fresenius J Anal Chem. 1991; 340 (3):186.
Bar-Even A, Noor E. Lewis N E, Milo R. Design and analysis of synthetic carbon fixation pathways. Proc Natl Acad Sci USA. 2010 May 11; 107(19):8889-94.
Bassham J A, Benson A A, Kay L D, Harris A Z, Wilson A T, Calvin M. The path of carbon in photosynthesis. XXI. The cyclic regeneration of carbon dioxide acceptor. J Am Chem Soc. 1954; 76:1760-70.
Bayer T S, Widmaier D M, Temme K, Mirsky E A. Santi D V, Voigt C A. Synthesis of methyl halides from biomass using engineered microbes. J Am Chem Soc. 2009 May 13; 131(18):6508-15.
Berríos-Rivera S J, San K Y, Bennett G N. The effect of NAPRTase overexpression on the total levels of NAD, the NADH/NAD+ratio, and the distribution of metabolites in *Escherichia coli*. Metab Eng. 2002 July; 4(3):238-47.
Brock T. Biotechnology: A Textbook of Industrial Microbiology. Second Edition. Sinauer Associates, Inc. Sunderland, Mass. 1989.
Brugna-Guiral M, Tron P, Nitschke W, Stetter K O, Burlat B, Guigliarelli B, Bruschi M, Giudici-Orticoni M T. [NiFe] hydrogenases from the hyperthermophilic bacterium *Aquifex aeolicus*: properties, function, and phylogenetics. Extremophiles. 2003 April; 7(2):145-57.
Buchanan B B, Arnon D I. A reverse KREBS cycle in photosynthesis: consensus at last. Photosynth Res. 1990; 24:47-53.
Burgdorf T, van der Linden E, Bernhard M. Yin Q Y, Back J W, Hartog A F, Muijsers A O, de Koster C G, Albracht S P, Friedrich B. The soluble $NAD^+$-Reducing [NiFe]-hydrogenase from *Ralstonia eutropha* H 16 consists of six subunits and can be specifically activated by NADPH. J Bacteriol. 2005 May; 187(9):3122-32.
Camilli A, Bassler B L. Bacterial small-molecule signaling pathways. Science. 2006 Feb. 24; 311(5764):1113-6.
Campbell B J, Jeanthon C, Kostka J E, Luther G W 3$^{rd}$, Cary S C. Growth and phylogenetic properties of novel bacteria belonging to the epsilon subdivision of the *Proteobacteria* enriched from *Alvinella pompejana* and deep-sea hydrothermal vents. Appl Environ Microbiol. 2001 October; 67(10):4566-72.
Campbell B J, Smith J L, Hanson T E, Klotz M G, Stein L Y. Lee C K, Wu D, Robinson J M, Khouri H M, Eisen J A, Cary S C. Adaptations to submarine hydrothermal environments exemplified by the genome of *Nautilia profundicola*. PLoS Genet. 2009 February; 5(2): e1000362.
Canton B, Labno A. Endy D. Refinement and standardization of synthetic biological parts and devices. Nat Biotechnol. 2008 July; 26(7):787-93.
Cheesbrough T M, Kolattukudy P E. Alkane biosynthesis by decarbonylation of aldehydes catalyzed by a particulate preparation from *Pisum sativum*. Proc Natl Acad Sci USA. 1984 November; 81(21):6613-7.

Chen S, von Bamberg D, Hale V, Breuer M, Hardt B, Miller R, Floss H G, Reynolds K A, Leistner E. Biosynthesis of ansatrienin (mycotrienin) and naphthomycin. Identification and analysis of two separate biosynthetic gene clusters in *Streptomyces collinus* Tü 1892. Eur J Biochem. 1999 April; 261(1):98-107.

Chin J W, Cirino P C. Improved NADPH supply for xylitol production by engineered *Escherichia coli* with glycolytic mutations. Biotechnol Prog. 2011 March-April; 27(2): 333-41. doi: 10.1002/btpr.559.

Cline J D. Spectrophotometric Determination of Hydrogen Sulfide in Natural Waters. Limnol Oceanogr. 1969; 14(3): 454-8.

Cronan J E, LaPorte D. Tricarboxylic Acid Cycle and Glyoxylate Bypass. In A. Böck, R. Curtiss III. J. B. Kaper, P. D. Karp, F. C. Neidhardt, T. Nystrom, J. M. Slauch, C. L. Squires, and D. Ussery (ed.), EcoSal—*Escherichia coli* and *Salmonella*: Cellular and Molecular Biology. http://www.ecosal.org. ASM Press, Washington, D C. 2010 Mar. 12.

Cropp T A, Wilson D J, Reynolds K A. Identification of a cyclohexylcarbonyl CoA biosynthetic gene cluster and application in the production of doramectin. Nat Biotechnol. 2000 September; 18(9):980-3.

Davis J H, Rubin A J, Sauer R T. Design, construction and characterization of a set of insulated bacterial promoters. Nucleic Acids Res. 2011 February; 39(3):1131-41.

de Mendoza D, Klages Ulrich A. Cronan J E Jr. Thermal regulation of membrane fluidity in *Escherichia coli*. Effects of overproduction of beta-ketoacyl-acyl carrier protein synthase I. J Biol Chem. 1983 Feb. 25; 258(4): 2098-101.

Dellomonaco C, Clomburg J M, Miller E N, Gonzalez R. Engineered reversal of the β-oxidation cycle for the synthesis of fuels and chemicals. Nature. 2011 Aug. 10; 476(7360):355-9.

Dennis M W, Kolattukudy P E. Alkane biosynthesis by decarbonylation of aldehyde catalyzed by a microsomal preparation from *Botryococcus braunii*. Arch Biochem Biophys. 1991 June; 287(2):268-75.

Denoya C D, Fedechko R W, Hafner E W, McArthur H A, Morgenstern M R, Skinner D D, Stutzman-Engwall K, Wax R G, Wernau W C. A second branched-chain alpha-keto acid dehydrogenase gene cluster (bkdFGH) from *Streptomyces avermitilis*: its relationship to avermectin biosynthesis and the construction of a bkdF mutant suitable for the production of novel antiparasitic avermectins. J Bacteriol. 1995 June; 177(12):3504-11.

Deshpande M V. Ethanol production from cellulose by coupled saccharification/fermentation using *Saccharomyces cerevisiae* and cellulase complex from *Sclerotium rolfsii* UV-8 mutant. Appl Biochem Biotechnol. 1992 September; 36(3):227-34.

Dettman D L, Reische A K, Lohmann K C. Controls on the stable isotope composition of seasonal growth bands in aragonitic fresh-water bivalves (unionidae). Geochim Cosmochim Acta. 1999; 63:1049-57.

Doolittle, R F (Editor). Computer Methods for Macromolecular Sequence Analysis. Methods in Enzymology. 1996; 266:3-711.

Edgar R C. MUSCLE: multiple sequence alignment with high accuracy and high throughput. Nucleic Acids Res. 2004 Mar. 19; 32(5):1792-7. (a)

Edgar R C. MUSCLE: a multiple sequence alignment method with reduced time and space complexity. BMC Bioinformatics. 2004 Aug. 19; 5:113. (b)

Edwards J S, Ramakrishna R, Palsson B O. Characterizing the metabolic phenotype: a phenotype phase plane analysis. Biotechnol Bioeng. 2002 Jan. 5; 77(1):27-36.

Eisenreich W, StraussG, Werz U, Fuchs G, Bacher A. Retrobiosynthetic analysis of carbon fixation in the phototrophic eubacterium *Chloroflexus aurantiacus*. Eur J Biochem. 1993 Aug. 1; 215(3):619-32.

Evans M C, Buchanan B B, Anon D I. A new ferredoxin-dependent carbon reduction cycle in a photosynthetic bacterium. Proc Natl Acad Sci USA. 1966 April; 55(4): 928-34.

Evans C T, Sumegi B, Sere P A, Sherry A D, Malloy C R. [13C]propionate oxidation in wild-type and citrate synthase mutant *Escherichia coli*: evidence for multiple pathways of propionate utilization. Biochem J. 1993 May 1; 291 (Pt 3):927-32.

Farquhar G D, Ehleringer J R, and Hubick K T. Carbon isotope discrimination and photosynthesis. Annu Rev Plant Physiol Plant Mol Biol. 1989; 40:503-37.

Ferenci T, Strom T, and Quayle J R. Purification and properties of 3-hexulose phosphate synthase and phospho-3-hexuloisomerase from *Methylococcus capsulatus*. Biochem J 1974 December; 144(3) 477-86.

Fogel G B, Collins C R, Li J, Brunk C F. Prokaryotic Genome Size and SSU rDNA Copy Number: Estimation of Microbial Relative Abundance from a Mixed Population. Microb Ecol. 1999 August; 38(2):93-113.

Fong S S, Palsson B Ø. Metabolic gene-deletion strains of *Escherichia coli* evolve to computationally predicted growth phenotypes. Nat Genet. 2004 October; 36(10): 1056-8.

Friedmann S, Steindorf A, Alber B E. Fuchs G Properties of succinyl-coenzyme A:L-malate coenzyme A transferase and its role in the autotrophic 3-hydroxypropionate cycle of *Chloroflexus aurantiacus*. J Bacteriol. 2006 April, 188(7):2646-55.

Friedmann S, Alber B E, Fuchs G Properties of R-citramalyl-coenzyme A lyase and its role in the autotrophic 3-hydroxypropionate cycle of *Chloroflexus aurantiacus*. J Bacteriol. 2007 April; 189(7):2906-14.

Gehring U and Arnon D I. Purification and properties of -ketoglutarate synthase from a photosynthetic bacterium. J Biol Chem 1972 Nov. 10; 247(21) 6963-9.

Gerhold D, Rushmore T, Caskey C T. DNA chips: promising toys have become powerful tools. Trends Biochem Sci. 1999 May; 24(5):168-73.

Goericke R, Montoya J P, Fry B. Physiology of isotopic fractionation in algae and cyanobacteria. Chapter 9 in "Stable Isotopes in Ecology and Environmental Science". Blackwell Publishing. 1994.

Grantham R, Gautier C, Gouy M, Mercier R, Pavé A. Codon catalog usage and the genome hypothesis. Nucleic Acids Res. 1980 Jan. 11; 8(1):r49-r62.

Greene D N, Whitney S M, Matsumura I, Artificially evolved *Synechococcus* PCC6301 Rubisco variants exhibit improvements in folding and catalytic efficiency. Biochem J. 2007 Jun. 15; 404(3):517-24.

Griesbeck C, Hauska G, Schutz M. Biological Sulfide Oxidation: Sulfide-Quinone Reductase (SQR), the Primary Reaction. Recent Research Developments in Microbiology. 2000; 4:179-203.

Gul-Karaguler N, Session R B, Clarke A R, Holbrook J J. A single mutation in the NAD-specific formate dehydrogenase from *Candida methylica* allows the enzyme to use NADP. Biotechnol Lett. 2001; 23(4):283-7.

Gutteridge S, Phillips A L, Kettleborough C A, Parry M A J. Expression of bacterial Rubisco genes in *Escherichia coli*. Phil Trans R Soc Lond B 313:433-45.

Han L. Reynolds K A. A novel alternate anaplerotic pathway to the glyoxylate cycle in streptomycetes. J Bacteriol. 1997 August; 179(16):5157-64.

Hatrongjit R, Packdibamrung K. A novel NADP+-dependent formate dehydrogenase from *Burkholderia stabilis* 15516: Screening, purification and characterization. Enzyme Microb Technol. 2010 Jun. 7; 46(7):557-61.

Hawley D K, McClure W R. Compilation and analysis of *Escherichia coli* promoter DNA sequences. Nucleic Acids Res. 1983 Apr. 25; 11(8):2237-55.

Hayes J M. Fractionation of Carbon and Hydrogen Isotopes in Biosynthetic Processes. Rev Mineral Geochem. 2001 January; 43(1):225-77.

Helling R B, Kukora J S. Nalidixic aed-resistant mutants of *Escherichia coli* deficient in isocitrate dehydrogenase. J Bacteriol. 1971 March, 105(3):1224-6.

Henry C S, Jankowski M D, Broadbelt L J, Hatzimanikatis V. Genome-scale thermodynamic analysis of *Escherichia coli* metabolism. Biophys J. 2006 Feb. 15; 90(4):1453-61.

Henstra A M, Sipma J, Rinzema A. Stams A J. Microbiology of synthesis gas fermentation for biofuel production. Curr Opin Biotechnol. 2007 June; 18(3):200-6.

Herter S, Fuchs G, Bacher A, Eisenreich W. A bicyclic autotrophic $CO_2$ fixation pathway in *Chloroflexus aurantiacus*. J Biol Chem. 2002 Jun. 7; 277(23):20277-83. (a)

Herter S, Busch A, Fuchs G. L-Malyl-coenzyme A lyase/beta-methylmalyl-coenzyme A lyase from *Chloroflexus aurantiacus*, a bifunctional enzyme involved in autotrophic $CO_2$ fixation. J Bacteriol. 2002 November; 184 (21):5999-6006. (b)

Ho N W, Chen Z, Brainard A P. Genetically engineered *Saccharomyces* yeast capable of effective cofermentation of glucose and xylose. Appl Environ Microbiol. 1998 May; 64(5):1852-9.

Hoffmeister M, Piotrowski M, Nowitzki U, Martin W. Mitochondrial trans-2-enoyl-CoA reductase of wax ester fermentation from *Euglena gracilis* defines a new family of enzymes involved in lipid synthesis. J Biol Chem. 2005 Feb. 11; 280(6):4329-38.

Holo H. *Chloroflexus aurantiacus* secretes 3-hydroxypropionate, a possible intermediate in the assimilation of $CO_2$ and acetate. Arch Microbiol. 1989:151(3):252-6.

Hügler M, Menendez C, Schägger H, Fuchs G. Malonyl-coenzyme A reductase from *Chloroflexus aurantiacus*, a key enzyme of the 3-hydroxypropionate cycle for autotrophic $CO_2$ fixation. J Bacteriol. 2002 May; 184(9):2404-10.

Hügler M, Huber H, Molyneaux S J, Vetriani C, Sievert S M. Autotrophic $CO_2$ fixation via the reductive tricarboxylic acid cycle in different lineages within the phylum Aquificae: evidence for two ways of citrate cleavage. Environ Microbiol. 2007 January; 9(1):81-92.

Hügler M, Sievert S M. Beyond the Calvin cycle: autotrophic carbon fixation in the ocean. Ann Rev Mar Sci. 2011; 3:261-89.

Huisman G W, Gray D. Towards novel processes for the fine-chemical and pharmaceutical industries. Curr Opin Biotechnol. 2002 August; 13(4):352-8.

Ikeda T, Yamamoto M, Arai H, Ohmori D, Ishii M, Igarashi Y. Two tandemly arranged ferredoxin genes in the *Hydrogenobacter thermophilus* genome: comparative characterization of the recombinant [4Fe-4S] ferredoxins. Biosci Biotechnol Biochem. 2005 June; 69(6):1172-7.

Inokuma K, Nakashimada Y, Akahoshi T, Nishio N. Characterization of enzymes involved in the ethanol production of *Moorella* sp. HUC22-1. Arch Microbiol. 2007 July; 188(1):37-45.

Ivlev A A. Carbon isotope effects ($^{13}C/^{12}C$) in biological systems. Separation Sci Technol. 2010; 36:1819-1914.

Janausch I G Zientz E. Tran Q H, Kröger A, Unden G. C4-dicarboxylate carriers and sensors in bacteria. Biochim Biophys Acta. 2002 Jan. 17; 1553(1-2):39-56.

Jukes T H, Osawa S. Evolutionary changes in the genetic code. Comp Biochem Physiol B. 1993 November; 106 (3):489-94.

Kalscheuer R, Steinbüchel A. A novel bifunctional wax ester synthase/acyl-CoA:diacylglycerol acyltransferase mediates wax ester and triacylglycerol biosynthesis in *Acinetobacter calcoaceticus* ADP1. J Biol Chem. 2003 Mar. 7; 278(10):8075-82.

Kalscheuer R, Stölting T, Steinbüchel A. Microdiesel: *Escherichia coli* engineered for fuel production. Microbiology. 2006 September; 152(Pt 9):2529-36.

Kanao T, Kawamura M, Fukui T, Atomi H and Imanaka T. Characterization of isocitrate dehydrogenase from the green sulfur bacterium *Chlorobium limicola*. A carbon dioxide-fixing enzyme in the reductive tricarboxylic acid cycle. Eur J Biochem 2002 April; 269(7) 1926-31. (a)

Kanao T, Fukui T, Atomi H, and Imanaka T. Kinetic and biochemical analyses on the reaction mechanism of a bacterial ATP-citrate lyase. Eur J Biochem 2002 July; 269(14) 3409-16. (b)

Kaneda T. Iso- and anteiso-fatty acids in bacteria: biosynthesis, function, and taxonomic significance. Microbiol Rev. 1991 June; 55(2):288-302.

Kapust R B, Waugh D S. *Escherichia coli* maltose-binding protein is uncommonly effective at promoting the solubility of polypeptides to which it is fused. Protein Sci. 1999 August; 8(8):1668-74.

Keasling J D, Jones K L, Van Dien S J. New Tools for Metabolic Engineering of *Escherichia coli*. Chapter 5 in Metabolic Engineering. Marcel Dekker. New York, N Y. 1999. (a)

Keasling J D. Gene-expression tools for the metabolic engineering of bacteria. Trends Biotechnol. 1999 November; 17(11):452-60. (b)

Kelly D P, Wood P, Gottschal J C, Kuenen J G Autotrophic metabolism of formate by *Thiobacillus* strain A2. J Gen Microbiol. 1979; 114:1-13.

Kelly J R, Rubin A J, Davis J H, Ajo-Franklin C M, Cumbers J, Czar M J, de Mora K. Glieberman A L, Monie D D, Endy D. Measuring the activity of BioBrick promoters using an in vivo reference standard. J Biol Eng. 2009 Mar. 20; 3:4.

Kemp M B. The hexose phosphate synthetase of *Methylococcus capsulatus*. Biochem J. 1972 April, 127(3):64P-65P.

Kemp M B. Hexose phosphate synthase from Methylcoccus *capsulatus* makes D-arabino-3-hexulose phosphate. Biochem J. 1974 April; 139(1):129-34.

Kim O B, Unden G. The L-tartrate/succinate antiporter TtdT (YgjE) of L-tartrate fermentation in *Escherichia coli*. J Bacteriol. 2007 March; 189(5):1597-603.

Kim J Y, Jo B H, Cha H J. Production of biohydrogen by heterologous expression of oxygen-tolerant *Hydrogenovibrio marinus* [NiFc]-hydrogenase in *Escherichia coli*. J Biotechnol. 2011 Jul. 20.

Klimke W, Agarwala R, Badretdin A, Chetvernin S, Ciufo S. Fedorov B, Kiryutin B, O'Neill K, Resch W. Resenchuk S, Schafer S, Tolstoy I, Tatusova T. The National Center for Biotechnology Information's Protein Clusters Database. Nucleic Acids Res. 2009 January; 37(Database issue):D216-23.

Knight T. Idempotent Vector Design for Standard Assembly of Biobricks. DOI: 1721.1/21168.

Knight T. BBF RFC10: Draft Standard for BioBrick™ biological parts. DOI: 1721.1/45138.

Larkum A W. Limitations and prospects of natural photosynthesis for bioenergy production. Curr Opin Biotechnol. 2010 June; 21(3):271-6.

Knothe G, Dunn R O, Bagby M O. Biodiesel: The use of vegetable oils and their derivatives as alternative diesel fuels. Am Chem Soc Symp Series. 1997; 666:172-208.

Knothe G. Rapid monitoring of transesterification and assessing biodiesel fuel quality by NIR spectroscopy using a fiber-optic probe. J Am Oil Chem Soc. 1999; 76(7):795-800.

Knothe G Dependence of biodiesel fuel properties on the structure of fatty acid alkyl Esters. Fuel Process Technol. 2005:86:1059-1070.

Kolkman J A, Stemmer W P. Directed evolution of proteins by exon shuffling. Nat Biotechnol. 2001 May; 19(5):423-8.

Komers K, Skopal F, Stloukal R. Determination of the neutralization number for biodiesel fuel production. Fett/Lipid. 1997; 99(2):52-54.

Larue T A, Kurz W G Estimation of nitrogenase using a colorimetric determination for ethylene. Plant Physiol. 1973 June; 51(6):1074-5.

Li Y, Florova G, Reynolds K A. Alteration of the fatty acid profile of *Streptomyces coelicolor* by replacement of the initiation enzyme 3-ketoacyl acyl carrier protein synthase III (FabH). J Bacteriol. 2005 June; 187(11):3795-9. Liu C L, Mortenson L E. Formate dehydrogenase of *Clostridium pasteurianum*. J Bacteriol. 1984 July; 159(1):375-80.

Marcia M, Ermler U, Peng G Michel H. Anew structure-based classification of sulfide:quinone oxidoreductases. Proteins. 2010 April; 78(5):1073-83.

Marrakchi H. Zhang Y M, Rock C O. Mechanistic diversity and regulation of Type H fatty acid synthesis. Biochem Soc Trans. 2002 November; 30(Pt 6):1050-5. (a)

Marrakchi H, Choi K H, Rock C O. Anew mechanism for anaerobic unsaturated fatty acid formation in *Streptococcus pneumoniae*. J Biol Chem. 2002 Nov. 22; 277(47): 44809-16. (b)

Martin V J J, Smolke C, Keasling J D. Redesigning cells for production of complex organic molecules. ASM News. 2002:68:336-343.

Martinez-Alonso M, Toledo-Rubio V, Noad R, Unzueta U, Ferrer-Miralles N, Roy P, Villaverde A. Rehosting of bacterial chaperones for high-quality protein production. Appl Eniron Microbiol. 2009 December; 75(24):7850-4.

Martínez-Alonso M, Garcia-Fruitós E, Ferrer-Miralles N, Rinas U, Villaverde A. Side effects of chaperone gene co-expression in recombinant protein production. Microb Cell Fact. 2010 Sep. 2; 9:64.

Marty J, Planas D. Comparison of methods to determine algal $\delta^{13}C$ in freshwater. Limnol Oceanogr: Methods. 2008; 6:51-63.

Menendez C, Bauer Z, Huber H, Gad'on N, Stetter K O, Fuchs Q Presence of acetyl coenzyme A (CoA) carboxylase and propionyl-CoA carboxylase in autotrophic Crenarchaeota and indication for operation of a 3-hydroxypropionate cycle in autotrophic carbon fixation. J Bacteriol. 1999 February; 181(4):1088-98.

Minshull J, Stemmer W P. Protein evolution by molecular breeding. Curr Opin Chem Biol. 1999 June; 3(3):284-90.

Miroshnichenko M L, Kostrikina N A, L'Haridon S, Jeanthon C, Hippe H, Stackebrandt E, Bonch-Osmolovskaya E A. *Nautilia lithotrophica* gen. nov., sp. nov., a thermophilic sulfur-reducing epsilon-proteobacterium isolated from a deep-sea hydrothermal vent. Int J Syst Evol Microbiol. 2002 July; 52(Pt 4):1299-304.

Mitsui R, Sakai Y, Yasueda H, Kato N. A novel operon encoding formaldehyde fixation: the ribulose monophosphate pathway in the gram-positive facultative methylotrophic bacterium *Mycobacterium gastri* MB19. J Bacteriol. 2000 February; 182(4):944-8.

Monson K D, Hayes J M. Biosynthetic control of the natural abundance of carbon 13 at specific positions within fatty acids in *Escherichia coli*. J Biol Chem. 1980; 255:11435-41.

Moriya Y, Itoh M, Okuda S, Yoshizawa A C. Kanehisa M. KAAS: an automatic genome annotation and pathway reconstruction server. Nucleic Acids Res. 2007 July; 35(Web Server issue):W182-5.

Morweiser M. Kruse O, Hankamer B, Posten C. Developments and perspectives of photobioreactors for biofuel production. Appl Microbiol Biotechnol. 2010 July; 87(4): 1291-301.

Murli S. Opperman T. Smith B T, Walker G C. A role for the umuDC gene products of *Escherichia coli* in increasing resistance to DNA damage in stationary phase by inhibiting the transition to exponential growth. J Bacteriol. 2000 February; 182(4):1127-35.

Murtagh, F. Complexities of Hierarchic Clustering Algorithms: the State of the Art. Computational Statistics Quarterly. 1984; 1:101-13.

Nature Genetics. 1999:21(1):1-60.

Ness J E, Del Cardayré S B, Minshull J, Stemmer W P. Molecular breeding: the natural approach to protein design. Adv Protein Chem. 2000; 55:261-92.

Ober J A. Sulfur. U.S. Geological Survey Minerals Report—2008. 2010; 74:1-17.

Orita I, Yurimoto H. Hirai R, Kawarabayasi Y, Sakai Y, Kato N. The archaeon *Pyrococcus horikoshii* possesses a bifunctional enzyme for formaldehyde fixation via the ribulose monophosphate pathway. J Bacteriol. 2005 June; 187(11):3636-42.

Orita I, Sato T, Yurinto H, Kato N, Atomi H. Imanaka T, Sakai Y. The ribulose mnonophosphate pathway substitutes for the missing pentose phosphate pathway in the archaeon *Thermococcus kodakaraensis*. J Bacteriol. 2006 July; 188(13):4698-704.

Orita I, Sakamoto N, Kato N, Yurimoto H, and Sakai Y. Bifunctional enzyme fusion of 3-hexulose-6-phosphate synthase and 6-phospho-3-hexuloisomerase. Appl Microbiol Biotechnol 2007 August; 76(2) 439-45.

Palaniappan N, Kim B S, Sekiyama Y, Osada H, Reynolds K A. Enhancement and selective production of phoslactomycin B, a protein phosphatase IIa inhibitor, through identification and engineering of the corresponding biosynthetic gene cluster. J Biol Chem. 2003 Sep. 12; 278 (37):35552-7.

Park M O. New pathway for long-chain n-alkane synthesis via 1-alcohol in *Vibrio furnissii* M1. J Bacteriol. 2005 February; 187(4):1426-9.

Parikh M R, Greene D N, Woods K K, Matsumura 1. Directed evolution of RuBisCO hypermorphs through genetic selection in engineered *E. coli*. Protein Eng Des Sel. 2006 March; 19(3):113-9.

Patton S M, Cropp T A, Reynolds K A. A novel delta(3), delta(2)-enoyl-CoA isomerase involved in the biosynthesis of the cyclohexanecarboxylic acid-derived moiety of the polyketide ansatrienin A. Biochemistry. 2000 Jun. 27; 39(25):7595-604.

Pinske C, Bönn M, Krüger S, Lindenstrauß U, Sawers R G. Metabolic Deficiencies Revealed in the Biotechnologically Important Model Bacterium *Escherichia coli* BL21 (DE3). PLoS One. 2011; 6(8):e22830.

Portis A R Jr. Parry M A. Discoveries in Rubisco (Ribulose 1,5-bisphosphate carboxylase/oxygenase): a historical perspective. Photosynth Res. 2007 October; 94(1):121-43.

Pramanik J, Keasling J D. Stoichiometric model of *Escherichia coli* metabolism: incorporation of growth-rate dependent biomass composition and mechanistic energy requirements. Biotechnol Bioeng. 1997 Nov. 20; 56(4): 398-421.

Pramanik J. Keasling J D. Effect of *Escherichia coli* biomass composition on central metabolic fluxes predicted by a stoichiometric model. Biotechnol Bioeng. 1998 Oct. 20; 60(2):230-8. (a)

Pramanik J, Trelstad P L, Keasling J D. A flux-based stoichiometric model of enhanced biological phosphorus removal metabolism. Wat Sci Technol. 1998; 37(4-5): 609-13. (b)

Pramanik J, Trelstad P L, Schuler A J, Jenkins D, Keasling J D. Development and validation of a flux-based stoichiometric model for enhanced biological phosphorus removal metabolism. Water Res. 1998; 33(2):462-76. ©.

Rathnasingh C, Raj S M, Lee Y, Catherine C, Ashok S, and Park S. Production of 3-hydroxypropionic acid via malonyl-CoA pathway using recombinant *Escherichia coli* strains. J Biotechnol 2011 Jun. 23.

Reading N C. Sperandio V. Quorum sensing: the many languages of bacteria. FEMS Microbiol Lett. 2006 January; 254(1):1-11.

Rock C O, Tsay J T, Heath R, Jackowski S. Increased unsaturated fatty acid production associated with a suppressor of the fabA6(Ts) mutation in *Escherichia coli*. J Bacteriol. 1996 September; 178(18):5382-7.

Roessner C A, Spencer J B, Ozaki S, Min C, Atshaves B P, Nayar P, Anousis N, Stolowich N J, Holderman M T, Scott A I. Overexpression in *Escherichia coli* of 12 vitamin B12 biosynthetic enzymes. Protein Expr Purif. 1995 April; 6(2):155-63.

Sachdev D, Chirgwin J M. Solubility of proteins isolated from inclusion bodies is enhanced by fusion to maltose-binding protein or thioredoxin. Protein Expr Purif. 1998 February; 12(1):122-32.

Sachdev D. Chirgwin J M. Fusions to maltose-binding protein: control of folding and solubility in protein purification. Methods Enzymol. 2000; 326:312-21.

Saitou N, Nei M. The neighbor-joining method: a new method for reconstructing phylogenetic trees. Mol Biol Evol. 1987 July; 4(4):406-25.

Sakata S, Hayes J M, McTaggart A R. Evans R A, Leckrone K J, Togasaki R K. Carbon isotopic fractionation associated with lipid biosynthesis by a cyanobacterium: relevance for interpretation of biomarker records. Geochim Cosmochim Acta. 1997; 61:5379-89.

Sambrook. J, Russell, D. Molecular Cloning: A Laboratory Manual, Third Edition. CSHL Press. Cold Spring Harbor, N.Y. 2001.

San K Y, Bennett G N, Berrios-Rivera S J, Vadali R V, Yang Y T, Horton E, Rudolph F B, Sariyar B, Blackwood K. Metabolic engineering through cofactor manipulation and its effects on metabolic flux redistribution in *Escherichia coli*. Metab Eng. 2002 April; 4(2):182-92.

Sauer U, Canonaco F, Heri S, Perrenoud A, Fischer E. The soluble and membrane-bound transhydrogenases UdhA and PntAB have divergent functions in NADPH metabolism of *Escherichia coli*. J Biol Chem. 2004 Feb. 20; 279(8):6613-9.

Schena M (editor). DNA Microarrays: A Practical Approach. The Practical Approach Series, Oxford University Press. 1999.

Schena M (editor). Microarray Biochip: Tools and Technology. Eaton Publishing Company/BioTechniques Books Division. 2000.

Schütz M, Shahak Y, Padan E, and Hauska G Sulfide-quinone reductase from *Rhodobacter capsulatus*. Purification, cloning, and expression. J Biol Chem 1997 Apr. 11; 272(15) 9890-4.

Self W T, Hasona A, Shanmugam K T. Expression and regulation of a silent operon, hyf, coding for hydrogenase 4 isoenzyme in *Escherichia coli*. J Bacteriol. 2004 January; 186(2):580-7.

Serov A E, Popova A S. Fedorchuk V V, Tishkov V I. Engineering of coenzyme specificity of formate dehydrogenase from *Saccharomyces cerevisiae*. Biochem J. 2002 Nov. 1; 367(Pt 3):841-7.

Shetty R P, Endy D, Knight T F Jr. Engineering BioBrick vectors from BioBrick parts. J Biol Eng. 2008 Apr. 14; 2:5. Shetty R, Lizarazo M, Rettberg R, Knight T F. Assembly of BioBrick standard biological parts using three antibiotic assembly. Methods Enzymol. 2011; 498: 311-26.

Shibata H and Kobayashi S. Sulfide oxidation in gram-negative bacteria by expression of the sulfide-quinone reductase gene of *Rhodobacter capsulatus* and by electron transport to ubiquinone. Can J Microbiol 2001 September; 47(9) 855-60.

Shpaer E Q GeneAssist. Smith-Waterman and other database similarity searches and identification of motifs. Methods Mol Biol. 1997; 70:173-87.

Sintsov N V, Ivanovskiĭ R N, and Kondrat'eva E N. [ATP-dependent citrate lyase in the green phototrophic bacterium. *Chlorobium limicola*]. Mikrobiologiia 1980 July-August; 49(4) 514-6.

Smith J L, Campbell B J, Hanson T E, Zhang C L. Cary S C. *Nautilia profundicola* sp. nov., a thermophilic, sulfur-reducing epsilonproteobacterium from deep-sea hydrothermal vents. Int J Syst Evol Microbiol. 2008 July; 58(Pt 7):1598-602.

Smolke C D, Carrier T A, Keasling J D. Coordinated, differential expression of two genes through directed mRNA cleavage and stabilization by secondary structures. Appl Environ Microbiol. 2000 December; 66(12): 5399-405. Smolke C D, Martin V J, Keasling J D. Controlling the metabolic flux through the carotenoid pathway using directed mRNA processing and stabilization. Metab Eng. 2001 October; 3(4):313-21.

Smolke C D, Keasling J D. Effect of copy number and mRNA processing and stabilization on transcript and protein levels from an engineered dual-gene operon. Biotechnol Bioeng. 2002 May 20; 78(4):412-24. (a)

Smolke C D, Keasling J D. Effect of gene location, mRNA secondary structures, and RNase sites on expression of two genes in an engineered operon. Biotechnol Bioeng. 2002 Dec. 30; 80(7):762-76. (b)

Sokal R, Michener. C. A Statistical Method for Evaluating Systematic Relationships. University of Kansas Science Bulletin. 1958:38:1409-38.

Strauss G, Fuchs G Enzymes of a novel autotrophic $CO_2$ fixation pathway in the phototrophic bacterium *Chloroflexus aurantiacus*, the 3-hydroxypropionate cycle. Eur J Biochem. 1993 Aug. 1; 215(3):633-43.

Strom T, Ferenci T, and Quayle J R. The carbon assimilation pathways of *Methylococcus capsulatus, Pseudomonas methanica* and *Methylosinus trichosporium* (OB3B) during growth on methane. Biochem J 1974 December; 144(3) 465-76.

Sun J, Hopkins R C, Jenney F E, McTernan P M, Adams M W. Heterologous expression and maturation of an NADP-dependent [NiFe]-hydrogenase: a key enzyme in biofuel production. PLoS One. 2010 May 6; 5(5):e10526.

Tabita F R, Small C L. Expression and assembly of active cyanobacterial ribulose-1,5-bisphosphate carboxylase/oxygenase in *Escherichia coli* containing stoichiometric amounts of large and small subunits. Proc Natl Acad Sci USA. 1985 September; 82(18):6100-3.

Tatusov R L, Koonin E V, Lipman D J. A genomic perspective on protein families. Science. 1997 Oct. 24; 278 (5338):631-7.

Tatusov R L, Fedorova N D, Jackson J D, Jacobs A R, Kiryutin B, Koonin E V, Krylov D M, Mazumder R, Mekhedov S L, Nikolskaya A N, Rao B S, Smirnov S, Sverdlov A V, Vasudevan S, Wolf Y I, Yin J J, Natale D A. The COG database: an updated version includes eukaryotes. BMC Bioinformatics. 2003 Sep. 11; 4:41.

van Wezel G P, Mahr K, König M, Traag B A, Pimentel-Schmitt E F, Willimek A, Titgemeyer F. GlcP constitutes the major glucose uptake system of *Streptomyces coelicolor* A3(2). Mol Microbiol. 2005 January; 55(2):624-36.

Venturi V. Regulation of quorum sensing in *Pseudomonas*. FEMS Microbiol Rev. 2006 March; 30(2):274-91.

Vignais P M, Colbeau A. Molecular biology of microbial hydrogenases. Curr Issues Mol Biol. 2004 July; 6(2):159-88.

Vignais P M, Billoud B. Occurrence, classification, and biological function of hydrogenases: an overview. Chem Rev. 2007 October; 107(10):4206-72.

Wells M A, Mercer J, Mott R A, Pereira-Medrano A G, Buja A M, Radianingtyas H, Wright P C. Engineering a non-native hydrogen production pathway into *Escherichia coli* via a cyanobacterial [NiFe] hydrogenase. Metab Eng. 2011 July; 13(4):445-53.

Wubbolts M G, Terpstra P, van Beilen J B, Kingma J, Meesters H A, Witholt B. Variation of cofactor levels in *Escherichia coli*. Sequence analysis and expression of the pncB gene encoding nicotinic acid phosphoribosyltransferase. J Biol Chem. 1990 Oct. 15; 265(29):17665-72.

Yamamoto M, Ikeda T, Arai H, Ishii M, and Igarashi Y. Carboxylation reaction catalyzed by 2-oxoglutarate:ferredoxin oxidoreductases from *Hydrogenobacter thermophilus*. Extremophiles 2010 January; 14(1) 79-85.

Yoon K S, Ishii M, Kodama T, Igarashi Y. Purification and characterization of pyruvate:ferredoxin oxidoreductase from *Hydrogenobacter thermophilus* TK-6. Arch Microbiol. 1997 May; 167(5):275-9.

Yoon Y G Cho J H, Kim S C. Cre/loxP-mediated excision and amplification of large segments of the *Escherichia coli* genome. Genet Anal. 1998 January; 14(3):89-95.

Zarzycki J. Brecht V, Miller M, Fuchs G Identifying the missing steps of the autotrophic 3-hydroxypropionate $CO_2$ fixation cycle in *Chloroflexus aurantiacus*. Proc Natl Acad Sci USA. 2009 Dec. 15; 106(50):21317-22.

Zarzycki J, Fuchs G Co-Assimilation of Organic Substrates via the Autotrophic 3-Hydroxypropionate Bi-Cycle in *Chloroflexus aurantiacus*. Appl Environ Microbiol. 2011 Jul. 15.

Zdobnov E M, Apweiler R. InterProScan—an integration platform for the signature-recognition methods in InterPro. Bioinformatics. 2001 September; 17(9):847-8.

Zhang C C, Durand M C, Jeanjean R, Joset F. Molecular and genetical analysis of the fructose-glucose transport system in the cyanobacterium *Synechocystis* PCC6803. Mol Microbiol. 1989 September; 3(9):1221-9.

Zhang Y M, Marrakchi H, Rock C O. The FabR (YijC) transcription factor regulates unsaturated fatty acid biosynthesis in *Escherichia coli*. J Biol Chem. 2002 May 3; 277(18):15558-65.

Zhu X, Yuasa M, Okada K, Suzuki K, Nakagawa T, Kawamukai M, Matsuda H. Production of ubiquinone in *Escherichia coli* by expression of various genes responsible for ubiquinone biosynthesis. J Ferm Bioeng. 1995; 79(5):493-5.

Zweiger G. Knowledge discovery in gene-expression-microarray data: mining the information output of the genome. Trends Biotechnol. 1999 November; 17(11):429-36.

The invention claimed is:

1. A chemoautotrophic host cell that comprises a heterologous polynucleotide encoding a hexulose-6-phosphate synthase (HPS), wherein the polynucleotide comprises a sequence that is at least 90% identical to SEQ ID NO: 46 or 47.

2. The chemoautotrophic host cell of claim 1, wherein the polynucleotide comprises SEQ ID NO: 46 or 47.

3. The chemoautotrophic host cell of claim 1, wherein the host cell is a bacterial cell.

4. The chemoautotrophic host cell of claim 3, wherein the bacterial cell is an *Escherichia coli* cell.

5. The chemoautotrophic host cell of claim 1, wherein the host cell further comprises a polynucleotide encoding a 6-phospho-3-hexuloisomerase (PHI).

6. The chemoautotrophic host cell of claim 5, wherein the host cell is capable of converting an inorganic carbon to a carbon-based central metabolite.

7. The chemoautotrophic host cell of claim 6, wherein the carbon-based central metabolite is fructose-6-phosphate.

8. A method for producing a carbon-based product, comprising culturing the chemoautotrophic host cell of claim 1.

9. A polynucleotide comprising a sequence that is at least 90% identical to SEQ ID NO: 46 or 47.

10. The polynucleotide of claim 9, wherein the polynucleotide comprises SEQ ID NO: 46 or 47.

11. A vector comprising the polynucleotide of claim 9.

12. A chemoautotrophic host cell that comprises a heterologous polynucleotide encoding a hexulose-6-phosphate synthase (HPS), wherein the HPS comprises a sequence that is at least 90% identical to the *Methylococcus capsulatus* HPS protein encoded by SEQ ID NO: 46 or 47, wherein the HPS protein encoded by SEQ ID NO: 46 corresponds to NCBI Reference Sequence YP_115138 and wherein the HPS protein encoded by SEQ ID NO: 47 corresponds to NCBI Reference Sequence YP_115430.

13. The chemoautotrophic host cell of claim 12, wherein the host cell is a bacterial cell.

14. The chemoautotrophic host cell of claim 13, wherein the bacterial cell is an *Escherichia coli* cell.

15. The chemoautotrophic host cell of claim 12, wherein the host cell further comprises a polynucleotide encoding a 6-phospho-3-hexuloisomerase (PHI).

16. The chemoautotrophic host cell of claim 15, wherein the chemoautotrophic host cell is capable of converting an inorganic carbon to a carbon-based central metabolite.

17. The chemoautotrophic host cell of claim 16, wherein the carbon-based central metabolite is fructose-6-phosphate.

18. A method for producing a carbon-based product, comprising culturing the chemoautotrophic host cell of claim 12.

* * * * *

```
                           SEQUENCE LISTING

<160> NUMBER OF SEQ ID NOS: 66

<210> SEQ ID NO 1
<211> LENGTH: 1161
<212> TYPE: DNA
<213> ORGANISM: Burkholderia stabilis

<400> SEQUENCE: 1
atggccactg ttctatgcgt gctatatcct gatccggttg atggttatcc accgcactat      60
gttcgtgata ccatcccggt gatcacccga tatgcagatg gccaaacagc ccccactccc     120
gcggggccgc caggatttcg tcccggtgaa ctggtgggca gtgtttctgg tgcgctggga     180
cttcgcggtt accttgaagc ccatggtcac actctcatcg tcacatcgga taaagatggt     240
ccggatagtg agtttgaaag acggctgcct gatgccgatg ttgtcatcag ccagccgttt     300
tggcccgcat atcttacggc tgaacgtatc gcgagggcgc cgaagttacg tctggctctg     360
```

```
actgctggta taggctcaga ccacgttgac ctcgatgccg cggcgcgtgc tcacattacg    420
gtcgccgaag tgactggaag taacagtatt tcagtggctg aacacgttgt tatgacaacg    480
ctggccttag tgcggaacta tttacctagc cacgcaattg cgcagcaagg tggttggaac    540
atcgccgact gtgtttcacg ctcttatgac gtcgaaggaa tgcatttcgg cacagtaggg    600
gcgggtagga ttggattggc tgttctgcgc cggcttaaac cgtttggtct gcatttgcat    660
tacacccaaa gacatcgctt ggatgcagcc atcgaacaag aactcggtct tacttaccat    720
gccgatccag ccagtcttgc ggcggcagta gacattgtta atttgcagat tccgctgtat    780
ccttccactg aacaccttt tgatgctgca atgattgcac gcatgaaaag aggtgcgtac    840
ctgattaata ctgcccgtgc gaagttagtg gaccgcgatg ccgtcgtcag ggctgtcaca    900
agcggacatc tggctggtta tggcggggac gtctggtttc cccagcctgc tccggctgat    960
catccgtggc gggcgatgcc ttttaatggc atgacacctc atattagcgg tacttcactt   1020
tctgctcagg cgcggtacgc agcggggacc cttgaaatcc tccagtgttg gtttgatggc   1080
agaccgatca ggaacgagta cctgatagtg gatggaggaa cattggccgg tacaggtgcc   1140
caatcatatc ggctgaagta a                                              1161

<210> SEQ ID NO 2
<211> LENGTH: 1095
<212> TYPE: DNA
<213> ORGANISM: Candida methylica

<400> SEQUENCE: 2
atgaaaattg tactggtgct ctatgatgca ggaaaacacg ccgcagacga ggaaaagctg    60
tatggctgca ctgagaacaa gctaggaatc gccaattggc tgaaggatca gggccatgaa    120
ttaatcacta cctccgataa agaaggtgaa acctcagagt tagataagca cattcccgat    180
gccgatataa tcattacgac gccttttcac ccagcttaca ttacaaaaga gcgtctggat    240
aaagcgaaaa acctcaaatc ggttgtagtc gccggcgtcg gttccgacca cattgacctg    300
gattatatta tcagactgg taagaagatc agcgtcctgg aagtcaccgg ctctaatgtg    360
gtatctgttg ctgagcatgt tgtaatgact atgctggttt tagtgcgcaa ttttgtgccc    420
gcacacgagc agatcataaa ccatgactgg gaagtagcag caatagctaa agatgcgtat    480
gatattgaag gcaaaactat cgctacgatc ggcgcgggcc ggatcggtta ccgggttctg    540
gagcggctgc tgccgttcaa tcctaaagag ctcctatact atgattatca ggcactgccc    600
aaggaagcag aggaaaaagt tggtgcgcgg agagtggaaa acattgaaga acttgtggct    660
caggccgaca ttgtaacggt aaatgctcca cttcacgcag gcaccaaagg ccttatcaat    720
aaagagttgc tttcaaagtt taagaaaggt gcctggttgg taaatacggc ccgtggagca    780
atttgcgttg cggaggatgt cgccgccgct ctggaatcgg acagctccg gggatacggt    840 ggggatgttt ggtttccca gccggcgcca aaggatcacc cgtggcgtga tatgcgaaac    900
aaatatggcg cagggaacgc catgacaccg cattactccg gacgaccctt agatgcacaa    960
actcgatacg ctgaaggtac caagaacatc ctggaaagtt tctttacggg caagtttgat   1020
tatcgccctc aggatattat tctgcttaat ggagaatatg taacaaaagc ttacggcaaa   1080
catgacaaaa agtaa                                                     1095

<210> SEQ ID NO 3
<211> LENGTH: 1095
<212> TYPE: DNA
```

<213> ORGANISM: Candida boidinii

<400> SEQUENCE: 3

```
atgaaaatcg tgttggtact gtatgacgct gggaaacatg ctgctgatga ggagaaattg      60
tatggctgta ccgagaataa actgggcatt gcgaactggt tgaaagatca agggcatgag     120
cttattacca cgagcgataa ggagggcgaa accagcgagc tggacaaaca tattcctgac     180
gcggatatta ttatcactac acccttcac cctgcgtaca ttactaaaga gcgtcttgat      240
aaggctaaga atctaaaact cgttgtcgtc gctggcgttg atctgatca tatcgatttg      300
gattacataa accagacagg aaagaagatc agcgtgctgg aagttacggg ctcgaacgtt     360
gttagcgtcg cagaacacgt ggttatgacc atgctagtcc tggtccgtaa cttcgtgccg     420
gcgcatgaac agatcattaa ccatgattgg gaagttgcgg ctattgcaaa ggatgcttat     480
gatatcgaag gtaaaaccat cgccaccatt ggcgctgggc gtattggcta cgcgtcttg      540
gagcgcctgc tgccatttaa cccgaaagaa ctgttgtatt acgactatca agccttacca     600
aaagaagcgg aagaaaaagt gggtgcacgt cgtgtagaaa atattgaaga attggtagcg     660
caggcagata tagttaccgt taatgctccc ctccacgccg gaacgaaagg tcttattaac     720
aaagaattac tgtctaagtt taaaaaaggg gcctggcttg tgaacacagc ccgaggcgct     780
atatgtgttg cagaagatgt tgcagctgcg ctggagagtg gtcaactgcg tgggtacgga     840
ggtgatgtgt ggtttcctca gccggcccca aaggatcacc cctggcgaga tatgcgcaat     900
aaatatgggg ccggaaatgc aatgacgcca cattatagtg gtacaaccct ggacgctcag     960
accagatatg cagaaggtac taagaatata cttgagtcgt tttttaccgg aaagtttgac    1020
tacagaccgc aagatatcat tttattgaat ggggagtatg tcaccaaagc atatggaaag    1080
catgataaaa agtaa                                                     1095
```

<210> SEQ ID NO 4
<211> LENGTH: 1131
<212> TYPE: DNA
<213> ORGANISM: Saccharomyces cerevisiae

<400> SEQUENCE: 4

```
atgtcgaaag caaagtgct ctcgtcctg tatgaaggtg ggaagcatgc agaagaacag      60
gagaaattac tgggctgtat cgaaaatgaa ttaggaatac gaaattttat cgaagaacaa     120
ggttatgaac tcgttactac gatcgataaa gatccggaac ctaccagtac tgtcgatcgc     180
gaattaaaag atgcggaaat cgttatcacc acccttttct ttcctgccta catatctagg     240
aaccgtattg ccgaagcccc gaacctcaaa ctatgcgtga ccgccggagt tgggtctgat     300
cacgtggatc tggaggcagc caatgaacgt aaaataacag taaccgaggt tactgggagt     360
aacgtggtca gcgtagctga gcacgttatg cgacaatcc tggtacttat ccgtaactac     420
aacgggggtc atcagcaagc gatcaatggt gaatgggata tcgctggcgt agcaaagaac     480
gaatatgatt tggaggataa gattattagt accgtgggag ccggcggat cgggtatcgt     540
gtactggaac gtcttgtagc tttcaatccg aaaaagcttc tgtattacga ctatcaagaa     600
ttgccggccg aagccatcaa tcggcttaat gaagcctcta agctgttcaa cggccgcggg     660
gacatcgttc agcgcgttga aagctggag acatggtgg cgcagtcaga tgtcgttaca     720
atcaattgtc cgctacataa agactccaga ggcttgttta caaaaaaact tatatcccat     780
atgaaagatg gagcctatct tgtaaatact gcacgcggcg ctatttgcgt agcagaggac     840
gttgccgagg ctgtaaaatc gggcaagctg gctggctatg gaggcgacgt gtgggacaaa     900
```

-continued

```
caacctgcgc ccaaggacca tccttggcgt acaatggata acaaggacca cgtaggaaat    960
gcgatgacgg ttcatatcag cggcacgagt ctggatgcac agaagcgtta tgcgcagggg   1020
gtcaagaata tccttaattc ctattttca aagaaatttg actatagacc ccaggatatc    1080
atagtgcaaa atggttcata cgccactaga gcttacggac aaaaaaagta a            1131
```

<210> SEQ ID NO 5
<211> LENGTH: 731
<212> TYPE: PRT
<213> ORGANISM: Clostridium pasteurianum

<400> SEQUENCE: 5

```
Met Tyr Lys Ile Lys Met His Cys Thr Gly Leu Leu Phe Cys Leu Ile
1               5                   10                  15

Gln Arg Ser Val Asn Met Glu Lys Lys Val Leu Thr Val Cys Pro Tyr
            20                  25                  30

Cys Gly Ser Gly Cys Asn Leu Tyr Leu Val Val Glu Gly Gly Lys Val
        35                  40                  45

Val Arg Ala Glu Pro Ala Lys Gly Arg Asn Asn Glu Gly Lys Leu Cys
    50                  55                  60

Leu Lys Gly Tyr Tyr Gly Trp Asp Phe Leu Asn Asp Pro Lys Leu Leu
65                  70                  75                  80

Thr Ser Arg Leu Lys Lys Pro Met Ile Arg Lys Asn Gly Val Leu Glu
                85                  90                  95

Glu Val Ser Trp Asp Glu Ala Ile Lys Phe Thr Ala Glu Asn Leu Met
            100                 105                 110

Lys Ile Lys Ala Gln Tyr Gly Pro Asp Ala Ile Met Gly Thr Gly Ser
        115                 120                 125

Ala Arg Gly Pro Gly Asn Glu Pro Asn Tyr Ile Met Gln Lys Phe Met
    130                 135                 140

Arg Ala Ala Ile Gly Thr Asn Asn Ile Asp His Cys Ala Arg Val Cys
145                 150                 155                 160

His Gly Pro Ser Val Ala Gly Leu Asp Tyr Ser Leu Gly Gly Ala Ala
                165                 170                 175

Met Ser Asn Ser Ile Pro Glu Ile Glu Asp Thr Asp Val Val Phe Val
            180                 185                 190

Phe Gly Tyr Asn Pro Ser Glu Thr His Pro Ile Val Ala Arg Arg Ile
        195                 200                 205

Val Lys Ala Arg Glu Lys Gly Ala Lys Ile Ile Val Ala Asp Pro Arg
    210                 215                 220

Lys Ile Glu Thr Val Lys Ile Ser Asp Leu Trp Leu Gln Leu Lys Gly
225                 230                 235                 240

Gly Thr Asn Met Ala Leu Val Asn Ala Leu Gly Asn Val Leu Ile Asn
                245                 250                 255

Glu Glu Leu Tyr Asp Glu Lys Phe Val Glu Asn Cys Thr Glu Gly Phe
            260                 265                 270

Glu Glu Tyr Lys Glu Ala Val Lys Lys Tyr Thr Pro Glu Tyr Ala Glu
        275                 280                 285

Lys Ile Thr Gly Val Ser Ala Glu Tyr Ile Arg Lys Ala Met Arg Ile
    290                 295                 300

Tyr Ala Lys Ala Lys Lys Ala Thr Ile Leu Tyr Gly Met Gly Val Cys
305                 310                 315                 320

Gln Phe Ser Gln Ala Val Asp Val Val Lys Gly Leu Ala Ser Leu Ala
                325                 330                 335
```

Leu Leu Thr Gly Asn Leu Gly Arg Pro Asn Val Gly Ile Gly Pro Val
            340                 345                 350

Arg Gly Gln Asn Asn Val Gln Gly Thr Cys Asp Met Gly Val Leu Pro
            355                 360                 365

Asn Arg Phe Pro Gly Tyr Gln Ser Val Thr Asp Glu Lys Ala Arg Glu
            370                 375                 380

Lys Phe Glu Lys Ala Trp Gly Val Lys Leu Ser Asp Arg Val Gly Tyr
385                 390                 395                 400

Phe Leu Thr Glu Val Pro Lys His Val Leu Lys Glu Asp Lys Ile Lys
            405                 410                 415

Ala Tyr Tyr Ile Phe Gly Glu Asp Pro Ala Gln Ser Asp Pro Asn Ala
            420                 425                 430

Ala Glu Val Arg Glu Ala Leu Asp Lys Ile Asp Phe Val Ile Val Gln
            435                 440                 445

Asp Ile Phe Met Asn Lys Thr Ala Leu His Ala Asp Val Val Leu Pro
            450                 455                 460

Ala Thr Ser Trp Gly Glu His Asp Gly Val Tyr Ser Ala Ala Asp Arg
465                 470                 475                 480

Ser Phe Gln Arg Ile Arg Lys Ala Val Glu Pro Met Gly Glu Ala Lys
            485                 490                 495

Asp Asp Trp Glu Ile Ile Cys Glu Ile Ser Thr Ala Met Gly Tyr Pro
            500                 505                 510

Met His Tyr Asn Asn Thr Glu Glu Ile Trp Asn Glu Met Arg Ser Leu
            515                 520                 525

Cys Pro Lys Phe Ala Gly Ala Ser Tyr Glu Lys Met Glu Lys Gln Gly
            530                 535                 540

Ala Val Pro Trp Pro Cys Thr Ser Glu Glu Asp Pro Gly Thr Asp Tyr
545                 550                 555                 560

Leu Tyr Asp Asp Gly Lys Phe Met Thr Glu Asn Gly Arg Gly Lys Leu
            565                 570                 575

Phe Ala Cys Glu Trp Arg His Pro Phe Glu Leu Thr Asp Glu Lys Tyr
            580                 585                 590

Pro Leu Val Leu Ser Thr Val Arg Glu Ile Gly His Tyr Ser Val Arg
            595                 600                 605

Thr Met Thr Gly Asn Cys Arg Thr Leu Gln Lys Leu Ala Asp Glu Pro
            610                 615                 620

Gly Tyr Ile Glu Ile Ser Val Glu Asp Ala Lys Glu Leu Asn Ile Lys
625                 630                 635                 640

Asp Gln Glu Leu Val Thr Val Ser Ser Arg Arg Gly Lys Ile Ile Thr
            645                 650                 655

Arg Ala Ala Val Ala Glu Arg Val Lys Lys Gly Ala Thr Tyr Met Thr
            660                 665                 670

Tyr Gln Trp Trp Val Gly Ala Cys Asn Glu Leu Thr Ile Asp Ser Leu
            675                 680                 685

Asp Pro Ile Ser Lys Thr Pro Glu Phe Lys Tyr Cys Ala Val Lys Val
            690                 695                 700

Glu Arg Ile Lys Asp Gln Gln Lys Ala Glu Gln Glu Ile Glu Glu Arg
705                 710                 715                 720

Tyr Ser Ser Leu Lys Lys Gln Met Lys Ala Glu
            725                 730

<210> SEQ ID NO 6
<211> LENGTH: 211

<212> TYPE: PRT
<213> ORGANISM: Clostridium pasteurianum

<400> SEQUENCE: 6

Met Asp Arg Phe Lys Thr Ala Val Ile Leu Ala Gly Gly Lys Ser Ser
1               5                   10                  15

Arg Met Gly Phe Asp Lys Gln Phe Leu Lys Ile Gly Glu Lys Arg Leu
            20                  25                  30

Met Asp Ile Leu Ile Asn Glu Ile Lys Glu Glu Phe Gln Asp Ile Ile
        35                  40                  45

Ile Val Thr Asn Lys Pro Lys Glu Tyr Lys Ser Leu Tyr Lys Ser Cys
    50                  55                  60

Arg Ile Val Ser Asp Glu Ile Glu Ser Gln Gly Pro Leu Ser Gly Ile
65                  70                  75                  80

His Ile Gly Leu Lys Glu Ser Lys Ser Lys Tyr Ala Tyr Phe Ile Ala
                85                  90                  95

Cys Asp Met Pro Lys Val Asn Ile Pro Tyr Ile Arg Tyr Met Lys Glu
            100                 105                 110

Glu Leu Ile Lys Thr Asp Ala Asp Ala Cys Val Thr Glu Ala Gly Cys
        115                 120                 125

Arg Met Gln Pro Phe Asn Ala Phe Tyr Ser Lys Glu Val Phe Tyr Lys
    130                 135                 140

Ile Glu Asp Leu Leu Arg Glu Gly Lys Arg Ser Met Phe Ser Phe Ile
145                 150                 155                 160

Asn Ile Ile Asn Thr His Phe Ile Asp Glu Asp Thr Ala Lys Lys Tyr
                165                 170                 175

Asn Lys Asp Phe Asn Met Phe Phe Asn Leu Asn Thr Pro Glu Asp Leu
            180                 185                 190

Lys Asp Phe Gln Val Lys Leu Tyr Asn Pro Lys Asn Met Asp Lys Asn
        195                 200                 205

Ile Glu Lys
    210

<210> SEQ ID NO 7
<211> LENGTH: 191
<212> TYPE: PRT
<213> ORGANISM: Clostridium pasteurianum

<400> SEQUENCE: 7

Met Arg Asn Phe Ile Lys Leu Phe Leu Tyr Arg Leu Ser Gly Lys Val
1               5                   10                  15

Gly Lys Ala Met Ser Arg Glu Val Asn Ser Phe Val Ile Gly Asp Ala
            20                  25                  30

Ser Lys Cys Val Gly Cys Arg Ala Cys Glu Val Ala Cys Phe Lys Ala
        35                  40                  45

His Ser Asn Arg Glu Glu Ser Ser Lys Pro Ile Phe Val Lys Gly Lys
    50                  55                  60

Arg Arg Asp Ile Ile Thr Arg Ile His Val Val Lys Asn Glu Lys Phe
65                  70                  75                  80

Ser Val Pro Val Gln Cys Arg Gln Cys Glu Asp Ala Pro Cys Ala Asn
                85                  90                  95

Ala Cys Pro Val Gly Ala Ile Lys Glu Lys Glu His Val Leu Val Val
            100                 105                 110

Glu Glu Glu Leu Cys Ile Gly Cys Lys Ala Cys Val Met Ala Cys Pro
        115                 120                 125

```
Phe Gly Ala Ile Glu Val Lys Arg Lys Ser Glu Glu Val Arg Lys Val
            130                 135                 140

Ala Tyr Lys Cys Asp Leu Cys Arg Asn Arg Asp Thr Lys Ala Cys Val
145                 150                 155                 160

Glu Ile Cys Ser Lys Lys Ala Leu Lys Leu Phe Asp Pro Val Lys Glu
                165                 170                 175

Arg Lys Gln Arg Asn Ile Asp Thr Val Asn Asn Leu Ile Asp Asp
            180                 185                 190
```

<210> SEQ ID NO 8
<211> LENGTH: 206
<212> TYPE: PRT
<213> ORGANISM: Clostridium pasteurianum

<400> SEQUENCE: 8

```
Met Thr Asn Leu Cys His Phe His Arg Gln Arg Glu Glu Arg Ile Ile
1               5                   10                  15

Met Asn Ser Phe Val Ile Ala Asn Pro Lys Lys Cys Ile Gly Cys Lys
            20                  25                  30

Thr Cys Glu Ala Gly Cys Ala Met Ala His Ser Glu Lys Asn Ile Leu
        35                  40                  45

Asn Arg Lys Ser Asp Glu Leu Lys Phe Asn Pro Arg Leu Lys Val Ile
    50                  55                  60

Lys Thr Trp Asp Val Thr Ala Pro Val Met Cys Arg His Cys Glu Asn
65                  70                  75                  80

Ser Pro Cys Ala Ser Val Cys Pro Asn Gly Ser Ile Thr Asn Lys Glu
                85                  90                  95

Gly Val Val Leu Ile Asn Gln Asp Thr Cys Ile Gly Cys Lys Ser Cys
            100                 105                 110

Met Val Ala Cys Pro Phe Gly Ala Ile Asn Leu Ile Val Gln Gln Asp
        115                 120                 125

Gly Glu Gly Lys Ala Ile Thr Gln Ser Gly Leu Lys Lys Thr Asp Gly
    130                 135                 140

Lys Glu Ile Ile His Lys Glu Lys Ile Val Ala Asn Lys Cys Asp Leu
145                 150                 155                 160

Cys Ile Glu Arg Asp Lys Gly Pro Ala Cys Val Glu Val Cys Pro Thr
                165                 170                 175

Glu Ala Leu Arg Leu Val Ser Gly Glu Asp Ile Glu Glu Ser Ile Lys
            180                 185                 190

Glu Lys Arg Glu Ala Ala Ala Leu Gly Leu Ser Arg Ile Gly
        195                 200                 205
```

<210> SEQ ID NO 9
<211> LENGTH: 1293
<212> TYPE: DNA
<213> ORGANISM: Aquifex aeolicus

<400> SEQUENCE: 9

```
atggccaaac atgtggttgt tattggcggc ggcgttggag gtattgcgac ggcctataac    60
ctgcgcaact tgatgccgga tttaaaaata acgttgatca gcgatcgccc atatttcggc   120
tttacgccag cattcccgca tctggcgatg ggctggcgca aatttgaaga tatcagcgtt   180
cccctggcgc ctttgttacc gaaattcaac atagagttta ttaacgaaaa ggctgaaagc   240
atcgatccag atgcgaacac ggttaccacg cagagcggaa aaaaaatcga gtatgattat   300
ctggttattg ccacaggccc gaaactggtg ttcggagcag aaggccagga ggagaactcg   360
```

```
acgagcattt gtaccgccga acatgcgcta gaaactcaga aaaaactgca agaattatat    420
gcgaatccgg gccctgtagt tattggtgcc ataccgggcg tgagttgttt cggccctgcc    480
tatgagttcg ccttgatgtt acattatgaa ctgaagaaac gtgggattcg ctataaagtg    540
ccgatgacgt tcatcacgag cgaaccgtat ttaggccatt ttggcgtggg tggtattggt    600
gcctctaaac gtctcgttga ggatttattc gccgaacgca acattgactg gatcgcgaac    660
gttgcggtaa aagccattga accagataaa gtgatttatg aagatctcaa cggcaacacg    720
catgaagtac cggctaaatt tacgatgttc atgccgagtt tccaaggccc agaggttgtg    780
gccagcgcag gcgataaggt cgcgaacccg gcgaacaaaa tggtgattgt gaaccgctgc    840
ttccagaacc cgacttataa aaacattttc ggcgttggtg tggttaccgc cattccgcca    900
attgaaaaaa cccccaattcc gacgggagtt cccaaaaccg gtatgatgat cgagcaaatg    960
gccatggccg ttgcccataa cattgttaac gatattcgca acaacccgga taaatatgcc   1020
cctcgtttaa gcgctatttg tattgccgat ttcggcgaag atgccggctt tttcttcgcg   1080
gatccggtta ttccacctcg cgaacgtgtt attacgaaaa tgggaaaatg gcgcattat    1140 ttcaaaacgg catttgaaaa atatttcctg tggaaagtac gcaacggcaa catagcgccg   1200
agctttgaag aaaaagttct ggaaattttc ctgaaagtgc atccgattga attatgtaaa   1260
gattgcgaag gcgcgccggg ctcccgctgc taa                                1293

<210> SEQ ID NO 10
<211> LENGTH: 1302
<212> TYPE: DNA
<213> ORGANISM: Nostoc sp.

<400> SEQUENCE: 10
atggcccaca ttgtgatcgt aggcgccgga ttaggcggcc tgcctactgc gtatgaactg     60
agacatatcc ttcctaaaca acatcaggtg actgtaatta gtgaaactcc atactttacg    120
tttattccaa gtttaccatg ggttgccatg ggcctgacct cttttggagag tattcaagtg    180 agcctccagc agagattgaa gcagaagggg attaactgga tattgggacg agttgattac    240
ttaaacccac agaatcagaa gatatcacta ggtgagcaga gcattagcta cgattacctg    300
attattgcaa cgggcgctga actcgccctg gatgcagttg cgggcctggg gcctgatggt    360 tatcccagt agtgtttgtaa ccccatcat gccatcaagg cttttcaagc gtggcagaat    420
tttcttctgg ccccgggacc gctggttgtt ggagccctgc cgaaaacaag ctgcctgggg    480
ccagcatacg agtttacatt gctggcggac tacgttccta ggaaacaagg tctgcgggag    540
caggttagta ttaccttcgt caccccggaa ccatacgccg gtcacttagg cataggcgga    600
atggcgaact cggcagagct ggtcacgaaa ttcatggccg aacgaggagt tgaggtgatt    660
gaaaatgttg ccgtgacggc cattgaggcc aaccaaattc atctcggtaa cgggcgggtt    720
ctgccgtttg cgtacagtat gttgcttccg cctttcagag gacccgtttt gtaagacag     780 gttccgggtc tgagcaacca agatggcttt attccggttt taccaacgta ccggcatcca    840
gaatatgcaa gtatttatgc cgtcggtgtg gttgttgaaa ttaaaccgag tgaggttacg    900
ccacttcctt taggtgttcc taaaaccggt cagatgacgg aagccatggg gatggccgtt    960
gcacataaca ttgcaattga attaggtgtt ttttcggcgc ccccagtcac cccgacgcta   1020
gatgcaattt gttttgcgga ctttggcaac agtggtattc tgtttcttgc gaatcctgtc   1080
ctgccggatc tggcaacggg taaacgcaga cgagcggttg ctttaagcgg cgcgtgggtt   1140
acctgggcga aagcagcctt tgaaaggtat tttttggcga aaatgcgttt cgggaccgcg   1200
```

```
gttccatggt ttgaaaaatt ggcgttaaaa ctgttaggtc tctcgctggt ggctccactc    1260
gccgttaaga gcagccggaa catctcccag gagaactatt aa                        1302

<210> SEQ ID NO 11
<211> LENGTH: 1458
<212> TYPE: DNA
<213> ORGANISM: Chlorobium tepidum

<400> SEQUENCE: 11
atggccaaag tcgtcgtcct cggggctggc gtcagcggac acacctgcgc aagtttcctg      60
aaaaagaagt tggggaaaca gcacgaagtc gtggtcatta gcccaaactc gtactatcag    120
tggatcccga gcaatatatg ggttggcgtg ggccacatga ccattgatga cgtgcgcttt    180
aaactgaaaa aagtctacga tcgctggggc attgactata acaggccaa ggcggtcagc     240 atccacccag aaggcgatgc gaacatttcg aaagggtatg ttaccattga atataccgat    300
gaagaacatg cggatatac cgaaacggtt gactatgatt atttggttaa cgcgaccggt     360
cctaaattaa actttgaagc taccgaagga ttgggacccg ataagaacag cttatcagtt    420
tgcacctatt cgcatgccgc tcacgcctgg gaagaactcc aaaagtcgat tgagaaaatg    480
aaaaatggtc agaaacagcg gtttctgatc ggcaccggcc acgccatggc tacctgtcag    540
ggcgcagctt tgaatacat tttaaacgtt gctcatgaga ttagtcggcg cggcttatcg     600
catatggccg aattaacctg gatctccaac gaatatgaat taggtgactt tggtatgggc    660
ggcgccttta ttaaacgcgg cggttatatc acgccgacca agttttcac cgagagctta     720 ctggctgaat atggcattaa atggattcgc cgtgccggtg tttataaagt ggaaccgggc    780
gtggcgcatt atgagacgct ggatggcgag atgttgagcc aggaatttga tttcgccatg    840
ttgatcccga gctttagtgg cgtcggctta accgcgtttg ataagtcggg caacgatatt    900
accgataaaa tgttcttacc gaacaaattt atgaaagttg acgccgatta taccgcgaaa    960
ccgtttggcg aatgggcgc taacgattgg ccgaccattt atcagacgcc gatgtattcg    1020
aatatttatg cggccggcat tgcgtttgcc ccgccgcaca gcattagcaa accaatgacg   1080
tcggtgaatg gccgccagat cttccgacg ccgccgcgca ccggcatgcc gagcggcgtc    1140
attggcaaaa ttatcgccct gaatattagt gaacagatta aaggcaacca taaagaacat   1200
caccataagg cgagcatggc gcgcatgggc gcagcgtgca tcgtgagcgc gggctttggt   1260
agcttcgatg gctgggcgc cagcatgacc gtgtttccaa ttgtgccaga ctgggaaaaa   1320
tacccggaat ggggccgcga tatgacctat agcgttggcg aggtgggatt ggcgggtcat   1380
tggttaaaat ttatgttaca ttatctgttt tttcataaag ccaagggcta cccgttttgg   1440
tatttaatcc cggaataa                                                  1458

<210> SEQ ID NO 12
<211> LENGTH: 1305
<212> TYPE: DNA
<213> ORGANISM: Acidithiobacillus ferrooxidans

<400> SEQUENCE: 12
atggcccatg tggtaatctt gggtgccggc acaggcggaa tgccggccgc gtacgaaatg     60
aaagaagctc tgggttctgg gcatgaggtg acgctgatta gcgcgaatga ttattttcag   120
tttgtcccgt cgaacccgtg ggtggggtg ggctggaaag agcgcgatga tattgctttt    180
cccattcgtc actatgtgga acggaaggga atacatttca ttgcccagtc ggcggaacag   240
```

```
attgatgcgg aagcccagaa tattaccctc gcggacggca acacggtaca ttacgactac    300
ctgatgattg ccacaggtcc gaaactggct tttgagaatg taccgggttc ggatccacat    360
gaaggcccgg tgcagtcgat ctgtacggtg gaccatgccg aacgtgcgtt cgcggaatac    420
caggctttgt tgcgcgagcc aggcccaatc gttattggtg cgatgcgggg cgcatcctgc    480
tttggaccgg cttacgaata tgcgatgatt gttgcttcgg acttaaagaa gcgtggcatg    540
cgcgacaaaa tcccgtcgtt taccttcatt acctccgagc catacattgg tcatctgggc    600
atccagggcg tgggcgattc gaaaggcatc ctgacgaaag gcttaaaaga agaaggtatt    660
gaagcctaca cgaactgtaa agttaccaaa gttgaagaca acaaaatgta tgtaacccag    720
gtggacgaga aggtgaaac cattaaagag atggtcctgc cggttaaatt tgggatgatg    780
attccggctt ttaaaggcgt gcccgccgtg gccggtgttg aaggattgtg caatccaggt    840
ggctttgtgc tggtggatga gcaccagcgc agcaaaaagt acgcaaatat tttcgccgcc    900
ggtattgcga ttgcgatccc gccggtagag acgaccccgg tgccgaccgg cgccccaaaa    960
accggttata tgattgaatc gatggtgagt gccgccgtgc acaacattaa agccgatctg   1020
gaaggccgca aggcgagca gaccatgggc acctggaatg ccgtgtgttt cgcggatatg   1080
ggtgatcgcg gcgccgcatt cattgcgttg ccacagttga aaccacggaa ggtggacgtt   1140
ttcgcgtacg ggcgctgggt gcatctggcc aaagtggcgt tcgaaaagta cttcattcgc   1200
aagatgaaaa tgggtgtttc ggagccattt tatgagaaag tgctgtttaa aatgatgggc   1260
atcacccggc tgaaagaaga agatacccat cggaaagcgt cgtaa                   1305
```

<210> SEQ ID NO 13
<211> LENGTH: 1458
<212> TYPE: DNA
<213> ORGANISM: Allochromatium vinosum

<400> SEQUENCE: 13

```
atggcccgca ttctgatatt aggagcgggt attagtggcc acgaccgc gcggtatctg      60 ggcaaatggg ttggcaaaca gcaccagatt accgttgtga gcccaaatag taagtggaac   120
tggatcccta gtaacatttg ggttggcgta ggtgagatga ccgaacgcca agtgaccttt   180
gaactggcac cagtgtacaa aaaaattaac gtgggttttc gtcaggcacg cgcggtgagc   240
attcacccag acggcggtgc gggacatgaa tcgccatttg tgaccattga atacacggat   300
ccgacacgtg cgggtcagtc ggatgaaatt gagtacgatt atctggtgaa tgcgaccggc   360
ccaaaattaa actttgatgc gacgccgggt ctggggccgg aaacgggcta caccatgagc   420
gtgtgcaccc cgagtcacgc cctggaagcg aacgaacagt tacagaaatg cgtgcaggaa   480
atgaaagcgg gtgcccgcaa aacctttgtg attggcaccg gcacggcat gtgcacctgc   540 cagggcgccg cgtttgaata catttacaac gtggaccatg tgctgcgggg agcgggcgtt   600
cgccacctgg cccgcgttgt gtggatttcg aacgaatacg agttaggcga ttttggcatg   660
ggaggcgttc atattacccg aggcggctat ctgaccaacg gcaaagtgtt tgcggaaagc   720
ctgatggtgg aacgcggcct ggaatggatt acccgcgccg ctgtgaccaa agtggaaccg   780
ggcaaaattc actacgaaca gttagatggc tccgtgcatg aactggaatt tgactttagt   840
atgttaattc cgccatttag cggcgttgga ttaaaggcgt atgataagag tgggtcggat   900
attaccgaac aattatttgc cccaaacggc tttatgaaag tggatgcgga ttacaatcca   960
aaaccatttg aggagtggtc gaaagcggat tggccgaaaa cctatcagac cccgaaatac  1020
aaaaacattt ttgcgattgg cattgcgttt gcgccgccgc acccgatttc gaaagttatg  1080
```

```
aaatccccgt cgggtctgca aatttcgccg actccgccgc gcaccggcat gccaagcgcc    1140
accatcggga aagctgttgc ggaaaacatt cgcgacctgt aaatggcgc  caccacgttg    1200 agccataccg cgagcatggg cgaaatgggc gccgcttgcg ttgcgagcac cggcatggac    1260
ttatttaaag gcacggccgc caccatgacc gtatttccgg ttgttccgga ttacgaaacc    1320
tatccagaat acggacgcga tatggacctg acctttggtg aaattggcct ggcgggacat    1380
tggatgaagt acctcctgca ccacgtgttt atttaccagg cgaaactgcg cccgggctgg    1440
agcgttctgc cagactaa                                                 1458
```

<210> SEQ ID NO 14
<211> LENGTH: 1284
<212> TYPE: DNA
<213> ORGANISM: Rhodobacter capsulatus

<400> SEQUENCE: 14

```
atggcccata ttgtggtcct gggggccggg ctcggcggcg ccattatggc atatgagctc     60
cgcgagcagg tgcgcaaaga ggataaagtt accgttatta ccaaagatcc gatgtatcat    120
tttgtgccaa gcaacccatg ggtggcgtg  ggctggcgcg atcgcaaaga aattaccgtg    180
gatttagcgc cgacgatggc gcgcaaaaac attgatttta ttccggtggc agcgaaacgc    240
ctgcatccgg cggagaaccg tgttgaactg gagaacggcc agagcgtttc gtacgatcag    300
attgttattg ccaccggccc ggagctggcc tttgatgaaa ttgaaggctt cggcccagaa    360
ggccacacgc aaagcatttg ccatattgat catgccgaag aagcgcggct ggccttcgat    420
cgcttctgcg agaacccagg cccgattttg attggtgcgg cgcagggcgc ctcgtgcttt    480
ggcccggctt acgagtttac ctttatttta gacaccgcgc tgcgcaaacg caaaattcgc    540
gataaagtgc cgatgacctt tgttaccagc gaaccatatg ttggtcatct gggtctggat    600
ggtgtgggcg ataccaaagg cctgttggag ggcaacctgc gcgataaaca cattaagtgg    660
atgaccagca cccgtattaa gcgcgttgag aaaggcaaaa tggtggttga agaagtgacc    720
gaagatggca cggttaaacc agaaaaggaa ctgccatttg ctatgcgat  gatgctgcca    780 gcgtttcgcg gcattaaagc gctgatgggt attgaaggtc tggttaatcc gcgcggcttt    840
gttattgttg accagcacca gcagaacccg acctttaaaa acgttttgc  ggttggcgtt    900 tgcgtggcga ttccgccgat tggtccgacg ccggtgccat gcggcgtgcc gaaaaccggc    960
tttatgattg agtcgatggt taccgccacc gcccacaaca ttggccgtat tgtgcgcggt   1020
ttcgaagccg atgaagttgg ctcgtggaac gccgtttgtc tggccgactt tggcgaccag   1080
ggcattgcct tcgttgcgca gccgcagatt ccgccgcgca acgtgaactg gagctcgcag   1140
ggcaagtggg tgcattgggc caaagaaggt tttgaacgct attttatgca caaactgcgc   1200
cgcggtacca gtgaaaacct ttatgagaaa gccgcgatga attcctggg  cattgataaa   1260 ctgaaagccg ttaagaaagg gtaa                                         1284
```

<210> SEQ ID NO 15
<211> LENGTH: 1269
<212> TYPE: DNA
<213> ORGANISM: Thiobacillus denitrificans

<400> SEQUENCE: 15

```
atggcccata ttgtaatatt aggcgccggc gtgggcggca tgaccatggc gtacgagatg     60
cgcgaaagcg cacgtgccga agataaagtg accgtgatca gtaacaatag ctattttcag    120
```

-continued

| | |
|---|---|
| tttacgccga gtaacccttg ggttggtgtt aactggcgca aacgggatga tgtgacgtta | 180 |
| gaagccgcgc cttatttaaa caaaaagaac attgatttta tcccggtggg cgccgcgcgc | 240 |
| gttcacccag atagaaacca gattgattta accgatggca gaaccgtgga ttacgatttt | 300 |
| ttagtgattg cgacgggtcc aaaattagcg tttgatgagg tgccgggctt aggcccagaa | 360 |
| gggtataccc agagcgtatg cacggtggat cacgcccagg ccgcgggccg cgcgtgggat | 420 |
| gacttcgtta aaaacccggg tccgattgtt gtgggcgcgg ttcagggtgc tagttgctat | 480 |
| ggcccggcgt atgaatatgc gatgattatg gataccgatc tgcgcaaacg caaaatccgg | 540 |
| gatcgtgttc cgatgaccta tgtgacggcc gaaccgtaca ttggccacct gggactgggc | 600 |
| ggcgtgggcg acagtaaagg catgttagag agcgtgttac gcgaacgcca tattaaatgg | 660 |
| atttgcaacg ccaaagtgac caaagtggaa gctggcaaaa tgtttgtggc cgaacataac | 720 |
| gataaaggcg aggttattaa agaacatgag ctgccgtttg gctatagcat gatgctgccg | 780 |
| gcgtttaaag gcattgacgc tgttttttggc attgaaggtc tgaccaatcc gcgcggcttt | 840 |
| attacgattg atccatatca gcgcaacgcg aaatatccga acgtgtatag tgtgggcgtt | 900 |
| tgcgtggcga ttcccccagt ggaagtgaca ccagttccga ccggcacgcc gaaaaccggc | 960 |
| tatatgattg agagcatggt tacggcgacc gcgcataaca ttcgcgccgt tttagatggc | 1020 |
| cgcgaacctg ccgaaaaagc gacctggaac gcgatttgct tagccgattt tggcgatacc | 1080 |
| ggcgccgcct ttgttgccct gccgcagatc ccgccgcgca atgtgaactg gtttaaagag | 1140 |
| ggcaaatggg ttcacctggc caaagtggcc tttgaaaaat attttattcg caaaatgaag | 1200 |
| aagggcagca ccgaaccgct gtatgaaaaa tatgttttag gcttaatggg cattaaaaag | 1260 |
| ttaaagtaa | 1269 |

<210> SEQ ID NO 16
<211> LENGTH: 1284
<212> TYPE: DNA
<213> ORGANISM: Magnetococcus sp.

<400> SEQUENCE: 16

| | |
|---|---|
| atggcccata ttgtggtgtt aggtggtggt gtaggggat ggccggctgc ctatgaatta | 60 |
| cgtggcgcct taggtaaaga acataaggtc actgtggtgc acaatagcac ccatttttct | 120 |
| tttacccccct ctaatccttg ggtagccgtc ggttggcgca aggcagagga gattcagctt | 180 |
| ccgatggagg gttatttaag caaaagggc atccatttta tttccgtcgc gtgcgaggaa | 240 |
| attaagcccg acgacaataa attagtgctg gcggatgggc agatcgtgga ttatgactat | 300 |
| ctggttatct gtaccggtcc tgaactggca tttgatgaag tcgagggatt aggtccgcat | 360 |
| ggtggttaca cgcagtccgt ttgctcaacg ccgcatgcgg aaaccgcatg cgagggatgg | 420 |
| gaggcgttct taaaagatcc aggcccgatc gtggtgggtg ccgtgcaggg cgcgtcatgt | 480 |
| tttggacccg cctatgaatt tgcatttatc atggatgcag acctgcgcaa gcgtcgtata | 540 |
| cgtgatcagg tgccgatgac ctatgtgacc tctgaacctt acattggcca tttagggctg | 600 |
| gcaggggtgg gtgactcgcg caccatgatg aatctgagc tgcgtggcca ccacattaac | 660 |
| tggatctgta acgcgaaggt aacccgtgtc gaacctggta aatgtttgt ggatgaacat | 720 |
| gatatgtcgg gtaatgtggt taagcagcac gaactgccgc acaaatactc tatgatgcta | 780 |
| ccagcattcc gtggggtgcc tgccgtggcc aaggtagggg ataagctgtg caatccacgt | 840 |
| ggttttgtga aggtggataa acatcagcgc aacaccgtgt ggccaaacat ttattcagcc | 900 |
| ggtgtgtgcg tggccattcc tcctgtcgaa gccacacctg tgccgaccgg taccccgaag | 960 |

```
acgggttata tgatcgaatc catggtgacg gcgattgtgc acaatattga actggacctg    1020
caaggcaagc cgttaaccca cgagggcacc tggaacgcga tctgtttagc cgatatgggg    1080
gatacagggg tggcctttgt ggccatgcca cagattggcc cgcgtaacgt cgcatggatg    1140
cgcaaaggta agtgggtgca tttagccaaa gtgggctttg aaaaatattt tatgcgcaag    1200
atgaagaccg gttcttctga accaatgttt gaaaagttta tgctgcgcat ggtgggtatt    1260
acccgcctga agaaggattc gtaa                                           1284

<210> SEQ ID NO 17
<211> LENGTH: 171
<212> TYPE: DNA
<213> ORGANISM: Clostridium pasteurianum

<400> SEQUENCE: 17
atggcctata aaatagcgga tagctgcgtg tcctgcgggg cgtgcgcgag cgaatgcccg     60
gttaacgcga ttagtcaggg cgattcgatt ttcgttattg atgcagatac ctgcatagac    120
tgcggtaatt gcgcgaatgt tgcccggtt ggcgccccgg tgcaggaata a              171

<210> SEQ ID NO 18
<211> LENGTH: 219
<212> TYPE: DNA
<213> ORGANISM: Hydrogenobacter thermophilus

<400> SEQUENCE: 18
atggccttgc gtaccatggt cgaccctgat acgtgtacct cttgcgaatt atgttatgat     60
cgcgtcccag aggtttataa gaaccgcggc gatggcattg cggaagtggt ttccccccggt   120 ccagatggtt ggatgatggt tcctcctgaa ttggaacaag aagtcaaaga ggtcaccgac    180
gaatgtccat ccgggtcgat aattacggag gaggtataa                           219

<210> SEQ ID NO 19
<211> LENGTH: 204
<212> TYPE: DNA
<213> ORGANISM: Hydrogenobacter thermophilus

<400> SEQUENCE: 19
atgcgcattt tgatcgacat tgatacgtgc acgacctgcc gtttatgcta tgatacactg     60
ccgactgttt ttgtggaccg cggcgatggg attccaatta cgttaccaat gaaaagcttc    120
ccggaccgta acctggttga ggcgattaag gaagtgatgg aaagctgccc aagcaattcg    180
attcagatgg aggaggtcgg gtaa                                           204

<210> SEQ ID NO 20
<211> LENGTH: 183
<212> TYPE: DNA
<213> ORGANISM: Methanosarcina barkeri

<400> SEQUENCE: 20
atgccagcga tcgtgaacgc ggatgaatgc tccggctgcg gcacttgcgt cgatgaatgt     60
cctaacgatg cgattacgct ggatgaggag aagggcatag cggttgtcga caacgacgaa    120
tgtgttgaat gtggtgcgtg tgaagaagcg tgtcccaatc aggcgattaa agttgaagaa    180
taa                                                                  183

<210> SEQ ID NO 21
<211> LENGTH: 243
<212> TYPE: DNA
```

<213> ORGANISM: Aquifex aeolicus

<400> SEQUENCE: 21

```
atggccaagt tgaaaacgat ggtggatcag gaaacgtgta ccgcctgcga gctctgttat      60
gaccgtgtgc cggaggtgta taaaaaccgc ggcgatggca ttgcagacgt ggtaaaatgt     120
gatattaagg atgaggaaga ccattgctgg atgattgtac ctgaaggcct cgaagatgaa     180
gtacgtgaag ttgaggagga gtgcccgagt ggttcgatca gtggaagaa actggaagaa     240
taa                                                                   243
```

<210> SEQ ID NO 22
<211> LENGTH: 80
<212> TYPE: PRT
<213> ORGANISM: Aquifex aeolicus

<400> SEQUENCE: 22

```
Met Ala Lys Leu Lys Thr Met Val Asp Gln Glu Thr Cys Thr Ala Cys
1               5                  10                  15
Glu Leu Cys Tyr Asp Arg Val Pro Glu Val Tyr Lys Asn Arg Gly Asp
                20                  25                  30
Gly Ile Ala Asp Val Val Lys Cys Asp Ile Lys Asp Glu Glu Asp His
            35                  40                  45
Cys Trp Met Ile Val Pro Glu Gly Leu Glu Asp Glu Val Arg Glu Val
        50                  55                  60
Glu Glu Glu Cys Pro Ser Gly Ser Ile Ile Val Glu Glu Leu Glu Glu
    65                  70                  75                  80
```

<210> SEQ ID NO 23
<211> LENGTH: 231
<212> TYPE: DNA
<213> ORGANISM: Aquifex aeolicus

<400> SEQUENCE: 23

```
atggggttaa aggtgcgtgt tgaccaggat acgtgcacgg cctgcgagct gtgctatgac      60
cgtataccgg aagtattcaa aaacgcaggc gatggcattg cagatgttgt aaaatgcgat     120
atagaagatg atgaaggctg ctggatgata gtgccggaag gcctggagga ggaagttcag     180
gaagtggcgg atgagtgccc gagtggcagc attatagttg aggaagaata a              231
```

<210> SEQ ID NO 24
<211> LENGTH: 76
<212> TYPE: PRT
<213> ORGANISM: Aquifex aeolicus

<400> SEQUENCE: 24

```
Met Gly Leu Lys Val Arg Val Asp Gln Asp Thr Cys Thr Ala Cys Glu
1               5                  10                  15
Leu Cys Tyr Asp Arg Ile Pro Glu Val Phe Lys Asn Ala Gly Asp Gly
                20                  25                  30
Ile Ala Asp Val Val Lys Cys Asp Ile Glu Asp Asp Glu Gly Cys Trp
            35                  40                  45
Met Ile Val Pro Glu Gly Leu Glu Glu Glu Val Gln Glu Val Ala Asp
        50                  55                  60
Glu Cys Pro Ser Gly Ser Ile Ile Val Glu Glu Glu
    65                  70                  75
```

<210> SEQ ID NO 25
<211> LENGTH: 3633

<212> TYPE: DNA
<213> ORGANISM: Unknown
<220> FEATURE:
<223> OTHER INFORMATION: gamma-proteobacterium

<400> SEQUENCE: 25

| | | | | | | |
|---|---|---|---|---|---|---|
| atgaacacag | aaactcgcac | caccagcggc | ggacggttgc | atgacaaggt | ggttatcttg | 60 |
| accggcgcgg | ccggaaacat | tggcagctac | attagccggt | ccttgctgcg | cgaaggggcg | 120 |
| aatttggtaa | tgaccgggcg | gaatgaaccg | aaattacagg | cgtttgtgga | aggtttagtt | 180 |
| gaggagggtt | ttgatcgtga | caatatatta | attgccatcg | gtgactccgc | gaaggcggat | 240 |
| atatgtcgcg | aaatcgttaa | ggcgactgtt | aatcatttcg | gcaacattga | tgtcctggtt | 300 |
| aataacgccg | gaggcgcggg | gcctcgtcgc | acgctgcggg | acattccgtt | ttctgagagt | 360 |
| gaacgcttag | cccgcggcga | cgatgagacc | atgttagatg | ccgccatgaa | tctattagct | 420 |
| ggcgcgtgga | acatgacccg | gccgccgtt | ccacacatga | gcgagggcgg | cagtattgtt | 480 |
| aatgttagta | ccatctttag | tcgcacccat | tactatggac | gcataccgta | cgtggtgccc | 540 |
| aaaagtggat | tgaatgccct | gagtataggc | ttagcgaaag | aactcggtga | agaacatggg | 600 |
| atccgcgtta | atacgctgtt | tccgggcccg | atcgagtcgg | aacgcattga | caccgttttt | 660 |
| ggcaatatgg | atgccctgca | aagcgcacca | gcaggtgcca | cttcgcagga | gttccgtgac | 720 |
| ctgatgatca | cccgtcgaga | aaacccggat | ggtgaatatg | agtaccgcta | cccaacgccc | 780 |
| aacgatgtgg | cgtcaacggt | gacctggctg | gcatcggagg | agagtgcggc | cctaagtgga | 840 |
| catcatattg | aagttaccaa | tggcatgcag | gtgccggccc | aaagccgctc | aaagttagta | 900 |
| agttggccgg | acaaacgact | ggaggacctg | tccgggcagg | tcgtattttt | gttagctggc | 960 |
| agcgactacg | aggacgcact | ggcatttgct | gagcgccaca | tggtttccgg | tgcgaaagtc | 1020 |
| gtcctcgcgt | tccgctccct | ggagtcgtta | gggttagctc | gctctttatg | cgcgtcgcgc | 1080 |
| gatttagaga | gcatccacct | actgcacctg | gagccactgc | gacgtgagtc | ggcagaccgg | 1140 |
| tgtttcgatt | acattcgcga | tcatttcggc | cgacttgacg | gcatcgtcgt | gcttccacgc | 1200 |
| tcgggcaacg | gagaacatgg | ctattcgtta | tccaccgcgg | gtgatgacga | tgtcgaggcg | 1260 |
| tttgtccgcg | atgagatcat | atcaccggta | gcatttgctg | ctgcattggc | cattaacctc | 1320 |
| gatcgctggg | gcattttaga | ggaggcacca | gcgctgacct | atgtcaccaa | tccgaccgat | 1380 |
| ggccacgggg | actacttaaa | cgaggtaaag | cgtgcagcta | ttgaggccct | gattcgcatc | 1440 |
| tggcggcatg | aggaccgcca | gatgcgcaag | aagggcgaac | gcgaatgggc | aatgctgcct | 1500 |
| aaccagctgt | tccgctatga | caacaacgag | gaggacaatt | taactttac | cgcagactgg | 1560 |
| gcggccacgc | taaccaaccg | tgttcgacgc | atggatccaa | taaacttatg | ggtgcctgag | 1620 |
| agcattatgc | gcgcaaccgg | caaaagcggt | atgccacaaa | gtatccagcg | cgtgttgcca | 1680 |
| ggcctgcata | aaggccggac | cgccgtgatc | accggtggct | ccctcggcat | cggcctgcaa | 1740 |
| ttgggccggt | tcctggctat | tgccggtgcg | cgggtattgt | tatcggctcg | ctccaaagag | 1800 |
| aaattagaag | aagcacgcca | cgagatcgtt | gaggagttac | gcggcgtcgg | ctacccgaac | 1860 |
| gcgcaccagc | gtgttcatat | tttaccagac | attgatgttg | gcgatgagga | ggccctcgaa | 1920 |
| cggttgtaca | atcactctat | agaattattc | ggaaatgtgg | acttcttaat | taacaacgcg | 1980 |
| ggcatcagtg | gcgctgagga | gatggtcgtt | gatatgtcgc | tcgaagcatg | gaatcgcacc | 2040 |
| atgtatgcga | acttaatcag | taactattct | ttgatccgca | aatatgcgcc | caagatgaaa | 2100 |
| gcgaatggct | acggcgttgt | actcaatgtt | agtagttatt | tcggcggcga | gaaatatgtt | 2160 |

```
gccgtggctt acccgaatcg tgccgactat gcggtctcta aggcaggtca gcgagtactg    2220
gcagagatcc tctctcggca ccttggccca gagatccgaa tcaacgcatt agcaccaggg    2280
ccagtggatg gcgcccgcct gcgcggcctt ggcggcgcac cgggattatt tgaacgacgc    2340
ggtcgactgg ttctcgagaa caaacgatta acagcgtgc ataaagcggt gttggcggcg    2400
ttgcgggagg gcgcaacccc cgaggttatc atggcgctgt cgagaaacgc cctgggcgac    2460
gcaaaaccga ccgccggaca gtccaaagca ttggacaaac tctttgccca ggtcgaagac    2520
tcccctgaag gcggtaatag taccgcattc ttattaaacc gagatttagc agagaaactg    2580
atgaaccggc tggttaccgg cgggttattt actcccgagt ccgctacaca attcatggaa    2640
ggctttgtcg atgcgccggc tatcttcttt gacgaaaagt cggtaaacaa ggcggcggca    2700
ggaattgagg ccggtatctt aaatcgactg cacttacata agatgccgac cgatgagcag    2760
atcggcctgt ctacggtgtt tcatctcgcg gacgatatcg cgagcggcga aacctttcat    2820
ccgagtggcg gcttaaaatt tgaccgctcg gtaaccgaag gggagttgct gctacccca    2880 gaccgtgaca gcttagcgaa gttaaaaggc aaacgtgtcg tgttaattgg tgattcgatg    2940
cgcgaggagc tgtcggccat cggcaatggc ttcattaatc agggcgtcgc ttctctgacg    3000
gtcttaacac gcagcccaga agcctgtgag gaggtgcagc atagcctcca gaaaagcaat    3060
tcggttacat tggatgtccg atgcattgaa gataatatcg aggacgcttt agatgatctg    3120
ttgcaaaacc agggtggctt tgatgtagtg gttagcgccc cgttcagtcg actgccgtat    3180
aacccattag cggccgagcg tgagggtagt tggaatcgtg tgttgtctca tacggacttt    3240
gcccgcctga ttgatgaaca gttaacccac catttccgcg tggcaagacg cgcggccctg    3300
gtaccgaact gccagattgt cttgttaaca ccagatacat ctttcgtatc gtctcgtgag    3360
gagttcgcgc tcgcccctgtt cgttaaaaac tcgctgcacg cgtttacggt aaccctgggg    3420
gtcgagaccg aacgcttacc gaccgtaccg gccgttaatc aggtgcagct tacccgtcgg    3480
gctcgcgctg aagaaccagc gaccgaaagc gagttgcagg aggagatgga gcgcctggtc    3540
tcggccgtac tgcaatgcgc cgttcctgca ccgtccccgt ctgaaagccg gtacctggcg    3600
cgcattttca gaggtaatgc ggtcaccgta tga                                3633
```

```
<210> SEQ ID NO 26
<211> LENGTH: 3690
<212> TYPE: DNA
<213> ORGANISM: Roseiflexus castenholzii

<400> SEQUENCE: 26
atgtcgactg tgcgacgact ggaaggaaag gtggcgctga ttaccggcgg cgctggcaac      60
atcggcgagg ttattacgcg ccgattcctg gcggaaggcg cgaccgttgt catcaccggt     120
cgcaatgcgg aaaagcttgc ggtgtaccgc cgtcgtctga ttgatgagga gcgcgtcgct     180
ccagagcgcg ttgtcgcgct gcggatggac ggcagtgata tcgctcaggt gcgcgcagga     240
gtcgcgcaga ttgttcatgg cggcactgac gtcccaatac cgctgcaccg gattgatatt     300
ctggttaaca acgccggcag tgccggacca cgccggcgcc tggtcgatat cccgttagaa     360
ccaagcgaag tgcaaccgcc tgactcggaa accctggcgc aggcggttgg taatctggtc     420
ggaatcacct ggaatctgac tcgcgcagcg gcgccgcaca tgccgtcagg ctcgtcggtg     480
attaatatca gcaccatttt ctcacgcacg gattattatg gtcggatcgc gtacgtcgcg     540
cccaaagcgg cgttaaatgc gctgtcggac ggtttggcgc gcgaattggg ggtgcgcggc     600
atccgcgtta atacgattta tccaggtccg attgagtcgg aacgcatcta caccatgttc     660
```

```
caggcgatgg acgcgttaaa ggggcaacca gagggcgaca cagcctccgg cttcctgaga      720
atgatgcgct tgtcgcgcat tgatcagaat ggcgaagtgg ttaagcgctt tccctcaccc      780
gtcgatgttg ccaataccgc ggtgttttta gcctcggatg agagcgcagc gtttacgggt      840
catgcctttg aggtgactca tggcatggag gtgcctacgg agagtcgcac taccttcgtg      900
agccgcccag gtctgcgctc ggttgatgcc acgggcaaag tcatcctgat ttgcgctggc      960
gatcaggtcg atgatgcggt cgcgctggcc gacaccttac gcagttgccg cgcgaccgtt     1020
gtgattggtt ttcgggatcc gcgcgcgctt gaaaaagcgt ctgtgttact gcgcgaacct     1080
cgccatgcgc ttgctgccga tatgtacggc cgcccgacca tgaccgcgga agcgcgcctg     1140
gtgcgcttag atccattaga cccgcgtgct gcggcacaga ccttagagca gatccacgcc     1200
gaattaggcg ccatccatca tgctgttgtc ctgcccggtc agagtcgtca cgcgcccagt     1260
gcatcgctga ttgaagtgga cgatcaggtt gttgagcgct ttctgcatca ggagctagta     1320
ggcaccatcg cgctgcgcg cgaactggcg cgcttttggg aggaataccc cagtggctcc      1380
tctatgcacc gcgtgctgtt cgtgtcgaat ccagacgatc agcaggggaa tcagtactcc     1440
catattctgc gcgctgcggt tgagcaattg gtgcgcgttt ggcgccacga gtcggagtat     1500
gacagcgtta atcctgcgca ccagcaggaa gggcagagct cggccgctgt gtgggcgaac     1560
caattgattc gctacgtgaa caatgagatg gccaacttag atttcacgtg cgcatgggtg     1620
gcaaagttat taggttcgga ccgtcgcatc gccgaaatta atttatactt accagaagaa     1680
attgtgggca ccatcggcgt gcacaatccg ggttttgggt gggcggaaag tctgttcggg     1740
ttacacatgg gtaaagtggc gttaattacg ggcggcagtc cggcattgg cgggcagatt      1800 ggtcggttac tggcgttaag tggcgcgcat gtgatgctgg cggcgcggaa cgccgatcag     1860
ttagagcaga tgcgcgcgag cattgtgcgg gaggtgcgtg atgccagtta ccccgatgcc     1920
gagagccgcg tggcgatttt tccaggctcg gatgttagtg acattgacgg tctcgaacgc     1980
ctggttaacc acaccgtgcg cgtgttcggc aaagtggatt atctgattaa caatgcgggc     2040
attgccggcg ccgaggagat ggtgattgat atgccggtgg acgcctggcg ccacactctg     2100
cgcgccaatc tgatttcgaa ttacgcgctg ctgcgccgct agcgccgca aatgaaagcg      2160 gcgggcggtg cgtacgtgct gaatgtgagc agttattttg gcggcgaaaa atacgtggcg     2220
attccttatc cgaaccgcag tgattacgcg gttagtaaag cggggcagcg cgccatggtt     2280
gaaagtctgg cgcgctttct tgggcccgag atccagatta acgcaattgc gccagggccg     2340
gtggaagggg aacgtctgaa gggcgccggt agtcggcccg ggctgtttat cgctccgggcg     2400 cgtttaatcc tggaaaacaa gcgcttaaat gaggttttg ctgcgctgct ggcagcgcgc      2460
catgagggcg cgacgattgc cgatctgtta ccagatctgt ttgccaatga catccagagt     2520
attgccaatt cggctgcgat gccggcgccg ctgcgccgcc tggcgaccat gctgcgcgag     2580
acctcggatg ctggcggttc ggcgcagagc tatctgatga atgcgactat cgcgcgcaag     2640
ttgttaaatc gtctggagaa tggcggttat atcaccttac atgaccgacg cgcgctgacg     2700
gtcgaaccgc cggagccgtt tttcacggaa gcgcagattg agcgcgaagc gattaaagtg     2760
cgggatggca tcctgggaat gttacatctg caacgaatgc cgacggagtt tgatgtggcg     2820
ctggcgaccg ttttttacct ggcggaccgt aatgtgaccg gcgagacctt tcacccgagc     2880
ggcggtctgc gcttcgagcg caccgttacg gaaggcgaac tgttcggcaa accgggacag     2940
cagcgcctgg aacgactgaa gggctcggtt gtttacctga ttggggagca tctgcgccaa     3000
```

| | | | |
|---|---|---|---|
| cacctggtgc | tgctggcgcg | cacgtttta gatgagatcc | acgttgcgcg cgttgtcctg | 3060 |
| ctgactgaaa | cgacccaggc | ggcaacggac ctggcagccg | aactgagtga ttacgaagcc | 3120 |
| gccggacgat | ttgtcgttat | ccgacctgt ggcgacatcg | aaggcgggat cgatcgagcg | 3180 |
| atggcagaat | atggccgccc | agggccggtc attagcaccc | cgtttcgccc gctgccggat | 3240 |
| cgcgccctga | gtgcccgaaa | cggggattgg agtagtgtgt | taacgacggc cgaatttgag | 3300 |
| gaattggttg | aacagcagat | tacgcaccat tttcgcgtcg | cgcgcaaagc gggtctgatt | 3360 |
| gagggcgcga | acgttacgct | ggtgaccccg ccgacgagcg | cgcgcagcac cagtgaggag | 3420 |
| tttgcgctgg | caaactttgt | taaaaccacc ttacatgcat | taaccgcgac ggctggcgcc | 3480 |
| gaaagtgaac | gcaccgtgcc | gcacgtgccg gttaatcagg | tggacctgac ccgtcgtgcc | 3540 |
| cgtagtgagg | agccccgtac | ccctagtgag gaggaggagg | aattacagcg gttcgtgaat | 3600 |
| gccgtgctgc | tgacgagtgc | gccgctgcct accccgttag | aaagtcgtta ccgtgcgcgt | 3660 |
| atttaccggg | gaaatgcgat | cacggtatga | | 3690 |

```
<210> SEQ ID NO 27
<211> LENGTH: 3651
<212> TYPE: DNA
<213> ORGANISM: Unknown
<220> FEATURE:
<223> OTHER INFORMATION: marine gamma proteobacterium

<400> SEQUENCE: 27
```

| | | | |
|---|---|---|---|
| atgaacgatt | tcgtgcaatt | caccgatgac atgaccagtc | agtcaaagtc cggaaaaaga | 60 |
| ctggacaaca | aatctattat | ccttacgggc gccgcgggg | ctattggccg atttattacc | 120 |
| cggcaattac | tctgcgaagg | tgcgagagtg atgatgacag | gcgtgatat cagcaagttg | 180 |
| gaagaatttg | tagattccct | ctgcgatgac ggttttgaca | gggagaatat ggtggttact | 240 |
| gtgggcgatt | gcgcggaccc | agaggtttgt cggcggatcg | ttgcagacac cgtggaagcg | 300 |
| ttcggcacca | ttgacgtgct | ggtcaacaac gcgggtgctg | ctggcccgaa atatacgcta | 360 |
| agagatattc | cgttttccga | tgtagagatg aagaccgcgg | gatcagatca aacgatgttc | 420 |
| gattcagcga | tgaatctatt | aggcgctccc tggaatatgg | cacgtgcagc ggcccctcac | 480 |
| atgtccgtgg | gtgcttcaat | catcaatgta tctacaatct | tttctcggac gcattacttt | 540 |
| ggtcgcatac | cgtatgtggt | tccgaagtcg ggcctaaatg | cgctatcaaa gggactcgca | 600 |
| ttggaattgg | gggaggaaca | aggcattcgt gtcaacactg | tatttccggg acccattgaa | 660 |
| tcggaacgta | tcgacacggt | gtttgcgcgc atggacgaat | tgcagaatct ggaacccggc | 720 |
| agcacgggcc | gcgagttccg | cgacctcatg attacgactc | gcgagggtga ggaggggttg | 780 |
| gagtatcgct | atcctacacc | gaccgatgtg gcgtcgtcca | ttacttggct cgcgtccggg | 840 |
| gagtcggccg | cagtttctgg | tcacgcagtt gaagtcacta | atggtatgca ggtgccagcc | 900 |
| cagagtcggt | cgcagttggt | gtcatggccg gataagcgac | tagaggatct ttccgatcac | 960 |
| attgtgctga | tattaggcgg | ctcagactat gaggaggcgg | tgaccttcgc cgaacggcat | 1020 |
| actgaaagtg | gcgctcgggt | gttactagct tttagaaact | ggaatccgt aggccatgct | 1080 |
| cgatctatta | tccaagctcg | ggaattggag tcagttcaat | tgtctcattt ggacccgtta | 1140 |
| cgccgagagt | cggtagacag | aaccatgcaa ttcatagacg | accatttcgg ccggttggat | 1200 |
| ggcgttattg | ttttgccccca | gaagaaaaac ggtcaatacg | ttattccat ctgttccgct | 1260 |
| accgacgacg | atgtagaaaa | cttcgtcaag gacgaagtcg | tggctccggt agcctttgcg | 1320 |
| tcaaccctcg | cgaccaatct | tagccgctgg tttggaaaat | gtgatccgcc ggcgattacc | 1380 |

```
tacgtcacca atgcgagtga tggacacggt aaccttctga acgaggtcat tcgcgcgtcg    1440
aacgaggcgc taattcgcgg ttggcgccac gaggatgaga cactaaaagc tgctggagag    1500
ttgtcgtggt ccgtgcaacc gaatcagtta gtgcgctatg acactgaaga tagagatgcg    1560
ctcccgtttg cagctgattg ggccgctacc ctcactaatc gcgtgcgaca gatggatccc    1620
attaatctct ggattcctaa ggatattaaa cgcgcgacag gtaaaggcgc gatgccgaca    1680
tctctgatgc gtgttcttcc gggcttacat aaaggaaaaa ccgcggtcat cacaggtggc    1740
agcttgggca taggcctaca attaggacgc tatctcgcca tcgcgggagc gcgagtgcta    1800
cttagtgccc gcagtgaggc gaaattgata gaagctaagg ccgagattgt tgcagaattg    1860
agtggcattg gctatccgaa cgccgacaac cggattcacg tgttggcgaa catcgacgtt    1920
ggagatcccg cagcactaga gacattacac cagcacgcgg tagaccttt cggtcaagtc     1980
gattttctta ttaataatgc aggcatttca ggtgcggagg agatggttgt tgatatgacc    2040
ctaaaagact gggatcgcac catggaggca aatctaatct caaattactc gctaatacgt    2100
aagtttggcc ccctaatgaa agataaaggg cgaggctcta tattgaatgt ttccagttac    2160
tttggtggta aaaaatatgt ggcggtggcg tatccgaatc gcgccgacta tgcggtgtca    2220
aaggcaggac aacgtgtgct cgcggaaatc ctgtcgcgcc acttgggacc tgagattcag    2280
atcaacgcgc tggctccagg cccagttgat ggagctcggt tgcggggatt aggcgatgcg    2340
cccggtcttt tgatcgtcg cgggagactt gttctcgaga ataaacgctt gaaccaggtc     2400
cacgcggcga tcatatcggc cgtcgcggat ggctacccca ttgaggaaat caggaaactc    2460
tcagccaacg cggttgaagt tttgccgacc cataatctac catccgtact aagccgtttg    2520
tattcccaag taaagactc cgggggaaca ggaagctcta gtaaatgcct gctgcatatg     2580
ggcatggctg tcaagctcgt cgaacggtta gtcaatgctg gtattttac gactgaggac     2640
aaagacgaat ttttaggctc gttcgtcgac gcaccgtcgc cgttctttga caaggaggcg    2700
tgcaaaagat ctgcaaccca gatcgaatct ggaatcctta accggctgca tttgcacaaa    2760
atgcctacag atgaacaagt cggcttatct accgtatttc atctcgcgga tgagatcgtc    2820
agtggtgaaa cttccatcc atcaggcggc ctgaaatttg accgctctgt aaccgagggc     2880
gagcttctct tgtcccctag tgagaaagat ttagcccgat tgagtggcaa gcgcgttgtg    2940
atacttggcg actgcatgcg taacgaaatc acagagattg caaggggtt taaatctaac     3000
ggtgttgaga agctctggat ccttacgcgc tcggaggaga ccaaaaccac gctataccat    3060
gctctcgaat gtgacagtgt ggagaacatc gacgtgcgct gcatcggtga cgatatcgaa    3120
ggtgcgctag ataatttact gcgccacgac ggcggattcg acgttgttgt cagcagcccg    3180
tttgaacgcc ttccgctaaa cgcactggca ggagaccgcg gtggtgactg ggatcgcgtg    3240
ctatcagatg agcagttccg acaactcgtt catcagcagt tgacccacca cttccgcagt    3300
gctcgaattg ctgccttaat accgagctgc caaatcgtat tattgacacc ggaaacctcg    3360
cttgcatcca cccgtgagga atttgcactt gcactgttcg tcaaaaatag tctgcacgct    3420
tttacggtga cgctaggtgt ggagggtgag cgtcttccca ccgttccagc tgtcaaccag    3480
gtgcagctta ctcgcagggc gcataccgag gagccaagta atgatcagga attaagtgag    3540
gagatggagc ggctggttgc tgctgtcatg caatgctcgg tcccagcccc ctctcctaaa    3600
gagagtcgtt acctgagtaa gatcttccgg ggaaacgccg tgacggtatg a             3651
```

<210> SEQ ID NO 28

<211> LENGTH: 3654
<212> TYPE: DNA
<213> ORGANISM: Erythrobacter sp.

<400> SEQUENCE: 28

```
atgtcgaagg aaggaaacgc cgccaaaggt cggttagaag gtaaagtggc gctgattacg      60
ggggcggcag gcaatttagg caacgagata tcgcgggcct tcgcccgcga aggcgccttc     120
gttgttatga cggggcgcac cgaggagcgg atctctgcgg cgcgtgaaca gttaattgcg     180
gataccggcg tggcgcctga gcgaattgat accgccgtgt tagacggcgg caatcccgac     240
tcgattcgcg cagcgatggc aaaattgcgc aaggaatacg gccgtattga cattttaatt     300
aacaatgcag gttctgctgg cccaaaacag ccgttacata acgtaccgtt aagccctcag     360
gagatggaag cgtgcggcga caccgagacc gtgcgcgacg cgatgttaaa tattttgggc     420
gttacctgga acatggcgcg cattgtcgcg ccaatgatgc cggttggcgg cgctatggtt     480
aatatttcga cgatctttag ccatacgcgc tactatggac gcacggctta cgtggttcca     540
aaagctgcgc tgaacgcgct ttcgaaccag ttggccagca gttaggaccc gcgcggcatt     600
cgcgttaaca cagtgtttcc aggcccgatc gaaagcgatc gcattcgcac cgtcttcgcc     660
gcgatggatg aggttcagag ccagccaaaa gatacgaccg caaactattt taccggtcgc     720
atggcgttaa cccgcagcgt gaacggaaaa gtagatggca aacctctgcc aaaccccaaa     780
gacattgcgg gacgtgcct gttttttggcc tcagaggaag ccgcaggaat cgcgggcgag     840
gaagttgatg ttacccatgg tcttagtgcc aaccgcacct cggcatcgac ctacatgacc     900
cgtcccagta tgcgctcgtt agatgggcg ggtttaaata tttttattgt gtcgggagag     960
aactgggatg acgcgctggt ggccgctcat acgctgattg gaagtggcgc aaaagttcgc    1020
ttaggcttag ctcgcaatgc cgatgtcgcg caggccaatg cgcgtctgaa ggcgcaaggg    1080
atcggcgagg agctgaccgt gacccgtttt aaccgtgcag agccagacgc gatggaagat    1140
gcgttagccg cgttcagtgg cgacgtggat ggggcgatta ccggcgcgat tattctgccg    1200
gtgaaaccct cgggccattt taccggatcg ctgttagccg ccgatgacga caccgtcacg    1260
aaatttatgg ataccgagtt ggttggcgcg atcgcagtgt cgcgaagctt ggcgcgttac    1320
tggcacgggc gagaggactt acagagtcct ccacgctgcg ttttttatgac caatccgggc    1380
gacccactcg gcaatagttt tgcctcggtg ttaagtgccg gcattaccca gctgattcgc    1440
atttggcgcg acgaggaacg cgttcaggcg ggcaatggct cgaccgagca tgccgtttgg    1500
tcgaaccaga ttgttcgcca taccaacacc gaagatgaga acaccccgctt cgcctcgggc    1560
cacgccaccc gcgtcttatt tcgcgaacag catattgccg agattgattt aaaactgcca    1620
gcgaatatta gcgaggaaac cggatcgcgc aaagccatgg tgggcttcgc cgagaacatt    1680
accgggcttc atttgggcaa agtcgctttt attaccggcg gctctgccgg gattggcggc    1740
caggttgcgc gcctcttagc gttagcaggc gcaaaagtta tgatggtggc aagacgcgaa    1800
agcgagttgg tggccgcccg ggatcgtatt gttggtgagt gcaggacat tggctttgcg    1860
ggcgtcgaac gccgtgtgaa gtatatggcc gatattgatg tgagcgattt tgcctcgtta    1920
gataaagcgg tcgatgcgac gttagaggag tttgggcgta tcgactattt aattaataac    1980
gcaggcgtcg cgggcgccga ggatatggtt attgatatgg agccagaggc atggcgcttt    2040
acgttagacg cgaacttaat tagtaattat cacctgatgc agcgcgtggt tccgctgatg    2100
aaagaacagg gcagtggcta tgtgttaaat gtgagtagtt actttggcgg tgaaaaattt    2160
ttagcggtgg cctatccaaa ccgtgccgac tacggactga gtaaggcggg ccagcgggcg    2220
```

```
atggtggagg cgtttagtcc gttttagggg cccgaggtac agtgcaacgc catcgcgccg   2280
ggccctgtgg acggcgatcg gcttagtggt accggtggaa agccaggtct gtttcagcgc   2340
cgtgccaaac tgattttgga gaacaaacga ctgaatgcgg tgtacagtgc agtgattcat   2400
gcgattcgcg agggcggcga cgcggcgaag attctgacgc gactctcgcg caattcgacc   2460
tcgaccttaa gccacgatgc agaagcacca gaggaactgc gcaaattagc attagatttt   2520
gcatcgcagg gtgacgggct gtgcacgtgg gaccagtact tactgaccga tgcgatggcg   2580
cagcggctct tagtgcggtt gcagttgggc ggctttctgt taggctcgaa cgaatgggcg   2640
agcctgtcga gcagcgagca gacgtggtta agttatcgc ctccagacga taaaccattt   2700
ttaccagctg cgcaggtgga taaagtggca acggcgtgg gcaaaggcgt tatttcgcag   2760
ttgcatttgg gtgcgatgcc gaccgaggcg gaggttgcgc aagcgaccgt gttttttta   2820 gccgatcgcg ctgttagcgg ggaaaccttt atgccgtccg gcggcttacg tgtggaacgc   2880
agtaacaccg agcgcgagat gtttggcagc ccaaaacaag agcgcattga taaaatgaaa   2940
gggaagaccg tgtggattat tggcgagcat ctgagtgact acgtggctgc gacaattgag   3000
gagttagtct ccggctgcgg cgtggccaaa gtggttctga ttgccaaaga taaaagtggc   3060
gaaaaagcgg ttcgcgatca gctcccaaac gatttgtcga aggatgcgtt agaagttctg   3120
attgcgggtg acgggttgga ggaagcgatg gatgaggcgt gggccactg ggcaaacca   3180 accacggtgc tgagtatgcc gggtgaacca ctcccagacc atctgtttga aggcggcaac   3240
ccgttgtcga ccaaagactt tgcgcacatg gtggaggcga acattacccg ccattaccgc   3300
gttacgcgca aagcgtcgtt gtacgatgga tgccaagtgg ttctcgtttc gccggatgtt   3360
ccgtatggca gtgacggccc aggagttgcg ttagccaatt tgttaaaaac gagcctgcat   3420
gcttttaccg cgacggtcgc ggttgagaat gagagactcg tgcatgacgt tccggtgaac   3480
cagattaact taacccgccg ggtgtcgagc gaggagccgc gcgacgctga tgaacacgcc   3540
gaggagttaa gacgctttac ccgcgctgtc ctgcttgtgg gcgcaccgct gccagacgcg   3600
caggatagtc gctatcgctc gaaaattac gcgcggcacgt cgatgacggt atga         3654
```

<210> SEQ ID NO 29
<211> LENGTH: 3660
<212> TYPE: DNA
<213> ORGANISM: Chloroflexus aurantiacus

<400> SEQUENCE: 29

```
atgtcgggaa ctggacgact ggcaggaaaa atcgcccctta tcaccggcgg tgcgggtaac     60
attggttcgg aattgactcg tcgcttttta gcagagggag ccacggttat catctcggga    120
cggaaccggc ccaaattgac cgcactggcg gaacggatgc aggcagaggc aggagtgccg    180
gcaaaacgca ttgatttaga agttatggat gggtcggatc cggttgccgt acgtgcgggc    240
attgaagcca tcgtggcgcg tcatggtcag attgacatcc tggttaataa cgcaggatcg    300
gcgggcgcgc agcgtcgtct ggcggagatc ccattaacag aagctgaact tggtcccggt    360
gcggaggaga cgctccacgc gagcattgcg aaccttctcg gcatgggatg gcacctgatg    420
cgtatcgccg caccccacat gccggtagga tcggccgtta ttaacgttag taccatttt    480 tcccgggctg agtattatgg gcggatcccg tacgttaccc ccaaggctgc tctcaacgct    540
ctatcacaac tcgctgcccg tgagcttggc gcacgtggta ttcgcgtcaa cacgattttt    600
cctggtccga tcgaatcgga tcgcattcgt actgtgttcc agcgtatgga tcagttaaaa    660
```

```
gggcggcctg aaggtgacac tgcccatcac ttttgaata ccatgcgatt gtgccgtgcg    720
aatgaccagg gtgccctcga acgtcggttc ccttctgttg gcgatgtggc agacgcggct    780
gttttctgg cgtcggcgga atctgcggct ttatctggcg agacgatcga ggtcacgcat    840
ggaatggagt tgccgcgtg ttcggagacc agcctgctgg cgcgtacaga tctgcgcacg    900
atcgatgcgt cgggtcgcac gacgttaatt tgtgcgggtg accagatcga ggaggtgatg    960
gccttaaccg gcatgttgcg tacctgcggg tcggaagtga ttattggttt ccgtagtgct   1020
gccgccctgg cgcagttcga gcaggcagtt aacgagtcgc ggcggctggc gggtgcagac   1080
tttacgcccc ctatcgcgtt gccattagat ccacgcgatc cggcaactat cgacgctgtt   1140
ttcgattggg cgggtgagaa caccggtggg atccacgcag ccgtgatcct gcccgctacc   1200
tcgcatgaac cggcaccgtg tgtgatcgag gtcgatgatg agcgggtgct gaactttctg   1260
gcggatgaaa ttaccgggac tatcgtgatc gcgtcgcgcc tggcgcgtta ttggcagagt   1320
caacggctca cccctggtgc acgtgcccgt gggccgcgtg ttatcttttt aagtaatggc   1380
gcggatcaaa acgggaacgt ctatggacgc atccaatcgg cggctattgg ccagttaatc   1440
cgtgtgtggc gtcatgaggc tgaactcgac taccagcgtg cgagcgcggc gggcgatcac   1500
gtgctgccgc cggtatgggc gaaccagatc gtgcgcttcg ctaatcgcag cctcgaaggg   1560
cttgaatttg cgtgcgcgtg gactgctcaa ttgttacact cgcaacgcca cattaacgag   1620
atcaccttaa atattcccgc gaatatcagc gcgaccaccg tgcacgctc ggccagtgtt   1680
ggatgggccg aaagcctgat tgggttacac ttggggaagg tcgcgttgat caccggcggt   1740
agcgcgggca tcggcgggca gattgggcgc ttactggctt tatcgggtgc ccgcgtgatg   1800
ctggcagcgc gtgatcggca caaattagaa cagatgcagg ccatgattca atcagagctg   1860
gctgaggtgg ggtacaccga tgttgaagat cgcgttcata tcgcaccggg ttgtgatgtg   1920
tcgagcgaag cccagctcgc cgatctcgtc gaacgtaccc tgtccgcttt tggtaccgtt   1980
gattacctga ttaataatgc ggggattgcg ggcgttgagg agatggtcat tgatatgcca   2040
gtcgagggat ggcgccacac cttattcgcg aacctgatta gcaattatag tttgatgcgc   2100
aagctggccc cgttgatgaa gaagcagggc agcggctata ttctcaatgt ttcctcctat   2160
tttggtggcg aaaaggatgc cgcgatccct tatcctaatc gtgcggatta tgcggttagt   2220
aaagctggcc agcgggcaat ggcggaagtt tttgcccgct tcctcggtcc ggagatacag   2280
attaacgcga tcgccccggg cccggttgaa ggcgatcgct tacgcggcac cggcgaacgt   2340
cctggtttat ttgcgcgtcg ggcccggctg atcttggaga ataaacggct gaacgagctc   2400
catgctgctc tcattgccgc tgcccgcacc gatgagcgat caatgcatga actggtcgaa   2460
ctgttacttc ctaacgatgt ggcggcacta gagcagaacc agcagcacc caccgccttg   2520
cgtgaactgg cacgacgttt tcgcagcgaa ggtgatccgg ccgcatcctc cagctcggcc   2580
ctgctgaatc gttccatcgc ggctaagttg ctggctcgtt tgcacaacgg cggttacgtg   2640
ttgcccgcgg acattttgc aaatctgcca atccgcctg atcctttctt cacccgagcg   2700
cagatcgatc gcgaggctcg caaagtccgt gacggtatta tggggatgtt atatctgcaa   2760
cggatgccga cagagtttga tgttgcaatg gcgaccgttt actatctcgc ggaccgcaac   2820
gtttcgggcg agactttcca tccatccggc ggcttgcgtt atgaacgcac ccccaccggc   2880
ggtgaattat tcggttttgcc ttccccggaa cggctggccg agctggttgg aagcacggtt   2940
tacctgatag gcgaacacct gacagaacat ctcaatctgc tcgcgcgtgc ctatttagaa   3000
cgttatgggg cacgtcaggt agtgatgatc gtcgagactg aaaccggggc agagactatg   3060
```

```
cgtcgcttgt tacatgatca tgttgaggct ggccggctga tgacaatcgt ggcgggcgat    3120
cagattgaag cggctattga ccaggctatt acacgctatg ccgcccagg gccggttgtt     3180 tgcaccccctt tccggccact gccgacggta ccactggttg ggcgtaagga ctcggactgg   3240
agcactgtgt tgtcggaggc tgaatttgcg gagttgtgtg aacatcagtt aacccatcac    3300
ttccgggtag cccgcaaaat cgcgctgtcg gatggcgcgt cgttagccct ggttacacct    3360
gaaacaacgg ctacctccac aaccgagcaa tttgctctgg ctaatttcat taagacgacc   3420
ctccatgctt ttacggctac gatcggcgtt gagagcgaaa ggacagctca gcgcatcctg    3480
attaaccaag ttgatctgac ccggcgtgcc cgtgcgaggg agccgcgtga tccgcatgag    3540
cgtcaacaag aactggaacg ttttattgag gcagttttac tggttacagc accattaccg    3600
cccgaagcgg atacccgtta tgcggggcgg atccaccgcg gacgggccat caccgtatga    3660

<210> SEQ ID NO 30
<211> LENGTH: 5469
<212> TYPE: DNA
<213> ORGANISM: Chloroflexus aurantiacus

<400> SEQUENCE: 30
atgatcgaca ctgcgcccct tgccccacca cgggcgcccc gctctaatcc gattcgggat      60
cgagttgatt gggaagctca gcgtgctgct gcgctggcag atcccggtgc ctttcatggc    120
gcgattgccc ggacagttat ccactggtac gacccacaac accattgctg gattcgcttc    180
aacgagtcta gtcagcgttg ggaagggctg atgccgcta ccggtgcccc tgtaacggta     240
gactatcccg ccgattatca gccctggcaa caggcgtttg atgatagtga agcgccgttt    300
taccgctggt ttagtggtgg gttgacaaat gcctgctta tgaagtaga ccggcatgtc      360 acgatgggct atggcgacga ggtggcctac tactttgaag gtgaccgctg ggataactcg    420
ctcaacaatg gtcgtggtgg tccggttgtc caggagacaa tcacgcgacg cgtctgttg     480 gtggaggtgg tgaaggctgc gcaggtgttg cgcgatctgg gcctgaagaa gggtgatcgg    540
attgctctga atatgccgaa tattatgccg cagatttatt tacgaagc ggcaaaacga      600 ctgggtattc tgtacacgcc ggtcttcggt ggcttctcgg acaagactct ttccgaccgt    660
attcacaatg ccggtgcacg agtggtgatt acctctgatg gcgcgtatcg caacgcgcag    720 gtggtgcccct acaaagaagc gtataccgat caggcgctcg ataagtatat tccggttgag    780
actgcgcagg cgattgttgc gcagaccctg gccaccttgc ccctgactga gtcgcagcgc    840
cagacgatca tcaccgaagt ggaggccgcc ctggcaggtg agattaccggt tgagcgttcg    900 gacgtgatgc gtggggttgg ttctgcccctc gcaaagctcc gcgatcttga tgcaagcgtg    960
caggcaaagg tgcgcacagt actggcgcag gcgctggtcg agtcgccgcc gcgggttgaa   1020
gctgtggtgg ttgtgcgtca taccggtcag agattttgt ggaacgaggg gcgagatcgc    1080
tggagtcacg acttgctgga tgctgcgctg gcgaagattc tggccaatgc gcgtgctgca    1140
ggctttgatg tgcacagtga gaatgatctg ctcaatctcc ccgatgacca gcttatccgt    1200
gcgctctacg ccagtattcc ctgtgaaccg gttgatgctg aatatccgat gtttatcatt    1260
tacacatcgg gtagcaccgg taagcccaag ggtgtgatcc acgttcacgg cggttatgtc    1320
gccggtgtgg tgcacacctt gagggtcagt tttgacgccg agcggggtga tacgatatat    1380
gtgatcgccg atccggcgct gatcaccggc cagagctata tgctcacagc cacaatggcc    1440
ggtagactga ccggggtgat tgccgaggga tcaccgcttt tcccctcagc cgggcgttat    1500
```

```
gccagcatca tcgagcgcta tggggtgcag atctttaagg cgggtgtgac cttcctcaag    1560
acagtgatgt ccaatccgca gaatgttgaa gatgtgcgac tctatgatat gcactcgctg    1620
agagttgcaa ccttctgcgc cgagccggta agtccggcgg tgcagcagtt tggtatgcag    1680
atcatgaccc cgcagtatat caattcgtac tgggcgaccg agcacggtgg aattgtctgg    1740
acgcatttct acggtaatca ggactttccg cttcgtcccg atgcccatac ctatcccttg    1800
ccctgggtga tgggtgatgt ctgggtggcc gaaactgatg agagcgggac gacgcgctat    1860
cgggtcgctg atttcgatga aagggcgag attgtgatta ccgccccgta tccctacctg    1920
acccgcacac tctggggtga tgtgcccggt ttcgaggcgt acctgcgcgg tgagattccg    1980
ctgcgagcct ggaagggtga tgccgagcgt ttcgtcaaga cctactggcg acgtgggcca    2040
aacggtgaat gggctatat ccaggtgat tttgccatca agtacccga tggtagcttc    2100
acgctccacg gacgctctga cgatgtgatc aatgtgtcgg gccaccgtat gggcaccgag    2160
gagattgagg tgccattttt gcgtgaccgc cagatcacgc ccgactcgcc tgtcggtaat    2220
tgtattgtgg tcggtgcgcc gcatcgtgag aagggtctga ccccggttgc cttcattcaa    2280
cctgcgcctg gccgtcatct gaccggtgca gacaggcgcc gtctcgatga gctggtgcgc    2340
accgagaagg gggcggtcag tgtcccagag gattacatcg aggtcagtgc ctttcccgaa    2400
acccgcagcg ggaagtatat gaggcgcttt ttgcgcaata tgatgctcga tgaaccactg    2460
ggtgatacga cgacgttgcg caatcctgaa gtgctcgaag aaattgcagc caagatcgct    2520
gagtggaaac gccgtcagcg tatggccgaa gaacagcaga tcatcgaacg ctatcgctac    2580
ttccggatcg agtatcatcc accaacggcc agtgcgggta actcgcggt agtgacggtg    2640
acaaatccgc cggtgaacgc actgaatgag cgtgcgttag atgagttgaa cacaattgtt    2700
gaccacctgg cccgtcgtca ggatgttgcc gcaattgtct tcaccggaca gggcgccagg    2760
agttttgtcg ccggtgctga tattcgccag ttgctcgaag aaattcatac ggttgaagaa    2820
gcaatggccc tgccgaataa cgcccatctt gctttccgca agattgagcg tatgaataag    2880
ccgtgtatcg cggcgatcaa cggtgtggcg ctcggtggtg gtctggaatt gccatggcc    2940
tgccattacc gggttgccga tgtctatgcc gaatttggtc agccagagat taatctgcgc    3000
ttgctacctg gttatggtgg cacgcagcgc ttgccgcgtc tgttgtacaa gcgcaacaac    3060
ggcaccggtc tgctccgagc gctggagatg attctgggtg ggcgtagcgt accggctgat    3120
gaggcgctgg agctgggtct gatcgatgcc attgctaccg gcgatcagga ctcactgtcg    3180
ctggcatgcg cgttagcccg tgccgcaatc ggtgccgatg gtcagttgat cgagtcggct    3240
gcggtgaccc aggctttccg ccatcgccac gagcagcttg acgagtggcg caaaccagac    3300
ccgcgctttg ccgatgacga actgcgctcg attatcgccc atccacgtat cgagcggatt    3360
atccggcagg cccataccgt tgggcgcgat gcggcagtgc accgggcact ggatgcaatc    3420
cgctatggca ttatccacgg cttcgaggcc ggtctggagc acgaggcgaa gctctttgcc    3480
gaggcagtgg ttgacccgaa cggtggcaag cgtggtattc gcgagttcct cgaccgccag    3540
agtgcgccgt tgccaacccg ccgaccattg attacacctg aacaggagca actcttgcgc    3600
gatcagaaag aactgttgcc ggttggttca cccttcttcc ccgtgttga ccggattccg    3660
aagtggcagt acgcgcaggc ggttattcgt gatccggaca ccggtgcggc ggctcacggc    3720
gatcccatcg tggctgaaaa gcagattatt gtgccggtgg aacgccccg cgccaatcag    3780
gcgctgattt atgttctggc ctcggaggtg aacttcaacg atatctgggc gattaccggt    3840
attccggtgt cacggtttga tgagcacgac cgcgactggc acgttaccgg ttcaggtggc    3900
```

```
atcggcctga tcgttgcgct gggtgaagaa gcgcgacgcg aaggccggct gaaggtgggt      3960
gatctggtgg cgatctactc cgggcagtcg gatctgctct caccgctgat gggccttgat      4020
ccgatggccg ccgatttcgt catccagggg aacgacacgc cagatggatc gcatcagcaa      4080
tttatgctgg cccaggcccc gcagtgtctg cccatcccaa ccgatatgtc tatcgaggca      4140
gccggcagct acatcctcaa tctcggtacg atctatcgcg ccctctttac gacgttgcaa      4200
atcaaggccg gacgcaccat ctttatcgag ggtgcggcga ccggcaccgg tctggacgca      4260
gcgcgctcgg cggcccggaa tggtctgcgc gtaattggaa tggtcagttc gtcgtcacgt      4320
gcgtctacgc tgctggctgc gggtgcccac ggtgcgatta accgtaaaga cccggaggtt      4380
gccgattgtt tcacgcgcgt gcccgaagat ccatcagcct gggcagcctg ggaagccgcc      4440
ggtcagccgt tgctggcgat gttccgggcg cagaacgacg ggcgactggc cgattatgtg      4500
gtctcgcacg cgggcgagac ggccttcccg cgcagtttcc agcttctcgg cgagccacgc      4560
gatggtcaca ttccgacgct cacattctac ggtgccacca gtggctacca cttcaccttc      4620
ctgggtaagc cagggtcagc ttcgccgacc gagatgctgc ggcgggccaa tctccgcgcc      4680
ggtgaggcgg tgttgatcta ctacggggtt gggagcgatg acctggtaga taccggcggt      4740
ctggaggcta tcgaggcggc gcggcaaatg ggagcgcgga tcgtcgtcgt taccgtcagc      4800
gatgcgcaac gcgagtttgt cctctcgttg ggcttcgggg ctgccctacg tggtgtcgtc      4860
agcctggcgg aactcaaacg acgcttcggc gatgagtttg agtggccgcg cacgatgccg      4920
ccgttgccga acgcccgcca ggacccgcag ggtctgaaag aggctgtccg ccgcttcaac      4980
gatctggtct tcaagccgct aggaagcgcg gtcggtgtct tcttgcggag tgccgacaat      5040
ccgcgtggct accccgatct gatcatcgag cgggctgccc acgatgcact ggcggtgagc      5100
gcgatgctga tcaagcccct tcaccggacgg attgtctact tcgaggacat tggtgggcgg      5160
cgttactcct tcttcgcacc gcaaatctgg gtgcgccagc gccgcatcta catgccgacg      5220
gcacagatct ttggtacgca cctctcaaat gcgtatgaaa ttctgcgtct gaatgatgag      5280
atcagcgccg gtctgctgac gattaccgag ccggcagtgg tgccgtggga tgaactaccc      5340
gaagcacatc aggcgatgtg ggaaaatcgc cacacgcgg ccacttatgt ggtgaatcat      5400
gccttaccac gtctcggcct aaagaacagg gacgagctgt acgaggcgtg gacggccggc      5460
gagcgctaa                                                              5469
```

<210> SEQ ID NO 31
<211> LENGTH: 1822
<212> TYPE: PRT
<213> ORGANISM: Chloroflexus aurantiacus

<400> SEQUENCE: 31

Met Ile Asp Thr Ala Pro Leu Ala Pro Pro Arg Ala Pro Arg Ser Asn
1               5                   10                  15

Pro Ile Arg Asp Arg Val Asp Trp Glu Ala Gln Arg Ala Ala Ala Leu
            20                  25                  30

Ala Asp Pro Gly Ala Phe His Gly Ala Ile Ala Arg Thr Val Ile His
        35                  40                  45

Trp Tyr Asp Pro Gln His His Cys Trp Ile Arg Phe Asn Glu Ser Ser
    50                  55                  60

Gln Arg Trp Glu Gly Leu Asp Ala Ala Thr Gly Ala Pro Val Thr Val
65                  70                  75                  80

Asp Tyr Pro Ala Asp Tyr Gln Pro Trp Gln Gln Ala Phe Asp Asp Ser

```
                85                  90                  95
Glu Ala Pro Phe Tyr Arg Trp Phe Ser Gly Gly Leu Thr Asn Ala Cys
            100                 105                 110
Phe Asn Glu Val Asp Arg His Val Thr Met Gly Tyr Gly Asp Glu Val
            115                 120                 125
Ala Tyr Tyr Phe Glu Gly Asp Arg Trp Asp Asn Ser Leu Asn Asn Gly
            130                 135                 140
Arg Gly Pro Val Val Gln Glu Thr Ile Thr Arg Arg Leu Leu
145                 150                 155                 160
Val Glu Val Val Lys Ala Ala Gln Val Leu Arg Asp Leu Gly Leu Lys
                165                 170                 175
Lys Gly Asp Arg Ile Ala Leu Asn Met Pro Asn Ile Met Pro Gln Ile
            180                 185                 190
Tyr Tyr Thr Glu Ala Ala Lys Arg Leu Gly Ile Leu Tyr Thr Pro Val
            195                 200                 205
Phe Gly Gly Phe Ser Asp Lys Thr Leu Ser Asp Arg Ile His Asn Ala
            210                 215                 220
Gly Ala Arg Val Val Ile Thr Ser Asp Gly Ala Tyr Arg Asn Ala Gln
225                 230                 235                 240
Val Val Pro Tyr Lys Glu Ala Tyr Thr Asp Gln Ala Leu Asp Lys Tyr
                245                 250                 255
Ile Pro Val Glu Thr Ala Gln Ala Ile Val Ala Gln Thr Leu Ala Thr
            260                 265                 270
Leu Pro Leu Thr Glu Ser Gln Arg Gln Thr Ile Ile Thr Glu Val Glu
            275                 280                 285
Ala Ala Leu Ala Gly Glu Ile Thr Val Glu Arg Ser Asp Val Met Arg
290                 295                 300
Gly Val Gly Ser Ala Leu Ala Lys Leu Arg Asp Leu Asp Ala Ser Val
            305                 310                 315                 320
Gln Ala Lys Val Arg Thr Val Leu Ala Gln Ala Leu Val Glu Ser Pro
                325                 330                 335
Pro Arg Val Glu Ala Val Val Val Arg His Thr Gly Gln Glu Ile
            340                 345                 350
Leu Trp Asn Glu Gly Arg Asp Arg Trp Ser His Asp Leu Leu Asp Ala
            355                 360                 365
Ala Leu Ala Lys Ile Leu Ala Asn Ala Arg Ala Gly Phe Asp Val
            370                 375                 380
His Ser Glu Asn Asp Leu Leu Asn Leu Pro Asp Asp Gln Leu Ile Arg
385                 390                 395                 400
Ala Leu Tyr Ala Ser Ile Pro Cys Glu Pro Val Asp Ala Glu Tyr Pro
            405                 410                 415
Met Phe Ile Ile Tyr Thr Ser Gly Ser Thr Gly Lys Pro Lys Gly Val
            420                 425                 430
Ile His Val His Gly Gly Tyr Val Ala Gly Val His Thr Leu Arg
            435                 440                 445
Val Ser Phe Asp Ala Glu Pro Gly Asp Thr Ile Tyr Val Ile Ala Asp
            450                 455                 460
Pro Gly Trp Ile Thr Gly Gln Ser Tyr Met Leu Thr Ala Thr Met Ala
465                 470                 475                 480
Gly Arg Leu Thr Gly Val Ile Ala Glu Gly Ser Pro Leu Phe Pro Ser
            485                 490                 495
Ala Gly Arg Tyr Ala Ser Ile Ile Glu Arg Tyr Gly Val Gln Ile Phe
            500                 505                 510
```

```
Lys Ala Gly Val Thr Phe Leu Lys Thr Val Met Ser Asn Pro Gln Asn
            515                 520                 525

Val Glu Asp Val Arg Leu Tyr Asp Met His Ser Leu Arg Val Ala Thr
        530                 535                 540

Phe Cys Ala Glu Pro Val Ser Pro Ala Val Gln Gln Phe Gly Met Gln
545                 550                 555                 560

Ile Met Thr Pro Gln Tyr Ile Asn Ser Tyr Trp Ala Thr Glu His Gly
                565                 570                 575

Gly Ile Val Trp Thr His Phe Tyr Gly Asn Gln Asp Phe Pro Leu Arg
            580                 585                 590

Pro Asp Ala His Thr Tyr Pro Leu Pro Trp Val Met Gly Asp Val Trp
        595                 600                 605

Val Ala Glu Thr Asp Glu Ser Gly Thr Thr Arg Tyr Arg Val Ala Asp
    610                 615                 620

Phe Asp Glu Lys Gly Glu Ile Val Ile Thr Ala Pro Tyr Pro Tyr Leu
625                 630                 635                 640

Thr Arg Thr Leu Trp Gly Asp Val Pro Gly Phe Glu Ala Tyr Leu Arg
                645                 650                 655

Gly Glu Ile Pro Leu Arg Ala Trp Lys Gly Asp Ala Glu Arg Phe Val
            660                 665                 670

Lys Thr Tyr Trp Arg Arg Gly Pro Asn Gly Glu Trp Gly Tyr Ile Gln
        675                 680                 685

Gly Asp Phe Ala Ile Lys Tyr Pro Asp Gly Ser Phe Thr Leu His Gly
    690                 695                 700

Arg Ser Asp Asp Val Ile Asn Val Ser Gly His Arg Met Gly Thr Glu
705                 710                 715                 720

Glu Ile Glu Gly Ala Ile Leu Arg Asp Arg Gln Ile Thr Pro Asp Ser
                725                 730                 735

Pro Val Gly Asn Cys Ile Val Val Gly Ala Pro His Arg Glu Lys Gly
            740                 745                 750

Leu Thr Pro Val Ala Phe Ile Gln Pro Ala Pro Gly Arg His Leu Thr
        755                 760                 765

Gly Ala Asp Arg Arg Leu Asp Glu Leu Val Arg Thr Glu Lys Gly
    770                 775                 780

Ala Val Ser Val Pro Glu Asp Tyr Ile Glu Val Ser Ala Phe Pro Glu
785                 790                 795                 800

Thr Arg Ser Gly Lys Tyr Met Arg Arg Phe Leu Arg Asn Met Met Leu
                805                 810                 815

Asp Glu Pro Leu Gly Asp Thr Thr Leu Arg Asn Pro Glu Val Leu
            820                 825                 830

Glu Glu Ile Ala Ala Lys Ile Ala Glu Trp Lys Arg Arg Gln Arg Met
        835                 840                 845

Ala Glu Glu Gln Gln Ile Ile Glu Arg Tyr Arg Tyr Phe Arg Ile Glu
    850                 855                 860

Tyr His Pro Pro Thr Ala Ser Ala Gly Lys Leu Ala Val Val Thr Val
865                 870                 875                 880

Thr Asn Pro Pro Val Asn Ala Leu Asn Glu Arg Ala Leu Asp Glu Leu
                885                 890                 895

Asn Thr Ile Val Asp His Leu Ala Arg Arg Gln Asp Val Ala Ala Ile
            900                 905                 910

Val Phe Thr Gly Gln Gly Ala Arg Ser Phe Val Ala Gly Ala Asp Ile
        915                 920                 925
```

Arg Gln Leu Leu Glu Glu Ile His Thr Val Glu Glu Ala Met Ala Leu
930             935                 940

Pro Asn Asn Ala His Leu Ala Phe Arg Lys Ile Glu Arg Met Asn Lys
945                 950                 955                 960

Pro Cys Ile Ala Ala Ile Asn Gly Val Ala Leu Gly Gly Gly Leu Glu
                965                 970                 975

Phe Ala Met Ala Cys His Tyr Arg Val Ala Asp Val Tyr Ala Glu Phe
                980                 985                 990

Gly Gln Pro Glu Ile Asn Leu Arg  Leu Leu Pro Gly Tyr  Gly Gly Thr
            995             1000                  1005

Gln Arg Leu Pro Arg Leu Leu  Tyr Lys Arg Asn Asn  Gly Thr Gly
    1010            1015                 1020

Leu Leu Arg Ala Leu Glu Met  Ile Leu Gly Gly Arg  Ser Val Pro
    1025            1030                 1035

Ala Asp Glu Ala Leu Glu Leu  Gly Leu Ile Asp Ala  Ile Ala Thr
    1040            1045                 1050

Gly Asp Gln Asp Ser Leu Ser  Leu Ala Cys Ala Leu  Ala Arg Ala
    1055            1060                 1065

Ala Ile Gly Ala Asp Gly Gln  Leu Ile Glu Ser Ala  Ala Val Thr
    1070            1075                 1080

Gln Ala Phe Arg His Arg His  Glu Gln Leu Asp Glu  Trp Arg Lys
    1085            1090                 1095

Pro Asp Pro Arg Phe Ala Asp  Asp Glu Leu Arg Ser  Ile Ile Ala
    1100            1105                 1110

His Pro Arg Ile Glu Arg Ile  Ile Arg Gln Ala His  Thr Val Gly
    1115            1120                 1125

Arg Asp Ala Ala Val His Arg  Ala Leu Asp Ala Ile  Arg Tyr Gly
    1130            1135                 1140

Ile Ile His Gly Phe Glu Ala  Gly Leu Glu His Glu  Ala Lys Leu
    1145            1150                 1155

Phe Ala Glu Ala Val Val Asp  Pro Asn Gly Gly Lys  Arg Gly Ile
    1160            1165                 1170

Arg Glu Phe Leu Asp Arg Gln  Ser Ala Pro Leu Pro  Thr Arg Arg
    1175            1180                 1185

Pro Leu Ile Thr Pro Glu Gln  Glu Gln Leu Leu Arg  Asp Gln Lys
    1190            1195                 1200

Glu Leu Leu Pro Val Gly Ser  Pro Phe Phe Pro Gly  Val Asp Arg
    1205            1210                 1215

Ile Pro Lys Trp Gln Tyr Ala  Gln Ala Val Ile Arg  Asp Pro Asp
    1220            1225                 1230

Thr Gly Ala Ala Ala His Gly  Asp Pro Ile Val Ala  Glu Lys Gln
    1235            1240                 1245

Ile Ile Val Pro Val Glu Arg  Pro Arg Ala Asn Gln  Ala Leu Ile
    1250            1255                 1260

Tyr Val Leu Ala Ser Glu Val  Asn Phe Asn Asp Ile  Trp Ala Ile
    1265            1270                 1275

Thr Gly Ile Pro Val Ser Arg  Phe Asp Glu His Asp  Arg Asp Trp
    1280            1285                 1290

His Val Thr Gly Ser Gly Gly  Ile Gly Leu Ile Val  Ala Leu Gly
    1295            1300                 1305

Glu Glu Ala Arg Arg Glu Gly  Arg Leu Lys Val Gly  Asp Leu Val
    1310            1315                 1320

Ala Ile Tyr Ser Gly Gln Ser  Asp Leu Leu Ser Pro  Leu Met Gly

```
                1325                1330                1335

Leu Asp Pro Met Ala Ala Asp Phe Val Ile Gln Gly Asn Asp Thr
        1340                1345                1350

Pro Asp Gly Ser His Gln Gln Phe Met Leu Ala Gln Ala Pro Gln
        1355                1360                1365

Cys Leu Pro Ile Pro Thr Asp Met Ser Ile Glu Ala Ala Gly Ser
        1370                1375                1380

Tyr Ile Leu Asn Leu Gly Thr Ile Tyr Arg Ala Leu Phe Thr Thr
        1385                1390                1395

Leu Gln Ile Lys Ala Gly Arg Thr Ile Phe Ile Glu Gly Ala Ala
        1400                1405                1410

Thr Gly Thr Gly Leu Asp Ala Ala Arg Ser Ala Ala Arg Asn Gly
        1415                1420                1425

Leu Arg Val Ile Gly Met Val Ser Ser Ser Ser Arg Ala Ser Thr
        1430                1435                1440

Leu Leu Ala Ala Gly Ala His Gly Ala Ile Asn Arg Lys Asp Pro
        1445                1450                1455

Glu Val Ala Asp Cys Phe Thr Arg Val Pro Glu Asp Pro Ser Ala
        1460                1465                1470

Trp Ala Ala Trp Glu Ala Ala Gly Gln Pro Leu Leu Ala Met Phe
        1475                1480                1485

Arg Ala Gln Asn Asp Gly Arg Leu Ala Asp Tyr Val Val Ser His
        1490                1495                1500

Ala Gly Glu Thr Ala Phe Pro Arg Ser Phe Gln Leu Leu Gly Glu
        1505                1510                1515

Pro Arg Asp Gly His Ile Pro Thr Leu Thr Phe Tyr Gly Ala Thr
        1520                1525                1530

Ser Gly Tyr His Phe Thr Phe Leu Gly Lys Pro Gly Ser Ala Ser
        1535                1540                1545

Pro Thr Glu Met Leu Arg Arg Ala Asn Leu Arg Ala Gly Glu Ala
        1550                1555                1560

Val Leu Ile Tyr Tyr Gly Val Gly Ser Asp Asp Leu Val Asp Thr
        1565                1570                1575

Gly Gly Leu Glu Ala Ile Glu Ala Ala Arg Gln Met Gly Ala Arg
        1580                1585                1590

Ile Val Val Val Thr Val Ser Asp Ala Gln Arg Glu Phe Val Leu
        1595                1600                1605

Ser Leu Gly Phe Gly Ala Ala Leu Arg Gly Val Val Ser Leu Ala
        1610                1615                1620

Glu Leu Lys Arg Arg Phe Gly Asp Glu Phe Glu Trp Pro Arg Thr
        1625                1630                1635

Met Pro Pro Leu Pro Asn Ala Arg Gln Asp Pro Gln Gly Leu Lys
        1640                1645                1650

Glu Ala Val Arg Arg Phe Asn Asp Leu Val Phe Lys Pro Leu Gly
        1655                1660                1665

Ser Ala Val Gly Val Phe Leu Arg Ser Ala Asp Asn Pro Arg Gly
        1670                1675                1680

Tyr Pro Asp Leu Ile Ile Glu Arg Ala Ala His Asp Ala Leu Ala
        1685                1690                1695

Val Ser Ala Met Leu Ile Lys Pro Phe Thr Gly Arg Ile Val Tyr
        1700                1705                1710

Phe Glu Asp Ile Gly Gly Arg Arg Tyr Ser Phe Phe Ala Pro Gln
        1715                1720                1725
```

```
Ile Trp Val Arg Gln Arg Arg Ile Tyr Met Pro Thr Ala Gln Ile
    1730                1735                1740

Phe Gly Thr His Leu Ser Asn Ala Tyr Glu Ile Leu Arg Leu Asn
    1745                1750                1755

Asp Glu Ile Ser Ala Gly Leu Leu Thr Ile Thr Glu Pro Ala Val
    1760                1765                1770

Val Pro Trp Asp Glu Leu Pro Glu Ala His Gln Ala Met Trp Glu
    1775                1780                1785

Asn Arg His Thr Ala Ala Thr Tyr Val Val Asn His Ala Leu Pro
    1790                1795                1800

Arg Leu Gly Leu Lys Asn Arg Asp Glu Leu Tyr Glu Ala Trp Thr
    1805                1810                1815

Ala Gly Glu Arg
    1820

<210> SEQ ID NO 32
<211> LENGTH: 1575
<212> TYPE: DNA
<213> ORGANISM: Metallosphaera sedula

<400> SEQUENCE: 32
atgaccgcca cgttcgagaa gcccgatatg tcgaagttgg ttgaggagct tcgtgcgttg     60
aaagcgaaag catatatggg tggcggcgaa gaacgtgtcc aggcacaaca cgcaaaagga    120
aaactcactg ctcgcgaacg cctaaattta ttgtttgatg aagggacctt caacgaagta    180
atgaccttcg cgacaactaa agcaacggaa tttggccttg ataagtccaa agtatatggc    240
gacggagtcg tcacgggctg gggccaggta gaaggccgca cggtcttcgc cttcgcgcag    300
gactttacaa gtattggcgg aacattgggg gaaacgcatg ctagtaagat tgcaaaagtt    360
tacgaattag ccctaaaagt tggcgcccct gtcgttggga ttaatgatag tggcggcgcg    420
cgtattcaag aaggagccgt agccttggaa ggttatggta cagtattcaa agcgaacgtg    480
atggccagtg gagtcgttcc gcagattacc attatggcag gtccagcagc tggcggtgcc    540
gtttattcgc cagcgttaac ggactttatt ataatgatta aggagacgc gtattatatg    600
ttcgtgaccg gtccagaaat aactaaagtg gtgcttggtg aagacgtttc gtttcaagac    660
ttgggtggcg cggtcatcca tgccacgaag tcgggagtgg ttcattttat cgctgaaaac    720
gagcaagata gcatcaacat taccaaacgc cttttaagtt atttgccgag taacaacatg    780
gaagaaccac cgtttatgga cacaggcgac cctgctgacc gcgagatgaa agacgtggaa    840
tccgttgttc aacggacac cgtaaaaccg ttcgatatgc gtgaagtcat ttatcgcacg    900
gtggacaacg gagaatttat ggaagtgcag aaacactggg cacagaacat ggtggttggc    960
ttcggccgcg tcgcggggaa cgtggtcggt attgtcgcca ataacagcgc gcacctcggg   1020
gccgcgattg atattgacgc gtcggacaaa gctgcgcgct ttattcgctt ttgcgacgca   1080
ttcaatatcc cgcttatctc ccttgtggac acgcctggtt atatgccggg cactgaccag   1140
gagtacaaag gaataatccg ccatggcgcc aaaatgcttt atgcgttcgc agaagccact   1200
gttccgaaag taacggtggt ggttcgtcgc agctatggtg agcacatat agcgatgtcc   1260
attaaatccc tgggcgctga tttaatttac gcatggccga gtgccgaaat tgctgtgacg   1320
gggcctgaag gggcggtgcg catactctat cgccgtgaga tccagaactc caaaagtcct   1380
gacgatttaa taaagaacg tattgcagaa tataaaaaac ttttttgcgaa cccgtactgg   1440
gccgcagaaa aaggccttat cgacgacgtc attgaaccga agatacacg caaagtcatt   1500
```

```
gcttcggcgc ttaaaatgct aaaaaacaaa cgcgaatttc gctatccgaa aaaacacggc    1560
aatattccgc tctaa                                                     1575

<210> SEQ ID NO 33
<211> LENGTH: 1533
<212> TYPE: DNA
<213> ORGANISM: Metallosphaera sedula

<400> SEQUENCE: 33
atgccaccgt tctctcgtgt tcttgttgcc aaccgcggcg agatcgccgt ccgcgtcatg     60
aaagccatta agagatggg catgactgcc attgcagttt atagtgaagc agacaaatat    120
gccgtacatg ttaaatacgc ggatgaggca tactacatcg gcccgtcacc cgcgcttgag    180
tcttatttaa acattccgca tataatcgac gccgctgaaa aagcacatgc agacgcagtt    240
caccctggct acggctttct ttcagaaaat gcagactttg tggaagccgt tgagaaagcc    300
ggcatgacgt atattggtcc gagtgcagaa gtaatgcgta aaattaaaga taaactcgat    360
gggaagcgca ttgcgcagct aagtggtgta ccgatcgcgc tggatcaga tggaccggtc    420 gagagcatcg acgaagcact gaaacttgca gaaaaaattg gctatccgat aatggttaaa    480
gcggcatccg ggggtggtgg cgtcggtatt actaaaattg atactcctga ccagttaatc    540
gacgcctggg agcgtaacaa acgcctagca actcaagcgt ttggccgaag tgatttgtat    600
attgagaagg cggcggtcaa ccctcgccat atcgaatttc agctaatcgg agataaatat    660
ggaaactacg tagttgcatg ggaacgcgag tgcacgatcc agcgtcgtaa ccagaaactt    720
attgaagaag ccccaagtcc agccataact atggaggagc gctcgcgaat gtttgaacct    780
atttataagt acgggaaact aatcaattat ttcaccctcg gtacgtttga aactgttttt    840
agtgatgcga ctcgcgaatt ttattttctg gaactcaaca agcgcctgca agtcgagcat    900
ccagttacgg aactaatttt tcgtatcgat ctcgtcaaat gcagattcg cttggcagcc    960 ggcgagcacc ttccatttac acaggaggag ttaaacaaac gcgctcgtgg tgccgccatt   1020
gaatttcgca ttaatgcgga agatccaatt aataattttt ccggctcctc gggttttatc   1080
acatattatc gcgaaccgac aggtcctggc gtgcgtatga ttccggtgt cacagaaggc   1140 tcctgggtcc ctccttttta tgacagtttg gtctcaaaac ttatcgtgta cggcgaggac   1200
cgccaatatg ccattcaaac ggcgatgcgc gccttggacg attataaaat cggaggcgta   1260
aagacaacga ttcccttgta taattaata atgcgcgatc cggacttcca ggagggccgc   1320
ttttctacgg cgtacatcag ccagaaaatc gactcgatgg ttaaaaagct caaagcggag   1380
gaagaaatga tggcatcggt ggcggccgtt ctgcaatccc gcggcttact gcgtaaaaaa   1440
gcatcggcac tcaggaaca ggctaagcca ggatcgggct ggaaatctta tggtataatg   1500
atgcagtcca cgcctcgcgt gatgtgggg taa                                 1533

<210> SEQ ID NO 34
<211> LENGTH: 504
<212> TYPE: DNA
<213> ORGANISM: Metallosphaera sedula

<400> SEQUENCE: 34
atgaaactct accgcgttca cgctgatact ggcgatacct ttatcgtggc gcatgatcaa     60
aaagagaaca agaccgtttt gaaacagag ataacgaat ttgaaattga atacgtaggt    120
cagggtactc gcgagggcga gattatactc aaaatcaacg gtgaaatgca tcgcgtattt    180
```

| | |
|---|---|
| attgacaacg gctggattat cctggacaat gcccgcattt ttcgcgccga acgtgttact | 240 |
| gaactgccga cgcaggaggg ccagactctc gacgaaatga taaagggtaa agaaggcgag | 300 |
| gtgttgtcgc ccctgcaagg acgtgtcgtt caggtacgcg ttaaagaggg agatgctgtg | 360 |
| aataaaggcc agccgctttt gtcaatcgaa gcgatgaagt ccgaaaccat tgtgtcagcc | 420 |
| ccaatttccg ggttggtgga aaaagtccta gttaaagccg gtcaaggcgt caaaaaaggc | 480 |
| gatatattgg tggtgattaa gtaa | 504 |

<210> SEQ ID NO 35
<211> LENGTH: 1548
<212> TYPE: DNA
<213> ORGANISM: Nitrosopumilus maritimus

<400> SEQUENCE: 35

| | |
|---|---|
| atgcactcgg aaaaacttga aaactataat aataaacaca aaacgtcgca gcagggaggt | 60 |
| ggtcaagatc gaataaaagc acaacatgat aaagggaaac tgacggcacg ggaacgcata | 120 |
| gatttactcc tggatgaggg tagttttact gaaatagacc cgatggttac gcatcattat | 180 |
| catgaatatg atatgcaaaa aagaagttc tttacggatg gtgttgtggg tggttatggc | 240 |
| aacgtcaatg gtcgccagat attcgttttt gcctatgatt tcacggtgtt aggtggcacg | 300 |
| ctcagtcaga tgggtgcaaa aaaaattacg aaactgatgg atcatgcggt gcgcacgggc | 360 |
| tgcccggtga taggcataat ggattcgggt ggtgcgcgca ttcaggaagg catcatgagt | 420 |
| ttagatggct ttgcggatat ttttatcat aaccagctgg ccagcggcgt ggtgccacag | 480 |
| attaccgcga gtattggtcc atcggcgggt gggagcgtat atagcccggc catgaccgac | 540 |
| tttgtcgtta tggtagaaaa ggcgggcagc atgtttgtga cgggtccaga tgtggttaag | 600 |
| accgtgttgg gtgaagaaat tagcatggat gatttaggtg gcgccatgac ccatggtagc | 660 |
| aaaagtggcg tggcgcattt tgtggcgcag aatgaatacg aatgcatgga ttacataaaa | 720 |
| aaactgatat cgtacatccc gcagaacaac tcggaagaac cgccgaaaat caaaactgat | 780 |
| gatgatccga atcgcctgga taacaacctt attaacgtga taccggaaaa cccgctgcaa | 840 |
| ccatatgata tgaaagaaat tataaactcg attgttgata accatgagtt ctttgaagtg | 900 |
| catgaactgt ttgcgccgaa cattgtcgtt ggttatgccc gcatggatgg tcaggttgtg | 960 |
| ggcatcattg cgaataaccc gatgcatctg gcgggcgcgt tagacattga tagcagcaac | 1020 |
| aaatcggcgc gtttcattcg cttctgcgat gcgtttaata ttcctattat aacgctggtt | 1080 |
| gatacccccgg gttacatgcc gggttcgaac caggaacaca atggtataat tcgccatggt | 1140 |
| agtaaattgc tttatgcgta ctgcgaagcg actgtgccgc gcattacctt agttattggc | 1200 |
| aaggcgtatg gtggggcgta cattgcgatg ggcagtaaga atttacggac ggacattaac | 1260 |
| tatgcgtggc cgacggcgcg ttgcgccgtt ctcggtggtg aagccgccgt taaaataatg | 1320 |
| aatcgcaaag atttggcgga cgcggataac ccagaagaat taaagaagaa attgattgat | 1380 |
| gagtttaccg aaaaattcga aaatccgtac gtggcggcga gccacggcac cgtggataac | 1440 |
| gttattgatc ctgcggaaac ccgcccaatg ttgattaaag cacttaaaat gttagcgaat | 1500 |
| aaacgcgaaa aacagttacc acgcaaacat ggcaacataa acctctaa | 1548 |

<210> SEQ ID NO 36
<211> LENGTH: 1488
<212> TYPE: DNA
<213> ORGANISM: Nitrosopumilus maritimus

<400> SEQUENCE: 36

```
atgatcgaga aagttttaat tgcgaatcgc ggcgaaattg cccttcgcgt tattcgcacc      60
tgcaacgcgc tgggtataaa gacggtggcg gtttactcgg atgaggatta caactcgctg     120
catgttaaga agccgatga atcgtatcac attggagaag cggccccagc gaaatcgtat     180
ttaaaccagg aaaaaatttt agaagtaatg ctaagctcgg gtgcggatgc cgttcatccg     240
ggttatggtt tcttatcgga aaacgatgac tttgcgcgcc tgtgcgaaaa aaacaaaatt     300
aacttcattg gtccgtcggc cgactccatg aacctctgcg gtgataagat ggaatgcaaa     360
gcggcgatgc tgaaagccca ggtgccgacc gttccaggca gtccgggcct ggttgatact     420
gcggaagaag cggaaaaaat tgcgaacgaa attggttatc cagttctttt gaaaagcgtg     480
tatggtggtg gcggtcgtgg catacgcctg gtgactacgg atcaggaact ccgggaaggt     540
tttgaaaccg ttacgtcgga atcgattgcc gccgttggca atcggcgat aattgtggaa     600
aaattcctcg aaaaaacccg ccacattgaa tatcagatgt gccgcgatca tcatggtaac     660
gccgttcacc tttttgagcg cgaatgctcg attcagcgcc gcaaccagaa actcattgaa     720
cagacgccat ccccagtggt tgatgaagcg aaacgggagg agattggtga actggtggtg     780
aaagcggcga agccgtcaa ctatacgaat ttaggtacgg cggaattttt acgcgcggat     840
aacggtgagt tttactttat tgagattaac gcgcgccttc aggttgaaca tccgataagt     900
gaaatggtga gcggcctgga ctttgttaaa ctgcaaattg atattgcgaa tggtgaaacc     960
ttaccgttca acagaaaga tctcaagatg aacggttatg cgattgaatg ccgcataaac    1020
gccgaagaca ccttttttgga ctttgcgcca agcacgggcc cagtgccgga tgttacaatt    1080
ccagcgggcc cgaacgtccg ctgcgacacg tatctctatc caggctgcac cgtttcgccg    1140
ttttacgata gcttgatggc gaaactttgc acctggggcc cgacctttga agaatcgcgc    1200
acgcgcatgt taacggcgct gaacgatatg tatgtgcagg gtgtggaaac cagcattccg    1260
ttatacaaaa ccattctcaa ttcggaagaa tacaaaaatg gtgaactcag cacggacttt    1320
ttgaaacgtt atgggatgat tgataaactc tcggaagact aaagaaaga aaaagaagac    1380
aagagtgaag ccgccttagc cgcggcaatt attcattcgg aatactttaa gaatcgcgtg    1440
cagaacgata atgcgtctag tgcgacgtgg aaaaacaaat tggactga                1488

<210> SEQ ID NO 37
<211> LENGTH: 513
<212> TYPE: DNA
<213> ORGANISM: Nitrosopumilus maritimus

<400> SEQUENCE: 37
atggactata agatcgccga tgtggaaaaa agctttgaag gcaaaattac ggaaaatctg      60
ggtaacaacg attatgtaat taagataaac gacaaagaac atcagttgaa aatattatct     120
atgaacgcga aggtatcga atttattctg gatcagcagt atcataaagc gaaatattta     180
gagacggcga cgaacgaaat gaacttagtt attgataacg tgccggtgac cctgaatatg     240
aacacgcact ttgacgaaat cgtgtacaaa aatagtgggg gtggtggggc gggtggtgcc     300
caggttgcgc ttaaaagtca gataccaggt aaagtggtaa gcattgcggt ggccgaaggt     360
gactcggtca agaaaggtga tgttgtgtgc acgctgaaa gcatgaagat gcaggtgggc     420
atcaaggcgc acaaagatgg tgaagtgaaa aaccttaaaa ttaaagaagg tgcgacggtc     480
gcgaagggg acgtgattgc ggatctggaa taa                                   513

<210> SEQ ID NO 38
```

```
<211> LENGTH: 1548
<212> TYPE: DNA
<213> ORGANISM: Cenarchaeum symbiosum

<400> SEQUENCE: 38
atgcactctg agaaattgga taaacgtagc gcgaacaacc gctcggcgtt aatgggtggc      60
ggtgaagcgc gaatcgaagc gcagcatggc aaaggcaaat taaccgcgcg cgaacgcatt     120
gcgatcatgt tagatgaagg tagttttacg gaagtggata gcctggccac ccatcattat     180
catgaatttg atatgcagaa aaagaaattc tttggtgatg gtgtagttgg cggttatggc     240
cgcattgatg gccgcaaagt ttttgttttc gcctatgatt ttaccgtgat gggcggcacg     300
ttaagtcaga tgggcgcaaa gaaaatcact aaactgatgg atcacgcagt ccgcactggc     360
tgcccggtga ttggtgttat ggactccggt ggtgcgagaa tccaggaagg tattatgagt     420
ttagatggtt ttgccgatat tttctatcat aaccagttgg catcgggtgt ggtgccgcag     480
atcactgcta gtattggtcc aagcgccggt ggctcggtgt atagcccggc gatgacggat     540
tttgtgatta tggttgagaa aagcgcgacc atgttcgtta cgggtccgga tgtggtgcag     600
acggttttag cgaatcgat cagctttgaa gatttaggcg gcgcgatgac ccatggttcg      660
aaaagtggcg tggcgcattt tgttgcaaaa acgaatatg actgcatgga ttacatccgc      720
aaactgttaa gctttatccc gcagaacaac cgcgaagaac caccagtcgt caaaacagcg     780
gatgatccgg atcgcttaga tcatggcttg atcgggatga tcccggaaaa cccactgcaa     840
acctatgata tgaagaatgt gattcatagc attgtggatg atcgtacgtt cttggaggtg     900
catgagaact ttgcgacgaa tatcattgtc ggtttcggcc ggttcaacgg ccgcgcggca     960
gggattgtgg cgaaccagcc agcgagtttg gccggcgcct agatattga tgcctcgagt    1020 aaagcggcac gcttcatccg gttctgcgat gccttcaaca ttccagtgat caccttggta    1080 gatacccccag gttatatgcc gggctcggat caggaacatg gcggtattat ccggcatggc    1140 agtaaaattat tatttgcata ttgcgaagcg accatcccga aaattacgct ggtcattggc    1200
aaagcgtatg gtggtgcgta tattgcgatg gcgagtaaaa acctggggac ggacatcaac    1260
tacgcctggc ccaccgcgcg ttgcgcggtg ttaggcgcag aggctgcggt caaaattatg    1320
aacaggaaag atctggctgc cgcatcggat ccggaaggtt aaagaaaga actgattggc    1380 aactttgcgg agaaattcga taacccatat gtagcggcct cgcatggtac tgtggatgcg    1440
gtcattgatc cggcagaaac ccgtccgatg ctgattaaag ccttagaaat gttaagctcg    1500
aaacgtgaag gccgtatatc gcgaaaacat gggaacatta acctctaa                  1548

<210> SEQ ID NO 39
<211> LENGTH: 1431
<212> TYPE: DNA
<213> ORGANISM: Cenarchaeum symbiosum

<400> SEQUENCE: 39
atgatccgca cctgccgcgc cttaggcttg ggtagcgtgg cagtctattc ggatgaagat      60
tacaacgccc tgcatgttaa gaaagcatcg gaatcctatc atattggcgg tgccgcgcca     120
gctgagtcgt atttaaacca gcagcgcatc attgaagccg ccttatcgtc gggcgccgac     180
gcgatacatc cagggtatgg cttttttaagc gaaaacggcg aatttgcggc cctgtgcgag     240
aaaaaccgca ttaactttat cggccccctcg gccaagagca tgaacctgtg cggcgataaa     300
atggaatgca aagcggcaat gttaaaagcg gacgtgccga cggtaccggg cagtccaggc     360
cttgtgggct ccgcggatga agccgcgggc attgcctcca aaattggcta ccccgtactg     420
```

```
ttaaaaagcg tttttggcgg tggcggccgt ggcatccgtc tggctgagga tgaaggcggt      480
ttacgcggcg ggtacgactc tgcgacagca gagagcattg ccgctgtcgg caaaagcgcg      540
attctggtgg agaaattctt aaaacgcacc cgtcacattg agtatcagat ggcccgtgat      600
aaacatggga acgcagttca tattttcgag cgcgaatgca gcattcagcg acgaaaccag      660
aaattaatcg aacagacccc gagcccgtc atggatgaag acaccgtaa acgcattggc       720 gacctggtgg ttaaagcagc ggaagcggtt gattacacca acctgggac ggcagaattt      780 cttcgtgccg actcgggcga attttacttc attgaaatca cgcccgcct gcaagtggaa      840 catccgatta cggaactggt tagcggtctg atctcgtta aactgcaaat tgatattgca      900
aacggcgaac cgctgccgtt caaacagaat gatctgcgca tgaacggcta tgcgattgaa      960
tgccgcatta acgcagagga cacgtttttg gattttgccc caagcgttgg tccagttcca     1020
gatgttaaac tgccttcggg tccaggcgtg cggtgcgata cttatctgta tcccgggtgc     1080
actgttagcc cattctacga ctctctgatg gcaaaactgt gcacctgggg tgccactttc     1140
gaagaatccc gcttacgcat gctgggcgcg ttaggcgatt tttatgtgga gggggtggaa     1200
acttcgatcc cgttatataa aacgattatg gcatcggatg aatataagaa cggcgaatta     1260
tcgacggatt ttttatcgcg ctataatatc attgatcgcc tggataagga tatcaagaaa     1320
gaacgcgcgg caaacggcga agctgccgca gcggcgcga ttatgcatag cgaatttctc     1380
agcagtcgcg ccggcggtaa cagtgggacc gcatggaaag ggggcgcctg a              1431

<210> SEQ ID NO 40
<211> LENGTH: 510
<212> TYPE: DNA
<213> ORGANISM: Cenarchaeum symbiosum

<400> SEQUENCE: 40
atgaaatatg aaattgagga tgccggctcg ttcgaaggcc gcatggccgc aaacccgggg       60
aacggggagt atactctgga aattaacggg aaggaagtgc ggttaaaagt cattagcatg      120
ggcccgcgtg gtatggaatt tctgctggat caaaaatatc atagcgcacg atatctggaa      180
cgcagtactt cgggcataga tatgattatc gatgggacgc cggttcgcgc aggcatgcac      240
gcagacctag ataaaattgt ttataagaat agcggcggcg tgggggcgg cggcccgggc      300 atagcgctgc ggagtcagat tcctggcaaa gttgtctccc ttgaagtctc ggaaggtgat      360
gaaattaaaa aaggcgatcc ggtggccgtt ttggaatcca tgaaaatgca ggtggcggtt      420
aaagcccata aggatggcac ggtcaagtcg gttagtatta agaaggcgg cagtgttgca      480 aaaaacgatg ttatcgcgga aattgaataa                                        510

<210> SEQ ID NO 41
<211> LENGTH: 1551
<212> TYPE: DNA
<213> ORGANISM: Halobacterium sp.

<400> SEQUENCE: 41
atgaccatgg aggaacgcat tgaagatttg cgcgaacaga ccgaacgcgc actgctgggc       60
ggcggagaag ctcgcattga aagtcaacat gaaaaaggta attaaccggc tcgcgaacgc      120
attgattatt ttctggatga tggcacgttt aacgaattgg accagttacg cacgcatcgc      180
agtacgaact ttgatatgga tgagacgaaa ctgccaggcg atggcgtggt gaccggctat      240
ggcgatgtga acggccgtac gacgtttgtt tttgcccatg attttaccgt gtttggtggt      300
```

```
tcgctggggg aagtttttgc ggaaaaggtt acgaaggtta tggaccgcgc gatggaagtg      360
ggcgcgccag tggttggtct gaacgatagc gcgggcgcac gcattcagga aggcgtggat      420
gcgttaggcg gttttgcgga aatttttacc cgcaacgaaa aagcctcggg cgtggtgcca      480
cagattagcg cgattatggg tccgtgtgcg ggcggggccg tgtatagccc ggcgattacg      540
gactttaccg tgatggttaa agatacgtcg catatgttta ttaccggtcc ggatgtgatt      600
gaaacggtta ccggcgaaca ggtgggcttt gaagaactgg gcggcgcgac cacccatgcc      660
gccgagagcg gtgtggcaca ctttgcctgc gattcggaag aagcggcctt agataacatt      720
aaacgcttac tgagctacct gccacagaac aacgtggaag atccgcctcg tgtggaacca      780
tatgatgatc cagaacgccg cgatgatgcc ctggagacca ttgtgccgga tgaacctcgt      840
aaaccatatg atatgaccga tgtggtggat tcggtggtgg atgaacagag cttctttgaa      900
gttcaggcgg attatgcgaa aaacattgtg gtgggttttg cgcggctgga tggccgtagc      960
gtgggcattg tggcgaacca gccacgcgtt aacgccggca ccctggatat tgatgcctcc     1020
gaaaaaggct cgcgttttgt tcgttttttgt gatagcttta acgtgccgat tttaacgctg     1080
gttgatgttc caggtttttt accgggcacc gatcaagaac atggcggcat tattcgtcat     1140
ggcgcgaaac tgttatatgc gttttcggaa gcgtcggttc cattaatgac ggtgattacg     1200
cgtaaagcct atggcggcgc ctatgatgtt atggcgtcga acatattgg cgcggatgtg     1260 aactatgcgt ggccgaccgc cgaaattgcc gttatgggtc cgaaaggcgc ggttaacgtg     1320
ctgtattccg acgagctgga ggcggccgat gataccgcgg cgcgtcgcca agaactgatt     1380
gatgaatatc gcgaagaatt tgccaaccct tatacgccg ccgatcgcgg ctatctggat     1440
gccgtgattg aaccgaccga aacccggccg cgtctgattg atgatctgga tatgttggcg     1500
tcgaaacgcg aagaaacgcc ggataaaaag catggcaaca ttccgctctg a             1551
```

<210> SEQ ID NO 42
<211> LENGTH: 1776
<212> TYPE: DNA
<213> ORGANISM: Halobacterium sp.

<400> SEQUENCE: 42

```
atgatcatga aggtacggat tggcgtgggg gcgacggatg cggaagccag tgcggtggcg       60
gcagcactgg cggcacatgt gagtgatgat gtcgcggttt acttaggcga tgccgatgaa      120
ccggcagcag tgcatgaacc agaaccaccc gccgatgatt cggccgatgc cgatgatctg      180
ggtccgaccg aacgcgaaga agttctgcgc gaagaaattg cggatattct ggatggcggc      240
ccagaaaaat ataagcagcg cttaccagaa caggataagt tatttgtgcg cgatcgcctg      300
gccctgtggt ttggcgatga tgatgatggc gatgatgacc tgctgtttga agatggcaga      360
tttgcgcact tgatggctg gcacccaaac tcgccagacg tggatgaagc agatgatggc      420
acacgtgtgc cggccgatgg tctgattacg ggcgcggcgg actttgatgg ccgtgatctg      480
cattttatgg ccaacgattt taccgttaag gcgggtagca tggccgaacg cggcgtggaa      540
aaatttctgc gcatgcagca gcgcgcgctg aaaaccggca agccagtttt gtatttaatg      600
gatagtagcg gtggtcgcat tgatcagcag agcggttttt ttgcgaaccg cgagggcatt      660
ggcaagtatt attttaatca gtcgtctg agtggccgcg tgccacagat ttgcgttta       720 tatggcccat gtattgccgg tgcagcgtat acgccggttt ttgcggattt tacgattatg      780
gtggaaggta tgagtgcgat ggccattgcc tcgccacgta tggttgaaat ggttaccggc      840
gaacagattg aaatgcagga tctgggcggc ccgcaggttc atgccgaaca gagtggctcg      900
```

-continued

```
gccgatttag tggcccgcga tgaagatcat gcccgcgaat tagtggcgga tctggttcag      960
tatctgccag ataactcgga tgaaaagccg ccatcccagc cggcgaaacc gcctgcgaaa     1020
ccgccaaaag gcattgatgg cttaattccg gaagcaccga accgcgccta tgatatgcat     1080
gatctgattg gccgcgttgt ggaccaggat agtttctttg aattacgtcc agaatatggg     1140
gccgaaattt taacgggtta tgcgcgcatt gatggccgta cggtgggcat tgtggcgaac     1200
cagccagccc agcgtgccgg cgccattttt ccggatgccg ccgaaaaagc gcggaatttt     1260
gtgtggaaaa gtgatgccta acattccg ttgttatatc tgtgtgatac gccaggcttt      1320
atgccgggta gcagtgtgga aaaggatgcc attttagaaa agggcaaaaa aatgatttat     1380
gccacctcgg aagccaccgt gccgaaacag agtgtggttg ttcgtaaagc ctatggcgcc     1440
ggcatttatg cgatgagtgg tccagcctat gatccagaaa gtaccattgc actgcctagt     1500
ggcgaaattg gtattatggg tccagaggcc gcgattaacg ccgtgtatgc gaacaaactg     1560
gatgccattg atgatccaga agaacgcaag cagcgcgaac aggaactgcg cgaagcgtat     1620
cgcgaagata ttgatgccca tcgtatggcc agtgaaacgg tgattgatga aattgttccg     1680
ccaagtgagc tgcgtacaga gctgagcaac cgttttttcgt tttatgaaga tgttgaaaag    1740
gatcgcccga gcaaaaagca tggcaccatt ctttga                              1776
```

```
<210> SEQ ID NO 43
<211> LENGTH: 1833
<212> TYPE: DNA
<213> ORGANISM: Halobacterium sp.

<400> SEQUENCE: 43
```

```
atgtttgaaa aagtactggt cgccaaccgc ggcgaaattg cggttcgagt tatgcgtgcg       60
tgtgatgatc tgggtgtgga tacggtggct gtttattcgg acgccgatgc gcatgccgga     120
catgttcgtt atgccgatga agcgtataac gtgggtccgg cgcgcgcggc ggatagttac     180
ctggatcatg atgccattat tgatgcggcc acgcgtgccg gtgccgatgc cattcatcca     240
ggctatggct ttctggccga aaacgccgaa tttgcgggca agtggaaga taccgatggc      300 gtgacgtggg tgggcccgag tgcggatagc atgccccagc tgggcaaaaa aacctcggcc    360
cgtaaaacga tgcgtgaagc cgatgttcca attgtgccag ggaccaccga tccagttgaa     420
agtgtggccg atattcatga atttggcgag agcatggct atccaattgc tattaaagcc      480
gaaggcggag gggcggccg tggcatgaaa attgttcgct cggccgatga agccgaggat      540
caattagaaa gcgcggaacg agaaggggaa gcgtattttg ataacgcgaa cgtgtactta     600
gaacgctatt tggaaaaccc acgccatatt gaagtgcaga ttctcgcgga tcatcatggt     660
aacgtgcgtc atctgggcga acgtgattgt agcttacagc gccgccatca gaaggtgatt     720
gaggagggcc cgtcgccagc gctgacggat gaacttcgcg aagaaattgg tacggcggcc    780
cgtcgaggag ccgatgccgc gggctattat aacgcaggca cctttgaatt tctggtggag    840
gaggataccg aacgtgaacc aggggatctg ctgggtccgg aaacggaatt ttatttttctg   900 gaggttaaca cccgtatcca ggtggaacat accgtgacgg aagcgctgac gggcgtggat    960
atcgttaaat ggcagctgaa aattgcaagt gatgatgaac tgacctttga acaggatgat     1020
gttgcattag atggccatgc cgtggaatat cgcattaacg cggaaaacgc ggccgatgat     1080
tttgcgccag ccacgggcgg cgaattagaa acctatgatc cgccgggcgg cattggcgtt    1140
cgtgtggatg atggcctgcg tcagggcgat gacctggtga ccgattatga tagcatggtg    1200
```

```
gcgaaactga ttgttcatgg ctcggatcgc gaagaatgtt tagcgcgtag tcgtcgcgcg   1260
ctggccgaat atgatattga aggcattccg acgattattc cgtttcaccg tttaatgtta   1320
accgatgatg cgtttgtggg tggcacgcat acgacgaaat acctggatcg cgatattgaa   1380
gaaagccgta ttagtgatgc ccaggcgaaa tggggtacga cgacggccag tgaaagtagt   1440
gccgacgaaa acgttgttga acgtgacttt acggttgagg tgaacggcaa acgttttgaa   1500
gtgaacttag aagaacgtgg tgcggcgcag tttgctgccc cagaggcgga taccggtggt   1560
ggtggtccgc cggaaccagc gggtggagca gatgatggtg aaacggtggt tgaaggtgat   1620
ggcgaaacgg tgacggcgga aatgcagggt acgattttag atgttgccgt tagtgaaggc   1680
gacgcggtgg atgcaggaga tgttttagtc gtttagagg cgatgaagat ggaaaacgat   1740
gtggttgcga gtcatggggg cacggtgacg caggtggccg tgtcggaaga tgattcggtg   1800
gatatggatg atgtttagt tgtgattgac tga                                1833

<210> SEQ ID NO 44
<211> LENGTH: 3129
<212> TYPE: DNA
<213> ORGANISM: Halobacterium sp.

<400> SEQUENCE: 44
atgaccgaag attcgcgtac gatattactg attggttcgg gcccaattca gattggccag     60
gcagcggaat ttgattatag cggcgcgcag gcttgtcgcg cgctgcaaga agaaggcgcg    120
cgtgtcgttc tggttaacag taaccctgcg accattatga ccgatccaga aatggccgat    180
gcggtgtata ttgaaccaat tgaaccagat gccattgccg aagtgattga acaggaagat    240
ccagatggcg tgattgccgg tttaggcggc cagaccggct taaacgtgac ggcagcgtta    300
gccgaacagg gcgtgctgga tgagcatgat gtggatgtta tgggtacgcc gttggatacc    360
atttatgcga ccgaagatcg cgatttattt cgccagcgca tggcggatct gggccagccg    420
gttccggcca gcacgaccat tgcgctgggc gatgatgaaa cggcaacgga tattgatgaa    480
ggtgcgttac gggaacgcgt ggatgatgcg gtggaagcgg tgggcggttt accggttatt    540
gcgcgtacga cgtatacgtt aggcggctcg ggcagtgggg tggtgcatga ttttgaagcg    600
ctggttgatc gtgttcgcac gggcttacgt ctgagccgta acgccgaagt tttagtgacg    660
gaaagtatta ccggttgggt ggagttagaa tatgaagtta tgcgtgatgc cggcgatagt    720
tgcattattg tgtgcaacat ggaaaacatt gatccgatgg gcattcatac cggcgaaagt    780
acggtggtga cgccatcgca gattattccg gatgatggcc atcaggaaat gcgcaacgcc    840
gccgtggcgg tgattcgcga attgggcatt cagggcggct gcaacattca gtttgcgtgg    900
cgcgatgatg cacgccagg cggcgaatat cgtgtggtgg aagtgaaccc gcgcgtgagc    960
cgtagtagcg cgttagcgag caaagcgacc ggctatccaa ttgcgcgtgt gaccgcgaaa   1020
gtggcgctgg gcaaacgcct gcatgaaatt gataacgaaa ttaccggcca gaccacggcg   1080
gcctttgaac cggccattga ttatgttgtt acgaaggttc cacgttggcc taacgataaa   1140
tttccagaag ttgattttga attaagcacg gcgatgaaaa gtacgggtga agcgatggcc   1200
attggtcgca cctttgaaga atcgttatta aaagcgttac gcagttcgga atatgacccg   1260
tcggtggatt gggcgaccgt gtcggatgat gagctggccg ccgattatct gcaacgcccg   1320
agtccagatc gtccatatgc cgtgtttgaa gcgtttgaac gtggttttac agtgggcgat   1380
gttaacgatc atacgggctt tcgtgaatgg tacttacagc gttttcagaa tgtggcagcg   1440
gccagtgcgg cagcaagtga aggtgatgtt gcgacgccgg cagcgctggg ttatacgaat   1500
```

```
agtgcggtgg cggcgttagc gagcgacggt ggagatgttg ccgtggatga tgttgcggcg      1560
actgccccag aacgtacgtt taaacaggtg gatacctgtg cgggcgaatt tgcggccagc      1620
acgccgtatt attatagcgc gcgcagccag ggaagcacgg gatcggatgt tcgtgccgat      1680
cgtgatgccc attcggttgt gattgtgggt ggcggcccaa ttcgcattgg tcagggcgtt      1740
gaatttgatt attgtacggt tcatgccgtt cgcgcgctgc gcgaagcggg cattgatgcc      1800
catgttgtta acaacaaccc ggaaacggtt agcacggatt atgataccag tgatggttta      1860
ttttttgaac cgattacggc ggaagaagtg gcggatgtgg ttgaagcgac gaacgccgat      1920
ggcgttatgg ttcagtttgg cggccagacc tcggttgatg ttggcgcgcc actggaggcc      1980
gaattagaac gccgcggcct ggattgtgaa attatgggta cggatgttga tgcgatggac      2040
ctggcggaag atcgcgatcg ctttaatcgt ttactggatg aacgcgatat ttcgcagcca      2100
gatggtggtt cagcgacctc cgttgcgggc gcgttagaac tggccgccga agtgggatac      2160
ccggttttgg tccgcccgtc gtatgttctg ggaggtcgcg cgatggaaat tgttcatgat      2220
gatgatgaac tgcgccgcta tgtggaagaa gccgtgcgtg tgtcgccaga aaaaccggtc      2280
ctggtggatg aatttctggc cgatgccgtg gaactggatg ttgatgccgt gtcggatggc      2340
gaagatgttt tagttggcgg cgttatggaa catattgaat cggcggggt gcatagtggt      2400 gatagcgcgt gcgttatccc gcctcggggt ctgggcgatg atattctggc gcgtgtccgt      2460
gaagtgacca ccgaaattgc gcgtgcgtta gatacggttg gattattaaa cgtgcaactg      2520
gccgtgcagg atggcgaggt ttatgtgctg gaggcgaacc cgcgtagtag ccgcaccgtc      2580
ccgtttgtga gcaaagcgac cggcgtgccg attgcgaaac tggcggcgaa agttatggcc      2640
ggcgaaagct tagccgatct ggatgcatcg gaaggcgtac cagaacagta ttcggtgaag      2700
gaagttgttt tgccgtttga tcgtctcccg ggtagcgacc cgcgcctggg cccggaaatg      2760
aaaagtacgg gcgaagttat gggcaccgcc tcggacccgg gtatggccta ttggaaagcc      2820
caggttgcgg cgagtaacgc accagtacca ggtagcacgg cggtggtgga tctcttagtg      2880
gaaggtctcg gcgaacgttt tgaagtggtt acggtgaagg atgttccggc ggcgattcga      2940
cgcggcgaag tggaatttct ggtgtcggat gatcgcgatg cgttaaccgc ggctgtggaa      3000
gccgaaattc cgtatgtgag tacggttgcg gcagcggaag cgatgcgaga aggtattgcg      3060
gcggccgatg gggcacgaga agcaatgccg gtggccgatc gtccggtgaa tgatgaaacg      3120
tggggatga                                                             3129
```

<210> SEQ ID NO 45
<211> LENGTH: 1437
<212> TYPE: DNA
<213> ORGANISM: Halobacterium sp.

<400> SEQUENCE: 45

```
atggcccgcg agtttacgct tcccgatgtg ggagaaggcg tggcggaagg cgagctggtt       60
cgttggctgg tggatgaagg cgataccgtg accgaagacc agccggtggc ggaagtggag      120
acggataagg cacaggtgga agttccagcg ccggtggatg gtacggtgca ggagctgcat      180
tgggcggagg gcgatgttgt tccggtgggc gatctgtttg ttacgtttga tgtcgatggc      240
gaagcgagcg ccaccgcgga tgatggtgat gagagtggtg atgaagccgc gagcgcgacc      300
agtgaagcca gtggtcgtac gtttgcgccg ccgagtgtcc gtacgctggc ccgtgaatta      360
ggcgtggatc tggatagtgt ggaaggtagt ggtccgagcg gtcgtattac cgatggcgat      420
```

```
gttcgtgccg ccgcggaagg tggtgaagat accacggaac cggccaccga agccacgagt    480
gcgacggagc gtgtggatga agatgatacc gcggcgagtg caggcagtca agaaccggcg    540
ggccgtgaaa aaacgcttgc ggcaccagcg acccgtggtg tggcccgaga attaggcgtg    600
gatattaacg atgttccggc ggtggagcag cgtgatggtg aagcgtttgt gaccgcggaa    660
gcggtgcagg cgtatgcaga aggtggtcag gcagcacagg gtgaagcggg tggtgcagcc    720
acccgtgaat ttgtggccgg cggtgaaacc accgaaccat atcgtggcat cgccgcacc     780 attggcgaac agatggccga agcaaatat acggcgcctc atgtgaccca tcatgatacc     840
gccgtgattg attcgctggt tgaaacgcga agcaaattaa aggcgcgcgc cgaagccgaa    900
gatgttaaat taacgtatat gccgtttgtt atgaaagcgg tggtggcggc gctgaaagaa    960
tttccagttt tgaacagtga actgcgcgaa gatgatgaag aaattgcgct gaaacaggac   1020
tataacattg gcgttgcggt ggcgaccgat gccggtttaa tggttccggt ggtggaacat   1080
gtggatcaga aaagcatgct cgaaattagt acgaaatga acgatctggt ggaacaggcc   1140
cgcgaacgca gcattgcgcc agcggatatg gatggcggaa cttttacgat tacgaacttt   1200
ggcgcgattg gcggcgaata tgcgaccccg attattaact atccagaaac ggcgatttta   1260
ggtttaggcg cgattgatga acgcccggtg gccgaagatg gcgatgttcg tgcggcccag   1320
acgttaccgt tgagcttaag cattgatcat cgcgtgattg atggcgcgga agccgcgcag   1380
tttacgaacc gcgttatgga atacttaaca gatccagagc ttcttcttct ggaataa      1437

<210> SEQ ID NO 46
<211> LENGTH: 1170
<212> TYPE: DNA
<213> ORGANISM: Methylcoccus capsulatus

<400> SEQUENCE: 46
atggcaaggc ccttaatcca gctggctctg gacagttggg atcgggatcg tacgttagag     60
ttagcgcgcg tgacggcccc ttacgtggat attttgaaa ttggcacgcc atgtattaag    120
tataacggca ttgagattgt gcgcgaatta aaacgccgtc atccggaccg tttagtgctg    180 gtggattta aaaccatgga cgcgggcgag tatgaagcgg ccccgttcta cgcggcgggc    240
gctgatattt gcaccgtttt aggtgtttcg ggtccggcca ccattgcggg tgtggtcaag    300
gccgcgcagg cccataatgc ggaggtgcag gttgacctga ttaacgttcc ggataaagct    360
gcgtgcgccc gcgaagccgc gcgtttaggc gcgcagatta ttggggttca taccgggctg    420
gacgcgcagg cgcaggggca gacgccgttt cggacttag agagcattgc gcgcctgaaa    480
ctgccggtga gaatttctgt tgctggtggt attaaccaga acaccgcgtc tcgtgtggcg    540
aaagccggtg cggatattgt ggtggtgggg gccgccattt atggcgcccc atgtccagcg    600
accgccgcgc gcacgatccg cgaactgctg gagggtgctc accataaatt tattgttagt    660
aaaattggcg gcgttcttgc ggcgactgat aaaagctatg aagcccggct gaccgggtta    720
ttagagcggg cgcgccggat ctttgtggcg ggcgcgggtc ggagtggcct ggtgggccgc    780
ttctttgcga tgcgtctgat gcatggcggc taccaggctt acatcgttgg cgaaattgtt    840
acgccaagca ttcggcaagg cgacctcctg attgttatca gtgggtcggg cgagaccgag    900
accatgattg cttatgcgaa aaaggcgaaa gagcagggtg cgagcattgc cctgattacc    960
acccgcgata aaagtacgat tggggatatg gcagatgttg ttttttcgtat tggcactcca   1020 gaacagtatg gcaaagttgt ggggatgccg atgggcacca cctttgaact gagtaccctg   1080
gttctgttag aggcgacgat cagtcatatt attcacacca aaaaaattcc agaagaacag   1140
```

```
atgcgtaccc gccatgcgaa tctggagtaa                                       1170
```

<210> SEQ ID NO 47
<211> LENGTH: 648
<212> TYPE: DNA
<213> ORGANISM: Methylcoccus capsulatus

<400> SEQUENCE: 47

```
atggcaaggc ccttgatcca gttagcgctg gatacgctgg atattccgca gaccctgaaa      60
ttagcaagct taaccgcccc atacgtggac attttttgaga ttggcacccc aagcattaaa   120
cataacggca ttgcgctggt taaagaattt aagaagcgct ttccaaacaa actgttactg    180
gtggatttaa agaccatgga tgcggggag tatgaggcga ccccattttt tgcggcgggc     240
gcggatatta ccaccgtgtt aggcgtggca ggactggcga ccattaaagg cgtgattaac    300
gcggcgaaca acataacgc ggaagtgcag gtggatctga ttaacgtgcc agataaagcg     360
gcgtgcgcgc gggaaaagtgc gaaagcgggc gcgcagattg tgggcattca taccggctta  420
gatgcgcagg cggcgggcca gaccccattt gcggatttac aggcgattgc gaaattaggc   480
ttaccagtgc gcattagtgt ggcggcggc attaaagcga gtaccgcgca acaggtggtg     540
aagaccgggg cgaacattat tgtggtggga gcggcgattt atggcgcggc gagtccagcg   600
gacgcggccc gcgagattta tgagcaggtg gtggcggcta gtgcgtaa                 648
```

<210> SEQ ID NO 48
<211> LENGTH: 534
<212> TYPE: DNA
<213> ORGANISM: Methylcoccus capsulatus

<400> SEQUENCE: 48

```
atgcaccaga agctgattat agataagatt agtggcattt tagcggcgac cgacgcgggc    60
tacgacgcaa agctgactgc gatgttagat caggcgagtc gcattttgt ggccggtgcg    120
ggccgttcgg gtctggtggc gaaatttttt gcgatgcgct taatgcatgg cggctacgat  180
gtgtttgtgg tgggcgagat tgtgaccccca agcattcgca aggcgatttt gctgattgtt  240
attagtggca gtggggagac cgagaccatg ttagcgttta ccaagaaggc gaaagaacag   300
ggcgcgagta ttgcgttaat tagtacccgc gatagcagta gtttaggcga tttagcggat  360
agtgtgtttc gcattggcag tcccgaatta tttggaaagg tggtgggcat gccaatgggc  420
accgtgtttg aattaagtac cttattattt ttagaagcga ccatttcaca tattattcat  480
gaaaagggca ttccagagga ggagatgagg actcggcatg cgaacctgga gtaa         534
```

<210> SEQ ID NO 49
<211> LENGTH: 1221
<212> TYPE: DNA
<213> ORGANISM: Mycobacterium gastri

<400> SEQUENCE: 49

```
atgaaattac aagttgcgat tgatctgctg agtaccgagg cggcgttaga actggcgggc    60
aaagtcgcgg aatatgttga tattattgag ctgggcaccc cactgattga agcggaaggc   120
ctgagcgtta ttaccgcggt taaaaaagct catccggata aaattgtttt tgcggatatg   180
aaaaccatgg atgcgggcga attagaggcg atattgcct ttaaagcggg cgctgatctg    240
gttacggttt taggcagcgc ggatgatagt accattgccg ggcggttaa agcggcgcag   300
gctcataaca aaggcgttgt tgttgatctg attggcattg aagataaagc gacccgggca   360
```

-continued

```
caggaggtcc gcgcgctggg ggcgaaattt gttgaaatgc atgctgggct ggatgaacag    420
gcgaaaccag gctttgatct gaacgggctg ttagcggcgg gcgaaaaagc tcgtgtcccg    480
tttagtgtgg cgggaggcgt gaaggtcgcc accattccag cagttcagaa agcgggtgca    540
gaggttgcgg ttgcgggagg tgcgatttat ggggcagcgg atccggcggc ggcggcaaaa    600
gagctgcgtg cggcaattgc gatgacgcaa gcggcagagg cggatggtgc ggtgaaagtt    660
gttggagatg atattaccaa caacctcagt cttgtccgtg atgaagttgc cgataccgcc    720
gccaaggttg atccggaaca ggtggctgtt ttagctcgcc aaattgttca gcccggacgt    780
gtctttgtgg ccggcgcggg gcgcagtggt ttagttctgc gcatggcggc gatgcgtctg    840
atgcattttg gcttaaccgt gcatgttgcc ggcgatacca ccaccccggc aatttctgcg    900
ggcgacctgc tgctggtggc tagtggcagc ggcaccacca gtggggtggt taaaagtgcg    960
gaaacggcga aaaagcgggg tgcacgtatt gcggcgttta ccaccaatcc ggactcaccg   1020
ctggcggggc tggcggatgc ggtggtgatt attccagcgg cccagaaaac cgaccatggc   1080
agccatatca gccgtcagta tgcgggatcc ctctttgaac aggtgctgtt tgttgttacc   1140
gaggcggtgt ttcagagcct gtgggaccat accgaagttg aagcggagga gttatggacg   1200
cgccatgcga acttagaatg a                                             1221
```

<210> SEQ ID NO 50
<211> LENGTH: 406
<212> TYPE: PRT
<213> ORGANISM: Mycobacterium gastri

<400> SEQUENCE: 50

```
Met Lys Leu Gln Val Ala Ile Asp Leu Leu Ser Thr Glu Ala Ala Leu
1               5                   10                  15

Glu Leu Ala Gly Lys Val Ala Glu Tyr Val Asp Ile Ile Glu Leu Gly
            20                  25                  30

Thr Pro Leu Ile Glu Ala Glu Gly Leu Ser Val Ile Thr Ala Val Lys
        35                  40                  45

Lys Ala His Pro Asp Lys Ile Val Phe Ala Asp Met Lys Thr Met Asp
    50                  55                  60

Ala Gly Glu Leu Glu Ala Asp Ile Ala Phe Lys Ala Gly Ala Asp Leu
65                  70                  75                  80

Val Thr Val Leu Gly Ser Ala Asp Asp Ser Thr Ile Ala Gly Ala Val
                85                  90                  95

Lys Ala Ala Gln Ala His Asn Lys Gly Val Val Asp Leu Ile Gly
            100                 105                 110

Ile Glu Asp Lys Ala Thr Arg Ala Gln Glu Val Arg Ala Leu Gly Ala
        115                 120                 125

Lys Phe Val Glu Met His Ala Gly Leu Asp Glu Gln Ala Lys Pro Gly
    130                 135                 140

Phe Asp Leu Asn Gly Leu Leu Ala Ala Gly Glu Lys Ala Arg Val Pro
145                 150                 155                 160

Phe Ser Val Ala Gly Gly Val Lys Val Ala Thr Ile Pro Ala Val Gln
                165                 170                 175

Lys Ala Gly Ala Glu Val Ala Val Ala Gly Gly Ala Ile Tyr Gly Ala
            180                 185                 190

Ala Asp Pro Ala Ala Ala Ala Lys Glu Leu Arg Ala Ala Ile Ala Met
        195                 200                 205

Thr Gln Ala Ala Glu Ala Asp Gly Ala Val Lys Val Val Gly Asp Asp
    210                 215                 220
```

```
Ile Thr Asn Asn Leu Ser Leu Val Arg Asp Glu Val Ala Asp Thr Ala
225                 230                 235                 240

Ala Lys Val Asp Pro Glu Gln Val Ala Val Leu Ala Arg Gln Ile Val
            245                 250                 255

Gln Pro Gly Arg Val Phe Val Ala Gly Ala Gly Arg Ser Gly Leu Val
        260                 265                 270

Leu Arg Met Ala Ala Met Arg Leu Met His Phe Gly Leu Thr Val His
    275                 280                 285

Val Ala Gly Asp Thr Thr Pro Ala Ile Ser Ala Gly Asp Leu Leu
290                 295                 300

Leu Val Ala Ser Gly Ser Gly Thr Thr Ser Gly Val Val Lys Ser Ala
305                 310                 315                 320

Glu Thr Ala Lys Lys Ala Gly Ala Arg Ile Ala Ala Phe Thr Thr Asn
                325                 330                 335

Pro Asp Ser Pro Leu Ala Gly Leu Ala Asp Ala Val Val Ile Ile Pro
            340                 345                 350

Ala Ala Gln Lys Thr Asp His Gly Ser His Ile Ser Arg Gln Tyr Ala
        355                 360                 365

Gly Ser Leu Phe Glu Gln Val Leu Phe Val Val Thr Glu Ala Val Phe
    370                 375                 380

Gln Ser Leu Trp Asp His Thr Glu Val Glu Ala Glu Glu Leu Trp Thr
385                 390                 395                 400

Arg His Ala Asn Leu Glu
                405
```

<210> SEQ ID NO 51
<211> LENGTH: 1020
<212> TYPE: DNA
<213> ORGANISM: Synechococcus elongatus

<400> SEQUENCE: 51

```
atgaccattc gagttgcgat caatggcttt ggccgtattg gccggaattt tctccgttgc      60
tggtttggac ggcagaacac cgatcttgag gttgtggcca ttaacaacac ctcggatgca     120
cggacggctg ctcacctgct ggagtacgac tctgttctcg gccggttcaa cgccgacatc     180
agctacgacg aaaattcgat caccgtcaac ggcaagacga tgaaaatcgt ctgcgatcgc     240
aaccccctca acctgccttg aaagagtgg gatatcgatc tcgtcattga atctacaggt     300
gtgttcgtca ccgctgaagg cgcatccaag cacatccaag ccggggccaa gaaagttctg     360
atcacggctc tggtaaaggc gaaggtgtc ggcacctacg tcatcggtgt caacgattcg     420
gaataccgcc acgaagactt cgcagtcatc agcaatgcaa gctgcaccac caactgctta     480
gcaccggtcg ccaaagttct gcatgacaac tttggcatca tcaaaggcac gatgaccacc     540
acccacagct acacgctgga ccagcgcatc ttggacgcca gcaccgtga tctacgtcgg     600 gctcgggctg ccgccgttaa catcgttccc accacgaccg cgctgctaa gccgttgct      660 ttggtgatcc ccgagctgaa aggcaaacta acgggattgc gctgcgcgt tcctacgcca     720 aacgtgtctg tcgttgactt ggtggttcaa gtcgagaaac cgacgatcac tgagcaggtc     780
aatgaagtcc tgcaaaaagc ttctcaaacg acgatgaagg gcatcatcaa gtactcggat     840
ctgcccttgg tatcttccga cttccggggt actgacgagt cttcgatcgt tgactccagc     900
ctgaccttgg taatggatgg cgatctcgtc aaagtaattg cttggtacga caacgagtgg     960
ggctacagcc aacgagttgt cgacttggct gaactggccg ctcgcaaatg ggccgcctaa    1020
```

<210> SEQ ID NO 52
<211> LENGTH: 1038
<212> TYPE: DNA
<213> ORGANISM: Synechococcus elongatus

<400> SEQUENCE: 52

| | | | | | |
|---|---|---|---|---|---|
| atggaaaaga | cgatcggtct | cgagattatt | gaagttgtcg | agcaggcagc | gatcgcctcg | 60 |
| gcccgcctga | tgggcaaagg | cgaaaagaat | gaagccgatc | gcgtcgcagt | agaagcgatg | 120 |
| cgggtgcgga | tgaaccaagt | ggaaatgctg | gccgcatcg | tcatcggtga | aggcgagcgc | 180 |
| gacgaagctc | cgatgctcta | tatcggtgaa | gaagtgggca | tctaccgcga | tgcagacaag | 240 |
| cgggctggcg | taccggctgg | caagctggtg | gaaatcgaca | tcgccgttga | ccctgcgaa | 300 |
| ggcaccaacc | tctgcgccta | cggtcagccc | ggctcgatgg | cagttttggc | catctccgag | 360 |
| aaaggcggcc | tgtttgcagc | tcccgacttc | tacatgaaga | aactggctgc | accccagct | 420 |
| gccaaaggca | agtagacat | caataagtcc | gcgaccgaaa | acctgaaaat | tctctcggaa | 480 |
| tgtctcgatc | gcgccatcga | tgaattggtg | gtcgtggtca | tggatcgtcc | ccgccacaaa | 540 |
| gagctaatcc | aagagatccg | ccaagcgggt | gcccgcgtcc | gtctgatcag | cgatggtgac | 600 |
| gtttcggccg | cgatctcctg | cggttttgct | ggcaccaaca | cccacgccct | gatgggcatc | 660 |
| ggtgcagctc | ccgagggtgt | gatttcggca | gcagcaatgc | gttgcctcgg | cggtcacttc | 720 |
| caaggccagc | tgatctacga | cccagaagtg | gtcaaaaccg | gctgatcgg | tgaaagccgt | 780 |
| gagagcaaca | tcgctcgcct | gcaagaaatg | ggcatcaccg | atcccgatcg | cgtctacgac | 840 |
| gccaacgaac | tggcttcggg | tcaagaagtg | ctgtttgcgg | cttgcggtat | caccccgggc | 900 |
| ttgctgatgg | aaggcgtgcg | cttcttcaaa | ggcggcgctc | gcacccagag | cttggtgatc | 960 |
| tccagccagt | cacggacggc | tcgcttcgtt | gacaccgttc | acatgttcga | cgatgtcaaa | 1020 |
| acggttagcc | tccgctaa | | | | | 1038 |

<210> SEQ ID NO 53
<211> LENGTH: 1002
<212> TYPE: DNA
<213> ORGANISM: Synechococcus elongatus

<400> SEQUENCE: 53

| | | | | | |
|---|---|---|---|---|---|
| atgtcgaagc | cagatcgtgt | tgttttgatc | ggcgttgccg | gtgactccgg | ttgcggcaaa | 60 |
| tcaaccttcc | taaatcgcct | tgccgacttg | tttggtacgg | aattgatgac | ggtcatctgc | 120 |
| ttggatgact | atcacagtct | cgatcgcaag | ggccggaagg | aagcaggcgt | aacggctttg | 180 |
| gatccccgcg | ccaacaactt | tgacttgatg | tatgaacagg | tcaaggcgtt | gaagaacggc | 240 |
| gaaacgatca | tgaagccgat | ctacaaccat | gaaaccggct | tgatcgatcc | gcccgaaaaa | 300 |
| atcgaaccca | atcgcatcat | tgtgatcgag | ggtctgcatc | cgctttacga | cgagcgcgtg | 360 |
| cgtgaactgc | tcgatttcag | cgtttacctc | gacatcgatg | acgaagtcaa | aatcgcttgg | 420 |
| aagatccaac | gcgatatggc | agaacgcggc | cactcctacg | aagatgtcct | cgcctcgatc | 480 |
| gaagcgcgcc | gccctgactt | caaggcctac | attgagcccc | agcgtggcca | tgcggacatc | 540 |
| gtcatccgcg | tcatgccgac | ccagctaatc | cccaatgaca | ccgagcgcaa | ggtgctgcgg | 600 |
| gtgcagttga | tccaacggga | aggccgcgat | ggttttgagc | cggcttacct | gttcgacgaa | 660 |
| ggttcgacca | tccagtggac | gccctgcggt | cgtaagctga | cctgctccta | tcgggcatt | 720 |
| cgcttagcct | acgccctga | cacctactac | ggtcacgaag | tctcagtgct | tgaggtcgac | 780 |
| ggtcagttcg | agaacctcga | ggagatgatc | tacgtcgagg | gccacctcag | caagaccgac | 840 |

```
acgcagtact acggtgagtt gacccacctg ctgctgcaac acaaagatta cccgggttcg      900
aacaacggca cgggtctgtt ccaagtgctg accggcctga aaatgcgggc ggcctatgag      960
cgtttgacct cccaagcagc acccgtcgcc gcaagcgtat aa                        1002
```

<210> SEQ ID NO 54
<211> LENGTH: 858
<212> TYPE: DNA
<213> ORGANISM: Escherichia coli

<400> SEQUENCE: 54

```
atgaaagctg acaacccttt tgatctttta cttcctgctg caatggccaa agtggccgag       60
gaggcgggtg tctataaagc aacgaaacat ccgcttaaga ctttctatct ggcgattacc      120
gccggtgttt tcatctcaat cgcattcgtc ttctatatca cagcaaccac tggcacaggc      180
acaatgccct tcggcatggc aaaactggtt ggcggcattt gcttctctct ggggctgatt      240
ctttgtgttg tctgcggagc cgatctcttt acttccaccg tgttgattgt tgttgctaag      300
gcgagtgggc gcatcaccctg ggtcagttg gcgaaaaact ggctaaatgt ctattttggc      360
aacctggtcg gcgcactgct gtttgtactt ttaatgtggc tttccggcga gtatatgacc      420
gcaaatggtc aatggggact aaacgtccta caaaccgccg accacaaagt gcaccatact      480
tttattgagg ccgtctgtct tggtatcctg caaacctga tggtatgtct ggcagtatgg       540
atgagttatt ctggccgcag cctgatggac aaagcgttca ttatggtgct gccggtcgcg      600
atgtttgttg ccagcggttt tgagcacagt atcgcaaaca tgtttatgat cccgatgggt      660
attgtaatcc gcgacttcgc atccccggaa ttttggaccg cagtcggttc tgcaccggaa      720 aattttctc acctgaccgt gatgaatttc atcactgata acctgattcc ggttacgatc      780
ggcaacatta tcggtggtgg tttgttggtt gggttgacat actgggtcat ttacctgcgt      840
gaaaacgacc accactaa                                                    858
```

<210> SEQ ID NO 55
<211> LENGTH: 849
<212> TYPE: DNA
<213> ORGANISM: Escherichia coli

<400> SEQUENCE: 55

```
atgcgcaaca aactctcttt cgacttgcag ttgagcgcca gaaaagcggc aatcgctgaa       60
cggattgccg cccataaaat tgcccgcagt aaagtgtcgg tctttttaat ggcgatgtcc      120
gctggcgtgt ttatggcgat cggatttact ttttaccttt ccgttatcgc cgatgccccg      180
tcttcacagg cattaaccca tctggtgggc ggcctttgct ttacactcgg ctttatttg       240 ctggcggttt gcgcaccag cctgttcacc tcgtcggtaa tgacggtgat ggcaaaaagt      300
cggggcgtta ttagttggcg aacttggctg attaacgcac ttctggtggc ctgcggtaat      360
ctggcaggta ttgcctgttt cagtttgtta atctggtttt ccgggctggt gatgagtgaa      420
aacgcgatgt ggggagtcgc ggttttacac tgcgccgagg gcaaaatgca tcatacattt      480
actgaatctg tcagcctcgg cattatgtgc aatctgatgg tttgcctggc gctgtggatg      540
agttattgcg ggcgttcgtt atgcgacaaa atcgtcgcca tgattttgcc catcaccctg      600
tttgtcgcca gtggctttga gcactgtatc gccaatttgt tgtgattcc gttcgccatt      660 gccattcgcc atttcgcccc tccccctttc tggcagctgg cgcacagtag cgcagacaat      720
tttccggcac tgacggtcag ccattttatt accgccaatc tgctcccggt gatgctgggt      780
```

| | |
|---|---:|
| aatattatcg gcggtgcggt gctggtgagt atgtgttatc gggctattta tttacgtcag | 840 |
| gaaccataa | 849 |

<210> SEQ ID NO 56
<211> LENGTH: 3461
<212> TYPE: DNA
<213> ORGANISM: Artificial Sequence
<220> FEATURE:
<223> OTHER INFORMATION: Synthetic DNA

<400> SEQUENCE: 56

| | |
|---|---:|
| aaaaaaaatc cttagctttc gctaaggatg atttctggaa ttcgcggccg cttctagagc | 60 |
| ccacagctaa caccacgtcg tccctatctg ctgccctagg tctatgagtg gttgctggat | 120 |
| aactttacgg gcatgcataa ggctcgtatg atatattcag ggagaccaca acggtttccc | 180 |
| tctacaaata attttgttta actttgcccg cgctctcccc cagtgtgaga gtgttcacac | 240 |
| aggaaagtac tagatggcca ctgttctatg cgtgctatat cctgatccgg ttgatggtta | 300 |
| tccaccgcac tatgttcgtg ataccatccc ggtgatcacc cgatatgcag atggccaaac | 360 |
| agcccccact cccgcgggc cgccaggatt tcgtcccggt gaactggtgg gcagtgtttc | 420 |
| tggtgcgctg gacttcgcg gttaccttga agcccatggt cacactctca tcgtcacatc | 480 |
| ggataaagat ggtccggata gtgagtttga aagacggctg cctgatgccg atgttgtcat | 540 |
| cagccagccg ttttggcccg catatcttac ggctgaacga atcgcgaggg cgccgaagtt | 600 |
| acgtctggct ctgactgctg gtataggctc agaccacgtt gacctcgatg ccgcggcgcg | 660 |
| tgctcacatt acgtcgccg aagtgactgg aagtaacagt atttcagtgg ctgaacacgt | 720 |
| tgttatgaca cgctggcct tagtgcggaa ctatttacct agccacgcaa ttgcgcagca | 780 |
| aggtggttgg aacatcgccg actgtgtttc acgtcttat gacgtcgaag gaatgcattt | 840 |
| cggcacagta ggggcgggta ggattggatt ggctgttctg cgccggctta accgtttgg | 900 |
| tctgcatttg cattacaccc aaagacatcg cttggatgca gccatcgaac aagaactcgg | 960 |
| tcttacttac catgccgatc cagccagtct tgcggcggca gtagacattg ttaatttgca | 1020 |
| gattccgctg tatccttcca ctgaacacct ttttgatgct gcaatgattg cacgcatgaa | 1080 |
| aagaggtgcg tacctgatta atactgcccg tgcgaagtta gtggaccgcg atgccgtcgt | 1140 |
| cagggctgtc acaagcggac atctggctgg ttatggcggg gacgtctggt ttccccagcc | 1200 |
| tgctccggct gatcatccgt ggcgggcgat gccttttaat ggcatgacac tcatattag | 1260 |
| cggtacttca ctttctgctc aggcgcggta cgcagcgggg acccttgaaa tcctccagtg | 1320 |
| ttggtttgat ggcagaccga tcaggaacga gtacctgata gtggatggag gaacattggc | 1380 |
| cggtacaggt gcccaatcat atcggctgaa gtaagccaca cgcgctctcc ccctccggt | 1440 |
| gtaatcgggg gagagcgcgt gtccgctgca gtccggcaaa aagggcaag gtgtcaccac | 1500 |
| cctgcccttt ttcttaaaa ccgaaaagat tacttcgcgt tatgcaggct tcctcgctca | 1560 |
| ctgactcgct gcgctcggtc gttcggctgc ggcgagcgg atcagctcac tcaaaggcgg | 1620 |
| taatacggtt atccacagaa tcaggggata acgcaggaaa gaacatgtga gcaaaaggcc | 1680 |
| agcaaaaggc caggaaccgt aaaaaggccg cgttgctggc gttttccac aggctccgcc | 1740 |
| cccctgacga gcatcacaaa atcgacgct caagtcagag gtggcgaaac ccgacaggac | 1800 |
| tataaagata ccaggcgttt ccccctggaa gctccctcgt gcgctctcct gttccgaccc | 1860 |
| tgccgcttac cggatacctg tccgcctttc tcccttcggg aagcgtggcg ctttctcata | 1920 |
| gctcacgctg taggtatctc agttcggtgt aggtcgttcg ctccaagctg ggctgtgtgc | 1980 |

```
acgaaccccc cgttcagccc gaccgctgcg ccttatccgg taactatcgt cttgagtcca    2040
acccggtaag acacgactta tcgccactgg cagcagccac tggtaacagg attagcagag    2100
cgaggtatgt aggcggtgct acagagttct tgaagtggtg gcctaactac ggctacacta    2160
gaagaacagt atttggtatc tgcgctctgc tgaagccagt taccttcgga aaaagagttg    2220
gtagctcttg atccggcaaa caaaccaccg ctggtagcgg tggttttttt gtttgcaagc    2280
agcagattac gcgcagaaaa aaaggatctc aagaagatcc tttgatcttt tctacggggt    2340
ctgacgctca gtggaacgaa aactcacgtt aagggatttt ggtcatgaga ttatcaaaaa    2400
ggatcttcac ctagatcctt ttaaattaaa aatgaagttt taaatcaatc taagtatat     2460 atgagtaaac ttggtctgac agctcgaggc ttggattctc accaataaaa aacgcccggc    2520
ggcaaccgag cgttctgaac aaatccagat ggagttctga ggtcattact ggatctatca    2580
acaggagtcc aagcgagctc gatatcaaat tacgccccgc cctgccactc atcgcagtac    2640
tgttgtaatt cattaagcat tctgccgaca tggaagccat cacaaacggc atgatgaacc    2700
tgaatcgcca gcggcatcag caccttgtcg ccttgcgtat aatatttgcc catggtgaaa    2760 acggggggcga agaagttgtc catattggcc acgtttaaat caaaactggt gaaactcacc    2820
cagggattgg ctgagacgaa aaacatattc tcaataaacc ctttagggaa ataggccagg    2880
ttttcaccgt aacacgccac atcttgcgaa tatatgtgta gaaactgccg gaaatcgtcg    2940
tggtattcac tccagagcga tgaaaacgtt tcagtttgct catggaaaac ggtgtaacaa    3000
gggtgaacac tatcccatat caccagctca ccgtctttca ttgccatacg aaattccgga    3060
tgagcattca tcaggcgggc aagaatgtga ataaaggccg gataaaactt gtgcttattt    3120
ttctttacgg tctttaaaaa ggccgtaata tccagctgaa cggtctggtt ataggtacat    3180
tgagcaactg actgaaatgc ctcaaaatgt tctttacgat gccattggga tatatcaacg    3240
gtggtatatc cagtgatttt tttctccatt ttagcttcct tagctcctga aaatctcgat    3300
aactcaaaaa atacgcccgg tagtgatctt atttcattat ggtgaaagtt ggaacctctt    3360
acgtgcccga tcaactcgag tgccacttga cgtctaagaa accattatta tcatgacatt    3420
aacctataaa aataggcgta tcacgaggca gaatttcaga t                        3461

<210> SEQ ID NO 57
<211> LENGTH: 3395
<212> TYPE: DNA
<213> ORGANISM: Artificial Sequence
<220> FEATURE:
<223> OTHER INFORMATION: Synthetic DNA

<400> SEQUENCE: 57
aaaaaaaatc cttagctttc gctaaggatg atttctggaa ttcgcggccg cttctagagc      60
ccacagctaa caccacgtcg tccctatctg ctgccctagg tctatgagtg gttgctggat     120
aactttacgg gcatgcataa ggctcgtatg atatattcag ggagaccaca acggtttccc     180
tctacaaata attttgttta actttgcccg cgctctcccc cagtgtgaga gtgttcacac     240
aggaaagtac tagatgaaaa ttgtactggt gctctatgat gcaggaaaac acgccgcaga     300
cgaggaaaag ctgtatggct gcactgagaa caagctagga atcgccaatt ggctgaagga     360
tcagggccat gaattaatca ctacctccga taaagaaggt gaaacctcag agttagataa     420
gcacattccc gatgccgata taatcattac gacgcctttt cacccagctt acattacaaa     480
agagcgtctg gataaagcga aaaacctcaa atcggttgta gtcgccggcg tcggttccga     540
```

```
ccacattgac ctggattata ttaatcagac tggtaagaag atcagcgtcc tggaagtcac    600
cggctctaat gtggtatctg ttgctgagca tgttgtaatg actatgctgg ttttagtgcg    660
caattttgtg cccgcacacg agcagatcat aaaccatgac tgggaagtag cagcaatagc    720
taaagatgcg tatgatattg aaggcaaaac tatcgctacg atcggcgcgg gccggatcgg    780
ttaccgggtt ctggagcggc tgctgccgtt caatcctaaa gagctcctat actatgatta    840
tcaggcactg cccaaggaag cagaggaaaa agttggtgcg cggagagtgg aaaacattga    900
agaacttgtg gctcaggccg acattgtaac ggtaaatgct ccacttcacg caggcaccaa    960
aggccttatc aataaagagt tgcttttcaa agtttaagaaa ggtgcctggt tggtaaatac   1020
ggcccgtgga gcaatttgcg ttgcggagga tgtcgccgcc gctctggaat cgggacagct   1080
ccggggatac ggtggggatg tttggtttcc ccagccggcg ccaaaggatc acccgtggcg   1140
tgatatgcga aacaaatatg cgcagggaa cgccatgaca ccgcattact ccgggacgac   1200
cttagatgca caaactcgat acgctgaagg taccaagaac atcctggaaa gtttctttac   1260
gggcaagttt gattatcgcc ctcaggatat tattctgctt aatggagaat atgtaacaaa   1320
agcttacggc aaacatgaca aaaagtaagc cacacgcgct ctcccccctc cggtgtaatc   1380
gggggagagc gcgtgtccgc tgcagtccgg caaaaaggg caaggtgtca ccaccctgcc   1440
cttttttcttt aaaaccgaaa agattacttc gcgttatgca ggcttcctcg ctcactgact   1500
cgctgcgctc ggtcgttcgg ctgcggcgag cggtatcagc tcactcaaag gcggtaatac   1560
ggttatccac agaatcaggg gataacgcag gaaagaacat gtgagcaaaa ggccagcaaa   1620
aggccaggaa ccgtaaaaag gccgcgttgc tggcgttttt ccacaggctc cgccccctg    1680
acgagcatca aaaaatcga cgctcaagtc agaggtggcg aaacccgaca ggactataaa   1740
gataccaggc gtttccccct ggaagctccc tcgtgcgctc tcctgttccg accctgccgc   1800
ttaccggata cctgtccgcc tttctccctt cgggaagcgt ggcgctttct catagctcac   1860
gctgtaggta tctcagttcg gtgtaggtcg ttcgctccaa gctgggctgt gtgcacgaac   1920
cccccgttca gcccgaccgc tgcgccttat ccggtaacta tcgtcttgag tccaacccgg   1980
taagacacga cttatcgcca ctggcagcag ccactggtaa caggattagc agagcgaggt   2040
atgtaggcgg tgctacagag ttcttgaagt ggtggcctaa ctacggctac actagaagaa   2100
cagtatttgg tatctgcgct ctgctgaagc cagttacctt cggaaaaaga gttggtagct   2160
cttgatccgg caaacaaacc accgctggta gcggtggttt ttttgtttgc aagcagcaga   2220
ttacgcgcag aaaaaaagga tctcaagaag atcctttgat cttttctacg ggtctgacg    2280
ctcagtggaa cgaaaactca cgttaaggga ttttggtcat gagattatca aaaaggatct   2340
tcacctagat ccttttaaat taaaatgaa gttttaaatc aatctaaagt atatatgagt   2400
aaacttggtc tgacagctcg aggcttggat tctcaccaat aaaaaacgcc cggcggcaac   2460
cgagcgttct gaacaaatcc agatggagtt ctgaggtcat tactggatct atcaacagga   2520
gtccaagcga gctcgatatc aaattacgcc ccgccctgcc actcatcgca gtactgttgt   2580
aattcattaa gcattctgcc gacatggaag ccatcacaaa cggcatgatg aacctgaatc   2640
gccagcggca tcagcacctt gtcgccttgc gtataatatt tgcccatggt gaaacggg     2700
gcgaagaagt tgtccatatt ggccacgttt aaatcaaaac tggtgaaact cacccaggga   2760
ttggctgaga cgaaaaacat attctcaata aaccctttag ggaaataggc caggttttca   2820
ccgtaacacg ccacatcttg cgaatatatg tgtagaaact gccggaaatc gtcgtggtat   2880
tcactccaga gcgatgaaaa cgtttcagtt tgctcatgga aaacggtgta acaagggtga   2940
```

-continued

| | |
|---|---|
| acactatccc atatcaccag ctcaccgtct ttcattgcca tacgaaattc cggatgagca | 3000 |
| ttcatcaggc gggcaagaat gtgaataaag gccggataaa acttgtgctt attttttcttt | 3060 |
| acggtcttta aaaaggccgt aatatccagc tgaacggtct ggttataggt acattgagca | 3120 |
| actgactgaa atgcctcaaa atgttcttta cgatgccatt gggatatatc aacggtggta | 3180 |
| tatccagtga ttttttttctc cattttagct tccttagctc ctgaaaatct cgataactca | 3240 |
| aaaaatacgc ccggtagtga tcttatttca ttatggtgaa agttggaacc tcttacgtgc | 3300 |
| ccgatcaact cgagtgccac ttgacgtcta agaaaccatt attatcatga cattaaccta | 3360 |
| taaaaatagg cgtatcacga ggcagaattt cagat | 3395 |

<210> SEQ ID NO 58
<211> LENGTH: 3556
<212> TYPE: DNA
<213> ORGANISM: Artificial Sequence
<220> FEATURE:
<223> OTHER INFORMATION: Synthetic DNA

<400> SEQUENCE: 58

| | |
|---|---|
| aaaaaaaatc cttagctttc gctaaggatg atttctggaa ttcgcggccg cttctagagc | 60 |
| ccacagctaa caccacgtcg tccctatctg ctgccctagg tctatgagtg gttgctggat | 120 |
| aactttacgg gcatgcataa ggctcgtagg ctatattcag ggagaccaca acggtttccc | 180 |
| tctacaaata attttgttta acttttcaca caggaaacct actagatggc ccatattgtg | 240 |
| gtcctggggg ccgggctcgg cggcgccatt atggcatatg agctccgcga gcaggtgcgc | 300 |
| aaagaggata aagttaccgt tattaccaaa gatccgatgt atcattttgt gccaagcaac | 360 |
| ccatgggtgg cggtgggctg gcgcgatcgc aaagaaatta ccgtggattt agcgccgacg | 420 |
| atggcgcgca aaacattga ttttattccg gtggcagcga acgcctgca tccggcggag | 480 |
| aaccgtgttg aactggagaa cggccagagc gtttcgtacg atcagattgt tattgccacc | 540 |
| ggcccggagc tggcctttga tgaaattgaa ggcttcggcc agaaggcca cacgcaaagc | 600 |
| atttgccata ttgatcatgc cgaagaagcg cggctggcct tcgatcgctt ctgcgagaac | 660 |
| ccaggcccga ttttgattgg tgcggcgcag ggcgcctcgt gctttggccc ggcttacgag | 720 |
| tttacccttta ttttagacac cgcgctgcgc aaacgcaaaa ttcgcgataa agtgccgatg | 780 |
| accttttgtta ccagcgaacc atatgttggt catctgggtc tggatggtgt gggcgatacc | 840 |
| aaaggcctgt tggagggcaa cctgcgcgat aaacacatta agtggatgac cagcacccgt | 900 |
| attaagcgcg ttgagaaagg caaaatggtg gttgaagaag tgaccgaaga tggcacggtt | 960 |
| aaaccagaaa aggaactgcc atttggctat gcgatgatgc tgccagcgtt tcgcggcatt | 1020 |
| aaagcgctga tgggtattga aggtctggtt aatccgcgcg gctttgttat tgttgaccag | 1080 |
| caccagcaga acccgacctt taaaaacgtt tttgcggttg gcgtttgcgt ggcgattccg | 1140 |
| ccgattggtc cgacgccggt gccatgcggc gtgccgaaaa ccggctttat gattgagtcg | 1200 |
| atggttaccg ccaccgccca aacattggc cgtattgtgc gcggtttcga agccgatgaa | 1260 |
| gttggctcgt ggaacgccgt ttgtctggcc gactttggcg accagggcat tgccttcgtt | 1320 |
| gcgcagccgc agattccgcc gcgcaacgtg aactggagct cgcagggcaa gtgggtgcat | 1380 |
| tgggccaaag aaggttttga acgctatttt atgcacaaac tgcgccgcgg taccagtgaa | 1440 |
| accttttatg agaagccgc gatgaaattc ctgggcattg ataaactgaa agccgttaag | 1500 |
| aaagggtaag ccacacgcgc tctcccccct ccggtgtaat cgggggagag cgcgtgtccg | 1560 |

| | |
|---|---|
| ctgcagtccg gcaaaaaagg gcaaggtgtc accaccctgc ccttttcctt taaaaccgaa | 1620 |
| aagattactt cgcgttatgc aggcttcctc gctcactgac tcgctgcgct cggtcgttcg | 1680 |
| gctgcggcga gcggtatcag ctcactcaaa ggcggtaata cggttatcca cagaatcagg | 1740 |
| ggataacgca ggaaagaaca tgtgagcaaa aggccagcaa aaggccagga accgtaaaaa | 1800 |
| ggccgcgttg ctggcgtttt tccacaggct ccgcccccct gacgagcatc acaaaaatcg | 1860 |
| acgctcaagt cagaggtggc gaaacccgac aggactataa agataccagg cgtttccccc | 1920 |
| tggaagctcc ctcgtgcgct ctcctgttcc gaccctgccg cttaccggat acctgtccgc | 1980 |
| ctttctccct tcgggaagcg tggcgctttc tcatagctca cgctgtaggt atctcagttc | 2040 |
| ggtgtaggtc gttcgctcca agctgggctg tgtgcacgaa ccccccgttc agcccgaccg | 2100 |
| ctgcgcctta tccggtaact atcgtcttga gtccaacccg gtaagacacg acttatcgcc | 2160 |
| actggcagca gccactggta acaggattag cagagcgagg tatgtaggcg gtgctacaga | 2220 |
| gttcttgaag tggtggccta actacggcta cactagaaga acagtatttg gtatctgcgc | 2280 |
| tctgctgaag ccagttacct tcggaaaaag agttggtagc tcttgatccg gcaaacaaac | 2340 |
| caccgctggt agcggtggtt ttttgtttg caagcagcag attacgcgca gaaaaaagg | 2400 |
| atctcaagaa gatcctttga tcttttctac ggggtctgac gctcagtgga acgaaaactc | 2460 |
| acgttaaggg attttggtca tgagattatc aaaaaggatc ttcacctaga tccttttaaa | 2520 |
| ttaaaaatga agttttaaat caatctaaag tatatatgag taaacttggt ctgacagctc | 2580 |
| gaggcttgga ttctcaccaa taaaaaacgc ccggcggcaa ccgagcgttc tgaacaaatc | 2640 |
| cagatggagt tctgaggtca ttactggatc tatcaacagg agtccaagcg agctcgatat | 2700 |
| caaattacgc cccgccctgc cactcatcgc agtactgttg taattcatta agcattctgc | 2760 |
| cgacatggaa gccatcacaa acggcatgat gaacctgaat cgccagcggc atcagcacct | 2820 |
| tgtcgccttg cgtataatat ttgcccatgg tgaaacggg ggcgaagaag ttgtccatat | 2880 |
| tggccacgtt taaatcaaaa ctggtgaaac tcacccaggg attggctgag acgaaaaaca | 2940 |
| tattctcaat aaaccctta gggaaatagg ccaggttttc accgtaacac gccacatctt | 3000 |
| gcgaatatat gtgtagaaac tgccggaaat cgtcgtggta ttcactccag agcgatgaaa | 3060 |
| acgtttcagt ttgctcatgg aaaacggtgt aacaagggtg aacactatcc catatcacca | 3120 |
| gctcaccgtc tttcattgcc atacgaaatt ccggatgagc attcatcagg cgggcaagaa | 3180 |
| tgtgaataaa ggccggataa aacttgtgct tatttttctt tacggtcttt aaaaaggccg | 3240 |
| taatatccag ctgaacggtc tggttatagg tacattgagc aactgactga atgcctcaa | 3300 |
| aatgttcttt acgatgccat tgggatatat caacggtggt atatccagtg atttttttct | 3360 |
| ccatttagc ttccttagct cctgaaaatc tcgataactc aaaaaatacg cccggtagtg | 3420 |
| atcttatttc attatggtga agttggaac ctcttacgtg cccgatcaac tcgagtgcca | 3480 |
| cttgacgtct aagaaaccat tattatcatg acattaacct ataaaaatag gcgtatcacg | 3540 |
| aggcagaatt tcagat | 3556 |

<210> SEQ ID NO 59
<211> LENGTH: 3555
<212> TYPE: DNA
<213> ORGANISM: Artificial Sequence
<220> FEATURE:
<223> OTHER INFORMATION: Synthetic DNA

<400> SEQUENCE: 59

| | |
|---|---|
| aaaaaaaatc cttagctttc gctaaggatg atttctggaa ttcgcggccg cttctagagc | 60 |

```
ccacagctaa caccacgtcg tccctatctg ctgccctagg tctatgagtg gttgctggat     120
aactttacgg gcatgcataa ggctcgtatg atatattcag ggagaccaca acggtttccc     180
tctacaaata attttgttta acttttcaca caggaaagta ctagatggcc catattgtgg     240
tcctggggc cgggctcggc ggcgccatta tggcatatga gctccgcgag caggtgcgca     300
aagaggataa agttaccgtt attaccaaag atccgatgta tcattttgtg ccaagcaacc     360
catgggtggc ggtgggctgg cgcgatcgca aagaaattac cgtggattta cgccgacga     420
tggcgcgcaa aaacattgat tttattccgg tggcagcgaa acgcctgcat ccggcggaga     480
accgtgttga actggagaac ggccagagcg tttcgtacga tcagattgtt attgccaccg     540
gcccggagct ggcctttgat gaaattgaag cttcggccc agaaggccac acgcaaagca     600
tttgccatat tgatcatgcc gaagaagcgc ggctggcctt cgatcgcttc tgcgagaacc     660
caggcccgat tttgattggt gcggcgcagg gcgcctcgtg ctttggcccg cttacgagt     720
ttacctttat tttagacacc gcgctgcgca aacgcaaaat tcgcgataaa gtgccgatga     780
cctttgttac cagcgaacca tatgttggtc atctgggtct ggatggtgtg ggcgatacca     840
aaggcctgtt ggagggcaac ctgcgcgata acacattaa gtggatgacc agcacccgta     900
ttaagcgcgt tgagaaaggc aaaatggtgg ttgaagaagt gaccgaagat ggcacggtta     960
aaccagaaaa ggaactgcca tttggctatg cgatgatgct gccagcgttt cgcggcatta    1020
aagcgctgat gggtattgaa ggtctggtta atccgcgcgg ctttgttatt gttgaccagc    1080
accagcagaa cccgaccttt aaaaacgttt ttgcggttgg cgtttgcgtg gcgattccgc    1140
cgattggtcc gacgccggtg ccatgcggcg tgccgaaaac cggctttatg attgagtcga    1200
tggttaccgc caccgcccac aacattggcc gtattgtgcg cggtttcgaa gccgatgaag    1260
ttggctcgtg gaacgccgtt tgtctggccg actttggcga ccagggcatt gccttcgttg    1320
cgcagccgca gattccgccg cgcaacgtga actggagctc gcagggcaag tgggtgcatt    1380
gggccaaaga aggttttgaa cgctatttta tgcacaaact gcgccgcggt accagtgaaa    1440
ccttttatga gaaagccgcg atgaaattcc tgggcattga taaactgaaa gccgttaaga    1500
aagggtaagc cacacgcgct ctccccctc cggtgtaatc ggggagagc gcgtgtccgc    1560
tgcagtccgg caaaaagggg caaggtgtca ccaccctgcc cttttctctt aaaaccgaaa    1620
agattacttc gcgttatgca ggcttcctcg ctcactgact cgctgcgctc ggtcgttcgg    1680
ctgcggcgag cggtatcagc tcactcaaag gcggtaatac ggttatccac agaatcaggg    1740
gataacgcag gaaagaacat gtgagcaaaa ggccagcaaa aggccaggaa ccgtaaaaag    1800
gccgcgttgc tggcgttttt ccacaggctc cgccccctg acgagcatca caaaaatcga    1860
cgctcaagtc agaggtggcg aaacccgaca ggactataaa gataccaggc gtttccccct    1920
ggaagctccc tcgtgcgctc tcctgttccg accctgccgc ttaccggata cctgtccgcc    1980
tttctccctt cgggaagcgt ggcgctttct catagctcac gctgtaggta tctcagttcg    2040
gtgtaggtcg ttcgctccaa gctgggctgt gtgcacgaac cccccgttca gcccgaccgc    2100
tgcgccttat ccggtaacta tcgtcttgag tccaacccgg taagacacga cttatcgcca    2160
ctggcagcag ccactggtaa caggattagc agagcgaggt atgtaggcgg tgctacagag    2220
ttcttgaagt ggtggcctaa ctacggctac actagaagaa cagtatttgg tatctgcgct    2280
ctgctgaagc cagttacctt cggaaaaaga gttggtagct cttgatccgg caaacaaacc    2340
accgctggta gcggtggttt ttttgtttgc aagcagcaga ttacgcgcag aaaaaaagga    2400
```

-continued

```
tctcaagaag atcctttgat cttttctacg gggtctgacg ctcagtggaa cgaaaactca    2460
cgttaaggga ttttggtcat gagattatca aaaaggatct tcacctagat ccttttaaat    2520
taaaaatgaa gttttaaatc aatctaaagt atatatgagt aaacttggtc tgacagctcg    2580
aggcttggat tctcaccaat aaaaaacgcc cggcggcaac cgagcgttct gaacaaatcc    2640
agatggagtt ctgaggtcat tactggatct atcaacagga gtccaagcga gctcgatatc    2700
aaattacgcc ccgccctgcc actcatcgca gtactgttgt aattcattaa gcattctgcc    2760
gacatggaag ccatcacaaa cggcatgatg aacctgaatc gccagcggca tcagcacctt    2820
gtcgccttgc gtataatatt tgcccatggt gaaaacgggg gcgaagaagt tgtccatatt    2880
ggccacgttt aaatcaaaac tggtgaaact cacccaggga ttggctgaga cgaaaaacat    2940
attctcaata acccttag ggaaataggc caggttttca ccgtaacacg ccacatcttg    3000
cgaatatatg tgtagaaact gccggaaatc gtcgtggtat tcactccaga gcgatgaaaa    3060
cgtttcagtt tgctcatgga aacggtgta acaagggtga acactatccc atatcaccag    3120
ctcaccgtct ttcattgcca tacgaaattc cggatgagca ttcatcaggc gggcaagaat    3180
gtgaataaag gccggataaa acttgtgctt attttcttt acggtcttta aaaaggccgt    3240
aatatccagc tgaacggtct ggttataggt acattgagca actgactgaa atgcctcaaa    3300
atgttcttta cgatgccatt gggatatatc aacggtggta tatccagtga tttttttctc    3360 catttttagct tccttagctc ctgaaaatct cgataactca aaaaatacgc ccggtagtga    3420
tcttatttca ttatggtgaa agttggaacc tcttacgtgc ccgatcaact cgagtgccac    3480
ttgacgtcta agaaaccatt attatcatga cattaaccta taaaaatagg cgtatcacga    3540
ggcagaattt cagat                                                     3555
```

<210> SEQ ID NO 60
<211> LENGTH: 7740
<212> TYPE: DNA
<213> ORGANISM: Artificial Sequence
<220> FEATURE:
<223> OTHER INFORMATION: Synthetic DNA

<400> SEQUENCE: 60

```
aaaaaaaatc cttagctttc gctaaggatg atttctggaa ttcgcggccg cttctagagc      60
ccacagctaa caccacgtcg tccctatctg ctgccctagg tctatgagtg gttgctggat     120
aactttacgg gcatgcataa ggctcgtatg atatattcag ggagaccaca acggtttccc     180
tctacaaata attttgttta acttttcaca caggaaagta ctagatgatc gacactgcgc     240
cccttgcccc accacgggcg ccccgctcta atccgattcg ggatcgagtt gattgggaag     300
ctcagcgtgc tgctgcgctg gcagatcccg gtgccttca tggcgcgatt gcccggacag     360
ttatccactg gtacgaccca caacaccatt gctggattcg cttcaacgag tctagtcagc     420
gttgggaagg gctggatgcc gctaccggtg cccctgtaac ggtagactat cccgccgatt     480
atcagccctg gcaacaggcg tttgatgata gtgaagcgcc gttttaccgc tggtttagtg     540
gtgggttgac aaatgcctgc tttaatgaag tagaccggca tgtcacgatg ggctatggcg     600
acgaggtggc ctactacttt gaaggtgacc gctgggataa ctcgctcaac aatggtcgtg     660
gtggtccggt tgtccaggag acaatcacgc gacggcgtct gttggtggag gtggtgaagg     720
ctgcgcaggt gttgcgcgat ctgggcctga gaagggtga tcggattgct ctgaatatgc     780
cgaatattat gccgcagatt tattatacgg aagcggcaaa acgactgggt attctgtaca     840
cgccggtctt cggtggcttc tcggacaaga ctctttccga ccgtattcac aatgccggtg     900
```

```
cacgagtggt gattacctct gatggcgcgt atcgcaacgc gcaggtggtg ccctacaaag    960
aagcgtatac cgatcaggcg ctcgataagt atattccggt tgagactgcg caggcgattg   1020
ttgcgcagac cctggccacc ttgcccctga ctgagtcgca gcgccagacg atcatcaccg   1080
aagtggaggc cgccctggca ggtgagatta cggttgagcg ttcggacgtg atgcgtgggg   1140
ttggttctgc cctcgcaaag ctccgcgatc ttgatgcaag cgtgcaggca aaggtgcgca   1200
cagtactggc gcaggcgctg tcgagtcgc cgccgcgggt tgaagctgtg gtggttgtgc   1260
gtcataccgg tcaggagatt ttgtggaacg aggggcgaga tcgctggagt cacgacttgc   1320
tggatgctgc gctggcgaag attctggcca atgcgcgtgc tgcaggcttt gatgtgcaca   1380
gtgagaatga tctgctcaat ctccccgatg accagcttat ccgtgcgctc tacgccagta   1440
ttccctgtga accggttgat gctgaatatc cgatgtttat catttacaca tcgggtagca   1500
ccggtaagcc caagggtgtg atccacgttc acggcggtta tgtcgccggt gtggtgcaca   1560
ccttgagggt cagttttgac gccgagccgg tgatacgat atatgtgatc gccgatccgg   1620
gctggatcac cggccagagc tatatgctca cagccacaat ggccggtaga ctgaccgggg   1680
tgattgccga gggatcaccg cttttcccct cagcccgggcg ttatgccagc atcatcgagc   1740
gctatggggt gcagatcttt aaggcgggtg tgaccttcct caagacagtg atgtccaatc   1800
cgcagaatgt tgaagatgtg cgactctatg atatgcactc gctgagagtt gcaaccttct   1860
gcgccgagcc ggtaagtccg gcggtgcagc agtttggtat gcagatcatg accccgcagt   1920
atatcaattc gtactgggcg accgagcacg gtggaattgt ctggacgcat ttctacggta   1980
atcaggactt tccgcttcgt cccgatgccc ataccctatcc cttgccctgg gtgatgggtg   2040
atgtctgggt ggccgaaact gatgagagcg ggacgacgcg ctatcgggtc gctgatttcg   2100
atgagaaggg cgagattgtg attaccgccc cgtatcccta cctgacccgc acactctggg   2160
gtgatgtgcc cggtttcgag gcgtacctgc gcggtgagat tccgctgcga gcctggaagg   2220
gtgatgccga gcgtttcgtc aagacctact ggcgacgtgg gccaaacggt gaatgggggct   2280 atatccaggg tgattttgcc atcaagtacc ccgatggtag cttcacgctc cacggacgct   2340
ctgacgatgt gatcaatgtg tcgggccacc gtatgggcac cgaggagatt gagggtgcca   2400
ttttgcgtga ccgccagatc acgcccgact cgcctgtcgg taattgtatt gtggtcggtg   2460
cgccgcatcg tgagaagggt ctgacccccgg ttgccttcat tcaacctgcg cctggccgtc   2520
atctgaccgg tgcagacagg cgccgtctcg atgagctggt gcgcaccgag aaggggggcgg   2580 tcagtgtccc agaggattac atcgaggtca gtgcctttcc cgaaacccgc agcgggaagt   2640
atatgaggcg ctttttgcgc aatatgatgc tcgatgaacc actgggtgat acgacgacgt   2700
tgcgcaatcc tgaagtgctc gaagaaattg cagccaagat cgctgagtgg aaacgccgtc   2760
agcgtatggc cgaagaacag cagatcatcg aacgctatcg ctacttccgg atcgagtatc   2820
atccaccaac ggccagtgcg ggtaaaactcg cggtagtgac ggtgacaaat ccgccggtga   2880
acgcactgaa tgagcgtgcg ttagatgagt tgaacacaat tgttgaccac ctggcccgtc   2940
gtcaggatgt tgccgcaatt gtcttcaccg gacagggcgc caggagtttt gtcgccggtg   3000
ctgatattcg ccagttgctc gaagaaattc atacggttga agaagcaatg ccctgccga   3060 ataacgccca tcttgctttc cgcaagattg agcgtatgaa taagccgtgt atcgcggcga   3120
tcaacggtgt ggcgctcggt ggtggtctgg aatttgccat ggcctgccat taccgggttg   3180
ccgatgtcta tgccgaattt ggtcagccag agattaatct gcgcttgcta cctggttatg   3240
```

```
gtggcacgca gcgcttgccg cgtctgttgt acaagcgcaa caacggcacc ggtctgctcc      3300
gagcgctgga gatgattctg ggtgggcgta gcgtaccggc tgatgaggcg ctggagctgg      3360
gtctgatcga tgccattgct accggcgatc aggactcact gtcgctggca tgcgcgttag      3420
cccgtgccgc aatcggtgcc gatggtcagt tgatcgagtc ggctgcggtg acccaggctt      3480
tccgccatcg ccacgagcag cttgacgagt ggcgcaaacc agacccgcgc tttgccgatg      3540
acgaactgcg ctcgattatc gcccatccac gtatcgagcg gattatccgg caggcccata      3600
ccgttgggcg cgatgcggca gtgcaccggg cactggatgc aatccgctat ggcattatcc      3660
acggcttcga ggccggtctg gagcacgagg cgaagctctt tgccgaggca gtggtttgacc     3720 cgaacggtgg caagcgtggt attcgcgagt tcctcgaccg ccagagtgcg ccgttgccaa      3780
cccgccgacc attgattaca cctgaacagg agcaactctt gcgcgatcag aaagaactgt      3840
tgccggttgg ttcacccttc ttccccggtg ttgaccggat tccgaagtgg cagtacgcgc      3900
aggcggttat tcgtgatccg gacaccggtg cggcggctca cggcgatccc atcgtggctg      3960
aaaagcagat tattgtgccg gtggaacgcc cccgcgccaa tcaggcgctg atttatgttc      4020
tggcctcgga ggtgaacttc aacgatatct gggcgattac cggtattccg gtgtcacggt      4080
ttgatgagca cgaccgcgac tggcacgtta ccggttcagg tggcatcggc ctgatcgttg      4140
cgctgggtga agaagcgcga cgcgaaggcc ggctgaaggt gggtgatctg gtggcgatct      4200
actccgggca gtcggatctg ctctcaccgc tgatgggcct tgatccgatg ccgccgatt      4260 tcgtcatcca ggggaacgac acgccagatg gatcgcatca gcaatttatg ctggcccagg      4320
ccccgcagtg tctgcccatc ccaaccgata tgtctatcga ggcagccggc agctacatcc      4380
tcaatctcgg tacgatctat cgcgccctct ttacgacgtt gcaaatcaag gccggacgca      4440
ccatctttat cgagggtgcg cgcgaccggca ccggtctgga cgcagcgcgc tcggcggccc     4500
ggaatggtct gcgcgtaatt ggaatggtca gttcgtcgtc acgtgcgtct acgctgctgg      4560
ctgcgggtgc ccacggtgcg attaaccgta aagacccgga ggttgccgat tgtttcacgc      4620
gcgtgcccga agatccatca gcctgggcag cctgggaagc cgccggtcag ccgttgctgg      4680
cgatgttccg ggcgcagaac gacgggcgac tggccgatta tgtggtctcg cacgcgggcg      4740
agacggcctt cccgcgcagt ttccagcttc tcggcgagcc acgcgatggt cacattccga      4800
cgctcacatt ctacggtgcc accagtggct accacttcac cttcctgggt aagccagggt      4860
cagcttcgcc gaccgagatg ctgcggcggg ccaatctccg cgccggtgag gcggtgttga      4920
tctactacgg ggttgggagc gatgacctgg tagataccgg cggtctggag gctatcgagg      4980
cggcgcggca aatgggagcg cggatcgtcg tcgttaccgt cagcgatgcg caacgcgagt      5040
ttgtcctctc gttgggcttc ggggctgccc tacgtggtgt cgtcagcctg gcggaactca      5100
aacgacgctt cggcgatgag tttgagtggc cgcgcacgat gccgccgttg ccgaacgccc      5160
gccaggaccc gcagggtctg aaagaggctg tccgccgctt caacgatctg gtcttcaagc      5220
cgctaggaag cgcggtcggt gtcttcttgc ggagtgccga caatccgcgt ggctaccccg      5280
atctgatcat cgagcgggct gcccacgatg cactggcggt gagcgcgatg ctgatcaagc      5340
ccttcaccgg acggattgtc tacttcgagg acattggtgg gcggcgttac tccttcttcg      5400
caccgcaaat ctgggtgcgc cagcgccgca tctacatgcc gacggcacag atctttggta      5460
cgcacctctc aaatgcgtat gaaattctgc gtctgaatga tgagatcagc gccggtctgc      5520
tgacgattac cgagccggca gtggtgccgt gggatgaact acccgaagca catcaggcga      5580
tgtgggaaaa tcgccacacg gcggccactt atgtggtgaa tcatgcctta ccacgtctcg      5640
```

```
gcctaaagaa cagggacgag ctgtacgagg cgtggacggc cggcgagcgc taagccacac    5700
gcgctctccc ccctccggtg taatcggggg agagcgcgtg tccgctgcag tccggcaaaa    5760
aagggcaagg tgtcaccacc ctgccctttt tctttaaaac cgaaaagatt acttcgcgtt    5820
atgcaggctt cctcgctcac tgactcgctg cgctcggtcg ttcggctgcg gcgagcggta    5880
tcagctcact caaaggcggt aatacggtta tccacagaat caggggataa cgcaggaaag    5940
aacatgtgag caaaaggcca gcaaaaggcc aggaaccgta aaaaggccgc gttgctggcg    6000 ttttccaca ggctccgccc cctgacgag catcacaaaa atcgacgctc aagtcagagg      6060
tggcgaaacc cgacaggact ataaagatac caggcgtttc ccctggaag ctccctcgtg     6120 cgctctcctg ttccgaccct gccgcttacc ggatacctgt ccgcctttct cccttcggga    6180
agcgtggcgc tttctcatag ctcacgctgt aggtatctca gttcggtgta ggtcgttcgc    6240
tccaagctgg gctgtgtgca cgaaccccc gttcagcccg accgctgcgc cttatccggt     6300
aactatcgtc ttgagtccaa cccggtaaga cacgacttat cgccactggc agcagccact    6360
ggtaacagga ttagcagagc gaggtatgta ggcggtgcta cagagttctt gaagtggtgg    6420
cctaactacg gctacactag aagaacagta tttggtatct gcgctctgct gaagccagtt    6480
accttcggaa aaagagttgg tagctcttga tccggcaaac aaaccaccgc tggtagcggt    6540
ggtttttttg tttgcaagca gcagattacg cgcagaaaaa aaggatctca agaagatcct    6600
ttgatctttt ctacggggtc tgacgctcag tggaacgaaa actcacgtta agggattttg    6660
gtcatgagat tatcaaaaag gatcttcacc tagatccttt aaattaaaa atgaagtttt     6720 aaatcaatct aaagtatata tgagtaaact tggtctgaca gctcgaggct tggattctca    6780
ccaataaaaa acgcccggcg gcaaccgagc gttctgaaca atccagatg gagttctgag    6840 gtcattactg gatctatcaa caggagtcca agcgagctcg atatcaaatt acgccccgcc    6900
ctgccactca tcgcagtact gttgtaattc attaagcatt ctgccgacat ggaagccatc    6960
acaaacggca tgatgaacct gaatcgccag cggcatcagc accttgtcgc cttgcgtata    7020
atatttgccc atggtgaaaa cggggcgaa gaagttgtcc atattggcca cgtttaaatc      7080
aaaactggtg aaactcaccc agggattggc tgagacgaaa acatattct caataaaccc     7140 tttagggaaa taggccaggt tttcaccgta acacgccaca tcttgcgaat atatgtgtag    7200
aaactgccgg aaatcgtcgt ggtattcact ccagagcgat gaaaacgttt cagtttgctc    7260
atggaaaacg gtgtaacaag ggtgaacact atcccatatc accagctcac cgtctttcat    7320
tgccatacga aattccggat gagcattcat caggcgggca agaatgtgaa taaaggccgg    7380
ataaaacttg tgcttatttt tctttacggt ctttaaaaag gccgtaatat ccagctgaac    7440
ggtctggtta taggtacatt gagcaactga ctgaaatgcc tcaaatgtt ctttacgatg     7500 ccattgggat atatcaacgg tggtatatcc agtgattttt ttctccattt tagcttcctt    7560
agctcctgaa aatctcgata actcaaaaaa tacgcccggt agtgatctta tttcattatg    7620
gtgaaagttg gaacctctta cgtgcccgat caactcgagt gccacttgac gtctaagaaa    7680
ccattattat catgacatta acctataaaa ataggcgtat cacgaggcag aatttcagat    7740
```

<210> SEQ ID NO 61
<211> LENGTH: 1959
<212> TYPE: DNA
<213> ORGANISM: Escherichia coli

<400> SEQUENCE: 61

| | |
|---|---|
| atgtcgcaaa ttcacaaaca caccattcct gccaacatcg cagaccgttg cctgataaac | 60 |
| cctcagcagt acgaggcgat gtatcaacaa tctattaacg tacctgatac cttctggggc | 120 |
| gaacagggaa aaattcttga ctggatcaaa ccttaccaga aggtgaaaaa cacctccttt | 180 |
| gcccccggta atgtgtccat taaatggtac gaggacggca cgctgaatct ggcggcaaac | 240 |
| tgccttgacc gccatctgca agaaaacggc gatcgtaccg ccatcatctg ggaaggcgac | 300 |
| gacgccagcc agagcaaaca tatcagctat aaagagctgc accgacgt ctgccgcttc | 360 |
| gccaataccc tgctcgagct gggcattaaa aaaggtgatg tggtggcgat ttatatgccg | 420 |
| atggtgccgg aagccgcggt tgcgatgctg cctgcgccc gcattggcgc ggtgcattcg | 480 |
| gtgattttcg gcggcttctc gccggaagcc gttgccgggc gcattattga ttccaactca | 540 |
| cgactggtga tcacttccga cgaaggtgtg cgtgccgggc gctccattcc gctgaagaaa | 600 |
| aacgttgatg acgcgctgaa aaacccgaac gtcaccagcg tagagcatgt ggtggtactg | 660 |
| aagcgtactg gcgggaaaat tgactggcag aagggcgcg acctgtggtg gcacgacctg | 720 |
| gttgagcaag cgagcgatca gcaccaggcg gaggagatga cgccgaaga tccgctgttt | 780 |
| attctctaca cctccggttc taccggtaag ccaaaaggtg tgctgcatac taccggcggt | 840 |
| tatctggtgt acgcggcgct gaccttaaa tatgtctttg attatcatcc gggtgatatc | 900 |
| tactggtgca ccgccgatgt gggctgggtg accggacaca gttacttgct gtacggcccg | 960 |
| ctggcctgcg gtgcgaccac gctgatgttt gaaggcgtac ccaactggcc gacgcctgcc | 1020 |
| cgtatggcgc aggtggtgga caagcatcag gtcaatattc tctataccgc acccacggcg | 1080 |
| atccgcgcgc tgatggcgga aggcgataaa gcgatcgaag caccgaccg ttcgtcgctg | 1140 |
| cgcattctcg gttccgtggg cgagccaatt aacccggaag cgtgggagtg gtactggaaa | 1200 |
| aaaatcggca acgagaaatg tccggtggtc gatacctggt ggcagaccga accggcggt | 1260 |
| ttcatgatca ccccgctgcc tggcgctacc gagctgaaag ccggtagtgc aacacgtccg | 1320 |
| ttcttcggcg tgcaaccggc gctggtcgat aacgaaggta acccgctgga ggggccacc | 1380 |
| gaaggtagcc tggtaatcac cgacagttgg ccgggtcagg cgcgtacgct gtttggcgat | 1440 |
| cacgaacgtt ttgaacagac ctacttctcc accttcaaaa atatgtattt cagcggcgac | 1500 |
| ggcgcgcgtc gcgatgaaga tggctattac tggataaccg ggcgtgtgga cgacgtgctg | 1560 |
| aacgtctccg gtcaccgtct ggggacggca gagattgagt cggcgctggt ggcgcatccg | 1620 |
| aagattgccg aagccgccgt agtaggtatt ccgcacaata ttaaaggtca ggcgatctac | 1680 |
| gcctacgtca cgcttaatca cggggaggaa ccgtcaccag aactgtacgc agaagtccgc | 1740 |
| aactgggtgc gtaaagagat tggcccgctg gcgacgccag acgtgctgca ctggaccgac | 1800 |
| tccctgccta aaacccgctc cggcaaaatt atgcgccgta ttctgcgcaa aattgcggcg | 1860 |
| ggcgatacca gcaacctggg cgatacctcg acgcttgccg atcctggcgt agtcgagaag | 1920 |
| ctgcttgagg agaagcaggc tatcgcgatg ccatcgtga | 1959 |

<210> SEQ ID NO 62
<211> LENGTH: 1461
<212> TYPE: DNA
<213> ORGANISM: Listeria monocytogenes

<400> SEQUENCE: 62

| | |
|---|---|
| atggcccttg aggacaaaga cctgcggagc atccaagagg taaggaactt aatagagagc | 60 |
| gcgaacaaag cccaaaaaga gctcgcggcc atgagtcaac aacaaataga cactatagtc | 120 |
| aaagctatag cggacgcagg gtatgggggcg agggagaaat tagccaaaat ggcccacgag | 180 |

| | |
|---|---|
| gagacagggt tcggcatatg gcaagataaa gtcataaaaa acgttttgc gtccaagcat | 240 |
| gtttacaatt acatcaaaga catgaaaacg atagggatgc tgaaagagga caacgagaag | 300 |
| aaagtcatgg aagtagccgt accgcttggg gtcgtagccg gcctgatacc atcgactaac | 360 |
| ccaacttcca cagtaatata caaaactctt atatctataa aagccggcaa ttcaatcgtc | 420 |
| ttctcgccgc acccgaacgc ccttaaagcc atactcgaga ctgtccgtat aatatcagag | 480 |
| gcggccgaga aagcgggatg tccgaaaggt gcgatcagtt gtatgacagt accgactatc | 540 |
| caaggcactg accaattgat gaaacataaa gacactgccg taatcctcgc cactggaggg | 600 |
| tcggccatgt caaagctgc gtatagctcg ggacaccgg ccataggcgt aggtccgggg | 660 |
| aatggtccgg ccttcatcga gcggtcagca acataccac gggccgtgaa acacatactc | 720 |
| gactccaaaa cttttgacaa cggcactata tgcgcctcgg aacaatcggt tgtagtagag | 780 |
| agggtgaata aagaggcggt tatagcggag ttccgtaaac aaggcgccca ttttctgagc | 840 |
| gacgccgagc cggtacaact cgggaaattt atcctgaggc cgaatgggag catgaatccg | 900 |
| gccatcgtcg ggaaaagtgt gcaacacatc gcgaacctcg cggggcttac tgtaccggcg | 960 |
| gatgcccgtg tcctcatcgc ggaggagact aaagtagggg cgaaaatccc atatagccgt | 1020 |
| gagaaactgg cgccgatcct agcgttttat actgccgaga catggcaaga ggcgtgcgag | 1080 |
| ctcagtatgg acatactcta tcacgagggc gcgggccaca cactgatcat ccattcggag | 1140 |
| gacaaagaga tcatccggga gtttgccttg aaaaaaccgg tatccaggct cctggtaaat | 1200 |
| actccgggcg ctctcggtgg cataggtgcc actactaatc tcgtcccagc gctgactctc | 1260 |
| gggtgtggag ccgtaggcgg ctcaagcagc tcggacaata tcggcccaga gaatctcttt | 1320 |
| aacatacggc ggatcgcgac tggcgtactg gaactggagg acataaggaa agaggagaac | 1380 |
| caagccactt cggagctccc tgtagacgcc gatgccttga tccaatcact ggtcgagaaa | 1440 |
| gtactggccg agctgaagta a | 1461 |

<210> SEQ ID NO 63
<211> LENGTH: 2919
<212> TYPE: DNA
<213> ORGANISM: Artificial Sequence
<220> FEATURE:
<223> OTHER INFORMATION: Synthetic DNA

<400> SEQUENCE: 63

| | |
|---|---|
| aaaaaaaatc cttagctttc gctaaggatg atttctggaa ttcgcggccg cttctagagc | 60 |
| ccacagctaa caccacgtcg tccctatctg ctgccctagg tctatgagtg gttgctggat | 120 |
| aactttacgg gcatgcataa ggctcgtatg atatattcag ggagaccaca acggtttccc | 180 |
| tctacaaata atttttgttta acttttcaca caggaaagta ctagatggca aggcccttga | 240 |
| tccagttagc gctggatacg ctggatattc cgcagaccct gaaattagca agcttaaccg | 300 |
| ccccatacgt ggacattttt gagattggca ccccaagcat taaacataac ggcattgcgc | 360 |
| tggttaaaga atttaagaag cgcttttcca acaaactgtt actggtggat ttaaagacca | 420 |
| tggatgcggg ggagtatgag gcgaccccat tttttgcggc gggcgcggat attaccaccg | 480 |
| tgttaggcgt ggcaggactg gcgaccatta aggcgtgat taacgcggcg aacaaacata | 540 |
| acgcggaagt gcaggtggat ctgattaacg tgccagataa agcggcgtgc gcgcgggaaa | 600 |
| gtgcgaaagc gggcgcgcag attgtgggca ttcataccgg cttagatgcg caggcggcgg | 660 |
| gccagacccc atttgcggat ttacaggcga ttgcgaaatt aggcttacca gtgcgcatta | 720 |

| | |
|---|---|
| gtgtggcggg cggcattaaa gcgagtaccg cgcaacaggt ggtgaagacc ggggcgaaca | 780 |
| ttattgtggt gggagcggcg atttatggcg cggcgagtcc agcggacgcg gcccgcgaga | 840 |
| tttatgagca ggtggtggcg gctagtgcgt aagccacacg cgctctcccc cctccggtgt | 900 |
| aatcggggga gagcgcgtgt ccgctgcagt ccggcaaaaa agggcaaggt gtcaccaccc | 960 |
| tgccctttt ctttaaaacc gaaaagatta cttcgcgtta tgcaggcttc ctcgctcact | 1020 |
| gactcgctgc gctcggtcgt tcggctgcgg cgagcggtat cagctcactc aaaggcggta | 1080 |
| atacggttat ccacagaatc aggggataac gcaggaaaga acatgtgagc aaaaggccag | 1140 |
| caaaaggcca ggaaccgtaa aaaggccgcg ttgctggcgt ttttccacag gctccgcccc | 1200 |
| cctgacgagc atcacaaaaa tcgacgctca agtcagaggt ggcgaaaccc gacaggacta | 1260 |
| taaagatacc aggcgtttcc ccctggaagc tccctcgtgc gctctcctgt tccgaccctg | 1320 |
| ccgcttaccg gatacctgtc cgcctttctc ccttcgggaa gcgtggcgct ttctcatagc | 1380 |
| tcacgctgta ggtatctcag ttcggtgtag gtcgttcgct ccaagctggg ctgtgtgcac | 1440 |
| gaaccccccg ttcagcccga ccgctgcgcc ttatccggta actatcgtct tgagtccaac | 1500 |
| ccggtaagac acgacttatc gccactggca gcagccactg gtaacaggat tagcagagcg | 1560 |
| aggtatgtag gcggtgctac agagttcttg aagtggtggc ctaactacgg ctacactaga | 1620 |
| agaacagtat ttggtatctg cgctctgctg aagccagtta ccttcggaaa aagagttggt | 1680 |
| agctcttgat ccggcaaaca aaccaccgct ggtagcggtg gtttttttgt ttgcaagcag | 1740 |
| cagattacgc gcagaaaaaa aggatctcaa gaagatcctt tgatcttttc tacggggtct | 1800 |
| gacgctcagt ggaacgaaaa ctcacgttaa gggattttgg tcatgagatt atcaaaaagg | 1860 |
| atcttcacct agatcctttt aaattaaaaa tgaagtttta atcaatcta aagtatatat | 1920 |
| gagtaaactt ggtctgacag ctcgaggctt ggattctcac caataaaaaa cgcccggcgg | 1980 |
| caaccgagcg ttctgaacaa atccagatgg agttctgagg tcattactgg atctatcaac | 2040 |
| aggagtccaa gcgagctcga tatcaaatta cgccccgccc tgccactcat cgcagtactg | 2100 |
| ttgtaattca ttaagcattc tgccgacatg gaagccatca caaacggcat gatgaacctg | 2160 |
| aatcgccagc ggcatcagca ccttgtcgcc ttgcgtataa tatttgccca tggtgaaaac | 2220 |
| gggggcgaag aagttgtcca tattggccac gtttaaatca aaactggtga actcacccca | 2280 |
| gggattggct gagacgaaaa acatattctc aataaaccct ttagggaaat aggccaggtt | 2340 |
| ttcaccgtaa cacgccacat cttgcgaata tatgtgtaga actgccgga atcgtcgtg | 2400 |
| gtattcactc cagagcgatg aaaacgtttc agtttgctca tggaaaacgg tgtaacaagg | 2460 |
| gtgaacacta tcccatatca ccagctcacc gtctttcatt gccatacgaa attccggatg | 2520 |
| agcattcatc aggcgggcaa gaatgtgaat aaaggccgga taaaacttgt gcttattttt | 2580 |
| ctttacggtc tttaaaaagg ccgtaatatc cagctgaacg gtctggttat aggtacattg | 2640 |
| agcaactgac tgaaatgcct caaaatgttc tttacgatgc cattgggata tatcaacggt | 2700 |
| ggtatatcca gtgatttttt tctccatttt agcttcctta gctcctgaaa atctcgataa | 2760 |
| ctcaaaaaat acgcccggta gtgatcttat ttcattatgg tgaaagttgg aacctcttac | 2820 |
| gtgcccgatc aactcgagtg ccacttgacg tctaagaaac cattattatc atgacattaa | 2880 |
| cctataaaaa taggcgtatc acgaggcaga atttcagat | 2919 |

<210> SEQ ID NO 64
<211> LENGTH: 2805
<212> TYPE: DNA
<213> ORGANISM: Artificial Sequence
<220> FEATURE:
<223> OTHER INFORMATION: Synthetic DNA

<400> SEQUENCE: 64

```
aaaaaaaatc cttagctttc gctaaggatg atttctggaa ttcgcggccg cttctagagc      60
ccacagctaa caccacgtcg tccctatctg ctgccctagg tctatgagtg gttgctggat     120
aactttacgg gcatgcataa ggctcgtatg atatattcag ggagaccaca acggtttccc     180
tctacaaata attttgttta acttttcaca caggaaagta ctagatgcac cagaagctga     240
ttatagataa gattagtggc attttagcgg cgaccgacgc gggctacgac gcaaagctga     300
ctgcgatgtt agatcaggcg agtcgcattt ttgtggccgg tgcgggccgt tcgggtctgg     360
tggcgaaatt ttttgcgatg cgcttaatgc atggcggcta cgatgtgttt gtggtgggcg     420
agattgtgac cccaagcatt cgcaaaggcg atttgctgat tgttattagt ggcagtgggg     480
agaccgagac catgttagcg tttaccaaga aggcgaaaga acagggcgcg agtattgcgt     540
taattagtac ccgcgatagc agtagtttag gcgatttagc ggatagtgtg tttcgcattg     600
gcagtcccga attatttgga aaggtggtgg gcatgccaat gggcaccgtg tttgaattaa     660
gtaccttatt attttttagaa gcgaccattt cacatattat tcatgaaaag ggcattccag     720
aggaggagat gaggactcgg catgcgaacc tggagtaagc cacacgcgct ctccccctc     780
cggtgtaatc gggggagagc gcgtgtccgc tgcagtccgg caaaaaggg caaggtgtca     840
ccaccctgcc cttttttcttt aaaaccgaaa agattacttc gcgttatgca ggcttcctcg     900
ctcactgact cgctgcgctc ggtcgttcgg ctgcggcgag cggtatcagc tcactcaaag     960
gcggtaatac ggttatccac agaatcaggg gataacgcag gaaagaacat gtgagcaaaa    1020
ggccagcaaa aggccaggaa ccgtaaaaag gccgcgttgc tggcgttttt ccacaggctc    1080
cgccccctg acgagcatca caaaaatcga cgctcaagtc agaggtggcg aaacccgaca    1140
ggactataaa gataccaggc gtttccccct ggaagctccc tcgtgcgctc tcctgttccg    1200
accctgccgc ttaccggata cctgtccgcc tttctccctt cgggaagcgt ggcgctttct    1260
catagctcac gctgtaggta tctcagttcg gtgtaggtcg ttcgctccaa gctgggctgt    1320
gtgcacgaac ccccgttca gcccgaccgc tgcgccttat ccggtaacta tcgtcttgag    1380
tccaacccgg taagacacga cttatcgcca ctggcagcag ccactggtaa caggattagc    1440
agagcgaggt atgtaggcgg tgctacagag ttcttgaagt ggtggcctaa ctacggctac    1500
actagaagaa cagtatttgg tatctgcgct ctgctgaagc cagttacctt cggaaaaaga    1560
gttggtagct cttgatccgg caaacaaacc accgctggta gcggtggttt ttttgtttgc    1620
aagcagcaga ttacgcgcag aaaaaaagga tctcaagaag atcctttgat cttttctacg    1680
gggtctgacg ctcagtggaa cgaaaactca cgttaaggga ttttggtcat gagattatca    1740
aaaaggatct tcacctagat ccttttaaat taaaaatgaa gttttaaatc aatctaaagt    1800
atatatgagt aaacttggtc tgacagctcg aggcttggat tctcaccaat aaaaaacgcc    1860
cggcggcaac cgagcgttct gaacaaatcc agatggagtt ctgaggtcat tactggatct    1920
atcaacagga gtccaagcga gctcgatatc aaattacgcc ccgccctgcc actcatcgca    1980
gtactgttgt aattcattaa gcattctgcc gacatggaag ccatcacaaa cggcatgatg    2040
aacctgaatc gccagcggca tcagcacctt gtcgccttgc gtataatatt tgcccatggt    2100
gaaaacgggg gcgaagaagt tgtccatatt ggccacgttt aaatcaaaac tggtgaaact    2160
cacccaggga ttggctgaga cgaaaaacat attctcaata aacccttag ggaaataggc    2220
```

| | |
|---|---|
| caggttttca ccgtaacacg ccacatcttg cgaatatatg tgtagaaact gccggaaatc | 2280 |
| gtcgtggtat tcactccaga gcgatgaaaa cgtttcagtt tgctcatgga aaacggtgta | 2340 |
| acaagggtga acactatccc atatcaccag ctcaccgtct ttcattgcca tacgaaattc | 2400 |
| cggatgagca ttcatcaggc gggcaagaat gtgaataaag gccggataaa acttgtgctt | 2460 |
| atttttcttt acggtcttta aaaaggccgt aatatccagc tgaacggtct ggttataggt | 2520 |
| acattgagca actgactgaa atgcctcaaa atgttcttta cgatgccatt gggatatatc | 2580 |
| aacggtggta tatccagtga ttttttttctc cattttagct tccttagctc ctgaaaatct | 2640 |
| cgataactca aaaaatacgc ccggtagtga tcttatttca ttatggtgaa agttggaacc | 2700 |
| tcttacgtgc ccgatcaact cgagtgccac ttgacgtcta agaaaccatt attatcatga | 2760 |
| cattaaccta aaaaatagg cgtatcacga ggcagaattt cagat | 2805 |

<210> SEQ ID NO 65
<211> LENGTH: 7393
<212> TYPE: DNA
<213> ORGANISM: Artificial Sequence
<220> FEATURE:
<223> OTHER INFORMATION: Synthetic DNA

<400> SEQUENCE: 65

| | |
|---|---|
| acacgcgctc tcccccgtca cgtacgtcgc agtacgtgct cttcgcggga tcgtacgtta | 60 |
| gagttagcgc gcgtgacggc cccttacgtg atattttg aaattggcac gccatgtatt | 120 |
| aagtataacg gcattgagat tgtgcgcgaa ttaaaacgcc gtcatccgga ccgtttagtg | 180 |
| ctggtggatt taaaaaccat ggacgcgggc gagtatgaag cggccccgtt ctacgcggcg | 240 |
| ggcgctgata tttgcaccgt tttaggtgtt tcgggtccgg ccaccattgc gggtgtggtc | 300 |
| aaggccgcg aggcccataa tgcggagtg caggttgacc tgattaacgt tccggataaa | 360 |
| gctgcgtgcg cccgcgaagc gcgcgttta ggcgcgcaga ttattggggt tcataccggg | 420 |
| ctggacgcgc aggcgcaggg gcagacgccg tttgcggact agagagcat tgcgcgcctg | 480 |
| aaactgccgg tgagaatttc tgttgctggt ggtattaacc agaacaccgc gtctcgtgtg | 540 |
| gcgaaagccg gtgcggatat tgtggtggtg ggggccgcca tttatggcgc ccatgtcca | 600 |
| gcgaccgccg cgcgcacgat ccgcgaactg ctggagggtg ctcaccataa atttattgtt | 660 |
| agtaaaattg gcggcgttct tgcggcgact gataaaagct atgaagcccg gctgaccggg | 720 |
| ttattagagc gggcgcgccg gatctttgtg gcgggcgcgg gtcggagtgg cctggtgggc | 780 |
| cgcttctttg cgatgcgtct gatgcatggc ggctaccagg cttacatcgt tggcgaaatt | 840 |
| gttacgccaa gcattcggca aggcgacctc ctgattgtta tcagtgggtc gggcgagacc | 900 |
| gagaccatga ttgcttatgc gaaaaaggcg aaagagcagg gtgcgagcat tgccctgatt | 960 |
| accacccgcg ataaaagtac gattgggat atggcagatg ttgtttttcg tattggcact | 1020 |
| ccagaacagt atggcaaagt tgtgggatg ccgatgggca ccacctttga actgagtacc | 1080 |
| ctggttctgt tagaggcgac gatcagtcat attattcaca ccaaaaaaat tccagaagaa | 1140 |
| cagatgcgta cccgccatgc gaatctggag taagcccaca gctaacacca cgtcgtccct | 1200 |
| atctgctgcc ctaggtctat gagtggttgc tggataactt tacgggcatg cataaggctc | 1260 |
| gtatgatata ttcagggaga ccacaacggt ttccctctac aaataatttt gtttaacttt | 1320 |
| aaagaggaga aatactagat gtcgcaaatt cacaaacaca ccattcctgc caacatcgca | 1380 |
| gaccgttgcc tgataaaccc tcagcagtac gaggcgatgt atcaacaatc tattaacgta | 1440 |
| cctgatacct tctggggcga acagggaaaa attcttgact ggatcaaacc ttaccagaag | 1500 |

```
gtgaaaaaca cctcctttgc ccccggtaat gtgtccatta aatggtacga ggacggcacg    1560
ctgaatctgg cggcaaactg ccttgaccgc catctgcaag aaaacggcga tcgtaccgcc    1620
atcatctggg aaggcgacga cgccagccag agcaaacata tcagctataa agagctgcac    1680
cgcgacgtct gccgcttcgc caatacccctg ctcgagctgg gcattaaaaa aggtgatgtg    1740
gtggcgattt atatgccgat ggtgccggaa gccgcggttg cgatgctggc ctgcgcccgc    1800
attggcgcgt gcattcggt gattttcggc ggcttctcgc cggaagccgt tgccgggcgc    1860
attattgatt ccaactcacg actggtgatc acttccgacg aaggtgtgcg tgccgggcgc    1920
tccattccgc tgaagaaaaa cgttgatgac gcgctgaaaa acccgaacgt caccagcgta    1980
gagcatgtgg tggtactgaa gcgtactggc gggaaaattg actggcagga agggcgcgac    2040
ctgtggtggc acgacctggt tgagcaagcg agcgatcagc accaggcgga ggagatgaac    2100
gccgaagatc cgctgtttat tctctacacc tccggttcta ccggtaagcc aaaaggtgtg    2160
ctgcatacta ccggcggtta tctggtgtac gcggcgctga cctttaaata tgtctttgat    2220
tatcatccgg gtgatatcta ctggtgcacc gccgatgtgg gctgggtgac cggacacagt    2280
tacttgctgt acgcccgct ggcctgcggt gcgaccacgc tgatgtttga aggcgtaccc    2340
aactggccga cgcctgcccg tatggcgcag gtggtggaca agcatcaggt caatattctc    2400
tataccgcac ccacggcgat ccgcgcgctg atggcggaag cgataaagc gatcgaaggc    2460 accgaccgtt cgtcgctgcg cattctcggt tccgtgggcg agccaattaa cccggaagcg    2520
tgggagtggt actggaaaaa aatcggcaac gagaaatgtc cggtggtcga tacctggtgg    2580
cagaccgaaa ccggcggttt catgatcacc ccgctgcctg gcgctaccga gctgaaagcc    2640
ggtagtgcaa cacgtccgtt cttcggcgtg caaccggcgc tggtcgataa cgaaggtaac    2700
ccgctggagg gggccaccga aggtagcctg gtaatcaccg acagttggcc gggtcaggcg    2760
cgtacgctgt ttggcgatca cgaacgtttt gaacagacct acttctccac cttcaaaaat    2820
atgtatttca gcgcgacgg cgcgcgtcgc gatgaagatg gctattactg gataaccggg    2880
cgtgtggacg acgtgctgaa cgtctccggt caccgtctgg ggacggcaga gattgagtcg    2940
gcgctggtgg cgcatccgaa gattgccgaa gccgccgtag taggtattcc gcacaatatt    3000
aaaggtcagg cgatctacgc ctacgtcacg cttaatcacg gggaggaacc gtcaccagaa    3060
ctgtacgcag aagtccgcaa ctgggtgcgt aaagagattg gcccgctggc gacgccagac    3120
gtgctgcact ggaccgactc cctgcctaaa acccgctccg gcaaaattat gcgccgtatt    3180
ctgcgcaaaa ttgcggcggg cgataccagc aacctgggcg atacctcgac gcttgccgat    3240
cctggcgtag tcgagaagct gcttgaggag aagcaggcta tcgcgatgcc atcgtgagcc    3300
cgaagagcac gtactgctaa gctgactgcg ggggagagcg cgtgtgccgg ccagtctaca    3360
tgtactcttt ttgataaaaa attggagatt cctttacaaa tatgctctta cgtgctatta    3420
tttaagtgac tatttaaaag gagttaataa atatgcggca aggtattctt aaataaactg    3480
tcaatttgat agcgggaaca aataattaga tgtcctttt taggagggct tagttttttg    3540
tacccagttt aagaatacct ttatcatgtg attctaaagt atccagagaa tatctgtatg    3600
ctttgtatac ctatggttat gcataaaaat cccggtgata aagtattta tcactgggat    3660 ttttatgccc ttttgggttt ttgaatggag gaatactaga tgaaaatcat aaatatcggt    3720
gtattagctc acgttgatgc aggaaaaaca acattaactg aatcactttt atataactct    3780
ggtgcaatta ctgaacttgg ttcagtagat aaaggtacta ctcgtactga taatacatta    3840
```

```
ttagaacgtc aacgtggaat cacaattcaa acaggtatca catcttttca atgggaaaat   3900
acaaaagtaa atattataga tacacctgga cacatggatt tccttgcaga agtataccgt   3960
agtctttcag tattagatgg tgctatttta cttatcagcg ctaaagatgg agttcaagct   4020
caaactcgta tcttatttca cgcattacgt aaaatgggta ttccaacaat tttctttata   4080
aacaaaattg accaaaacgg aattgattta agtacagttt atcaagatat caagaaaaa    4140 ctttctgctg aaatcgttat taaacaaaaa gttgaattat acccaaacgt tgcgtaaca    4200 aattttactg aatcagaaca atgggataca gttatagaag gtaatgatga tttattagaa   4260
aaatacatgt caggtaaatc attagaagca ttagaattag aacaagaaga agtattcgt    4320 ttccaaaact gttctttatt ccctttatac catggaagcg ctaaagtaa cataggtatt    4380 gataacttaa ttgaagttat tactaacaaa ttttattctt caactcatcg tgggccttct   4440
gaattatgcg gtaacgtttt caaaattgaa tatacaaaaa aacgtcaacg tttagcttat   4500
atacgtcttt atagtggtgt tttacattta cgtgatagtg ttcgtgttag tgaaaaagaa   4560
aagattaaag ttacagaaat gtatacttct attaacggtg aattatgcaa aattgaccgt   4620
gcatattcag gtgaaattgt aattttacaa acgaatttc ttaaacttaa tagtgtactt    4680
ggtgacacaa aacttttacc acaacgtaag aaaattgaaa atccacaccc attacttcaa   4740
acaacagtag aaccaagcaa acctgaacaa cgtgaaatgc ttttagatgc tcttttagaa   4800
attagtgact ctgacccact tttacgttac tatgtagatt ctactactca tgaaattatt   4860
ctttctttcc ttggtaaagt tcaaatggaa gttatttctg cattattaca agaaaaatat   4920
catgttgaaa tcgaattaaa agaacctact gtaatttata tggaacgtcc attaaaaaat   4980
gctgaatata caattcatat tgaagttcca ccaaatccat tttgggcttc tattggtctt   5040
tctgtttctc cacttccact tggtagcgga atgcaatatg aaagtagcgt aagtttaggt   5100
tatcttaatc aaagtttcca aaacgcagtt atggaaggta ttcgttacgg ttgcgaacaa   5160
ggtttatacg gttggaatgt tacagactgc aaaatctgtt ttaagtatgg actttactat   5220
tcacctgtat caacacctgc tgactttcgt atgcttgcac caattgtttt agaacaagtt   5280
ttaaagaaag ctggaactga acttttagaa ccataccttt cttttaaaat ctatgcacca   5340
caagaatact aagtcgtgc ttataacgat gcacctaaat actgtgctaa tattgttgat   5400
actcaattaa agaacaacga agtaattta agcggagaaa ttcctgcacg ttgtattcaa   5460
gaatatcgta gtgatttaac attttcact aatggacgtt ctgtttgctt aactgaatta    5520
aaaggttatc atgttactac tggtgaacct gtatgccaac cacgtcgtcc taatagtcgt   5580
attgataaag ttcgttatat gttcaacaaa atcacataat aaaaaaaaaa accccgcccc   5640
tgacagggcg gggttttttt tttagttagt tagagatgtg tataagagac agctggccat   5700
ggaatagact ggatggaggc ggataaagtt gcaggaccac ttctgcgctc ggcccttccg   5760
gctggctggt ttattgctga taaatctgga gccggtgagc gtgggtctcg cggtatcatt   5820
gcagcactgg ggccagatgg taagccctcc cgtatcgtag ttatctacac gacggggagt   5880
caggcaacta tggatgaacg aaatagacag atcgctgaga taggtgcctc actgattaag   5940
cattggtaac tgtcagacca gtttactca tatatacttt agattgattt aaaacttcat    6000
ttttaattta aaaggatcta ggtgaagatc cttttttgata atctcatgac caaaatccct   6060
taacgtgagt tttcgttcca ctgagcgtca gacccttaa taagatgatc ttcttgagat    6120
cgttttggtc tgcgcgtaat ctcttgctct gaaaacgaaa aaaccgcctt gcagggcggt   6180
ttttcgaagg ttctctgagc taccaactct ttgaaccgag gtaactggct tggaggagcg   6240
```

```
cagtcaccaa aacttgtcct ttcagtttag ccttaaccgg cgcatgactt caagactaac    6300
tcctctaaat caattaccag tggctgctgc cagtggtgct tttgcatgtc tttccgggtt    6360
ggactcaaga cgatagttac cggataaggc gcagcggtcg gactgaacgg ggggttcgtg    6420
catacagtcc agcttggagc gaactgccta cccggaactg agtgtcaggc gtggaatgag    6480
acaaacgcgg ccataacagc ggaatgacac cggtaaaccg aaaggcagga acaggagagc    6540
gcacgaggga gccgccaggg gaaacgcctg gtatctttat agtcctgtcg ggtttcgcca    6600
ccactgattt gagcgtcaga tttcgtgatg cttgtcaggg gggcggagcc tatggaaaaa    6660
cggctttgcc gcggccctct cacttccctg ttaagtatct tcctggcatc ttccaggaaa    6720
tctccgcccc gttcgtaagc catttccgct cgccgcagtc gaacgaccga gcgtagcgag    6780
tcagtgagcg aggaagcgga atatatcctg tatcacatat tctgctgacg caccggtgca    6840
gccttttttc tcctgccaca tgaagcactt cactgacacc ctcatcagtg ccaacatagt    6900
aagccagtat acactccgct agcgctgagg tctgcctcgt gaagaaggtg ttgctgactc    6960
ataccaggcc tgaatcgccc catcatccag ccagaaagtg agggagccac ggttgatgag    7020
agctttgttg taggtggacc agttggtgat tttgaactt tgctttgcca cggaacggtc    7080
tgcgttgtcg ggaagatgcg tgatctgatc cttcaactca gcaaaagttc gatttattca    7140
acaaagccac gttgtgtctc aaaatctctg atgttacatt gcacaagata aaaatatatc    7200
atcatgaaca ataaaactgt ctgcttacat aaacagtaat acaaggggtg ttgcccagct    7260
gtctcttata cacatctccg gcttatcggt cagtttcacc tgatttacgt aaaaaccgc     7320 ttcggcgggt ttttgctttt ggaggggcag aaagatgaat gactgtccac gacgctatac    7380
ccaaaagaaa gcc                                                        7393

<210> SEQ ID NO 66
<211> LENGTH: 4269
<212> TYPE: DNA
<213> ORGANISM: Artificial Sequence
<220> FEATURE:
<223> OTHER INFORMATION: Synthetic DNA

<400> SEQUENCE: 66
gaattcgcgg ccgcttctag aggccgatct cgatcccgcg aaattaatac gactcactat      60 agggaattg tgagcggata caattcccc tctagaaata attttgttta actttaagaa       120
ggagactctt ctatggccct tgaggacaaa gacctgcgga gcatccaaga ggtaaggaac     180
ttaatagaga gcgcgaacaa agcccaaaaa gagctcgcgg ccatgagtca acaacaaata    240
gacactatag tcaaagctat agcggacgca gggtatgggg cgagggagaa attagccaaa    300
atggcccacg aggagacagg gttcggcata tggcaagata aagtcataaa aaacgttttt    360
gcgtccaagc atgtttacaa ttacatcaaa gacatgaaaa cgatagggat gctgaaagag    420
gacaacgaga agaaagtcat ggaagtagcc gtaccgcttg gggtcgtagc ggcctgata    480 ccatcgacta acccaacttc cacagtaata tacaaaactc ttatatctat aaaagccggc    540
aattcaatcg tcttctcgcc gcacccgaac gcccttaaag ccatactcga gactgtccgt    600
ataatatcag aggcggccga gaaagcggga tgtccgaaag gtgcgatcag ttgtatgaca    660
gtaccgacta tccaaggcac tgaccaattg atgaaacata agacactgc cgtaatcctc    720 gccactggag ggtcggccat ggtcaaagct gcgtatagct cggggacacc ggccataggc    780
gtaggtccgg ggaatggtcc ggccttcatc gagcggtcag caaacatacc acgggccgtg    840
```

```
aaacacatac tcgactccaa aacttttgac aacggcacta tatgcgcctc ggaacaatcg      900
gttgtagtag agagggtgaa taaagaggcg gttatagcgg agttccgtaa acaaggcgcc      960
cattttctga gcgacgccga ggcggtacaa ctcgggaaat ttatcctgag gccgaatggg     1020
agcatgaatc cggccatcgt cgggaaaagt gtgcaacaca tcgcgaacct cgcggggctt     1080
actgtaccgg cggatgcccg tgtcctcatc gcggaggaga ctaaagtagg ggcgaaaatc     1140
ccatatagcc gtgagaaact ggcgccgatc ctagcgtttt atactgccga gcatggcaa      1200 gaggcgtgcg agctcagtat ggacatactc tatcacgagg gcgcgggcca cacactgatc     1260
atccattcgg aggacaaaga gatcatccgg gagtttgcct tgaaaaaacc ggtatccagg     1320
ctcctggtaa atactccggg cgctctcggt ggcataggtg ccactactaa tctcgtccca     1380
gcgctgactc tcgggtgtgg agccgtaggc ggctcaagca gctcggacaa tatcggccca     1440
gagaatctct ttaacatacg gcggatcgcg actggcgtac tggaactgga ggacataagg     1500
aaagaggaga accaagccac ttcggagctc cctgtagacg ccgatgcctt gatccaatca     1560
ctggtcgaga aagtactggc cgagctgaag taagcccgaa gagctactag tagcggccgc     1620
tgcagcgtca aaagggcgac acaaaattta ttctaaatgc ataataaata ctgataacat     1680
cttatagttt gtattatatt ttgtattatc gttgacatgt ataattttga tatcaaaaac     1740
tgattttccc tttattattt tcgagattta ttttcttaat tctctttaac aaactagaaa     1800
tattgtatat acaaaaaatc ataaataata gatgaatagt ttaattatag gtgttcatca     1860
atcgaaaaag caacgtatct tatttaaagt gcgttgcttt tttctcattt ataaggttaa     1920
ataattctca tatatcaagc aaagtgacag gcgcccttaa atattctgac aaatgctctt     1980
tccctaaact ccccccataa aaaaacccgc cgaagcgggt ttttacgtta tttgcggatt     2040
aacgattact cgttatcaga accgcccagg gggcccgagc ttaagactgg ccgtcgtttt     2100
acaacacaga aagagtttgt agaaacgcaa aaaggccatc cgtcagggcc ttctgcttta     2160
gtttgatgcc tggcagttcc ctactctcgc cttccgcttc ctcgctcact gactcgctgc     2220
gctcggtcgt tcggctgcgg cgagcggtat cagctcactc aaaggcggta atacggttat     2280
ccacagaatc aggggataac gcaggaaaga acatgtgagc aaaaggccag caaaaggcca     2340
ggaaccgtaa aaaggccgcg ttgctggcgt ttttccatag gctccgcccc cctgacgagc     2400
atcacaaaaa tcgacgctca agtcagaggt ggcgaaaccc gacaggacta taaagatacc     2460
aggcgtttcc ccctggaagc tccctcgtgc gctctcctgt tccgaccctg ccgcttaccg     2520
gatacctgtc cgcctttctc ccttcgggaa gcgtggcgct ttctcatagc tcacgctgta     2580
ggtatctcag ttcggtgtag gtcgttcgct ccaagctggg ctgtgtgcac gaaccccccg     2640
ttcagcccga ccgctgcgcc ttatccggta actatcgtct tgagtccaac ccggtaagac     2700
acgacttatc gccactggca gcagccactg gtaacaggat tagcagagcg aggtatgtag     2760
gcggtgctac agagttcttg aagtggtggg ctaactacgg ctacactaga agaacagtat     2820
ttggtatctg cgctctgctg aagccagtta ccttcggaaa aagagttggt agctcttgat     2880
ccggcaaaca aaccaccgct ggtagcggtg gtttttttgt ttgcaagcag cagattacgc     2940
gcagaaaaaa aggatctcaa gaagatcctt tgatcttttc tacggggtct gacgctcagt     3000
ggaacgacgc gcgcgtaact cacgttaagg gattttggtc atgagcttgc gccgtcccgt     3060
caagtcagcg taatgctctg cttttagaaa aactcatcga gcatcaaatg aaactgcaat     3120
ttattcatat caggattatc aataccatat ttttgaaaaa gccgtttctg taatgaagga     3180
gaaaactcac cgaggcagtt ccataggatg caagatcct ggtatcggtc tgcgattccg     3240
```

```
actcgtccaa catcaataca acctattaat ttccctcgt caaaaataag gttatcaagt    3300
gagaaatcac catgagtgac gactgaatcc ggtgagaatg gcaaaagttt atgcatttct    3360
ttccagactt gttcaacagg ccagccatta cgctcgtcat caaaatcact cgcatcaacc    3420
aaaccgttat tcattcgtga ttgcgcctga gcgaggcgaa atacgcgatc gctgttaaaa    3480
ggacaattac aaacaggaat cgagtgcaac cggcgcagga acactgccag cgcatcaaca    3540
atattttcac ctgaatcagg atattcttct aatacctgga acgctgtttt tccggggatc    3600
gcagtggtga gtaaccatgc atcatcagga gtacggataa aatgcttgat ggtcggaagt    3660
ggcataaatt ccgtcagcca gtttagtctg accatctcat ctgtaacatc attggcaacg    3720
ctacctttgc catgtttcag aaacaactct ggcgcatcgg gcttcccata caagcgatag    3780
attgtcgcac ctgattgccc gacattatcg cgagcccatt tatacccata taaatcagca    3840
tccatgttgg aatttaatcg cggcctcgac gtttcccgtt gaatatggct catattcttc    3900 cttttcaat attattgaag catttatcag ggttattgtc tcatgagcgg atacatattt    3960
gaatgtattt agaaaaataa acaaatacgg gtcagtgtta caaccaatta accaattctg    4020
aacattatcg cgagcccatt tatacctgaa tatggctcat aacacccctt gtttgcctgg    4080
cggcagtagc gcggtggtcc cacctgaccc catgccgaac tcagaagtga aacgccgtag    4140
cgccgatggt agtgtgggga ctccccatgc gagagtaggg aactgccagg catcaaataa    4200
aacgaaaggc tcagtcgaaa gactgggcct ttcgcccggg ctaattaggg ggtgtcgccc    4260
ttcgctgaa                                                            4269
```